US007820181B2

(12) United States Patent
Skiadopoulos et al.

(10) Patent No.: US 7,820,181 B2
(45) Date of Patent: Oct. 26, 2010

(54) RECOVERY OF RECOMBINANT HUMAN PARAINFLUENZA VIRUS TYPE 2 (HPIV2) FROM CDNA AND USE OF RECOMBINANT HPIV2 IN IMMUNOGENIC COMPOSITIONS AND AS VECTORS TO ELICIT IMMUNE RESPONSES AGAINST PIV AND OTHER HUMAN PATHOGENS

(75) Inventors: Mario H. Skiadopoulos, Potomac, MD (US); Brian R. Murphy, Bethesda, MD (US); Peter L. Collins, Kensington, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 1311 days.

(21) Appl. No.: 10/667,141

(22) Filed: Sep. 18, 2003

(65) Prior Publication Data
US 2004/0204581 A1    Oct. 14, 2004

Related U.S. Application Data

(60) Provisional application No. 60/412,053, filed on Sep. 18, 2002.

(51) Int. Cl.
*A61K 39/155*    (2006.01)

(52) U.S. Cl. ............ 424/211.1; 424/199.1; 424/184.1; 435/69.1; 435/69.52

(58) Field of Classification Search ............ None
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 5,993,824 | A | 11/1999 | Murphy |
| 6,264,957 | B1 | 7/2001 | Collins |
| 6,410,023 | B1 | 6/2002 | Durbin et al. |
| 6,689,367 | B1 | 2/2004 | Collins |
| 2004/0142448 | A1 | 7/2004 | Murphy |

FOREIGN PATENT DOCUMENTS

| | | |
|---|---|---|
| WO | WO 9706270 | 2/1997 |
| WO | WO 9712032 | 4/1997 |
| WO | WO 9802530 | 1/1998 |
| WO | WO 98/53078 | * 11/1998 |
| WO | WO 9853078 | 11/1998 |
| WO | WO 0061611 | 10/2000 |
| WO | WO 0061737 | 10/2000 |
| WO | WO 0104320 | 1/2001 |
| WO | WO 0104335 | 1/2001 |
| WO | WO 0142445 | 6/2001 |

OTHER PUBLICATIONS

Skiadapoulos et al. Journal of Virology, 1998, vol. 72, p. 1762-1768.*
Skiadapoulos et al. Journal of Virology, 1999, vol. 73, p. 1374-1381.*
Kawano et al. (Virology, vol. 284, p. 99-112).*
Skidapoulos et al. (Journal of Virology 2003, vol. 77, p. 270-279).*
Anderson et al., Antigenic Characterization of Respiratory Syncytial Virus Strains With Monoclonal Antibodies, Journal Infectious Diseases, vol. 151, No. 4, 626-633 (1985).
Baron et al., Rescue of Rinderpest Virus From Cloned cDNA, Journal of Virology, vol. 71, No. 2, 1265-1271 (1997).
Beeler et al., Neutralization Epitopes of F Glycoprotein of Respiratory Syncytial Virus Effect of Mutation Upon Fusion Function, Journal of Virology, vol. 63, No. 7, 2941-2950 (1989).
Belshe et al., Cold Adaptation of Parainfluenza Virus Type 3, Journal Medical Virology, vol. 10(4), 235-242 (1982).
Belshe et al., Comparison of Enzyme-Linked Immunosorbent Assay and Neutralization Techniques for Measurement of Antibody, Infection and Immunity, vol. 37, No. 1, 160-165 (1982).
Belshe et al., Further Characterization of the Complementation Group B Temperature Sensitive Mutant of Respiratory Syncytial Virus, Journal of Virology, vol. 24, No. 1, 8-12 (1977).
Biacchesi et al., Recovery of NV Knockout Infectious Hematopoietic Necrosis Virus, Journal of Virology vol. 74, No. 23, 11247-11253 (2000).
Bilsel et al., Polymerase Errors Accumulating During Natural Evolution of the Glycoprotein Gene of Vesicular Stomatitis Virus, Journal of Virology, vol. 64, No. 10, 4873-4883 (1990).
Buchholz et al., Generation of Bovine Respiratory Syncytial Virus (BRSV) from cDNA, Journal of Virology, vol. 73, No. 1, 251-259 (1999).
Bukreyev et al., Recovery of Infectious Respiratory Syncytial Virus Expressing An Additional, Foreign Gene, Journal of Virology, vol. 70, No. 10, 6634-6641 (1996).
Bukreyev et al., Granulocyte-Macrophage Colony-Stimulating Factor Expressed By Recombinant Respiratory Syncytial Virus, Journal of Virology vol. 75, No. 24, 12128-12140 (2001).

(Continued)

*Primary Examiner*—Zachariah Lucas
*Assistant Examiner*—Agnieszka Boesen
(74) *Attorney, Agent, or Firm*—Woodcock Washburn LLP

(57) ABSTRACT

Recombinant human parainfluenza virus type 2 (HPIV2) viruses and related immunogenic compositions and methods are provided. The recombinant HPIV2 viruses, including HPIV2 chimeric and chimeric vector viruses, provided according to the invention are infectious and attenuated in permissive mammalian subjects, including humans, and are useful in immunogenic compositions for eliciting an immune responses against one or more PIVs, against one or more non-PIV pathogens, or against a PIV and a non-PIV pathogen. Also provided are isolated polynucleotide molecules and vectors incorporating a recombinant HPIV2 genome or antigenome.

6 Claims, 29 Drawing Sheets

OTHER PUBLICATIONS

Bukreyev et al., Interferon Expressed By A Recombinant Respiratory Syncytial Virus Attenuates Virus Replication In Mice, Proc. Natl. Acad. Sci. USA vol. 96, 2367-2372 (1999).

Calain et al., The Rule of Six, A Basic Feature for Efficient Replication of Sendai Virus, Journal of Virology, vol. 67, No. 8, 4822-4830 (1993).

Chanock et al., Parainfluenza Viruses, Fields Virology, 4th Ed., vol. 1, 1341-1379 (2001).

Chanock et al., Association of A New Type of Cytopathogenic Myxovirus With Infantile Croup, Journal of Experimental Medicine, vol. 104, Plate 47, 555-577 (1956).

Cheng et al., Effective Amplification of Long Targets From Cloned Inserts, Proc. Natl. Acad. Sci. USA, vol. 91, 5695-5699 (1994).

Clarke et al, Rescue of Mumps Virus From cDNA, Journal of Virology, vol. 74, No. 10, 4831-4838 (2000).

Clements et al., Evaluation of Bovine Cold-Adapted Human, and Wild Type Human Parainfluenza Type 3 Viruses in Adult Volunteers, Journal of Clinical Microbiology, vol. 29, 1175-1182 (1991).

Coelingh et al., Antigenic and Functional Organization of Human Parainfluenza Virus Type 3 Fusion Glycoprotein, Journal of Virology, vol. 63, No. 1, 375-382 (1989).

Coelingh et al., Antigenic Variation in the Hemaggultinin Neuraminidase Protein of Human Parainfluenza Type 3 Virus, Virology, vol. 143, 569-582 (1985).

Coelingh et al., Nucleotide and Deduced Amino Acid Sequence of Hemagglutinin Neuraminidase Genes of Human Type 3 Parainfluenza Viruses, Virology, vol. 162, 137-143 (1988).

Collins et al., Fields Virology, Third Edition, Parainfluenza Viruses, Chapter 41, 1205-1241 (1996).

Collins et al., Production of Infectious Human Respiratory Syncytial Virus From Cloned cDNA, Pro. Natl. Acad. Sci., vol. 92, 11563-11567 (1995).

Collins et al., Respiratory Syncytial Virus Reverse Genetics and Vaccine Strategies, Virology, vol. 296 204-211 (2002).

Connors et al., Respiratory Syncytial Virus (RSV) F, G, M2 (22K), and N Proteins Each Induce Resistance to RSV Challenge, Journal of Virology, vol. 65, No. 3, 1634-1637 (1991).

Conzelmann et al., Genetic Manipulation of Non-Segmented Negative-Strand RNA Viruses, Journal of General Virology, vol. 77, 381-389 (1996).

Corsoro and Pearson, Enhancing the Efficiency of DNA Mediated Gene Transfer In Mammalian Cells, Somatic Cell Genetics, vol. 7, No. 5, 603-616 (1981).

Crookshanks et al., Evaluation of Cold-Adapted And Temperature-Sensitive Mutants Of Parainfluenza Virus Type 3, Journal of Medical Virology, vol. 13, 243-249 (1984).

Crowe et al., Cold-Passaged, Temperature-Sensitive Mutants of Human Respiratory Syncytial Virus (RSV), Vaccine, vol. 13, No. 9, 847-855 (1995).

Curran et al., Ribosomal Initiation From An ACG Condon In the Sendai Virus, EMBO Journal, vol. 7, No. 1, 245-251 (1988).

Curran et al., Sendai Virus Nonstructural C Proteins Specifically Inhibit Viral mRNA Synthesis, Virology, vol. 189, 647-656 (1992).

Didcock et al., The V Protein of Simian Virus 5 Inhibits Interferon Signaling By Targeting STAT1, Journal of Virology, vol. 73, No. 12, 9928-9933 (1999).

Didcock et al., Sendai Virus and Simian Virus 5 Block Activation of Interferon Responsive Genes, Journal of Virology, vol. 73, No. 4, 3125-3133 (1999).

Dillon et al., Expression Of Five Proteins From The Sendai Virus PC mRNA In Infected Cells, Journal of Virology, vol. 63, No. 2, 974-977 (1989).

Dimock et al., Rescue of Synthetic analogs of Genomic RNA and Replicative Intermediate RNA of Human Parainfluenza Virus Type 3, Journal of Virology, vol. 67, No. 5, 2772-2778 (1993).

Duprex et al., In Vitro And In Vivo Infection Of Neural Cells By A Recombinant Measles Virus Expressing Enhanced Green Fluorescent Protein, Journal of Virology, vol. 74, No. 17, 7972-7979 (2000).

Durbin et al., Comparison of the Immunogenicity and Efficacy of A Replication-Defective Vaccinia Virus, Journal of Infectious Diseases, vol. 179, 1345-1351 (1999).

Durbin et al., Human Parainfluenza Virus Type 3 (PIV3) Expressing Hemagglutinin Protein of Measles Virus, Journal of Virology, vol. 74, No. 15, 6821-6831 (2000).

Durbin et al., The Immunogenicity And Efficacy of Intranasally or Parenterally Administered Replication Deficient Vaccinia Parainfluenza Virus Type 3, Vaccine, vol. 16, No. 13, 1324-1330 (1998).

Durbin et al., Mini. Protein Requirements for Transcription, RNA Replication of Minigenome of Human Parainfluenza Virus Type 3 and Evaluation of the Rule of Six, Virology, vol. 234, 74-83 (1997).

Durbin et al., Recovery of Infections Human Parainfluenza Virus Type 3 from cDNA, Virology, vol. 235, 323-332 (1997).

Durbin et al., Mutations In C, D, and V Open Reading Frames of Human Parainfluenza Virus Type 3 Attenuate Replication In Rodents and Primates, Virology, vol. 261, 319-330 (1999).

Elango et al., Human Parainfluenza Type 3 Virus Hemagglutinin-Neuraminidase Glycoprotein, Journal of Virology, vol. 57, No. 2, 481-489 (1986).

Elroy-Stein et al., Cap-Independent Translation of mRNA Conferred By Encephalomyocarditis Virus 5 Sequence, Proc. Natl, Acad. Sci. USA, vol. 86, 6126-6130 (1989).

Feller et al., Comparison of Identical Temperature Sensitive Mutations in the L Polymerase Proteins of Sendai and Parainfluenza3 Viruses, Virology, vol. 276, 190-201 (2000).

Fenner et al., Monoclonal Antibodies Specific For Sendai Virus, Scand. Journal of Immunology, vol. 24, 341-349 (1986).

Fernie et al., Classification of Hybridomas to Respiratory Syncytial Virus Glycoproteins, Proceedings of the Society for Experimental Biology and Medicine, vol. 171, 266-271 (1982).

Finke et al., Ambisense Gene Expression From Recombinant Rabies Virus, Journal of Virology, vol. 71, No. 10, 7281-7288 (1997).

Galinski, Annotated Nucleotide and Protein Sequences for Selected Paramyxoviridae, Nucleotide and Protein Sequences, Appendix, 537-568 (1991).

Garcia-Barreno et al., Oligo(A) Sequences of Human Respiratory Syncytial Virus G Protein Gene, Journal of Virology, vol. 68, No. 9, 5460-5468 (1994).

Garcia-Barreno et al., Frame Shift Mutations As Novel Mechanism For Generation Of Neutralization Resistant Mutants, EMBO Journal, vol. 9, No. 12, 4181-4187 (1990).

Garcia-Sastre et al., Inhibition of Interferon Mediated Antiviral responses by Influenza A Viruses and Other Negative Strand RNA Viruses, Virology, vol. 279, 375-384 (2001).

Garcin et al., A Highly Recombinogenic System For Recovery of Infectious Sendai Paramyxovirus For cDNA, EMBO Journal, vol. 14, No. 24, 6087-6094 (1995).

Garcin et al., Longer And Shorter Forms Of Sendai Virus C Proteins Play Different Roles In Modulating The Cellular Antiviral Response, Journal of Virology, vol. 75, No. 15, 6800-6807 (2001).

Garcin et al., All Four Sendai Virus C Proteins Bind Stst1, But Only the Larger Forms Also Induce Its Mono Ubiquitination and Degradation, Virology, vol. 295, 256-265 (2002).

Gassen et al., Establishment Of A Rescue System For Canine Distemper Virus, Journal of Virology, vol. 74, No. 22, 10737-10744 (2000).

Goodbourn et al., Interferons Cell Signaling, Immune Modulation, Antiviral Responses and Virus Countermeasures, Journal of General Virology, vol. 81, 2341-2364 (2000).

Graham et al., A New Technique for The Assay of Infectivity of Human Adenovirus 5 DNA, Virology, vol. 52, 456-467 (1973).

Griffin et al., Measles Virus, Fields Virology, Third Edition, Chapter 43, 1267-1312 (1991).

Haas et al., Codon Usage Limitation In The Expression Of HIV-1 Envelope Glycoprotein, Current Biology, vol. 6, No. 3, 315-324 (1996).

Hall et al., Cold Passaged Human Parainfluenza Type 3 Viruses Contain ts and Non ts Mutations Leading To Attenuation In Rhesus Monkeys, Virus Research vol. 22, 173-184 (1992).

Halsey et al., Response to Measles Vaccine In Haitian Infants 6 to 12 Months Old, New England Journal of Medicine, vol. 313, No. 9, 544-548 (1985).

Hasan et al., Creation of An Infectious Recombinant Sendai Virus Expressing The Firefly Luciferase Gene From The 3' Proximal First Locus, Journal of General Virology, vol. 78, 2813-2820 (1997).

Hausmann et al., Paramyxovirus RNA Editing and the Requirement for Hexamer Genome Length, RNA, vol. 2, 1033-1045 (1996).

Hawley-Nelson et al., A New Higher Efficiency Polycationic Liposome Transfection Reagent, Focus, vol. 15, No. 3, 73-79 (1993).

He et al., Recovery of Infectious SV5 From Cloned DNA and Expression of A Foreign Gene, Virology, vol. 237, 249-260 (1997).

Heikkinen et al., Prevalence of Various Respiratory Viruses In The Middle Ear During Acute Ottitis Media, New England Journal of Medicine, vol. 340, 260-264 (1999).

Hoffman et al., An Infectious Clone of Human Parainfluenza Virus Type 3, Journal of Virology, vol. 71, No. 6, 4272-4277 (1997).

Huang et al., High Level Expression Of A Foreign Gene From The Most 3 Proximal Locus Of A Recombinant Newcastle Disease Virus, Journal of General Virology, vol. 82, 1729-1736 (2001).

Johnson et al., Specific Targeting to CD4 Cells of Recombinant Vesicular Stomatitis Viruses Encoding Human Immunodeficiency Virus, Journal of Virology, vol. 71, No. 7, 5060-5068 (1997).

Jin et al., Recombinant Human Respiratory Syncytial Virus (RSV) from cDNA and Construction of Subgroup A and B Chimeric RSV, Virology, vol. 251, 206-214 (1998).

Juhasz et al., The Temperature-Sensitive (ts) Phenotype of a Cold-Passaged (cp) Live Attenuated Respiratory Syncytial Virus, Journal of Virology, vol. 71, No. 8, 5814-5819 (1997).

Kahn et al., Replication Competent Or Attenuated, Nonpropagating Vesicular Stomatitis Viruses Expressing Respiratory Syncytial Virus, Journal Virology, vol. 75, No. 22, 11079-11087 (2001).

Kahn et al., Recombinant Vesicular Atomatitis Virus Expressing Respiratory Syncytial Virus (RSV) Glycoproteins, Virology, vol. 254, 81-91 (1999).

Karron et al., A. Live Attenuated Bovine Parainfluenza Virus Type 3 Vaccine Is Safe, Infectious, Immunogenic, and Phenotypically Stable In Infants And Children, Journal of Infectious Diseases, vol. 171, 1107-1104 (1995).

Karron et al., A Live Human Parainfluenza Type 3 Virus Vaccine Is attenuated and Immunogenic In Healthy Infants and Children, Journal Infectious Diseases, vol. 172, 1445-1450 (1995).

Karron et al., Evaluation of a Live Attenuated Bovine Parainfluenza Type 3 Vaccine In Two To Six Month Old Infants, Pediatric Infectious Diseases Journal, vol. 15, 650-654 (1996).

Kato et al., The Paramyxovirus, Sendai Virus, V Protein encodes A Luxury Function Required For viral Pathogenesis, EMBO Journal, vol. 16, No. 3, 578-587 (1997).

Kato et al., Initiation of Sendai Virus Multiplication From Transfected cDNA or RNA with Negative or Positive Sense, Genes To Cells, vol. 1, 569-579 (1996).

Kawano et al., Characterization of the Human Parainfluenza Type 2 Virus Gene Encoding the L Protein and the Intergenic Sequences, Nucleic Acids Research, vol. 19, No. 10, 2739-2746 (1991).

Kawano et al., Sequence Determination of the Hemagglutinin Neuraminidase (HN) Gene of Human Parainfluenza Type 2 Virus, Virology, vol. 174, 308-313 (1990).

Kawano et al., Sequence of the Fusion Protein Gene of Human Parainfluenza Type 2 Virus and Its 3 Intergenic Region, Virology, vol. 178, 289-292 (1990).

Kawano et al., Complete Nucleotide Sequence of the Matrix Gene of Human Parainfluenza Type 2 Virus and Expression of the M Protein In Bacteria, Virology, vol. 179, 857-861 (1990).

Kawano et al., Recovery of Infectious Human Parainfluenza Type 2 Virus From CDNA Clones and Properties of the Defective Virus, Virology, vol. 284, 99-112 (2001).

Kolakofsky et al., Paramyxovirus RNA synthesis ad the Requirement for Hexamer Genome Length, Journal of Virology, vol. 72, No. 2, 891-899 (1998).

Kretzschmar et al., Normal Replication of Vesicular Stomatitis Virus Without C Proteins, Virology, vol. 216, 309-316 (1996).

Kretzschmar et al., High Efficiency Incorporation of Functional Influenza Virus Glycoproteins Into Recombinant Vesicular Stomatitis Viruses, Journal of Virology, vol. 71, No. 8, 5982-5989 (1997).

Krishnamurthy et al., Recovery of a Virulent Strain of Newcastle Disease Virus from Cloned CDNA, Virology, vol. 278, 168-182 (2000.

Kroutil et al., Exonucleolytic Proofreading During Replication of Repetitive DNA, Biochemistry, vol. 35, 1046-1053 (1996).

Kulkarni et al., The Cytolytic Activity of Pulmonary CD8 Lymphocytes, Induced by Infection with a Vaccinia Virus, Journal of Virology, vol. 67, No. 2, 1044-1049 (1993).

Lamb et al., Paramyxoviridae The Viruses and Their Replication, Virology, vol. 1, No. 41, 1305-1337 (2001).

Latorre et al., Sendai Virus Y Proteins Are Initiated by a ribosomal Shunt, Molecular and Cellular Biology, vol. 18, No. 9, 5021-5031 (1998).

Lawson et al., Recombinant Vesicular Stomatitis Viruses From DNA, Proc. Natl. Acad. Sci., vol. 92, 4477-4481 (1995).

Liston et al., Ribosomal Frameshifting During Translation of Measles Virus P Protein mRNA Is Capable of Directing Synthesis, Journal of Virology, vol. 69, No. 11, 6742-6750 (1995).

Marx et al., Pediatric Hospitalizations for Croup, Journal of Infectious Diseases, vol. 176, 1423-1427 (1997).

Matsuoka et al., The P Gene of Human Parainfluenza Virus Type 1 Encodes P and C Proteins But Not a Cysteine Rich V Protein, Journal of Virology, vol. 65, No. 6, 3406-3410 (1991).

McGettigan et al., Expression and Immunogenicity of Human Immunodeficiency Virus Type 1 Gag Expressed By A Replication, Journal of Virology, vol. 75, No. 18, 8724-8732 (2001).

McGettigan et al., Rabies Virus Based Vectors Expressing Human Immunodeficiency Virus Type 1 (HIV-1), Journal of Virology, vol. 75, No. 9, 4430-4434 (2001).

Mebatsion et al., Highly Stable Expression of a Foreign Gene From Rabies Virus Vectors, Proc. Natl. Acad. Sci., vol. 93, 7310-7314 (1996).

Moeller et al., Recombinant Measles Viruses Expressing Altered Hemagglutinin (H) Genes, Journal of Virology, vol. 75, No. 16, 7612-7620 (2001).

Moriya et al., Large Quantity Production With Extreme Convenience of Human SDF-1 Alpha and SDF-1 Beta By a Sendai Virus Vector, FEBS Letters, vol. 425, 105-111 (1998).

Mucke et al., Extragenic and Intragenic Suppression of a Transport Mutation in the Hemagglutinin Gene of an Influenza A Virus, Virology, vol. 158, 112-117 (1987).

Murphy et al., Live Attenuated Virus Vaccines for Respiratory Syncytial ad Parainfluenza Viruses, Journal of Clinical Investigation, vol. 110, 21-27 (2002).

Murphy et al., An Influenza A Live Attenuated Reassortant Virus Possessing Three Temperature Sensitive Mutations in the PB2 Polymerase Gene, Vaccine, vol. 15, No. 12, 1372-1378 (1997).

Murphy et al., Genome Nucleotide Lengths That Are Divisible by Six Are Not Essential but Enhance Replication, Virology, vol. 232, 145-157 (1997).

Murphy et al., Current Approaches to the Development of Vaccines Effective Against Parainfluenza, Virus Research, vol. 11, 1-15 (1988).

Needleman and Wunsch, A General Method Applicable To The Search For Similarities In The Amino Acid Sequence Of Two Proteins, Journal of Molecular Biology, vol. 48, 443-453 (1970).

Neumann et al., Gene Transfer Into Mouse Lymoa Cells By Electroporation In High Electric Fields, EMBO Journal, vol. 1, 841-845 (1982).

Newman et al., Sequence Analysis of the Washington 1964 Strain of Human Parainfluenza Virus Type 1, Virus Genes, vol. 24, 77-92 (2002).

Olmsted et al., Processing Surface Expression and Immunogenicity of Carboxy Terminally Truncated Mutants of G Protein, Journal Virology, vol. 63, No. 1, 411-420 (1989).

Osterhaus et al., Vaccine Strategies to Overcome Maternal Antibody Mediated Inhibition of Measles Vaccine, Vaccine, vol. 16, No. 14, 1479-1481 (1998).

Parisien et al., The V Protein of Human Parainfluenza Virus 2 Antagonizes Type I, Virology, vol. 283, 230-239 (2001).

Pearson et al., Improved Tools For Biological Sequence Comparison, Proc. Natl. Acad. Sci. USA, vol. 85, 2444-2448 (1988).

Peeters et al., Genome Replication of Newcastls Disease Virus Involvement of the Rule of Six, Archives of Virology, vol. 145, 1829-1845 (2000).

Pelet et al., Partial Characterization of a Sendai Virus Replication Promoter and the Rule of Six, Virology, vol. 224, 405-414 (1996).

Perrotta et al., A Pseudoknot-Like Structure Required For Efficient Self-Cleavage Of Hepatitis Delta Virus RNA, Nature, vol. 350, 434-436 (1991).

Peeters et al., Rescue Of Newcastls Disease Virus From Cloned cDNA Evidence That Cleavability Of The Fusion Protein Is A Major Determinant For Virulence, Journal of Virology, vol. 73, No. 6, 5001-5009 (1999).

Polo et al., Mutational Analysis of A Virulence Locus In the E2 Glycoprotein Gene of Sindbis Virus, Journal of Virology, vol. 65, No. 11, 6358-6361 (1991).

Radecke et al., Rescue of Measled Viruses from Cloned DNA, EMBO Journal, vol. 14, 5773-5784 (1995).

Radecke et al., The Nonstructural C Protein Is Not Essential For Multiplication of Edmonston B Strain Measles Virus In Cultured Cells, Virology, vol. 217, 418-421 (1996).

Ray et al., Monoclonal Antibodies Reveal Extensive Antigenic Differences Between the Hemagglutinin, Virology, vol. 148, 232-236 (1986).

Reed et al., Epidemiology and clinical Impact of Parainfluenza Virus Infections In Otherwise Health Infants and Young Children 5 Years Old, Journal Infectious Diseases, vol. 175, 807-813 (1997).

Richardson et al., Isolation and Characterization of Further Defective Clones of Temperature Sensitive Mutant (ts-1), Archives Virology, vol. 54, 53-60 (1977).

Roberts et al., Vaccination with Recombinant Vesicular Stomatitis Virus Expressing Influenza Virus Hemagglutinin, Journal Virology, vol. 72, No. 6, 4704-4711 (1998).

Roberts et al., Attenuated Vesicular Stomatitis Viruses As Vaccine Vectors, Journal of Virology, vol. 73, No. 5, 3723-3732 (1999).

Roberts et al., Recovery of Negative Strand RNA Viruses From Plasmid DNAs, Virology, vol. 247, 1-6 (1998).

Rochat et al., Loss of V Protein Expression In Human Parainfluenza Virus Type 1 Is Not A Recent Event, Virus Research, vol. 24, 137-144 (1992).

Rose et al., Glycoprotein exchange Vectors Based On Vesicular Stomatitis Virus, Journal of Virology, vol. 74, No. 23, 10903-10910 (2000).

Rydbeck et al., Characterization of Four Parainfluenza Virus Type 3 Proteins by Use of Monoclonal Antibodies, Journal of General Virology, vol. 67, 1531-1542 (1986).

Sakai et al., Accommodation of Foreign Genes Into Sendai Virus Genome Sizes of Inserted Genes and Viral Replication, FEBS Letters, vol. 456, 221-226 (1999).

Samal et al., RNA Replication By A Respiratory Syncytial Virus, Journal of Virology, vol. 70, No. 8, 5075-5082 (1996).

Samuel et al., Antiviral Actions of Interferons, Clinical Microbiology Reviews, vol. 14, No. 4, 778-809 (2001).

Sato et al., Characterization of Major Structural Proteins of Measles Virus with Monoclonal Antibodies, Journal of General Virology, vol. 66, 1397-1409 (1985).

Schmidt et al., Recombinant Bovine Human Parainfluenza Virus Type 3 (BHPIV3), Journal of Virology, vol. 75, No. 10, 4594-4603 (2001).

Schmidt et al., Bovine Parainfluenza Virus Type 3 (BPIV3) Fusion and Hemagglutinin Neuraminidase Glycoproteins, Journal of Virology, vol. 74, 8922-8929 (2000).

Schneider et al., Recombinant Measles Viruses Defective for RNA Editing, Virology, vol. 227, 314-322 (1997).

Schnell et al., Construction of A Novel Virus That Targets HIV-1-Infected Cells and Controls HIV-1 Infection, Cell, vol. 90, 849-857 (1997).

Schnell et al., Infectious Rabies Viruses from Cloned cDNA, EMBO Journal, vol. 13, No. 18, 4195-4203 (1994).

Schnell et al., The Minimal Conserved Transcription Stop Start Signal Promotes Stable Expression of A Foreign Gene, Journal Virology, vol. 70, No. 4, 2318-2323 (1996).

Schnell et al., Foreign Glycoproteins Expressed From Recombinant Vesicular Stomatitis Viruses Are Incorporated Efficiently, Proc. Natl. Acad. Sci., vol. 93, 11359-11365 (1996).

Schoepp et al., Directed Mutagenesis of A Sindbis Virus Pathogenesis Site, Virology, vol. 193, 149-159 (1993).

Sidhu et al., Rescue of Synthetic Measles Virus Minireplicons Measles Genomic Termini Direct, Virology, vol. 208, 800-807 (1995).

Singh et al., A Recombinant Measles Virus Expressing Biologically Active Human Interleukin12, Journal of General Virology, vol. 80, 101-106 (1999).

Singh et al., A Recombinant Measles Virus Expressing Hepatitis B Virus Surface Antigen Induces Humeral Immune Responses, Journal Virology, vol. 73, No. 6, 4823-4828 (1999).

Skiadopoulos et al., The Bovine Papillomavirus Type 1 E2 Transactivator and Repressor Proteins Use Different Nuclear Localization Signals, Journal of Virology, vol. 70, No. 2, 1117-1124 (1996).

Skiadopoulos et al., Three Amino Acid Substitutions In L Protein of Human Parainfluenza Virus Type 3 cp45 Live Attenuated Vaccine, Journal Virology, vol. 72, No. 3, 1762-1768 (1998).

Skiadopoulos et al., Identification of Mutations Contributing to Temperature Sensitive Cold Adapted, Journal Virology, vol. 73, No. 2, 1374-1381 (1999).

Skiadopoulos et al., A Chimeric Human Bovine Parainfluenza Virus Type 3 Expressing Measles Virus, Journal Virology, vol. 75, No. 21, 10498-10504 (2001).

Skiadopoulos et al., Generation of Parainfluenza Virus Type 1 Vaccine Candidate By Replacing HN and F Glycoproteins, Vaccine, vol. 18, 503-510 (1999).

Skiadopoulos et al., Attenuation of Recombinant Human Parainfluenza Virus Type 3 cp45 Candidate Vaccine Virus, Virology, vol. 260, 125-135 (1999).

Skiadopoulos et al., Long Nucleotide Insertions Between the HN and L Protein Coding Regions of Human PIV, Virology, vol. 272, 225-234 (2000).

Skiadopoulos et al., Evaluation of the Replication and Immunogenicity of Recombinant Human Parainfluenza Virus Type 3 Vectors, Virology, vol. 297, 136-152 (2002).

Smith & Waterman, Comparison of Biosequences, Advances In Applied Mathematics, vol. 2, 482-489 (1981).

Spielhofer et al., Chimeric Measles Viruses With A Foreign Envelope, Journal of Virology, vol. 72, No. 3, 2150-2159 (1998).

Stokes et al., The Complete Nucleotide Sequence of JS Strain of Human Parainfluenza Virus Type 3, Virus Research, vol. 25, 91-103 (1992).

Stokes et al., Virus Research, Erratum vol. 27 p. 96 (1993).

Stope et al., Chimeric Bovine Respiratory Syncytial Virus with Attachment and Fusion Glycoproteins Replaced, Journal of Virology, vol. 75, No. 19, 9367-9377 (2001).

Subash et al., Recovery and Characterization of a Chimeric Rinderpest Virus with the Glycoproteins, Journal of Virology, vol. 74, No. 19, 9039-9047 (2000).

Tao et al., Recovery of A Fully Viable Chimeric Human Parainfluenza Virus (PIV) Type 3, Journal Virology, vol. 72, No. 4, 2955-2961 (1998).

Tao et al., Replacement of the Ectodomains of the Hemagglutinin Neuraminidase and Fusion Glycoproteins, Journal of Virology, vol. 74, No. 14, 6448-6458 (2000).

Tao et al., A Live Attenuated Chimeric Recombinant Parainfluenza Virus (PIV) Encoding the Internal Proteins of PIV Type 3, Vaccine, vol. 17, 1100-1108 (1999).

Tao et al., A Live Attenuated Recombinant Chimeric Parainfluenza virus (PIV) Candidate, Vaccine, vol. 18, 1359-1366 (2000).

Tao et al., Construction of A Live Attenuated Bivalent Vaccine Virus Against Human Parainfluenza Virus (PIV) Types 1 and 2, Vaccine, vol. 19, 3620-3631 (2001).

Tolpin et al., Genetic Factors Associated with Loss of the Temperature Sensitive Phenotype of the Influenza, Virology, vol. 112, 505-517 (1981).

Treanor et al., Evaluation of the Genetic Stability of the Temperature Sensitive PB2 Gene, Journal of Virology, vol. 68, No. 12, 7684-7688 (1994).

Van Den Hoogen et al., Analysis of the Genomic Sequence of a Human Metapneumovirus, Virology, vol. 295, 119-132 (2002).

Van Wyke Coelingh et al., Antigenic and Functional Organization of Human Parainfluenza Virus Type 3 Fusion Glycoprotein, Journal Virology, vol. 63, No. 1, 375-382 (1989).

Van Wyke Coelingh et al., Attenuation of Bovine Parainfluenza Virus Type 3 In Nonhuman Primates, Journal Infectious Diseases, vol. 157, No. 4, 655-662 (1988).

Van Wyke Coelingh et al., Antigenic and Structural Properties of Hemagglutinin Neuraminidase Glycoprotein of Human Parainfluenza Virus Type 3, Journal Virology, vol. 61, No. 5, 1473-1477 (1987).

Vulliemoz et al., Rule of Six How Does the Sendai virus RNA Polymerase keep Count, Journal of Virology, vol. 75, No. 10, 4506-4518 (2001).

Walsh et al., Analysis of the Respiratory Syncytial Virus Fusion Protein Using Monoclonal and Polyclonal Antibodies, Journal of General Virology, vol. 67, 505-513 (1986).

Whelan et al., Efficient Recovery of Infectious Vesicular Stomatitis Virus Entirely from cDNA Clones, Proc. Natl. Acad. Sci., vol. 92, 8388-8392 (1995).

Whitehead et al., Recombinant Respiratory Syncytial Virus (RSV) Bearing A Set of Mutations, Journal Virology, vol. 72, No. 5, 4467-4471 (1998).

Whitehead et al., Recombinant Respiratory Syncytial Virus Bearing A Deletion of Either the NS2 or SH Gene, Journal Virology, vol. 73, No. 4, 3438-3442 (1999).

Whitehead et al., A Single Nucleotide Substitution In Transcription Start Signal of M2 Gene, Virology, vol. 247, 232-239 (1998).

Wigler et al., Biochemical Transfer of Single Copy Eucaryotic Genes Using Total Cellular DNA As Donor, Cell, vol. 14, 725-731 (1978).

Wright et al., Evaluation of a Live Cold Passaged Temperature Sensitive Respiratory Syncytial Virus Vaccing Candidate In Infancy, Journal Infectious Diseases, vol. 182, 1331-1342 (2000).

Wyatt et al. Replication Deficient Vaccinia Virus Encoding Bacteriophage T7 RNA, Virology, vol. 210, 202-205 (1995).

Yu et al., Sendai Virus Based Expression of HIV-a gp120 Reinforcement By The V- Version, Genes to Cells, vol. 2, 457-466 (1997).

* cited by examiner

A.

HPIV3 L aa 456 (RSV L aa 521) F→L
AEISYEYTLKHWKEISLIEFRKCFDFDPGEELSIFMKDKA-HPIV2 F460
SAISYENAVDYYQSFIGIKFNKFIEPQLDEDLTIYMKDKA-HPIV3
SAISYECAVDNYSSFIGFKFLKFIEPQLDEDLTIYMKDKA-HPIV1

B.

**HPIV3 *cp*45 L aa 942 Y→H**
LLPSQLGGLNYLACSRLFNRN-HPIV2 Y948
LIPASVGGFNYMAMSRCFVRN-HPIV3
LIPANIGGFNYMSTARCFVRN-HPIV1

C.

**HPIV3 *cp*45 L aa 992 L→F**
LARKPGKGSWATLAADPYSLN-HPIV2 A998
MNQEPGESSFLDWASDPYSCN-HPIV3
MNQEPGDSSFLDWASDPYSCN-HPIV1

D.

**HPIV3 *cp*45 L aa 1558 T→I**
DIITPIHAPYLASLDYVKLSI-HPIV2 L1566
GVLNPIYGPNTASQDQIKLAL-HPIV3
GVVEPVYGPNLSNQDKILLAI-HPIV1

E.

BPIV3 L aa 1711 T→I
EQLETDIILHSTLTA-HPIV2 S1724
EDNILDNIVKTVNDN-BPIV3
EDNMLDNIVKTVNDN-HPIV3
ADSMLDNITAEVQHN-HPIV1

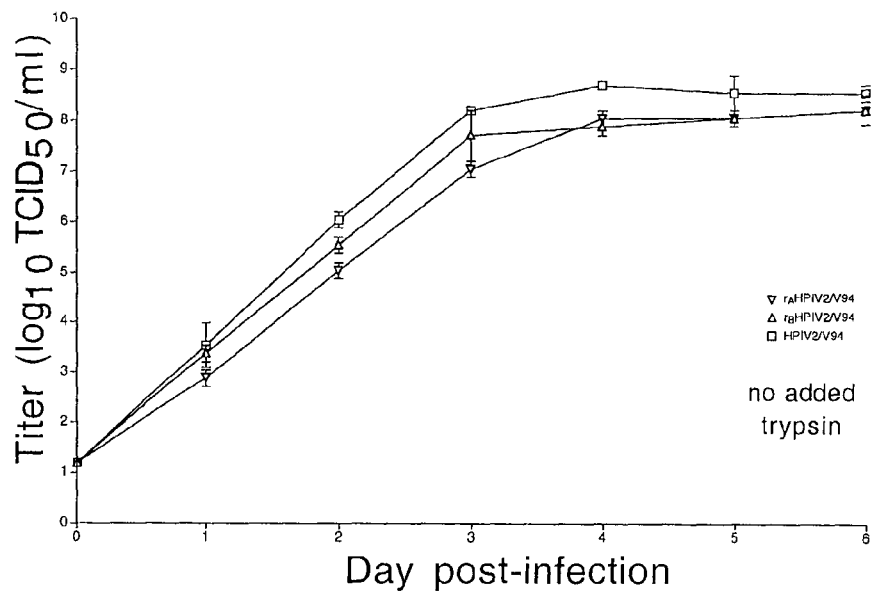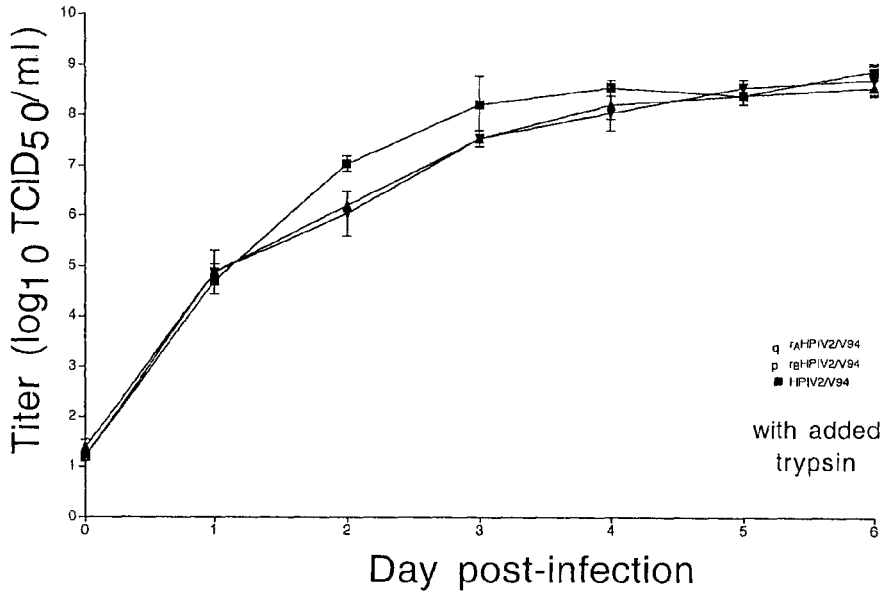
FIGURE 4

A
```
 51 TACGTAGGTCCGGAACCACTAGATT.CGGTGCCGGTAACGATTCCAGTTT  99   Toshiba
    ||||||||||||||||||||||||| |||||||||||||||||||||||||
 51 TACGTAGGTCCGGAACCACTAGATTCCGGTGCCGGTAACGATTCCAGTTT 100   Greer
```

B
```
700 ATGACTGCTCCTGATCAACCACCAGTATCAGTAGCAAA...GATGGCTAA  746   Toshiba
    ||||||||||||||||||||||||||||||||||||||   |||||||||
701 ATGACTGCTCCTGATCAACCACCAGTATCAGTAGCAAAGCGGATGGCTAA  750   Greer
```

C
```
1897 TCTCTCATAATTTAAAGAAAAAATCATAGG.CCGGACGGGTTAGAAATCC 1945   Toshiba
     |||||||||||| ||||||||||||||||| |||||||||||||||||||
1901 TCTCTCATAATTT.AAGAAAAAATCATAGGCCCGGACGGGTTAGAAATCC 1949   Greer
```

D
```
2896 AGTAATTGCCGGTCCAACTAGTGGAGGCTTCACAGCCGAA.CAGGTGATA 2944   Toshiba
     ||||||||||||||||||||||||||||||||||||||||    ||||||
2900 AGTAATTGCCGGTCCAACTAGTGGAGGCTTCACAGCCGAAGGCAGTGATA 2949   Greer
```

E
```
2945 TTGATTTCAATGGATGAACTAGCTAGACCTACACTCTCATCAACAAAAAG 2994   Toshiba
      |||||||||||||||||||||||||||||||||||||||||||||||||
2950 .TGATTTCAATGGATGAACTAGCTAGACCTACACTCTCATCAACAAAAAG 2998   Greer
```

F
```
8595 TTATACGTTTTGGCTGTATTAGAATGTTATAG.ATTCTGCTGTTTTTCCC 8643   Toshiba
     ||||||||||||||||||||||||||||||||  ||||||||||||||||
8599 TTATACGTTTTGGCTGTATTAGAATGTTATAGCATTCTGCTGTTTTTCCC 8648   Greer
```

G
```
9894 TGGGGTCATCCCACTCTTACTGCTGCGCAA...GTGGGTAAAGTGAGAGA 9940   Toshiba
     ||||||||||||||||||||||||||||||   | |||||||||||||||
9899 TGGGGTCATCCCACTCTTACTGCTGCGCAAGCTGCAGGTAAAGTGAGAGA 9948   Greer
```

H
```
10991 TGATATCTTTATAGTCT...CCAAGGGAGGTATTGAAGGCCTATGTCAGA 11037   Toshiba
      |||||||||||||||||   |||||||||||||||||||||||||||||||
10999 TGATATCTTTATAGTCTCTCCCAAGGGAGGTATTGAAGGCCTATGTCAGA 11048   Greer
```

I
```
13938 ACAGATATAATTCTTCACTCTACTTTAACTGCTCCTTATGATAATTCAGA 13987   Toshiba
      |||||||||||||||||||||||||||||||||||||||||||||||||
13949 ACAGATATAATTCTTCACTCTACTTTAACTGCTCCTTATGATAATTCAG. 13997   Greer
```

J
```
13988 AAACTCTAACAAAGTTCGATTTATCCCTTTCGACATCTTTCCACATCCAG 14037   Toshiba
      |||||||||||||||||||||||||||||||  |||||||||||||||||
13998 AAACTCTAACAAAGTTCGATTTATCCCTT..GACATCTTTCCACATCCAG 14045   Greer
```

FIGURE 6

A. Site of insertion of oligonucleotides at an *EcoRV* restriction site in the L polymerase coding sequence

```
        EcoRV↓
        GAT ATC GAG AGG GGT ATC GAT GGC GAA GAA TTA TGA CAA CAG TGA
HPIV2 nt 15554↑

FIGURE 8

Human Parainfluenza Virus Type 2 Strain V94 antigenomic sense cDNA Sequence Range: 1 to 15654

```
        10         20         30         40         50         60         70         80         90        100
ACCAAGGGGA GAATCAGATG GCATCGTTAT ATGACGAATT GCAAAAAGAT TACGTAGGTC CGGAACCACT AGATTCCGGT GCCGGTAACG ATCTCAGTTT 110        120        130        140        150        160        170        180        190        200
TATACTATCT GATCATTCTT TATCTCTACT AAGGATATTT CTAATCTAAG GTTCAAAATG TCAAGTGTCT TAAAGACATT TGAAAGATTT ACTATACAAC 210        220        230        240        250        260        270        280        290        300
AGGAGCTTCA GGAGCAATCT GAAGACACTC CAATACCTCT TGAAACAATC AGACCTACAA TCAGAGTATT TGTCATCAAT AATAATGATC CTATTGTAAG 310        320        330        340        350        360        370        380        390        400
ATCTAGACTT TTATTCTTTA ATCTACGAAT TATTATGAGT AACACTGCAA GAGAGGGACA TAGAGCTGGT GCTCTCCTCA GTCTTTTATC ACTACCTTCT 410        420        430        440        450        460        470        480        490        500
GCAGCTATGA GTAATCACAT CAAACTAGCC ATGCATTCAC CAGAAGCCAG CATAGATAGA GTAGAAATAA CAGGGTTTGA GAATAATTCA TTCCGAGTTA 510        520        530        540        550        560        570        580        590        600
TTCCAGATGC TCGATCAACT ATGTCCAGAG GAGAAGTGCT GGCCTTCGAA GCATTAGCTG AGGACATTCC TGATACCCTT AATCACCAAA CTCCATTTGT 610        620        630        640        650        660        670        680        690        700
AAATAATGAT GTGGAAGATG ACATATTTGA TGAAACAGAG AAATTCTTGG ATGTTTGCTA TAGTGTACTT ATGCAGGCAT GGATAGTAAC ATGCAAGTGC 710        720        730        740        750        760        770        780        790        800
ATGACTGCTC CTGATCAACC ACCAGTATCA GTAGCAAAGC GGATGGCTAA ATATCAACAA CAAGGGAGAA TCAATGCTAG ATATGTACTA CAACCTGAAG 810        820        830        840        850        860        870        880        890        900
CACAAAGACT AATTCAGAAT GCCATCCGCA AGTCAATGGT AGTAAGGCAT TTCATGACCT ATGAGCTTCA ACTTTCACAA TCAAGATCTT TGCTAGCGAA 910        920        930        940        950        960        970        980        990       1000
CCGTTATTAT GCCATGGTGG GAGACATTGG CAAGTATATT GAACACAGCG GAATGGGAGG GTTTTTCTTA ACACTTAAAT ATGGACTTGG AACAAGATGG 1010       1020       1030       1040       1050       1060       1070       1080       1090       1100
CCTACATTGG CTCTTGCAGC ATTCTCTGGG GAACTCCAGA AATTAAAGGC TCTCATGCTA CATTATCAGA GTCTAGGACC CATGGCCAAG TACATGGCTC 1110       1120       1130       1140       1150       1160       1170       1180       1190       1200
TATTAGAATC ACCAAAGCTG ATGGATTTTG TCCCATCTGA ATATCCATTA GTTTATAGCT ATGCAATGGG TATTGGAACT GTCCTTGATA CAAACATGAG 1210       1220       1230       1240       1250       1260       1270       1280       1290       1300
AAACTATGCA TATGGTAGAT CATATCTAAA TCCACAATAT TTTCAGCTAG GGGTAGAAAC AGCAAGGAAA CAGCAAGGAG CTGTTGACAA CAGGACAGCA 1310       1320       1330       1340       1350       1360       1370       1380       1390       1400
GAGGACCTCG GCATGACTGC TGCAGATAAA GCAGACCTCA CTGCAACCAT ATCAAAGCTA TCTTTATCCC AATTACCTAG GGGTAGACAA CCAATATCCG 1410       1420       1430       1440       1450       1460       1470       1480       1490       1500
ACCCATTTGC TGGAGCAAAT GACAGAGAAA CAGGAGGACA AGCAACTGAT ACACCTGTGT ATAACTTCAA TCCAATCAAT AATCGGAGGT ATGACAACTA 1510       1520       1530       1540       1550       1560       1570       1580       1590       1600
TGACAGTGAT AGTGAGGACA GAATTGACAA CGATCAAGAT CAGGCTATCA GAGAGAACAG AGGAGAACCT GGACAACCAA ACAACCAGAC AAGCGAAAAC 1610       1620       1630       1640       1650       1660       1670       1680       1690       1700
CAGCAGAGAC TCAATCTCCC TGTACCGCAA AGAACATCAG GTATGAGTAG TGAAGAGTTC CAACATTCAA TGAATCAGTA CATCCGTGCT ATGCATGAGC 1710       1720       1730       1740       1750       1760       1770       1780       1790       1800
AATACAGAGG CTCCCAGGAT GATGATGCCA ATGATGCCAC AGATGGGAAT GACATTTCAC TTGAGCTAGT TGGAGATTTT GATTCCTAAC TCTCACTTTC 1810       1820       1830       1840       1850       1860       1870       1880       1890       1900
ACATAACCAG ACATACACAT CCACACCACC CAGAGACATA GCTACCATCC ACACACTCAC CCAGACAAAT CAAACTAGAT TCAAATCATT CGGAAACAAT 1910       1920       1930       1940       1950       1960       1970       1980       1990       2000
TCTCCTAGAA TTTAAGAAAA AAACATAGGC CCGGACGGGT TAGAGATCCG GTGCTCGTCT GTGGCCAGAC AACCTCCACA CCAGAGCCAC ACAATCATGG 2010       2020       2030       2040       2050       2060       2070       2080       2090       2100
CCGAGGAACC AACATACACC ACTGAGCAAG TTGATGAATT AATCCATGCT GGACTAGGAA CAGTAGATTT CTTCCTATCT AGACCCATAG ATGCTCAGTC 2110       2120       2130       2140       2150       2160       2170       2180       2190       2200
TTCTTTAGGT AAAGGCAGCA TCCCACCAGG TGTCACGGCT GTTCTAACCA ATGCAGCAGA GGCAAAATCC AAACCAGTTG CTGCTGGTCC AGTAAAACCC 2210       2220       2230       2240       2250       2260       2270       2280       2290       2300
AGACGGAAGA AAGTGATCAG CAATACCACT CCATACACTA TTGCAGACAA CATCCCACCT GAGAAGCTAC CGATCAACAC TCCAATACCC AATCCATTAC 2310       2320       2330       2340       2350       2360       2370       2380       2390       2400
TTCCACTGGC ACGCCCTCAC GGAAAGATGA CAGACATTGA CATTGTCACT GGGAACATTA CAGAAGGATC ATACAAAGGT GTGGAGCTTG CCAAATTAGG 2410       2420       2430       2440       2450       2460       2470       2480       2490       2500
GAAGCAAACA CTACTCACAA GGTTCACCTC GAATGAGCCA GTCTCCTCAG CTGGATCCGC CCAAGACCCC AACTTTAAGA GGGGGGGAGC TAATAGAGAA 2510       2520       2530       2540       2550       2560       2570       2580       2590       2600
AGAGCAAGAG GCAACCATAG GAGAGAATGG AGTATTGCAT GGGTCGGAGA TCAGGTCAAA GTCTTCGAGT GGTGTAATCC CAGGTGTGCC CCAGTCACGG 2610       2620       2630       2640       2650       2660       2670       2680       2690       2700
CTTCAGCTCG CAAGTTCACC TGCACATGTG GATCCTGCCC CAGCATCTGC GGAGAATGTG AAGGAGATCA TTGAGCTCTT AAAAGGGCTT GATCTTCGCC 2710       2720       2730       2740       2750       2760       2770       2780       2790       2800
TTCAGACTGT AGAAGGGAAA GTAGATAAAA TTCTTGCAAC CTCTGCAACT ATAATCAATC TTAAAAATGA AATGACTAGT CTTAAGGCGA GCGTTGCAAC 2810       2820       2830       2840       2850       2860       2870       2880       2890       2900
TGTGGAAGGT ATGATAACAA CAATTAAAAT CATGGATCCC AGTACACCAA CCAATGTCCC TGTAGAGGAG ATCAGAAAGA GTTTACACAA TGTTCCAGTA
```

FIGURE 9A

```
       2910       2920       2930       2940       2950       2960       2970       2980       2990       3000
GTAATTGCTG GTCCGACTAG TGGAGGCTTC ACAGCCGAAG GCAGTGACAT GATTTCAATG GATGAACTAG CTAGGCCTAC ACTCTCATCA ACAAAAAAGA 3010       3020       3030       3040       3050       3060       3070       3080       3090       3100
TCACACGAAA GCCTGAATCC AAGAAAGATT TAACAGGCAT AAAACTAACC CTGATGCAGC TTGCAAATGA CTGCATCTCG CGTCCAGATA CCAAGACTGA 3110       3120       3130       3140       3150       3160       3170       3180       3190       3200
GTTTGTGACT AAGATTCAAG CAGCAACCAC AGAATCACAG CTCAACGAAA TCAAACGGTC AATAATACGC TCTGCAATAT AAAATGCGGT GCAATCACAC 3210       3220       3230       3240       3250       3260       3270       3280       3290       3300
AAGAGACATT CAACATGCAT CCGATCAAGA TCCAAACTCC TTCCATCCGA AAACACACTC ACCACTGTCA ACACCAAGAA ACAACTACAG CCGAACCATG 3310       3320       3330       3340       3350       3360       3370       3380       3390       3400
CTCAACCAAA AGACCCAAAC AACATCTCAA ATCGACAGAA GGCTAGACAT GATAAATTTA ATAAAAAATT AAAAGAAGTT AAGTAAAATT TAAAGAACAC 3410       3420       3430       3440       3450       3460       3470       3480       3490       3500
AATAGAGAAA ACCTAGGTCC GAAAGCTTGC CTTTCAGACA GATCCCAAAA TCATAGTTCA AACTTCAAAC ACAGCAGCAG ACATGCCTAT AATATCATTA 3510       3520       3530       3540       3550       3560       3570       3580       3590       3600
CCAGCAGATC CAACTTCACC CAGTCAATCC CTTACTCCGT TTCCAATACA ACTTGATACC AAAGATGGCA AGGCAGGGAA ACTCCTTAAA CAGATTAGAA 3610       3620       3630       3640       3650       3660       3670       3680       3690       3700
TTAGGTATCT AAATGAACCT AACTCTCGTC ATACACCAAT AACTTTCATC AATACGTATG GATTTGTTTA TGCTCGAGAC ACTTCAGGAG GCATTCACAG 3710       3720       3730       3740       3750       3760       3770       3780       3790       3800
CGAGATCAGC AGTGACCTAG CTGCAGGGTC CATAACGGCA TGCATGATGA CACTAGGTCC TGGTCCAAAT ATTCAGAATG CAAATCTAGT GCTAAGATCC 3810       3820       3830       3840       3850       3860       3870       3880       3890       3900
CTGAATGAAT TCTACGTAAA AGTCAAGAAG ACATCAAGCC AGAGGGAGGA AGCAGTGTTT GAATTAGTTA ACATTCCAAC CTTATTGAGA GAACATGCTC 3910       3920       3930       3940       3950       3960       3970       3980       3990       4000
TTTGCAAACG CAAAACGTTA GTATGCTCTG CAGAAAAATT CCTCAAGAAC CCATCAAAGC TACAAGCTGG ATTTGAATAT GTATACATCC CAACTTTTGT 4010       4020       4030       4040       4050       4060       4070       4080       4090       4100
CTCCATTACA TACTCACCAC GAAATCTGAA TTACCAAGTT GCCAGACCTA TCCTTAAGTT CAGATCACGC TTTGTGTATA GCATTCATTT GGAATTAATC 4110       4120       4130       4140       4150       4160       4170       4180       4190       4200
CTGAGATTGC TATGCAAATC TGACTCCCCT TTGATGAAAT CTTATAATGC AGATCGAACA GGTCGAGGAT GCCTCGCATC AGTCTGGATC CACGTATGTA 4210       4220       4230       4240       4250       4260       4270       4280       4290       4300
ACATTCTGAA AAACAAAAGC ATCAAGCAAC AAGGCAGAGA ATCATATTTC ATAGCTAAGT GCATGAGTAT GCAGCTGCAG GTGTCCATTG CAGATCTTTG 4310       4320       4330       4340       4350       4360       4370       4380       4390       4400
GGGACCAACA ATCATAATTA AATCATTGGG TCACATCCCC AAGACTGCAC TTCCTTTTTT CAGCAAAGAC GGGATTGCCT GTCATCCACT ACAAGATGTT 4410       4420       4430       4440       4450       4460       4470       4480       4490       4500
TCCCCTACTC TGACAAAATC ACTGTGGTCA GTGGGATGTG AGATAGAATC TGCCAAGTTG ATACTTCAAG AATCTGATAT TAATGAGCTA ATGGGCCACC 4510       4520       4530       4540       4550       4560       4570       4580       4590       4600
AGGACTTGAT TACTGATAAG ATTGCCATTA GATCAGGTCA ACGGACATTT GAGAGGTCCA AATTCAGCCC ATTCAAAAAA TACGCATCAA TTCCAAACTT 4610       4620       4630       4640       4650       4660       4670       4680       4690       4700
AGAAGCCATC AACTGAATGC TCCAGCATCT AGGAATAGAA CAACAACTAG GTCATACCAT TATTGACCAT ACAATAATCA ACAATTTTAG CCAACTGATT 4710       4720       4730       4740       4750       4760       4770       4780       4790       4800
ACTAAGATAT TATCATAGGT CCGAACTGAT CAATCTAACA AAAAAACTAA ACATTCAATA ATAAATCAAA GTTCAGGCCA AATTATCCAG CCATGCATCA 4810       4820       4830       4840       4850       4860       4870       4880       4890       4900
CCTGCATCCA ATGATAGTAT GCATTTTTGT TATGTACACT GGAATTGTAG GTTCAGATGC CATTGCTGGA GATCAACTCC TCAATGTAGG GGTCATTCAA 4910       4920       4930       4940       4950       4960       4970       4980       4990       5000
TCAAAGATAA GATCACTCAT GTACTACACT GATGGTGGCG CTAGCTTTAT TGTTGTAAAA TTACTACCCA ATCTTCCCCC AAGCAATGGA ACATGCAACA 5010       5020       5030       5040       5050       5060       5070       5080       5090       5100
TCACCAGTCT AGATGCATAT AATGTTACCC TATTTAAGTT GCTAACACCC CTGATTGAGA ACCTGAGCAA AATTTCTGCT GTTACAGATA CCAAACCCCG 5110       5120       5130       5140       5150       5160       5170       5180       5190       5200
CCGAGAACGA TTTGCAGGAG TCGTTATTGG GCTTGCTGCA CTAGGAGTAG CTACAGCTGC ACAAATAACC GCAGCTGTAG CAATAGTAAA AGCCAATGCA 5210       5220       5230       5240       5250       5260       5270       5280       5290       5300
AATGCTGCTG CGATAAACAA TCTTGCATCT TCAATTCAAT CCACCAACAA GGCAGTATCC GATGTGATAA CTGCATCAAG AACAATTGCA ACCGCAGTTC 5310       5320       5330       5340       5350       5360       5370       5380       5390       5400
AAGCCATTCA GGATCACATC AATGGAGCCA TTGTCAACGG GATAACATCT GCATCATGCC GTGCCCATGA TGCACTAATT GGGTCAATAT TAAATTTGTA 5410       5420       5430       5440       5450       5460       5470       5480       5490       5500
TCTCACTGAG CTTACTACAA TATTTCATAA TCAAATAACA AACCCTGCGC TGACACCACT TTCCATCCAA GCTTTAAGAA TCCTCCTCGG TAGCACCTTG 5510       5520       5530       5540       5550       5560       5570       5580       5590       5600
CCAATTGTCA TTGAATCCAA ACTCAACACA AAACTCAACA CAGCAGAGCT GCTCAGTTCC GGACTGTTAA CTGGTCAAAT AATTTCCATT TCCCCAATGT 5610       5620       5630       5640       5650       5660       5670       5680       5690       5700
ACATGCAAAT GCTAATTCAA ATCAATGTTC CGACATTTAT AATGCAACCC GGTGCGAAGG TAATTGATCT AATTGCTATC TCTGCAAACC ATAAATTACA 5710       5720       5730       5740       5750       5760       5770       5780       5790       5800
AGAAGTAGTT GTACAAGTTC CTAATAGAAT TCTAGAATAT GCAAATGAAC TACAAAACTA CCCAGCCAAT GATTGTGTCG TGACACCAAA CTCTGTATTT
```

FIGURE 9B

```
      5810       5820       5830       5840       5850       5860       5870       5880       5890       5900
TGTAGATACA ATGAGGGTTC CCCGATCCCT GAATCACAAT ATCAATGCTT AAGGGGGAAT CTTAATTCTT GCACTTTTAC CCCTATTATC GGGAACTTTC 5910       5920       5930       5940       5950       5960       5970       5980       5990       6000
TCAAGCGATT CGCATTTGCC AATGGTGTGC TCTATGCCAA CTGCAAATCT TTGCTATGTA AGTGTGCCGA CCCTCCCCAT GTTGTGTCTC AAGATGACAA 6010       6020       6030       6040       6050       6060       6070       6080       6090       6100
CCAAGGCATC AGCATAATTG ATATTAAGAG GTGCTCTGAG ATGATGCTTG ACACTTTTTC ATTTAGGATC ACATCTACAT TCAATGCTAC ATACGTGACA 6110       6120       6130       6140       6150       6160       6170       6180       6190       6200
GACTTCTCAA TGATTAATGC AAATATTGTA CATCTAAGTC CTCTAGACTT GTCAAATCAA ATCAATTCAA TAAACAAATC TCTTAAAAGT GCTGAGGATT 6210       6220       6230       6240       6250       6260       6270       6280       6290       6300
GGATTGCAGA TAGCAACTTC TTCGCTAATC AAGCCAGAAC AGCCAAGACA CTTTATTCAC TAAGTGCAAT CGCATTAATA CTATCAGTGA TTACTTTGGT 6310       6320       6330       6340       6350       6360       6370       6380       6390       6400
TGTTGTGGGA TTGCTGATTG CCTACATCAT CAAGCTGGTT TCTCAAATCC ATCAATTCAG AGCACTAGCT GCTACAACAA TGTTCCACAG GGAGAATCCT 6410       6420       6430       6440       6450       6460       6470       6480       6490       6500
GCCGTCTTTT CCAAGAACAA TCATGGAAAC ATATATGGGA TATCTTAAGA ATTCTATCAT AAGTCCATAT ATGTCCATGA TTGACCTTTA AGAGCCAACC 6510       6520       6530       6540       6550       6560       6570       6580       6590       6600
TCCAATGATT ATCCGTTAAA TTCAGATATA ACAATTCAAA AATCAATATT AAGCCTCCAG ATACCAATGA ATATGAATAT ATCTCTTAGA AAACTTGATT 6610       6620       6630       6640       6650       6660       6670       6680       6690       6700
ATTATGTGAT AACATAGTAC AATTTAAGAA AAAACCTAAA ATAAGCACGA ACCCTTAAGG TGTCGTAACG TCTCGTGACG CCGGGTTCAG TTCAAACATC 6710       6720       6730       6740       6750       6760       6770       6780       6790       6800
GACCCCTGAC CCAATTCAAT ACCCATTTTC ATAAAGGAAC ACAGTATAAT TTAATCATAA AAGACCTCAA AATCTGATAC AGCTTAATCC ACTCAACATA 6810       6820       6830       6840       6850       6860       6870       6880       6890       6900
TAATTATAAG ACTAATAATA ATGGAAGATT ACAGCAATCT ATCTCTTAAA TCAATTCCTA AAAGGACATG TAGAATCATT TTCCGAACTG CCACAATTCT 6910       6920       6930       6940       6950       6960       6970       6980       6990       7000
TGGCATATGC ACATTAATTG TGCTATGTTC AAGTATTCTT CATGAGATAA TTCATCTTGA TGTTTCCTCT GGTCTTATGA ATTCTGATGA GTCACAGCAA 7010       7020       7030       7040       7050       7060       7070       7080       7090       7100
GGCATTATTC AGCCTATCAT AGAATCATTA AAATCATTGA TTGCTTTGGC CAACCAGATT CTATATAATG TTGCAATAGT AATTCCTCTT AAAATTGACA 7110       7120       7130       7140       7150       7160       7170       7180       7190       7200
GTATCGAAAC TGTAATACTC TCTGCTTTAA AAGATATGCA CACCGGGAGT ATGTCCAATG CCAACTGCAC GCCAGGAAAT CTGCTTCTGC ATGATGCAGC 7210       7220       7230       7240       7250       7260       7270       7280       7290       7300
ATACATCAAT GGAATAAACA AATTCCTTGT ACTTGAATCA TACAATGGGA CGCCTAAATA TGGACCTCTC CTAAATATAC CCAGCTTTAT CCCCTCAGCA 7310       7320       7330       7340       7350       7360       7370       7380       7390       7400
ACATCTCCCC ATGGGTGTAC TAGAATACCA TCATTTTCAC TCATCAAGAC CCATTGGTGT TACACTCACA ATGTAATGCT TGGAGATTGT CTTGATTTCA 7410       7420       7430       7440       7450       7460       7470       7480       7490       7500
CGGCATCTAA CCAGTATTTA TCAATGGGAA TAATACAACA ATCTGCTGCA GGGTTTCCAA TTTTCAGGAC TATGAAAACC ATTTACCTAA GTGATGGAAT 7510       7520       7530       7540       7550       7560       7570       7580       7590       7600
CAATCGCAAA AGCTGTTCAG TCACTGCTAT ACCAGGAGGT TGTGTCTTGT ATTGCTATGT AGCTACAAGG TCTGAAAAAG AAGATTATGC CACGACTGAT 7610       7620       7630       7640       7650       7660       7670       7680       7690       7700
CTAGCTGAAC TGAGACTTGC TTTCTATTAT TATAATGATA CCTTTATTGA AAGAGTCATA TCTCTTCCAA ATACAACAGG GCAGTGGGCC ACAATCAACC 7710       7720       7730       7740       7750       7760       7770       7780       7790       7800
CTGCAGTCGG AAGCGGGATC TATCATCTAG GCTTTATCTT ATTTCCTGTA TATGGTGGTC TCATAAATGG GACTACTTCT TACAATGAGC AGTCCTCACG 7810       7820       7830       7840       7850       7860       7870       7880       7890       7900
CTATTTTATC CCAAAACATC CCAACATAAC TTGTGCCGGT AACTCCAGCA AACAGGCTGC AATAGCACGG AGTTCCTATG TCATCCGTTA TCACTCAAAC 7910       7920       7930       7940       7950       7960       7970       7980       7990       8000
AGGTTAATTC AGAGTGCTGT TCTTATTTGT CCATTGTCTG ACATGCATAC AGAAGAGTGT AATCTAGTTA TGTTTAACAA TTCCCAAGTC ATGATGGGTG 8010       8020       8030       8040       8050       8060       8070       8080       8090       8100
CAGAAGGTAG GCTCTATGTT ATTGGTAATA ATTTGTATTA TTATCAACGC AGTTCCTCTT GGTGGTCTGC ATCGCTCTTT TACAGGATCA ATACAGATTT 8110       8120       8130       8140       8150       8160       8170       8180       8190       8200
TTCTAAAGGA ATTCCTCCGA TCATTGAGGC TCAATGGGTA CCGTCCTATC AAGTTCCTCG TCCTGGAGTC ATGCCATGCA ATGCAACAAG TTTTTGCCCT 8210       8220       8230       8240       8250       8260       8270       8280       8290       8300
GCTAATTGCA TCACAGGGGT GTACGCAGAT GTGTGGCCGC TTAATGATCC AGAACTCATG TCACGTAATG CTCTGAACCC CAACTATCGA TTTGCTGGAG 8310       8320       8330       8340       8350       8360       8370       8380       8390       8400
CCTTTCTCAA AAATGAGTCC AACCGAACTA ATCCCACATT CTACACTGCA TCGGCTAACT CCCTCTTAAA TACTACCGGA TTCAACAACA CCAATCACAA 8410       8420       8430       8440       8450       8460       8470       8480       8490       8500
AGCAGCATAT ACATCTTCAA CCTGCTTTAA AAACACTGGA ACCCAAAAAA TTTATTGTTT AATAATAATT GAAATGGGCT CATCTCTTTT AGGGGAGTTC 8510       8520       8530       8540       8550       8560       8570       8580       8590       8600
CAAATAATAC CATTTTTAAG GGAACTAATG CTTTAATCCT ATTGAATGAA GACTCCAGAT TCAAGAATAA TTGGAAGGCT CTTTATTTTA TGCGATAGTT 8610       8620       8630       8640       8650       8660       8670       8680       8690       8700
ATACGTTTTG GCTGTATTAG AATGCTATAG CATTCTGCTG TTTTTCCCAT ATGGAAAAAT CCTTCAACAC CAACTTAGGT TCAATTTTCT CATCATTTAC
```

FIGURE 9C

```
        8710       8720       8730       8740       8750       8760       8770       8780       8790       8800
   TGTTGTAATT CAATCTTACT AAAGTTATTC TGATATTTAA GAAAAAATAA TGTTTATATA ATGTAACAAT ACTACTAAGA TTATAATATA GGCCAGAATG
        8810       8820       8830       8840       8850       8860       8870       8880       8890       8900
   GCGGCCTCTT CTGAGATACT CCTTCCTGAA GTCCATTTGA ACTCACCAAT AGTCAAACAC AAACTCATAT ACTACTTATT ACTAGGGCAC TTCCCGCATG
        8910       8920       8930       8940       8950       8960       8970       8980       8990       9000
   ATCTTGACAT TTCTGAAATA AGCCCCCTTC ACAATAATGA TTGGGATCAG ATTGCCAGAG AAGAATCCAA TCTTGCTGAA CGACTCGGAG TAGCTAAATC
        9010       9020       9030       9040       9050       9060       9070       9080       9090       9100
   TGAATTAATT AAACGTGTGC CCGCATTTAG AGCAACCAGA TGGCGTAGTC ATGCAGCCGT CCTTATATGG CCTTCTTGTA TACCATTCCT TGTTAAATTC
        9110       9120       9130       9140       9150       9160       9170       9180       9190       9200
   CTACCCCATT CTAAGCTTCA ACCAATAGAA CAATGGTACA AGTTGATCAA TGCTTCATGC AATACTATAT CTGACTCAAT TGATAGAGT ATGGAGAATA
        9210       9220       9230       9240       9250       9260       9270       9280       9290       9300
   TTTCTATTAA GCTTACTGGG AAAAACAATC TATTCTCTCG ATCCAGAGGA ACTGCAGGCG CAGGTAAAAA CAGTAAAATC ACCCTCAATG ATATCCAATC
        9310       9320       9330       9340       9350       9360       9370       9380       9390       9400
   TATTTGGGAA TCAAACAAAT GGCAGCCTAA TGTATCTTTA TGGCTTACAA TTAAATACCA AATGCGACAA CTTATAATGC ATCAAAGTTC TCGTCAGCCA
        9410       9420       9430       9440       9450       9460       9470       9480       9490       9500
   ACTGATTTAG TTCACATTGT TGACACACGA TCTGGTCTAA TAGTTATCAC CCCTGAACTT GTTATTTGCT TTGATCGGTT GAATAATGTT TTAATGTATT
        9510       9520       9530       9540       9550       9560       9570       9580       9590       9600
   TTACATTTGA GATGACTTTA ATGGTAAGTG ACATGTTTGA GGGACGGATG AATGTTGCCG CGCTCTGCAC TATTAGTCAT TACTTATCAC CACTAGGGCC 9610       9620       9630       9640       9650       9660       9670       9680       9690       9700
   AAGGATAGAT AGATTGTTTT CTATTGTAGA TGAATTAGCA CAACTATTGG GTGACACTGT ATATAAAATT ATTGCATCTC TTGAATCTTT AGTATATGGG
        9710       9720       9730       9740       9750       9760       9770       9780       9790       9800
   TGTCTACAAC TTAAAGATCC AGTGGTTGAA TTAACAGGAT CATTTCATTC CTTTATTACG CAAGAGATTA TAGATATCCT AATTGGGTCA AAAGCCCTTG
        9810       9820       9830       9840       9850       9860       9870       9880       9890       9900
   ATAAGGATGA ATCAATAACT GTCACTACAC AATTGCTAGA TATATTTTCC AACCTTTCTC CAGATTTAAT CGCTGAGATG TTGTGTCTCA TGAGACTTTG
        9910       9920       9930       9940       9950       9960       9970       9980       9990      10000
   GGGTCATCCC ACTCTTACTG CTGCGCAAGC TGCAGGTAAA GTGAGAGAAT CTATGTGTGC AGGTAAGTTA CTTGATTTCC CTACAATAAT GAAAACTCTT
       10010      10020      10030      10040      10050      10060      10070      10080      10090      10100
   GCTTTTTTCC ACACAATTTT AATCAATGGT TATCGTAGAA AGAAGAATGG AATGTGGCCT CCACTTATAC TTCCTAAAAA TGCATCAAAA AGCTTAATAG
       10110      10120      10130      10140      10150      10160      10170      10180      10190      10200
   AGTTTCAACA TGATAATGCT GAAATATCTT ATGAGTATAC ACTCAAGCAT TGGAAAGAAA TCTCTCTCAT AGAATTTAGA AAGTGCTTTG ACTTTGATCC
       10210      10220      10230      10240      10250      10260      10270      10280      10290      10300
   TGGTGAGGAG CTAAGCATTT TTATGAAAGA CAAGGCAATA AGTGCTCCAA AAAGTGATTG GATGAGTGTA TTCCGTAGAA GTCTAATAAA ACAACGACAT
       10310      10320      10330      10340      10350      10360      10370      10380      10390      10400
   CAGAGACATC ATATTCCTAT GCCCAATCCA TTTAACAGAC GTCTATTACT CAATTCTTA GAAGATGACA GTTTTGATCC AGTTGCTGAG CTTCAATATG
       10410      10420      10430      10440      10450      10460      10470      10480      10490      10500
   TTACCAGTGG TGAATATCTC CGAGATGACA CATTTTGTGC ATCTTACTCA TTAAAAGAGA AAGAAATAAA ACCAGATGGA AGGATATTTG CTAAGCTTAC
       10510      10520      10530      10540      10550      10560      10570      10580      10590      10600
   TAATAGAATG CGGTCTTGTC AAGTAATTGC GGAAGCAATT CTTGCAAATC ACGCAGGTAC TCTAATGAAG GAAAACGGAG TTGTCTTGAA TCAATTATCT
       10610      10620      10630      10640      10650      10660      10670      10680      10690      10700
   CTGACTAAAT CATTGCTTAC TATGAGTCAA ATTGGCATAA TATCAGAAAA AGCAAAGAGA TATACCCGAG ATAACATCTC ATCTCAAGGT TTCCATACAA
       10710      10720      10730      10740      10750      10760      10770      10780      10790      10800
   TCAAGACTGA CTCAAAAAAT AAGAAGAAAA GCAAAATTGC ATCATCATAC CTCACAGATC CTGATGATAC ATTTGAACTT AGTGCATGTT TTATAACTAC
       10810      10820      10830      10840      10850      10860      10870      10880      10890      10900
   TGATCTTGCT AAATACTGTC TTCAATGGAG ATATCAGACC ATAATCCATT TTGCTCGAAC ATTAAACAGA ATGTATGGAG TTCCACATTT ATTTGAATGG
       10910      10920      10930      10940      10950      10960      10970      10980      10990      11000
   ATTCATCTTC GTTTGATTAG ATCTACATTA TATGTTGGTG ATCCATTCAA TCCTCCTGCC ACAACTGATG CCTTCGATCT AGATAAAGTA TTAAATGGTG
       11010      11020      11030      11040      11050      11060      11070      11080      11090      11100
   ATATCTTTAT AGTCTCTCCC AAGGGAGGTA TTGAAGGCCT ATGTCAGAAA ATGTGGACAA TGATCTCTAT TTCTGTGATC ATCCTTTCTT CAGCCGAATC
       11110      11120      11130      11140      11150      11160      11170      11180      11190      11200
   CAAAACAAGA GTAATGAGCA TGGTTCAAGG AGATAATCAG GCGATTGCAG TTACAACAAG AGTTCCTAGA TCATTGCCTA GTGTTCAGAA AAAGGAGTTA
       11210      11220      11230      11240      11250      11260      11270      11280      11290      11300
   GCCTACGCAG CAAGCAAGTT ATTCTTTGAA AGACTTAGGG CAAATAATTA TGGTTTGGGT CATCAACTAA AGGCTCAAGA GACTATAATA AGTTCCACGT
       11310      11320      11330      11340      11350      11360      11370      11380      11390      11400
   TCTTCATATA TAGTAAACGG GTATTCTATC AAGGACGTAT ACTAACACAG GCACTAAAA ATGCTAGCAA GTTATGTCTT ACTGCAGATG TATTAGGTGA
       11410      11420      11430      11440      11450      11460      11470      11480      11490      11500
   ATGTACTCAG GCTTCCTGCT CAAATTCTGC TACTACAATC ATGAGATTAA CAGAAAATGG GGTTGAGAAA GATACATGTT ATAAGCTTAA TATTTATCAA
       11510      11520      11530      11540      11550      11560      11570      11580      11590      11600
   TCTATTCGTC AACTCACATA TGATCTAATA TTTCCCCAAT ACTCCATACC AGGTGAAACA ATAAGTGAAA TTTTCTTACA GCATCCAAGA TTAATCTCAC
```

FIGURE 9D

```
       11610      11620      11630      11640      11650      11660      11670      11680      11690      11700
   GTATTGTTCT GCTCCCTTCA CAGCTAGGTG GTCTTAATTA CCTCGCATGT AGCAGATTAT TTAACCGCAA TATCGGAGAT CCCCTTGGTA CAGCCGTGGC 11710      11720      11730      11740      11750      11760      11770      11780      11790      11800
   AGACCTCAAG AGGTTAATTA AATGTGGTGC TCTTGAATCA TGGATACTGT ACAATTTACT GGCAAGAAAA CCAGGGAAAG GTTCATGGGC CACTTTAGCA 11810      11820      11830      11840      11850      11860      11870      11880      11890      11900
   GCCGATCCAT ACTCATTGAA TCAAGAATAT CTTTATCCTC CTACTACTAT ACTTAAAAGA CATACTCAAA ATACTTTAAT GGAGATATGT CGGAATCCTA 11910      11920      11930      11940      11950      11960      11970      11980      11990      12000
   TGTTAAAGGG AGTTTTTACA GATAATGCAA AAGAGGAGGA AAATCTCCTT GCAAAATTTC TTCTTGATCG TGATATAGTA TTGCCAAGAG TCGCACACAT 12010      12020      12030      12040      12050      12060      12070      12080      12090      12100
   TATAATAGAT CAATCCAGCA TTGGAAGGAA GAAACAGATA CAAGGGTTTT TTGACACCAC AAGGACCATA ATGAGACGAT CATTTGAGAT CAAACCACTC 12110      12120      12130      12140      12150      12160      12170      12180      12190      12200
   TCAACTAAGA AGACACTTTC AGTCATAGAA TATAATACTA ATTATTTATC TTATAACTAC CCTGTCATAC TTAATCCTTT ACCTATTCCT GGATATTTAA 12210      12220      12230      12240      12250      12260      12270      12280      12290      12300
   ATTATATTAC TGACCAAACT TGCAGTATTG ATATATCTAG AAGTTTAAGA AAATTATCAT GGTCTTCTTT ATTGAATGGA AGAACTTTAG AAGGATTAGA 12310      12320      12330      12340      12350      12360      12370      12380      12390      12400
   AACTCCAGAT CCAATTGAAG TTGTCAATGG TTCCTTGATT GTAGGTACAG GAGATTGTGA CTTTTGTATG CAGGGTGACG ATAAATTCAC TTGGTTCTTT 12410      12420      12430      12440      12450      12460      12470      12480      12490      12500
   TTACCTATGG GGATAATTAT TGATGGAAAT CCTGAAACTA ATCCACCCAT CAGAGTTCCA TACATTGGGT CTAGAACAGA GGAAAGAAGA GTTGCATCAA 12510      12520      12530      12540      12550      12560      12570      12580      12590      12600
   TGGCATATAT TAAAGGTGCC ACACACAGTT TGAAGGCTGC TCTTAGAGGC GCAGGGGTAT ACATTTGGGC ATTCGGAGAT ACAGTAGTGA ACTGGAATGA 12610      12620      12630      12640      12650      12660      12670      12680      12690      12700
   TGCACTTGAT ATCGCAAATA CTAGGGTTAA GATATCCCTA GAGCAACTTC AGACTCTTAC ACCTCTTCCT ACATCTGCAA ACATTACACA TCGTTTAGAT 12710      12720      12730      12740      12750      12760      12770      12780      12790      12800
   GATGGAGCCA CAACACTTAA ATTCACTCCA GCTAGTTCCT ATGCATTTTC TAGTTATACT CATATATCAA ATGATCAACA ATATTTAGAA ATAGATCAGA 12810      12820      12830      12840      12850      12860      12870      12880      12890      12900
   GAGTAGTCGA TTCCAATATT ATTTATCAAC AATTAATGAT AACAGGGCTT GGGATCATTG AGACCTACCA TAACCCACCT ATCAGGACCT CTACACAGGA 12910      12920      12930      12940      12950      12960      12970      12980      12990      13000
   AATCACCCTC CATTTGCACA CTAGCTCATC TTGTTGTGTT AGAAGTGTAG ATGGTTGCCT TATATGTGAG AGCAATGGAG AGGTTCCTCA GATCACTGTT 13010      13020      13030      13040      13050      13060      13070      13080      13090      13100
   CCCTACACTA ATTCATTTGT ATATGATCCT GATCCACTAG CAGATTATGA GATTGCACAT CTAGATTATC TCTCCTACCA AGCTAAAATT GGAAGTACAG 13110      13120      13130      13140      13150      13160      13170      13180      13190      13200
   ATTACTACTC ACTTACTGAT AAAATTGATC TATTGGCACA TTTAACTGCA AAACAAATGA TAAACTCAAT AATTGGGTTA GATGAAACAG TATCAATTGT 13210      13220      13230      13240      13250      13260      13270      13280      13290      13300
   CAATGATGCG GTTATTCTAT CTGATTATAC TAATAACTGG ATTAGTGAAT GTTCTTATAC TAAGATAGAT TTAGTTTTTA AATTAATGGC ATGGAATTTC 13310      13320      13330      13340      13350      13360      13370      13380      13390      13400
   CTTCTTGAGC TTGCATTCCA GATGTACTAC CTAAGAATAT CATCTTGGAC AAATATATTT GACTATACTT ACATGACTTT ACGCAGGATA CCCGGAACTG 13410      13420      13430      13440      13450      13460      13470      13480      13490      13500
   CTCTAAAATAA TATTGCAGCT ACTATTAGCC ACCCAAAATT ATTAAGACGT GCAATGAATC TTGATATTAT CACTCCTATA CATGCACCGT ATTTGGCTTC 13510      13520      13530      13540      13550      13560      13570      13580      13590      13600
   ATTAGATTAT GTCAAATTAA GTATTGATGC AATTCAGTGG GGGGTTAAAC AAGTTCTTGC TGATTTATCA AATGGAATTG ATCTTGAAAT CTTGATTCTT 13610      13620      13630      13640      13650      13660      13670      13680      13690      13700
   TCAGAGGATT CAATGGAAAT TAGTGATAGG GCAATGAATC TCATTGCTAG AAAAACTAACT CTCCTTGCAC TTGTTAAAGG TGAGAACTAT ACATTCCAA 13710      13720      13730      13740      13750      13760      13770      13780      13790      13800
   AAATTAAAGG GATGCCACCA GAGGAAAAGT GTTTAGTCTT AACTGAATAC CTAGCAATGT GTTATCAGAA TACTCACCAC TTAGATCCAG ATCTTCAAAA 13810      13820      13830      13840      13850      13860      13870      13880      13890      13900
   GTATTTATAT AATCTAACTA ATCCAAAATT GACTGCATTT CCCAGTAACA ACTTCTACTT AACAAGGAAA ATCCTTAATC AAATTAGAGA ATCAGACGAA 13910      13920      13930      13940      13950      13960      13970      13980      13990      14000
   GGACAATATA TTTATCACCTC ATATTATGAA TCCTTCGAAC AATTAGAAAC AGATATAATT CTTCACTCTA CTTTAACTGC TCCTTATGAT AATTCAGAAA 14010      14020      14030      14040      14050      14060      14070      14080      14090      14100
   CTCTAACAAA GTTTGATTTA TCCCTTGACA TCTTTCCACA TCCAGAATCT CTCGAGAAAT ATCCTTCCTTC AGTTGATCAT GACTCTCAAT CTGCAATTTC 14110      14120      14130      14140      14150      14160      14170      14180      14190      14200
   AACACTAATT CCAGGCCCTC CCTCTCATCA TGTATTACGA CCACTAGGAG TGTCATCTAC AGCTTGGTAT AAAGGGATAA GTTATTGCAG ATACCTGGAA 14210      14220      14230      14240      14250      14260      14270      14280      14290      14300
   ACGCAAAAGA TACAGACTGG TGATCATCTT TATTTAGCTG AAGGAAGCGG TGCTTCAATG TCACTTCTAG AACTCCTATT TCCAGGAGAT ACTGTCTATT 14310      14320      14330      14340      14350      14360      14370      14380      14390      14400
   ATAATAGTCT TTTTAGTAGT GGAGAGAATC CTCCACAGAG AAATTATGCT CCTCTTCCAA CTCAATTTGT ACAGAGTGTT CCATATAAAT TGTGGCAAGC 14410      14420      14430      14440      14450      14460      14470      14480      14490      14500
   TGATCTTGCT GATGATAGTA ACTTAATAAA AGATTTTGTC CCATTATGGA ATGGAAACGG AGCAGTTACA GACTTATCGA CAAAGGATGC AGTTGCATTC
```

FIGURE 9E

```
        14510      14520      14530      14540      14550      14560      14570      14580      14590      14600
ATAATACATA AAGTAGGAGC GGAGAAAGCA TCCCTTGTTC ATATAGATCT CGAATCGACT GCTAATATAA ATCAGCAAAC TCTGTCCAGA TCCCAGATTC 14610      14620      14630      14640      14650      14660      14670      14680      14690      14700
ATTCGTTAAT TATAGCAACT ACTGTTCTTA AGAGGGGTGG GATATTAGTT TACAAAACAT CATGGCTTCC GTTTTCTAGG TTTAGTCAAC TAGCAAGCCT 14710      14720      14730      14740      14750      14760      14770      14780      14790      14800
ACTTTGGTGC TTTTTTGACC GGATCCATCT AATACGTAGT AGTTATTCTG ATCCTCACAG TCATGAGGTT TATCTTGTAT GTAGACTTGC TGCGGATTTT 14810      14820      14830      14840      14850      14860      14870      14880      14890      14900
AGAACTATCG GTTTCAGTGC AGCTCTAGTA ACTGCTACTA CTCTTCACAA TGACGGATTC ACAACAATAC ATCCTGATGT TGTTTGTAGT TATTGGCAAC 14910      14920      14930      14940      14950      14960      14970      14980      14990      15000
ACCATCTTGA GAATGTTGGG AGAGTCGAAA AAGTAATTGA TGAGATACTT GATGGTTTAG CCACCAACTT CTTCGCAGGA GATAATGGGC TTATTCTAAG 15010      15020      15030      15040      15050      15060      15070      15080      15090      15100
ATGTGGAGGA ACTCCCAGCT CTAGAAAATG GTTAGAGATT GATCAGTTAG CATCATTTGA TTCAGTTCAA GATGCTCTAG TGACACTTAT CACCATACAC 15110      15120      15130      15140      15150      15160      15170      15180      15190      15200
CTAAAGGAAA TTATAGAAGT GCAGTCATCA CATACAGAGG ATTATACATC TCTCCTTTTC ACACCTTATA ATATTGGTGC AGCAGGGAAA GTAAGAACTA 15210      15220      15230      15240      15250      15260      15270      15280      15290      15300
TCATCAAATT AATTCTAGAA CGATCTTTAA TGTATACAGT CCGAAATTGG TTAGTTTTAC CCAGTTCCAT CCGGGATTCC GTACGACAAG ATCTAGAGTT 15310      15320      15330      15340      15350      15360      15370      15380      15390      15400
AGGGTCATTT AGATTAATGT CTATTTTAAG TGAACAGACA TTTCTTAAAA AGACACCCAC CAAAAAATAC TTACTTGATC AGCTTACAAG GACATATATA 15410      15420      15430      15440      15450      15460      15470      15480      15490      15500
TCAACCTTCT TTAATTCTCA CTCAGTCCTC CCCCTCCACC GTCCATATCA AAAACAAATA TGGAAAGCCT TAGGTAGTGT AATATATTGT TCGGAGACGG 15510      15520      15530      15540      15550      15560      15570      15580      15590      15600
TTGATATACC TCTAATTAGA GACATTCAGA TAGAAGATAT TAATGATTTT GAAGATATCG AGAGGGGTAT CGATGGCGAA GAATTATGAC AACAGTGATT 15610      15620      15630      15640      15650
ATAAGAACTC ATGATAGTTT TATTTAAGAA AAACATATTG ATTTTCCCCT TGGT
```

FIGURE 9F

Human Parainfluenza Virus Type 2 Strain V98 Antigenomic sense cDNA Sequence Range: 1 to 15654

10 20 30 40 50 60 70 80 90 100
ACCAAGGGGA GAATTAGATG GCATCGTTAT ATGACGAATT GCAAAAAGAT TACGTAGGTC CGGAACCACT AGATTCCGGT GCCGGTAACG ATTCCATTTT 110 120 130 140 150 160 170 180 190 200
TATACTATCT GATCATTCTC TATCTCTACT AAGGATATTT CTAGTCTAAA GTTCAAAATG TCAAGTGTCT TAAAGACATT TGAAAGGTTT ACTATACAAC 210 220 230 240 250 260 270 280 290 300
AAGAGCTTCA GGAGCAATCT GATGACACTC CAGTACCTCT TGAGACAATC AAACCTACAA TAAGGGTATT TGTCATCAAT AATAATGATC CTGCCATAAG 310 320 330 340 350 360 370 380 390 400
GTCTAGACTT TTATTCTTTA ATCTACGAAT TATTATGAGT AACACCGCAA GAGAGGGACA TAGAGCTGGT GCTCTCCTCA GTCTCTTATC ACTACCTTCT 410 420 430 440 450 460 470 480 490 500
GCAGCTATGA GTAATCACAT CAAACTAGCC ATGCATTCAC CAGAAGCCAG CATAGATAGA GTAGAGATAA CAGGGTTTGA GAATAATTCA TTCCGAGTTA 510 520 530 540 550 560 570 580 590 600
TTCCAGATGC TCGATCAACT ATGTCCAGAG GAGAGGTGCT GGCCTTTGAA GCATTAGCTG AAGACATTCC TGATACCCTT AATCACCAAA CTCCATTTGT 610 620 630 640 650 660 670 680 690 700
AAATAATGAT GTAGAAGATG ACATGTTTGA TGAAACAGAG AAATTCTTAG ATGTTTGCTA CAGTGTACTT ATGCAGGCAT GGATAGTAAC ATGCAAGTGT 710 720 730 740 750 760 770 780 790 800
ATGACTGCTC CTGATCAGCC GCCAGTATCA GTAGCAAAGC GGATGGCTAA ATATCAACAA CAAGGGAGAA TCAATGCTAG GTATGTACTA CAGCCTGAAG 810 820 830 840 850 860 870 880 890 900
CACAAAGACT AATTCAGAAT GCCATCCGCA AGTCAATGGT AGTGAGGCAT TTCATGACTT ATGAGCTTCA ACTTTCACAA TCAAGATCTT TGCTAGCAAA 910 920 930 940 950 960 970 980 990 1000
CCGCTACTAT GCTATGGTGG GAGACATTGG CAAGTACATT GAACACAGCG GAATGGGAGG TTTTTTCTTA ACACTTAAAT ATGGACTTGG AACAAGATGG 1010 1020 1030 1040 1050 1060 1070 1080 1090 1100
CCTACATTGG CTCTTGCAGC ATTCTCTGGG GAACTCCAGA AATTAAAAGC TCTCATGCTA CATTATCAGA GCCTAGGACC CATGGCCAAG TACATGGCTC 1110 1120 1130 1140 1150 1160 1170 1180 1190 1200
TATTAGAATC ACCAAAGCTG ATGGATTTTG TCCCATCTGA ATATCCATTA GTTTATAGTT ATGCAATGGG TATTGGAACT GTCCTTGATA CAAATATGAG 1210 1220 1230 1240 1250 1260 1270 1280 1290 1300
AAACTATGCA TATGGTAGAT CATATTTAAA TCCGCAATAT TTTCAGCTAG GAGTAGAAAC AGCAAGGAAA CAGCAGGGAG CTGTTGACAA CAGGACAGCA 1310 1320 1330 1340 1350 1360 1370 1380 1390 1400
GAGGACCTCG GCATGACTGC TGCAGACAAA GCAGACCTCA CTGCAACCAT ATCAAAGCTA TCTTTGTCCC AATTACCTAG GGGTAGACAA CCAATATCTG 1410 1420 1430 1440 1450 1460 1470 1480 1490 1500
ACCCATTTGC TGGAGCAAAT GACAGAGAAA TAGGAGGCCA AGCAAATGAT ACACCTGTAT ACAACTTCAA TCCAATCAAT ACTCGGAGGT ATGACAACTA 1510 1520 1530 1540 1550 1560 1570 1580 1590 1600
TGACAGTGAT GGTGAGGACA GAATTGACAA CGATCAAGAT CAAGCTATCA GAGAGAACAG AGGAGAGCCT GGACAACTAA ACAACCAGAC AAGTGACAAC 1610 1620 1630 1640 1650 1660 1670 1680 1690 1700
CAGCAGAGAC TCAATCTCTC CATACCGCAA AGAACATCAG GTATGAGCAG TGAAGAGTTC CAACATTCAA TGAATCAGTA CATCCGTGCC ATGCATGAGC 1710 1720 1730 1740 1750 1760 1770 1780 1790 1800
AATACAGAGG ACCCCAGGAT GATGATACCA ATGATGCCGC AGATGGGAAT GACATTTCTC TTGAGCTAGT TGGGGATTTT GATTCCTAAT TCTCAATGTC 1810 1820 1830 1840 1850 1860 1870 1880 1890 1900
ATACAACCAG ATATACACAT CCACATCACT TAAAGATACA GCTGCCACCC ACACACTCAT CCAGACAAAT CAAACCAGAC TCACATCATT CAGAAACAAT 1910 1920 1930 1940 1950 1960 1970 1980 1990 2000
TCTCTCATAA TTTAAGAAAA AAACATAGGC CCGGACGGGT TTAAAATCTG GTGCTCGTTC GTGGTCTGAC AACCTCCAAA CCAGAATCAC ACAATTATGG 2010 2020 2030 2040 2050 2060 2070 2080 2090 2100
CCGAGGAACC AACATACACC ACTGAGCAAG TTGATGAACT AATCCATGCT GGACTGGGAA CAGTAGATTT CTTCCTATCT AGACCCATAG ATGCTCAATC 2110 2120 2130 2140 2150 2160 2170 2180 2190 2200
TTCCCTAGGC AAGGGCAGCA TCCCACCAGG TGTCACAGCT GTTCTAACTA GTGCAGCAGA GGCAAAATCC AAACCAGTTG CCGCTGGTCC AGTGAAACCC 2210 2220 2230 2240 2250 2260 2270 2280 2290 2300
AGGCGGAAGA AAGTGATCAG CAATGCTACC CCATACACTG TTGCAGACAA TACTCCACCT GAGAAGCTAC CAATCAACAC CCCAATACCC AATCCATTAC 2310 2320 2330 2340 2350 2360 2370 2380 2390 2400
TTCCACTGGC ACGCCCCCAA GGAAAGATGA CAGACATTGA CATTGTCACT GGGACCATTA CAGAAGGATC GTACAAAGGT GTGGAGCTTG CTAAATTAGG 2410 2420 2430 2440 2450 2460 2470 2480 2490 2500
GAAGCAAACA CTACTCACAA GGTTCACCTC GAACGAGCCA GTCTCCTCAG CTGGATCCGC CCAAGACCCC AACTTTAAGA GGGGGGGAGC TAATAGAGAA 2510 2520 2530 2540 2550 2560 2570 2580 2590 2600
AGAGCAAGAG GCAACCATAG GAGAGAATGG AGTATTGCAT GGGTCGGAGA TCAGGTCAAA GTCTTCGAGT GGTGTAATCC CAGGTGTGCC CCAGTCACGG 2610 2620 2630 2640 2650 2660 2670 2680 2690 2700
CCTCAGCTCG CAAGTTCACC TGCACATGCG GATCCTGCCC CAGCATCTGC GGAGAATGTG AAGGAGATCA TTGAGCTCTT AAAGGGGCTT GATCTTCGCC 2710 2720 2730 2740 2750 2760 2770 2780 2790 2800
TTCAGACTGT AGAAGGGAAG GTAGATAAAA TTCTTGCAAC TTCCGCAACT ATAATCAATC TTAAAAATGA AATGACTAGT CTCAAGGCGA GCGTTGCAAC 2810 2820 2830 2840 2850 2860 2870 2880 2890 2900
TGTGGAAGGT ATGATAACAA CAATTAAAAT CATGGATCCC AGCACACCAA CCAATGTCCC TGTAGAGGAG ATCAGAAAGA GCTTACACAA TGCTCCAGTA

FIGURE 10A

```
       2910       2920       2930       2940       2950       2960       2970       2980       2990       3000
GTAATTGCCG GTCCAACTAG TGGAGGCTTC ACAGCCGAAG GCAGTGATAT GATTTCAATG GATGAACTAG CTAGACCTAC ACTCTCATCA ACAAAAAAGA 3010       3020       3030       3040       3050       3060       3070       3080       3090       3100
TCACACGAAA GCCTGAATCC AAGAAAGACT TAACAGGCAC AAAACTAACC TTGATGCAGC TTGCAAATGA CTGCATCTCG CGTCCAGATA CCAAGACTGA 3110       3120       3130       3140       3150       3160       3170       3180       3190       3200
GTTCGTGACT AAGATTCAAG CAGCAACCAC AGAATCACAG CTTAATGAAA TCAAGCGGTC AATAATACGC TCTGCAATAT AAAATGAGGT GCAATCACAC 3210       3220       3230       3240       3250       3260       3270       3280       3290       3300
AAGAGACACT CAACATGCAT CCAATCAAGA TCCAAATTCT GTCCATCCGA AAACACACCC ACAATTGTTA ACACCAAGAA ACAACCACAG CCGAACCATG 3310       3320       3330       3340       3350       3360       3370       3380       3390       3400
CTTAATCAAA AGATCCAAAC AACATCTCAC ATCGACAGAA GGCTGGACAT GATAAATTTA ATAAAAAAGA AAAAAAAGTC AAGTAAAATT TAAAGGACAC 3410       3420       3430       3440       3450       3460       3470       3480       3490       3500
AATAGAGAAA ATCTAGGTCC GAAAGCTTGC TTCCCGGACA GATCTCAAAA TCATAGTCTA AACCTCAAAC ACAGCAGCAG ACATGCCCAT AATATCATTA 3510       3520       3530       3540       3550       3560       3570       3580       3590       3600
CCAGCAGATC CAACTTCACC CAGTCAATCC CTTACTCCGT TTCCAATACA ACTTGACACC AAAGATGGCA AGGCAGGGAA ACTCCTTAAA CAGATTCGAA 3610       3620       3630       3640       3650       3660       3670       3680       3690       3700
TTAGGTATCT AAATGAGCCT AATTCTCGCC ATACACCAAT AACTTTCATC AATACGTATG GATTTGTTTA TGCTCGAGAC ACTTCAGGGG GCATTCACAG 3710       3720       3730       3740       3750       3760       3770       3780       3790       3800
TGAGCTTAGT AGTGACCTAG CTGCAGGGTC TATAACAGCA TGCATGATGA CGCTAGGCCC TGGTCCAAAT ATTCAGAATG CAAATCTAGT GCTAAGATCT 3810       3820       3830       3840       3850       3860       3870       3880       3890       3900
CTGAATGAAT TCTACGTGAA AGTCAAGAAG ACATCAAGCC AGAGAGAGGA AGCAGTGTTT GAATTAGTTA ACATTCCAAC TTTATTGAGA GAACATGCTC 3910       3920       3930       3940       3950       3960       3970       3980       3990       4000
TTTGCAAACG CAAAATGTTA GTTTGCTCTG CAGAAAAGTT CCTCAAGAAC CCGTCAAAGC TACAAGCTGG ATTTGAGTAT GTATACATAC CAACTTTTGT 4010       4020       4030       4040       4050       4060       4070       4080       4090       4100
CTCCATTACA TACTCACCAC GAAATCTGAA TTACCAAGTT GCCAGACCTA TCCTTAAGTT CAGATCACGT TTTGTGTATA GCATTCATTT GGAATTAATT 4110       4120       4130       4140       4150       4160       4170       4180       4190       4200
CTGAGATTGC TATGCAAATC TGAATCCCCC TTAATGAAAT CCTACAATGC AGACAAAACA GGTCGGGGAT GCCTTGCATC AGTCTGGATC CATGTATGTA 4210       4220       4230       4240       4250       4260       4270       4280       4290       4300
ACATTCTGAA AAACAAAAGC ATCAAGCAAC AAGGCAGAGA ATCATATTTC ATAGCCAAGT GCATGAGCAT GCAGCTGCAG GTGTCCATTG CAGATCTTTG 4310       4320       4330       4340       4350       4360       4370       4380       4390       4400
GGGACCAACA ATCATAATCA AATCATTGGG TCACATCCCC AAGACTGCAC TTCCTTTTTT CAGCAAAGAT GGGATTGCCT GTCATCCATT ACAAGATGTT 4410       4420       4430       4440       4450       4460       4470       4480       4490       4500
TCCCCCACTC TGACAAAATC ACTGTGGTCA GTTGGATGTG AGATAGAATC TGCCAAGTTG ATACTTCAAG AATCTGATCT TAATGAGCTA ATGGGCCACC 4510       4520       4530       4540       4550       4560       4570       4580       4590       4600
AGGACCTTAT CACTGATAAG ATTGCCATCA GATCAGGTCA ACGGACATTT GAGAGGTCCA AATTCAGCCC ATTTAAAAAA TATGCATCAA TTCCAAACTT 4610       4620       4630       4640       4650       4660       4670       4680       4690       4700
GGAAGCCATC AACTGAATGC TCCAGCATCT GAGAATAGAA CCACAATTAA ATCATACTAT TAGTAACTAT ACAATAATAA ACAATTTTAG TCAACAGATT 4710       4720       4730       4740       4750       4760       4770       4780       4790       4800
ACCAAGATGT TATCATAGGT CCGAACTGAT CAATCTAACA AAAAAACTAA ACGTTCCATA ATAAATCAAC GTTCAGGTCA AAATACTCAA CCATGCATCA 4810       4820       4830       4840       4850       4860       4870       4880       4890       4900
CCTACATCCA ATGATAGTAT GCATCTTTGT TATGTACACT GGAATTGTAG GTTCAGGTGC CATTGCCGGA GACCAACTAC TTAATATAGG GGTCATTCAA 4910       4920       4930       4940       4950       4960       4970       4980       4990       5000
TCAAAGATAA GATCACTCAT GTACTATACT GATGGTGGTG CTAGCTTTAT TGTTGTTAAA TTGCTACCTA ATCTTCCCCC AAGCAATGGA ACATGCAACA 5010       5020       5030       5040       5050       5060       5070       5080       5090       5100
TTACCAGTCT AGATGCATAC AATGTTACCC TATTTAAATT ACTGACACCC CTGATTGAGA ACCTGAGCAA AATCTCCGCT GTTACAGATA CCAAAACCCG 5110       5120       5130       5140       5150       5160       5170       5180       5190       5200
CCAAGAACGA TTTGCAGGAG TCGTTGTTGG ACTTGCTGCA TTAGGAGTAG CCACAGCTGC ACAAATAACC GCAGCTGTAG CAATAGTTAA AGCTAATGCA 5210       5220       5230       5240       5250       5260       5270       5280       5290       5300
AATGCTGCCG CGATTAATAA TCTTGCATCT TCAATTCAAT CAACAAAACAA GGCAGTATCC GATGTGATAG ATGCATCAAA AACAATTGCA ACTGCAGTTC 5310       5320       5330       5340       5350       5360       5370       5380       5390       5400
AAGCAATCCA GGATCATATC AATGGAGCTA TTGTTAATGG GATAACATCT GCATCATGCC GTGCCCATGA TGCACTCATT GGGTCAATAT TAAATCTTTA 5410       5420       5430       5440       5450       5460       5470       5480       5490       5500
TCTCACTGAG CTTACCACAA TATTTCACAA TCAAATAACA AACCCTGCGC TGACACCGCT CTCCATCCAA GCTTTAAGAA TTCTCCTCGG TAGCACCTTG 5510       5520       5530       5540       5550       5560       5570       5580       5590       5600
CCAATTGTCA TTGAGTCCAA ACTCAACACA AACCTCAACA CAGCAGAGCT GCTCAGCTCC GGACTGTTAA CTGGTCAAAT AATTTCAATT TCCCCAATGT 5610       5620       5630       5640       5650       5660       5670       5680       5690       5700
ACATGCAAAT GCTAATTCAA ATCAATGTTC CGACATTTAT AATGCAACCC GGTGCGAAGG TAATTGATCT AATTGCTATC TCTCAAACC ATAAATTGCA 5710       5720       5730       5740       5750       5760       5770       5780       5790       5800
AGAAGTAGTT GTACAAGTTC CGAATAGGAT TCTAGAGTAT GCAAATGAAC TACAAATTA TCCAGCCAAT GACTGTGTTG TGACACCGAA CTCTGTATTC
```

FIGURE 10B

```
       5810       5820       5830       5840       5850       5860       5870       5880       5890       5900
   TGTAGATACA ATGAGGGTTC CCCTATCCCT GAATCACAAT ACCAATGCTT GAGGGGGAAT CTTAATTCTT GCACTTTTAC CCCTATTATC GGGAACTTTC 5910       5920       5930       5940       5950       5960       5970       5980       5990       6000
   TTAAGCGATT TGCATTTGCC AATGGTGTGC TCTATGCCAA CTGCAAATCT TTGCTATGTA AGTGTGCCGA CCCTCCCCAT GTGGTGTCCC AAGATGATAC 6010       6020       6030       6040       6050       6060       6070       6080       6090       6100
   CCAAGGCATC AGCATAATTG ATATTAAGAG ATGCTCTGAG ATGATGCTTG ACACTTTCTC ATTTAGGATC ACATCTACGT TCAATGCTAC ATACGTGACA 6110       6120       6130       6140       6150       6160       6170       6180       6190       6200
   GACTTCTCAA TGATTAAATGC AAATATTGTA CATCTAAGTC CTCTAGATTT GTCAAACCAA ATCAATTCAA TAAACAAATC TCTTAAAAGT GCTGAGGATT 6210       6220       6230       6240       6250       6260       6270       6280       6290       6300
   GGATTGCAGA TAGCAACTTC TTTGCTAATC AAGCCAGGAC AGCCAAGACA CTTTATTCAT TAAGTGCAAT AGCATTAATA CTATCAGTGA TTACCTTGGT 6310       6320       6330       6340       6350       6360       6370       6380       6390       6400
   TGTTGTGGGA TTGCTGATTG CCTACATCAT CAAACTAGTT TCCCAAATCC ATCAATTCAG AGCGCTAGCT GCTACAACAA TGTTCCACAG GGAAAATCCT 6410       6420       6430       6440       6450       6460       6470       6480       6490       6500
   GCCTTCTTTT CCAAGAACAA TCATGGAAAC ATATATGGGA TATCTTAAGA AATCTATCAC AAGTCCATAT ATGTCCACAA TTGATTCTTA AGAACCAACT 6510       6520       6530       6540       6550       6560       6570       6580       6590       6600
   TCCAATGATT ATCCTTTAAA CTTAAGTATA ATAGTTTAAA AATTAACATT AAGCCTCCAG ATACCAATGA ATATGAATAT ATCTCTAAGA AAACCTGATT 6610       6620       6630       6640       6650       6660       6670       6680       6690       6700
   ATTATGTGAT AGTGTAGTAC AATTTAAGAA AAAACCTAAA ATAAGCACGA ACCCTTAAGG TGTCGTAACG TCTCGTGACA CTGGGTTCAG TTCAAAAATC 6710       6720       6730       6740       6750       6760       6770       6780       6790       6800
   GACTTCTAAT CTAATTTAAC ACCCATTCTT ATATAAGAAC ACAGTATAAC TTAATTACAA AAGACCTCAA AAACTGACAC AGCTTAATCC ACTCAACATA 6810       6820       6830       6840       6850       6860       6870       6880       6890       6900
   TAATTGTAAG ATTAATAATA ATGGAAGATT ACAGCAATCT ATCTCTTAAA TCAATTCCTA AAAGGACATG TAGAATCATT TTCCGAACTG CCACAATTCT 6910       6920       6930       6940       6950       6960       6970       6980       6990       7000
   TGGAATATGC ACATTGATTG TTCTATGTTC AAGTATTCTT CATGAAATAA TTCATCTTGA TGCTTCCTCT GGTCTCATGA ATTCTGATGA TTCACAGCAA 7010       7020       7030       7040       7050       7060       7070       7080       7090       7100
   GGCATTATTC AGCCTATTGT AGAATCATTA AAATCATTGA TTGCTTTGGC TAACCAGATT CTGTACAATG TTGCAATAAT AATTCCTCTT AAAATTGACA 7110       7120       7130       7140       7150       7160       7170       7180       7190       7200
   GTATTGAGAC CGTAATACTC TCTGCTTYAA AGGAYATGCA TACTGGGAGC ATGTCCAACA CCAACTGTAC ACCCGGAAAT CTGCTTCTGC ATGATGCAGC 7210       7220       7230       7240       7250       7260       7270       7280       7290       7300
   ATACATCAAT GGAATAAACA AATTCCTTGT ACTTAAATCA TACAATGGTA CGCCTAAATA TGGACCTCTC CTAAATATTC CTAGCTTTAT CCCCTCAGCA 7310       7320       7330       7340       7350       7360       7370       7380       7390       7400
   ACATCTCCCC ACGGGTGCAC TAGAATACCA TCATTTTCAC TCAGTAAGAC TCATTGGTGT TACACTCACA ATGTAATACT TGGAGATTGC CTCGATTTCA 7410       7420       7430       7440       7450       7460       7470       7480       7490       7500
   CGACATCTAA TCAGTATTTA GCAATGGGGA TAATACAACA ATCTGCTGCA GCATTTCCAA TCTTCAGGAC TATGAAAACC ATTTACCTAA GTGATGGAAT 7510       7520       7530       7540       7550       7560       7570       7580       7590       7600
   CAATCGCAAA AGCTGTTCAG TCACTGCCAT ACCAGGAGGT TGTGTCTTGT ACTGCTATGT AGCTACAAGA TCTGAGAAAG AAGATTATGC CACAACTGAT 7610       7620       7630       7640       7650       7660       7670       7680       7690       7700
   CTAGCTGAAC TGAGACTTGC TTTCTATTAT TATAATGATA CCTTTGTTGA AAGAGTCATA TCTCTTCCAA ATACAACAGG GCAATGGGCC ACAATCAATC 7710       7720       7730       7740       7750       7760       7770       7780       7790       7800
   CTGCAGTTGG AAGCGGGATC TATCATCTAG GCTTTATTTT ATTTCCTGTA TATGGTGGTC TCATAAATGG GACTCCTTCC TACAACGAGC AGTCCTCACG 7810       7820       7830       7840       7850       7860       7870       7880       7890       7900
   CTATTTTATC CCAACACATC CCAACATAAC CTGTGCCGGA AACTCCAGTG AACGGGCTGC AGCAGCACGG GGTTCCTATG TCATCCGTTA TCATTCAAAC 7910       7920       7930       7940       7950       7960       7970       7980       7990       8000
   AGGTTGATTC AGAGTGCTAT TCTTATTTGC CCATTATCTG ACATGCAAAC AGCAAGGTGT GATCTAGTTA TGTTTAACAA TTCTCAAGTC ATGATGGGTG 8010       8020       8030       8040       8050       8060       8070       8080       8090       8100
   CAGAAGGTAG GCTCTATGTT ATTGACAACA ATTTGTATTA TTATCAACGT AGTTCCTCTT GGTGGTCTGC ATCGCTTTTC TACAGGATCA ATACAGATTT 8110       8120       8130       8140       8150       8160       8170       8180       8190       8200
   CTCTAAAGGA ATTCCTCCTA TCATTGAGGC TCAATGGGTA CCGTCCTATC AAGTTCCCCG CCCTGGAGTC ATGCCATGTA ATGCAACAAG TTTTTGCCCT 8210       8220       8230       8240       8250       8260       8270       8280       8290       8300
   GCTAATTGCA TCACAGGAGT GTATGCAGAT GTGTGGCCGC TTAACGATCC AGAACTCACA TCACAAAATG CTCTGAATCC CAACTATCGA TTTGCTGGAG 8310       8320       8330       8340       8350       8360       8370       8380       8390       8400
   CCTTTCTAAA AAATGAGTCC AACCGAACCA ATCCCACATT TTACACTGCA TCAGCCAACT CCCTACTAAA TACTACCGGA TTCAACAACA CCAATCACAA 8410       8420       8430       8440       8450       8460       8470       8480       8490       8500
   AGCAGCATAT ACGTCTTCAA CCTGCTTTAA GAATACTGGA ACTCAGAAGA TTTATTGTTT GATAATAATC GAAATGGGCT CATCTCTTTT AGGGGAGTTC 8510       8520       8530       8540       8550       8560       8570       8580       8590       8600
   CAAATAATAC CATTTCTAAG GGAACTAATA CCTTAATACT ATTGAATGAA AACTTAAGAT TCAATAATAA TTGAAAGGCT CTCTATCTTA TGTAATAGTT 8610       8620       8630       8640       8650       8660       8670       8680       8690       8700
   ATACGTTTTG GCTGTATTAG AATGTTATAG CATTCTGCTG TGTTTCCCAT ATGAAGCAAG CCTCAACAC CGACTTAGGT TCAATTTTCT CATCATTTAC
```

FIGURE 10C

```
        8710       8720       8730       8740       8750       8760       8770       8780       8790       8800
   TGTTGTAATC CAATCTTACT AAAGTTATTC TGATATTTAA GAAAAAATAA CCTTTATATA ATATAACAAT ACTATTAAGA TTATGATATA GGCCAGAATG
        8810       8820       8830       8840       8850       8860       8870       8880       8890       8900
   GCGGCCTCTT CTGAGATACT CCTTCCTGAA GTCCACTTGA ACTCACCAAT AGTCAAACAC AAACTCTATAT ACTACTTATT ACTAGGGCAC TTCCCGCATG
        8910       8920       8930       8940       8950       8960       8970       8980       8990       9000
   ATCTTGACAT TTCTGAAATA AGCCCTCTTC ACAATAATGA TTGGGATCAA ATTGCCAGAG AAGAATCCAA TCTTGCTGAA CGACTTGGAG TAGCTAAATC
        9010       9020       9030       9040       9050       9060       9070       9080       9090       9100
   TGAATTAATT AAACGTGTGC CCGCATTTAG AGCAACTAGA TGGCGTAGTC ATGCAGCTGT CCTTATATGG CCTTCTTGTA TACCATTTCT TGTTAAATTC
        9110       9120       9130       9140       9150       9160       9170       9180       9190       9200
   CTACCTCATT CTAAGCTTCA ACCAATAGAA CAATGGTACA AGTTGATCAA TGCTTCATGT AATACTATAT CTGACTCAAT TGATAGATGT ATGGAGAATA
        9210       9220       9230       9240       9250       9260       9270       9280       9290       9300
   TTTCTATTAA GCTTACTGGG AAAAACAATC TATTCTCTCG ATCCAGAGGA ACTGCAGGTG CAGGTAAAAA CAGTAAAATC ACCCTCAATG ATATCCAATC
        9310       9320       9330       9340       9350       9360       9370       9380       9390       9400
   TATTTGGGAA TCAAACAAGT GGCAGCCTAA TGTATCTTTA TGGCTTACAA TTAAATATCA AATGCGACAA CTTATAATGC ATCAAAGTTC TCGTCAGCCG
        9410       9420       9430       9440       9450       9460       9470       9480       9490       9500
   ACTGATTTAG TTCACATTGT TGACACACGA TCTGGTCTAA TAGTTATCAC CCCTGAACTT GTTATTTGTT TTGATCGGTT GAATAGTGTT TTAATGTATT
        9510       9520       9530       9540       9550       9560       9570       9580       9590       9600
   TTACATTTGA GATGACTTTA ATGGTAAGCG ACATGTTCGA GGGGAGGATG AATGTCACTG CTCTCTGCAC TATTAGTCAT TACTTATCTC CACTAGGGCC
        9610       9620       9630       9640       9650       9660       9670       9680       9690       9700
   AAGGATCGAT AGATTGTTTT CCATTGTAGA TGAATTAGCA CAACTATTAG GTGACACTGT ATATAAAGTT ATTGCATCTC TTGAATCTTT AGTATATGGG
        9710       9720       9730       9740       9750       9760       9770       9780       9790       9800
   TGTCTACAAC TTAAAGATCC AGTAGTGGAA TTAGCAGGGT CATTTCATTC CTTTATTACA CAAGAGATTA TAGATATCCT AATTGGTTCA AAAGCCCTTG
        9810       9820       9830       9840       9850       9860       9870       9880       9890       9900
   ATAAGGATGA ATCAATAACT GTTACTACAC AATTGTTAGA TATATTTTCC AACCTTTCTC CAGATTTAAT TGCTGAGATG TTGTGTCTCA TGAGACTTTG
        9910       9920       9930       9940       9950       9960       9970       9980       9990      10000
   GGGTCATCCT ACTCTTACTG CTGCGCAAGC TGCAGGTAAA GTGAGAGAAT CTATGTGTGC AGGTAAGTTG CTTGATTTCC CTACAATAAT GAAAACTCTT
       10010      10020      10030      10040      10050      10060      10070      10080      10090      10100
   GCTTTTTTCC ACACAATTTT AATTAATGGT TACCGTAGAA AGAAAAATGG AATGTGGCCT CCACTTATAC TTCCTAAAAA TGCATCAAAA AGCTTAATAG
       10110      10120      10130      10140      10150      10160      10170      10180      10190      10200
   AATTTCAACA TGATAATGCT GAAATATCTT ACGAATATAC ACTCAAGCAT TGGAAAGAGA TCTCTCTCAT AGAATTTAGA AAGTGCTTTG ACTTTGATCC
       10210      10220      10230      10240      10250      10260      10270      10280      10290      10300
   TGGTGAGGAG CTAAGCATTT TTATGAAGGA CAAGGCAATA AGTGCTCCAA AAAGTGATTG GATGAGTGTA TTTCGTAGAA GTCAATAAAA ACAACGACAT
       10310      10320      10330      10340      10350      10360      10370      10380      10390      10400
   CAGAGACATC ATATTCCTAT GCCCAATCCA TTTAATAGAC GTCTATTACT CAATTTCTTA GAAGATGACA GTTTTGACCC AGTTGCTGAG CTCCAATATG
       10410      10420      10430      10440      10450      10460      10470      10480      10490      10500
   TTACCAGTGG TGAATACCTC CAAGATGACA CATTTTGTGC ATCTTACTCA TTAAAAGAGA AAGAAATAAA ACCAGATGGA AGGATATTCG CTAAGCTTAC
       10510      10520      10530      10540      10550      10560      10570      10580      10590      10600
   TAATAGAATG CGGTCCTGTC AAGTAATTGC GGAAGCAATT CTTGCAAATC ATGCAGGTAC TCTAATGAAG GAAAACGGAG TTGTCTTGAA TCAATTATCA
       10610      10620      10630      10640      10650      10660      10670      10680      10690      10700
   CTGACCAAGT CATTGCTTAC TATGAGTCAA ATTGGCATAA TATCAGAAAA GGCAAAGAGA TATACGCGAG ATAACATCTC ATCTCAAGGT TTCCATACAA
       10710      10720      10730      10740      10750      10760      10770      10780      10790      10800
   TCAAGACTAC CTCTAAAAAT AAGAGGAAAA GCAAAACTGC ATCATCATAC CTCACAGATC CTGATGATAC ATTTGAACTT AGTGCATGTT TTATAACTAC
       10810      10820      10830      10840      10850      10860      10870      10880      10890      10900
   TGATCTTGCT AAATACTGTC TTCAATGGAG ATATCAGACC ATAATCCATT TTGCTCGAAC ATTAAACAGA ATGTATGGAG TTCCACATTT ATTTGAATGG
       10910      10920      10930      10940      10950      10960      10970      10980      10990      11000
   ATTCATCTTC GTTTAATTAG GTCTACATTA TATGTTGGTG ATCCATTCAA TCCCCCTGCT GCGACTGATG CTTTCGATCT AGATAAAGTA TTAAATGCTG
       11010      11020      11030      11040      11050      11060      11070      11080      11090      11100
   ATATCTTTAT AGTCTCTCCC AAAGGAGGTA TTGAAGGCCT ATGTCAGAAA ATGTGGACAA TGATCTCTAT TTCTGTGATC ATCCTCTCCT CAGCCGAATC
       11110      11120      11130      11140      11150      11160      11170      11180      11190      11200
   CAAAACAAGA GTAATGAGCA TGGTTCAAGG AGATAATCAG GCAATTGCAG TTACAACAAG AGTTCCTAGA TCATTACCTA GTATTCAGAA AAAGGAGTTA
       11210      11220      11230      11240      11250      11260      11270      11280      11290      11300
   GCCTATGCAG CAAGCAAGTT ATTTTTTGAA AGACTTAGGG CAAATAATTA TGGGTTGGGT CATCAGCTAA AGGCTCAAGA AACTATAATA AGTTCCACAT
       11310      11320      11330      11340      11350      11360      11370      11380      11390      11400
   TCTTCATATA TAGTAAACGG GTATTTTATC AAGGACGTAT ACTAACACAG GCACTCAAAA ACGCTAGCAA GCTATGTCTT ACTGCGGATG TATTAGGTGA
       11410      11420      11430      11440      11450      11460      11470      11480      11490      11500
   ATGTACTCAA GCTTCCTGTT CAAATTCTGC TACTACCATC ATGAGATTAA CAGAAAATGG GGTTGAGAAA GATACATGTT ATAAGCTTAA TATTTATCAG
       11510      11520      11530      11540      11550      11560      11570      11580      11590      11600
   TCCATTCGTC AACTCACATA TGATCTAATA TTTCCCCAAT ATTCCATACC AGGTGAAACG ATAAGTGGGA TTTTCCTGCA GCATCCAAGA CTAATCTCAC
```

FIGURE 10D

```
       11610      11620      11630      11640      11650      11660      11670      11680      11690      11700
   GTATTGTTCT GCTCCCTTCA CAGCTAGGTG GTCTTAATTA CCTCGCATGC AGCAGATTAT TTAACCGCAA TATCGGAGAT CCTCTTGGTA CAGCTGTGGC 11710      11720      11730      11740      11750      11760      11770      11780      11790      11800
   GGACCTCAAG AGGTTAATTA AATGTGGTGC TCTTGAATCA TGGATACTGT ACAATTTACT AGCAAGAAAA CCAGGGAAAG GTTCATGGGC AACTTTAGCA 11810      11820      11830      11840      11850      11860      11870      11880      11890      11900
   GCCGATCCGT ACTCATTGAA TCAAGAATAT CTTTATCCTC CTACTACTAT ACTTAAAAGA CATACTCAAC ATACTTTAAT GGAGATATGT AGGAATCCTA 11910      11920      11930      11940      11950      11960      11970      11980      11990      12000
   TGTTAAAGGG AGTTTCACA GATAATGCAA AAGAGGAGGA AAATCTCCTT GCAAAATTTC TTCTTGATCG TGATATAGTA TTGCCAAGAG TTGCGCACAT 12010      12020      12030      12040      12050      12060      12070      12080      12090      12100
   TATAATAGAT CAATCTAGCA TCGGAAGGAA GAAACAGATA CAAGGATTTT TTGACACCAC AAGGACCATT ATGAGACGAT CATTTGAAAT CAAACCACTC 12110      12120      12130      12140      12150      12160      12170      12180      12190      12200
   TCAACTAAGA AGACTCTTTC AGTTATAGAA TATAATACAA ATTACTTATC TTATAACTAC CCTGTCATAC TTAATCCTTT ACCTATTCCC GGATATTTAA 12210      12220      12230      12240      12250      12260      12270      12280      12290      12300
   ATTATATTAC TGACCAAACT TGCAGTATTG ATATATCTAG AAGTTAAGA AAATTATCAT GGTCTTCTTT ATTGAATGGA AGAACTTTAG AAGGATTAGA 12310      12320      12330      12340      12350      12360      12370      12380      12390      12400
   AACTCCAGAT CCAATTGAAG TTGTCAATGG TTCCTTGATT GTAGGTACAG GAGATTGTGA TTTTTGTATG CAGGGTGATG ACAAATTTAC TTGGTTCTTT 12410      12420      12430      12440      12450      12460      12470      12480      12490      12500
   TTACCTATGG GGATAATTAT TGATGGAAAT CCTGAAACTA ATCCACCCAT CAGAGTTCCA TACATTGGGT CTAGAACAGA GGAAAGAAGA GTTGCATCAA 12510      12520      12530      12540      12550      12560      12570      12580      12590      12600
   TGGCATATAT TAAAGGTGCC ACACACAGTT TGAAGGCTGC TCTTAGGGGT GCAGGGGTAT ATATTTGGGC ATTCGGGGAT ACTATAGTGA ACTGGAATGA 12610      12620      12630      12640      12650      12660      12670      12680      12690      12700
   TGCACTTGAT ATTGCAAATA CTAGAGTTAA GATATCCCTA GAGCAACTTC AGACTCTCAC ACCTCTTCCT ACATCTGCAA ACATTACACA CCGTTTAGAT 12710      12720      12730      12740      12750      12760      12770      12780      12790      12800
   GATGGAGCCA CAACACTTAA ATTCACTCCA GCTAGTTCCT ATGCATTTTC TAGTTATACT CATATATCAA ATGATCAACA ATATTTAGAA ATAGATCAGA 12810      12820      12830      12840      12850      12860      12870      12880      12890      12900
   GAGTAGTTGA TTCCAATATT ATTTATCAAC AATTAATGAT AACAGGACTT GGGATTATTG AGACCTACCA TAACCCACCT ATAAGAACTT CTACACAAGA 12910      12920      12930      12940      12950      12960      12970      12980      12990      13000
   AATCACTCTC CATTTGCACA CTAGCTCATC TTGTTGTGTT AGAAGTGTAG ATGGCTGCCT TATATGTGAA AGCAATGGAG AGGTTCCCCA GATCACTGTT 13010      13020      13030      13040      13050      13060      13070      13080      13090      13100
   CCCTATACTA ATACATTTGT ATATGATCCT GACCCACTAG CAGATTATGA GATTGCACAT CTAGATTACC TCTCCTACCA AGCTAAAATT GGAAGTACAG 13110      13120      13130      13140      13150      13160      13170      13180      13190      13200
   ATTACTACTC ACTCACTGAT AAAATTGACC TATTAGCACA TTTAACTGCA AAACAAATGA TAAACTCAAT AATTGGGTTA GATGAAACAG TATCGATTGT 13210      13220      13230      13240      13250      13260      13270      13280      13290      13300
   CAATGATGCG GTTATCCTAT CTGACTATAC TAATAACTGG ATTAGTGAAT GTTCTTATAC TAAAATAGAT CTAGTTTTTA AATTAATGGC ATGGAATTTT 13310      13320      13330      13340      13350      13360      13370      13380      13390      13400
   CTTCTTGAGC TTGCATTCCA GATGTACTAC TTAAGGATAT CATCTTGGAC AAATATATTT GACTATACTT ACATGACTTT ACGCAGAATA CCCGGAACTG 13410      13420      13430      13440      13450      13460      13470      13480      13490      13500
   CTCTAAATAA TATTGCAGCT ACTATTAGCC ATCCAAAATT ACTGAGACGT GCAATGAATC TTGATATTAT CACTCCTATA CATGCACCGT ATCTAGCTTC 13510      13520      13530      13540      13550      13560      13570      13580      13590      13600
   ATTAGATTAT GTCAAATTAA GTATTGATGC AATTCAGTGG GGAGTTAAAC AAGTTCTTGC TGATTTATCA AATGGAATTG ATCTTGAAAT CTTGATTCTT 13610      13620      13630      13640      13650      13660      13670      13680      13690      13700
   TCAGAGGATT CAATGGAAAT TAGTGATAGG GCAATGAATC TCATTGCTAG AAAACTAACT CTCCTTGCAC TTGTTAAAGG TGAGAACTAC ACTTTTCCAA 13710      13720      13730      13740      13750      13760      13770      13780      13790      13800
   AAATTAAAGG GATGCCACCA GAAGAAAAGT GTTTAGTCTT AACTGAATAT CTAGCAATGT GTTATCAAAA TACTCACCAC TTAGATCCAG ATCTTCAAAA 13810      13820      13830      13840      13850      13860      13870      13880      13890      13900
   GTATTTATAT AATCTAACTA ATCCAAAATT GACCGCATTT CCCAGTAACA ACTTCTACTT AACTAGGAAA ATCCTCAATC AAATTAGAGA ATCAGACGAA 13910      13920      13930      13940      13950      13960      13970      13980      13990      14000
   GGACAATATA TTATCACCTA ATATTATGAA TCCTTCGAAC AATTAGAAAC AGATATAATT CTTCATTCTA CTTTAACTGC TCCTTATGAT AATTCAGAAA 14010      14020      14030      14040      14050      14060      14070      14080      14090      14100
   CTCTAACAAA GTTTGATTTA TCCCTTGACA TCTTTCCACA TCCAGAATCT CTCGAGAAAT ATCCTCTTCC AGTTGATCAT GACTCTCAAT CTGCAATTTC 14110      14120      14130      14140      14150      14160      14170      14180      14190      14200
   AACACTAATT CCAGGCCCTC CTTCTCATCA TGTATTACGA CCACTGGGAG TGTCCTCTAC AGCTTGGTAT AAAGGGATAA GTTATTGTAG GTATCTAGAA 14210      14220      14230      14240      14250      14260      14270      14280      14290      14300
   ACACAAAAGA TACAGACTGG TGATCATCTT TATTTAGCTG AAGGAAGCGG CGCTTCAATG TCACTCCTAG AACTCCTATT TCCAGGAGAT ACTGTCTATT 14310      14320      14330      14340      14350      14360      14370      14380      14390      14400
   ATAATAGTCT TTTTAGTAGT GGAGAGAATC CTCCACAGAG AAACTACGCC CCTCTTCCAA CTCAATTTGT ACAGAGTGTT CCATATAAAT TGTGGCAAGC 14410      14420      14430      14440      14450      14460      14470      14480      14490      14500
   TGATCTTGCT GATGATAGCA ACTTGATAAA AGATTTTGTC CCATTATGGA ATGGAAATGG TGCAGTTACA GACTTATCAA CAAAGGATGC AGTTGCATTC
```

FIGURE 10E

```
       14510      14520      14530      14540      14550      14560      14570      14580      14590      14600
ATAATACATA AAGTAGGAGC AGAAAAAGCA TCTCTTGTCC ATATAGATCT CGAATCGACT GCTAATATAA ATCAGCAAAC TCTGTCCAGA TCCCAGATTC 14610      14620      14630      14640      14650      14660      14670      14680      14690      14700
ATTCATTAAT TATAGCAACT ACTGTTCTTA AGAGGGGTGG GATATTAATT TATAAGACAT CATGGCTTCC TTTTTCTAGA TTTAGTCAAC TAGCAAGCCT 14710      14720      14730      14740      14750      14760      14770      14780      14790      14800
TCTTTGGTGC TTTTTTGACC GGATCCATCT AATACGTAGT AGCTATTCTG ATCCTCACAG TCATGAGGTT TATCTTGTAT GTAGACTTGC CGCAGATTTT 14810      14820      14830      14840      14850      14860      14870      14880      14890      14900
AGAACTATCG GTTTCAGTGC AGCTCTAGTA ACTGCTACTA CTCTTCACAA TGACGGATTC ACAACAATAC ATCCTGATGT TGTTTGTAGT TATTGGCAAC 14910      14920      14930      14940      14950      14960      14970      14980      14990      15000
ACCATCTTGA AAATGTTGGG AGAGTCGGAA AAGTAATTGA TGAGATACTT GATGGTTTAG CCACCAACTT CTTTGCAGGA GATAATGGAC TTATTCTAAG 15010      15020      15030      15040      15050      15060      15070      15080      15090      15100
ATGTGGAGGA ACTCCCAGCT CCAGAAAATG GTTGGAGATT GACCAGTTAG CATCATTTGA TTTGGTTCAA GATGCTCTGG TGACACTTAT CACTATACAC 15110      15120      15130      15140      15150      15160      15170      15180      15190      15200
CTAAAGGAAA TTATAGAAGT GCAATCATCA CATACAGAAG ATTATACATC TCTCCTCTTC ACACCTTATA ATATTGGTGC AGCAGGGAAA GTTAGAACTA 15210      15220      15230      15240      15250      15260      15270      15280      15290      15300
TCATCAAATT AATTCTAGAA CGATCTTTAA TGTATACAGT CCGAAATTGG TTAGTGTTAC CCAGTTCCAT CCGGGATTCT GTACGACAAG ATTTGGAATT 15310      15320      15330      15340      15350      15360      15370      15380      15390      15400
AGGGTCATTT AGATTAATGT CTATTTTAAG TGAACAGACA TTTCTTAAAA AGACACCCAC AAAAAAATAC TTACTTGATC AGCTTACAAG GACATATATA 15410      15420      15430      15440      15450      15460      15470      15480      15490      15500
TCAACCTTCT TTAACTCTCA CTCAGTCCTT CCTCTTCACC GTCCATATCA AAAACAAATA TGGAAAGCCT TAGGTAGTGT AATATATTGT TCGGAGACAG 15510      15520      15530      15540      15550      15560      15570      15580      15590      15600
TTGATATACC TCTAATTAAA GACATTCAGA TAGAAGATAT TAATGATTTT GAGGATATCG AGAGGGGTAT CGATGGCGAA GAATTATGAC AACAATGATT 15610      15620      15630      15640      15650
ATAAGAACTC ATGATAGTTT TATTTAAGAA AAACATATTG ATTTTCCCCT TGGT
```

FIGURE 10F

Human Parainfluenza Virus Type 2 Strain Greer antigenomic sense cDNA Sequence Range: 1 to 15654

```
         10         20         30         40         50         60         70         80         90        100
ACCAAGGGGA GAATCAGATG GCATCGTTAT ATGACGAATT GCAAAAAGAT TACGTAGGTC CGGAACCACT AGATTCCGGT GCCGGTAACG ATTCCAGTTT
        110        120        130        140        150        160        170        180        190        200
TATACTATCT GATCATTCTC TATCTCTATT AAGGATATTT CTAGTCTAAA GTTCAAAATG TCAAGTGTTT TAAAGACATT TGAAAGATTT ACTATACAAC
        210        220        230        240        250        260        270        280        290        300
AGGAGCTTCA GGAGCAATCT GATGACACTC CAGTACCTCT TGAGACAATC AAACCTACAA TCAGGGTATT TGTCATCAAT AATAATGATC CTGTCGTAAG
        310        320        330        340        350        360        370        380        390        400
ATCTAGACTT TTATTCTTTA ATCTACGAAT CATTATGAGT AACACTGCAA GAGAGGGACA TAGAGCTGGT GCTCTCCTCA CTCTTTTATC ACTACCTTCT
        410        420        430        440        450        460        470        480        490        500
GCAGCTATGA GTAATCACAT CAAATTAGCC ATGCATTCAC CAGAAGCCAG CATAGATAGA GTAGAGATAA CAGGGTTTGA GAATAATTCA TTCCGAGTCA
        510        520        530        540        550        560        570        580        590        600
TTCCAGATGC TCGATCAACT ATGTCCAGAG GAGAGGTGCT GGCTTTTGAA GCATTAGCTG AGGACATTCC TGATACCCTT AATCACCAAA CTCCATTTGT
        610        620        630        640        650        660        670        680        690        700
AAATAATGAT GTAGAAGATG ACATATTTGA TGAAACAGAG AAATTCTTAG ATGTTTGCTA CAGTGTGCTT ATGCAGGCAT GGATAGTAAC ATGCAAGTGT
        710        720        730        740        750        760        770        780        790        800
ATGACTGCTC CTGATCAACC ACCAGTATCA GTAGCAAAGC GGATGGCTAA ATATCAACAA CAAGGGAGAA TCAATGCTAG GTATGTACTA CAACCTGAAG
        810        820        830        840        850        860        870        880        890        900
CACAAAGACT AATTCAGAAT GCCATCCGCA AGTCAATGGT AGTAAGGCAT TTCATGACTT ATGAGCTTCA ACTTTCACAA TCAAGATCTT TGCTAGCAAA
        910        920        930        940        950        960        970        980        990       1000
CCGCTACTAT GCTATGGTGG GAGACATTGG CAAGTACATT GAACACAGCG GAATGGGAGG ATTTTTCTTA ACACTTAAAT ATGGACTTGG AACAAGATGG
       1010       1020       1030       1040       1050       1060       1070       1080       1090       1100
CCTACATTGG CTCTTGCAGC ATTTTCTGGG GAACTCCAGA AATTAAAAGC TCTCATGCTA CATTATCAGA GTCTAGGACC CATGGCCAAG TACATGGCTC
       1110       1120       1130       1140       1150       1160       1170       1180       1190       1200
TATTAGAATC ACCAAAACTG ATGGATTTTG TCCCATCTGA ATATCCATTA GTTTATAGCT ATGCAATGGG TATTGGAACT GTCCTTGATA CAAATATGAG
       1210       1220       1230       1240       1250       1260       1270       1280       1290       1300
AAATTATGCA TACGGTAGAT CATATTTAAA TCCGCAATAT TTTCAGCTAG GAGTAGAAAC AGCAAGGAAA CAGCAGGGAG CTGTTGACAA CAGGACAGCA
       1310       1320       1330       1340       1350       1360       1370       1380       1390       1400
GAGGACCTCG GCATGACTGC TGCAGACAAA GCAGACCTCA CTGCAACCAT ATCAAAGCTA TCCTTGTCCC AATTACCTAG GGGTAGACAA CCAATATCTG
       1410       1420       1430       1440       1450       1460       1470       1480       1490       1500
ACCCATTTGC TGGAGCAAAT GACAGAGAAA TGGGAGGACA AGCAAATGAT ACACCTGTGT ATAACTTCAA TCCAATCAAT ACTCGGAGGT ATGACAACTA
       1510       1520       1530       1540       1550       1560       1570       1580       1590       1600
TGACAGTGAT GGTGAGGACA GAATTCACAA CGATCAAGAT CAAGCTATCA GAGAGAATAA AGGAGAGCCT GGACAACCAA ACAACCAGAC AAGTGACAAC
       1610       1620       1630       1640       1650       1660       1670       1680       1690       1700
CAGCAGAGAT TCAACCCCCC CATACCGCAA AGAACATCAG GTATGAGCAG TGAAGAGTTC CAACATTCAA TGAATCAGTA CATCCGTGCT ATGCATGAGC
       1710       1720       1730       1740       1750       1760       1770       1780       1790       1800
AATACAGAGG CTCCCAGGAT GATGATGCCA ATGATGCCAC AGATGGGAAT GACATTTCTC TTGAGCTAGT TGGAGATTTT GATTCCTAAC TCTCAATGTC
       1810       1820       1830       1840       1850       1860       1870       1880       1890       1900
ATACAACCAG ATATACACAT CCACATCACT CAGAGATACA CCTGCCACTC ACACACTCAT CCAGACAAAT CAAACTAGAC TCACATCATT CGGAAACAAT
       1910       1920       1930       1940       1950       1960       1970       1980       1990       2000
TCTCTCATAA TTTAAGAAAA AATCATAGCC CCGGACGGGT TAGAAATCCG GTGCTTGTTC GTGATCAGAT AACCTCCACA CCAGAATCAT ACAATCATGG
       2010       2020       2030       2040       2050       2060       2070       2080       2090       2100
CCGAGGAACC AACATACACC ACTGAGCAAG TTGATGAATT AATCCATGCT GGACTGGGAA CAGTAGATTT CTTCCTATCT AGACCCATAG ATGCTCAGTC
       2110       2120       2130       2140       2150       2160       2170       2180       2190       2200
TTCTTTAGGC AAAGGCAGCA TCCCACCAGG TGTCACAGCT GTTCTAACTA GTGCAGCGGA GGCAAAATCC AAACCAGTTG CTGCTGGTCC AGTTAAACCC
       2210       2220       2230       2240       2250       2260       2270       2280       2290       2300
AGGCGGAAGA AAGTGATCAG CAATACTACT CCATACACTA TTGCAGACAA TATTCCACCT GAGAAGCTAC CGATCAACAC TCCAATACCC AATCCATTAC
       2310       2320       2330       2340       2350       2360       2370       2380       2390       2400
TTCCACTGGC ACGCCCTCAC GGAAAGATGA CAGACATTGA CATTGTCACT GGGAACATTA CAGAAGGATC GTACAAAGGT GTGGAGCTTG CTAAATTAGG
       2410       2420       2430       2440       2450       2460       2470       2480       2490       2500
GAAGCAGACA CTACTCACAA GGTTCACCTC GAATGAGCCA GTCTCCTCAG CTGGATCCGC CCAAGACCCC AACTTTAAGA GGGGGGGAGC TAATAGAGAA
       2510       2520       2530       2540       2550       2560       2570       2580       2590       2600
AGAGCAAGAG GCAACCATAG GAGAGAATGG AGTATTGCAT GGGTCGGAGA TCAGGTCAAA GTCTTCGAGT GGTGTAATCC CAGGTGTGCC CCAGTCACGG
       2610       2620       2630       2640       2650       2660       2670       2680       2690       2700
CCTCAGCTCG CAAGTTCACC TGCACATGCG GATCCTGCCC CAGCATCTGC GGAGAATGTG AAGGAGATCA TTGAGCTCTT AAAGGGACTT GATCTTCGCC
       2710       2720       2730       2740       2750       2760       2770       2780       2790       2800
TTCAGACTGT AGAAGGGAAA GTAGATAAAA TTCTTGCAAC TTCTGCAACT ATAATCAATC TTAAAAATGA AATGACTAGT CTCAAGGCGA GTGTTGCAAC
       2810       2820       2830       2840       2850       2860       2870       2880       2890       2900
TGTGGAAGGT ATGATAACAA CAATTAAAAT CATGGATCCC AGTACACCAA CTAATGTCCC TGTAGAGGAG ATCAGAAAGA GTTTACACAA TGTTCCAGTA
```

FIGURE 11A

```
       2910      2920      2930      2940      2950      2960      2970      2980      2990      3000
  GTAATTGCCG GTCCAACTAG TGGAGGCTTC ACAGCCGAAG GCAGTGATAT GATTTCAATG GATGAACTAG CTAGACCTAC ACTCTCATCA ACAAAAAGGA 3010      3020      3030      3040      3050      3060      3070      3080      3090      3100
  TCACACGAAA GCCTGAATCC AAGAAAGATT TAACAGGCAT AAAACTAACT TTGATGCAGC TTGCAAATGA CTGCATCTCG CGTCCAGATA CCAAGACTGA 3110      3120      3130      3140      3150      3160      3170      3180      3190      3200
  GTTCGTGACT AAGATTCAGG CAGCAACCAC AGAATCACAG CTTAACGAAA TTAAACGGTC AATAATACGC TCTGCAATAT AAAATGAGGT GCAGTCACAC 3210      3220      3230      3240      3250      3260      3270      3280      3290      3300
  AAGAGACACT CAACATGCAT CCAATCAAGA TCCAGACTCC ATCCATCCAA AAACACGCCC ACAATTGTCA ACACCAAGAA ACAACCACAG CCGAACCATG 3310      3320      3330      3340      3350      3360      3370      3380      3390      3400
  CTCAACCAAA AGACCCAAAC AACACCTCAC ATCAATAGAA GGCTGGACAT GATAAATTTA ATAAAAAAAG AAAAGAAGTT AAGTAAAATT TAAAGGACAC 3410      3420      3430      3440      3450      3460      3470      3480      3490      3500
  AATAGAGAAA ATCTAGGTCC GAAAGCTTGC CTCTCAGACA GATCCCAAAA TCATAGTCCA AACCCCAAAC ACAGCAGCAG ACATGCCTAT AATATCATTA 3510      3520      3530      3540      3550      3560      3570      3580      3590      3600
  CCAGCAGATC CAACTTCACC CAGTCAATCC CTTACTCCGT TTCCAATACA ACTTGACACC AAAGATGGCA AGGCAGGGAA ACTCCTTAAA CAGATTCGAA 3610      3620      3630      3640      3650      3660      3670      3680      3690      3700
  TTAGGTATCT AAATGAGCCT AATTCTCGCC ATACACCAAT AACTTTCATC AATACGTATG GATTTGTTTA TGCTCGAGAC ACTTCAGGGG GCATTCACAG 3710      3720      3730      3740      3750      3760      3770      3780      3790      3800
  TGAGATCAGC AGTGACCTAG CTGCAGGGTC CATAACAGCA TGCATGATGA CGCTAGGTCC TGGTCCAAAT ATTCAGAATG CAAATCTAGT GCTAAGATCT 3810      3820      3830      3840      3850      3860      3870      3880      3890      3900
  CTGAATGAAT TCTACGTAAA AGTCAAGAAG ACATCAAGCC AGAGAGAGGA AGCAGTGTTT GAATTAGTTA ACATTCCAAC TTTATTGAGA GAACATGCTC 3910      3920      3930      3940      3950      3960      3970      3980      3990      4000
  TTTGCAAACG CAAAATGTTA GTATGCTCTG CAGAAAAATT CCTCAAGAAC CCGTCAAAGC TACAAGCTGG ATTTGAGTAT GTATACATAC CAACTTTTGT 4010      4020      4030      4040      4050      4060      4070      4080      4090      4100
  CTCCATTACA TACTCACCAC GAAATCTGAA TTACCAAGTT GCCAGACCTA TCCTTAAGTT CAGATCACGC TTTGTGTATA GCATTCATTT GGAATTAATC 4110      4120      4130      4140      4150      4160      4170      4180      4190      4200
  CTGAGATTGC TATGCAAATC TGACTCCCCC TTGATGAAAT CCTACAATGC AGACAGAACA GGTCGGGGAT GCCTCGCATC AGTCTGGATC CTTGTATGTA 4210      4220      4230      4240      4250      4260      4270      4280      4290      4300
  ACATTCTGAA AAACAAAAGC ATCAAGCAAC AAGGCAGAGA ATCATATTTC ATAGCTAAGT GCATGAGCAT GCAGCTGCAG GTGTCCATTG CAGATCTTTG 4310      4320      4330      4340      4350      4360      4370      4380      4390      4400
  GGGACCAACA ATCATAATCA AATCATTGGG TCACATCCCC AAGACTGCAC TTCCTTTTTT CAGCAAAGAT GGGATTGCCT GTCATCCATT ACAAGATGTT 4410      4420      4430      4440      4450      4460      4470      4480      4490      4500
  TCCCCTAATC TGACAAAATC ACTGTGGTCA GTTGGATGTG AGATAGAATC TGCCAAGTTA ATACTTCAAG AATCTGATCT TAATGAGCTA ATGGGCCACC 4510      4520      4530      4540      4550      4560      4570      4580      4590      4600
  AGGACCTTAT CACTGATAAG ATTGCCATTA GATCAGGTCA ACGGACATTT GAGAGGTCCA AATTCAGCCC ATTCAAAAAA TATGCATCAA TTCCAAACTT 4610      4620      4630      4640      4650      4660      4670      4680      4690      4700
  GGAAGCCATC AACTGAATGC TCCAGCATCT GAGAATAGAA CCACAATCAA GTCATACTAC TAGTCACTAT ACAATAATCA ACAATTTTAG TCAACTGATT 4710      4720      4730      4740      4750      4760      4770      4780      4790      4800
  ACCAAGATGT TATCATAGGT CCGAACTGAT CAATCTAACA AAAAAACTAA ACGTTCCACA ATAAATCAAC GTTCAGGCCA AAATATTCAG CCATGCATCA 4810      4820      4830      4840      4850      4860      4870      4880      4890      4900
  CCTGCATCCA ATGATAGTAT GCATCTTTGT TATGTACACT GGAATTGTAG GTTCAGATGC CATTGCTGGA GATCAACTAC TTAATATAGG GGTCATTCAA 4910      4920      4930      4940      4950      4960      4970      4980      4990      5000
  TCAAAGATAA GATCACTCAT GTACTATACT GATGGTGGTG CTAGCTTTAT TGTTGTAAAA TTGCTACCTA ATCTTCCCCC AAGCAATGGA ACATGCAACA 5010      5020      5030      5040      5050      5060      5070      5080      5090      5100
  TCACCAGTCT AGATGCATAT AATGTTACCC TATTTAAGTT ACTAACACCC CTGATTGAGA ACCTGAGTAA AATTTCCACT GTTACAGATA CCAAAACCCG 5110      5120      5130      5140      5150      5160      5170      5180      5190      5200
  CCAAGAACGA TTTGCAGGAG TAGTTGTTGG ACTTGCTGCA TTAGGAGTAG CCACAGCCGC ACAAATAACT GCAGCTGTAG CAATAGTGAA AGCTAATGCA 5210      5220      5230      5240      5250      5260      5270      5280      5290      5300
  AATGCTGCTG CGATAAACAA TCTTGCATCT TCAATTCAAT CCACCAACAA GGCAGTATCC GATGTGATAG ATGCATCAAG AACAATTGCA ACCGCAGTTC 5310      5320      5330      5340      5350      5360      5370      5380      5390      5400
  AAGCAATTCA GGATCACATC AATGGAGCTA TTGTTAATGG GATAACATCT GCATCATGCC GTGCCCATGA TGCACTCATT GGGTCAATAT TAAATCTTTA 5410      5420      5430      5440      5450      5460      5470      5480      5490      5500
  TCTCACTGAG CTTACCACAA TATTTCATAA TCAAATAACA AACCCTGCGC TGACACCCACT CTCCATCCAA GCTTTAAGAA TCCTCCTCGG TAGCACCTTG 5510      5520      5530      5540      5550      5560      5570      5580      5590      5600
  CCAATTGTCA TTGAGTCCAA ACTCAACACA AACCTCAACA CAGCAGAGCT GCTCAGTTCC GGACTGTTAA CTGGTCAAAT AATTTCCATT TCCCCAATGT 5610      5620      5630      5640      5650      5660      5670      5680      5690      5700
  ACATGCAAAT GCTAATTCAA ATCAATGTTC CGACATTTAT AATGCAACCC GGTGCGAAGG TAATTGATCT AATTGCTATC TCCCAAAACC ATAAATTGCA 5710      5720      5730      5740      5750      5760      5770      5780      5790      5800
  AGAAGTGGTT GTACAAGTTC CGAATAGGAT TCTAGAGTAT GCAAATGAAC TACAAAATTA CCCAGCCAAT GACTGTGTCG TGACACCGAA CTCTGTATTT
```

FIGURE 11B

```
      5810       5820       5830       5840       5850       5860       5870       5880       5890       5900
TGTAGATACA ATGAGGGTTC CCCTATCCCT GAATCACAAT ATCAATGCTT GAGGGGGAAT CTTAATTCTT GCACTTTTAC CCCTATTATC GGGAACTTTC
      5910       5920       5930       5940       5950       5960       5970       5980       5990       6000
TTAAGCGATT CGCATTTGCT AATGGTGTGC TCTATGCCAA CTGCAAATCT TTGCTATGTA GGTGTGCCGA CCCCCCCCAT GTTGTATCCC AGGATGATAC
      6010       6020       6030       6040       6050       6060       6070       6080       6090       6100
CCAAGGCATC AGCATAATTG ATATTAAGAG ATGCTCTGAG ATGATGCTTG ACACTTTTTC ATTTAGGATC ACATCTACTT TCAATGCTAC GTACGTGACA
      6110       6120       6130       6140       6150       6160       6170       6180       6190       6200
GACTTCTCAA TGATTAATGC AAATATTGTA CATCTAAGTC CTCTAGATTT GTCAAATCAA ATCAATTCAA TAAACAAATC TCTTAAAAGT GCTGAGGATT
      6210       6220       6230       6240       6250       6260       6270       6280       6290       6300
GGATTGCAGA TAGCAACTTC TTTGCTAATC AAGCCAGGAC AGCCAAGACA CTTTATTCAC TAAGTGCAAT AGCATTAATA CTATCAGTGA TTACTTTGGT
      6310       6320       6330       6340       6350       6360       6370       6380       6390       6400
TGTCGTGGGA TTGCTGATTG CCTACATCAT CAAGCTGGTT TCTCAAATCC ATCAATTCAG ATCGCTAGCT GCTACAACAA TGTTCCACAG GGAAAATCCT
      6410       6420       6430       6440       6450       6460       6470       6480       6490       6500
GCCTTCTTTT CCAAGAATAA CCATGGAAAC ATATATGGGA TATCTTAAGA AATCTATCAC AAGTCTATAT ATGTCCACAA TTGACCCTTA AGAACCAACT
      6510       6520       6530       6540       6550       6560       6570       6580       6590       6600
TCCAACGATT ATCCGTTAAA TTTAAGTATA ATAGTTTAAA AATTAACATT AAGCCTCCAG ATACCAATGA ATATGAATAT ATCTCTTAGA AAACCTGATT
      6610       6620       6630       6640       6650       6660       6670       6680       6690       6700
ATTATGTGAT AGCGTAGTAC AATTTAAGAA AAAACCTAAA ATAAGCACGA ACCCTTAAGG TGTCGTAACG TCTCGTGACA CCGGGTTCAG TTCAAATATC
      6710       6720       6730       6740       6750       6760       6770       6780       6790       6800
GACCTCTAAC CCAATTTAAC ACCCATTCTT ATATAAGAAC ACAGTATAAT TTAATCACAA AAGACCTCAA AAACTGACAC AGCTTGATCC ACTCAACATA
      6810       6820       6830       6840       6850       6860       6870       6880       6890       6900
TAATTGTAAG ATTAATAATA ATGGAAGATT ACAGCAATCT ATCTCTTAAA TCAATTCCTA AAAGGACATG TAGAATCATT TTCCGAACTG CCACAATTCT
      6910       6920       6930       6940       6950       6960       6970       6980       6990       7000
TGGAATATGC ACATTGATTG TTCTATGTTC AAGTATTCTT CATGAGATAA TTCATCTTGA TGTTTCCTCT GGTCTCATGG ATTCCGATGA TTCACAGCAA
      7010       7020       7030       7040       7050       7060       7070       7080       7090       7100
GGCATTATTC AGCCTATTAT AGAATCATTA AAATCATTAA TTGCTTTGGC TAACCAGATT CTGTACAATG TTGCAATAAT AATTCCTCTT AAAATTGACA
      7110       7120       7130       7140       7150       7160       7170       7180       7190       7200
GTATCGAGAC TGTAATATAC TCTGCTTTAA AGGATATGCA TACTGGGAGC ATGTCCAACA CCAACTGTAC ACCCGGAAAT CTGCTTCTGC ATGATGCAGC
      7210       7220       7230       7240       7250       7260       7270       7280       7290       7300
GTACATCAAT GGAATAAACA AATTCCTTGT ACTTAAATCA TACAATGGGA CGCCTAAATA TGGACCTCTC CTAAATATTC CCAGCTTTAT CCCCTCAGCA
      7310       7320       7330       7340       7350       7360       7370       7380       7390       7400
ACATCTCCCA ACGGGTGCAC TAGAATACCA TCATTTTCAC TCATTAAGAC CCATTGGTGT TACACTCACA ATGTAATACT TGGAGATTGC CTCGATTTCA
      7410       7420       7430       7440       7450       7460       7470       7480       7490       7500
CGACATCTAA TCAGTATTTA GCAATGGGGA TAATACAACA ATCTGCTGCA GCATTTCCAA TCTTCAGGAC TATGAAAACC ATTTACCTAA GTGATGGAAT
      7510       7520       7530       7540       7550       7560       7570       7580       7590       7600
CAATCGCAAA AGCTGTTCAG TCACTGCTAT ACCAGGAGGT TGTGTCTTGT ATTGCTATGT AGCTACAAGA TCTGAGAAAG AAGATTATGC CACAACTGAT
      7610       7620       7630       7640       7650       7660       7670       7680       7690       7700
CTAGCTGAAC TGAGACTTGC TTTCTATTAT TATAATGATA CCTTTATTGA AAGAGTCATA TCTCTTCCAA ATACAACAGG GCAATGGGCC ACAATCAATC
      7710       7720       7730       7740       7750       7760       7770       7780       7790       7800
CTGCAGTTGG AAGCGGGATC TATCATCTAG GCTTTATTTT ATTTCCTGTA TATGGTGGTC TCATAAAGGG GACTCCTTCC TACAACAAGC AGTCCTCACG
      7810       7820       7830       7840       7850       7860       7870       7880       7890       7900
CTATTTTATC CCAAAACATC CCAACATAAC CTGTGCCGGT AAATCCAGCG AACAGGCTGC AGCAGCACGG AGTTCCTATG TAATCCGTTA TCACTCAAAC
      7910       7920       7930       7940       7950       7960       7970       7980       7990       8000
AGGTTGATTC AGAGTGCTGT TCTTATTTGC CCATTGTCTG ACATGCACAC AGCAAGGTGT AATCTAGTTA TGTTTAACAA TTCTCAAGTC ATGATGGGTG
      8010       8020       8030       8040       8050       8060       8070       8080       8090       8100
CAGAAGGTAG GCTCTATGCT ATTGACAATA ATTTGTATTA TTATCAACGT AGTTCCTCTT GGTGGGCTGC ATCGCTTTTT TACAGGATCA ATACAGATTT
      8110       8120       8130       8140       8150       8160       8170       8180       8190       8200
TTCTAAAGGA ATTCCTCCTA TCATTGAGGC TCAATGGGTA CCGTCCTATC AAGTTCCCCG TCCTGGAGTC ATGCCATGCA ATGCAACAAG TTTTTGCCCT
      8210       8220       8230       8240       8250       8260       8270       8280       8290       8300
GCTAATTGCA TCACAGGGGT GTACGCAGAT GTGTGGCCGC TTAACGATCC AGAACCCACA TCACAAAATG CTCTGAATCC CAACTATCGA TTTGCTGGAG
      8310       8320       8330       8340       8350       8360       8370       8380       8390       8400
CCTTTCTCAG AAATGAGTCC AACCGAACCA ATCCCACATT CTACACTGCA TCAGCCAGCG CCCTACTAAA TACTACCGGA TTCAACAACA CCAATCACAA
      8410       8420       8430       8440       8450       8460       8470       8480       8490       8500
AGCAGCATAT ACGTCTTCAA CCTGCTTTAA GAATACTGGA ACTCAAAAGA TTTATTGTTT GATAATAATT GAAATGGGCT CATCTCTTTT AGGGGAGTTC
      8510       8520       8530       8540       8550       8560       8570       8580       8590       8600
CAAATAATAC CATTTCTAAG GGAACTAATA CCTTAATACT ATTGAATGAA GACTCCAGAT TCAATAATAA TTGAAAGGCT CTCTATCTTA TGCAATAGTT
      8610       8620       8630       8640       8650       8660       8670       8680       8690       8700
ATACGTTTTG GCTGTATTAG AATGTTATAG CATTCTGCTG TTTTTCCCAT ATGAAGCAAT CCTTCAACAC CGACTTAGGT TCAATTTTCT CATCATTTAC
```

FIGURE 11C

```
       8710       8720       8730       8740       8750       8760       8770       8780       8790       8800
TGTTGTAATT CAATCTTACT AAAGTTATTC CGATATTTAA GAAAAAATAA CCTTTATATA ATGTAACAAT ACTATTAAGA TTATGATATA GGCCAGAATG 8810       8820       8830       8840       8850       8860       8870       8880       8890       8900
GCGGCCTCTT CTGAGATACT CCTTCCTGAA GTCCACTTGA ACTCACCAAT AGTCAAACAC AAACTCATAT ACTACTTATT ACTAGGGCAC TTCCCGCATG 8910       8920       8930       8940       8950       8960       8970       8980       8990       9000
ATCTTGACAT TTCTGAAATA AGCCCCCTTC ACAATAATGA TTGGGATCAA ATTGCCAGAG AAGAATCCAA TCTTGCTGAA CGACTTGGAG TAGCTAAATC 9010       9020       9030       9040       9050       9060       9070       9080       9090       9100
TGAATTAATT AAACGTGTGC CCGCATTTAG AGCAACTAGA TGGCGTAGTC ATGCAGCCGT CCTTATATGG CCTTCTTGTA TACCATTTCT TGTTAAATTC 9110       9120       9130       9140       9150       9160       9170       9180       9190       9200
CTACCTCATT CTAAGCTTCA ACCAGTAGAA CAATGGTACA AGTTGATCAA TGCTTCATGT AATACTATAT CTGACTCAAT TGATAGATGT ATGGAGAATA 9210       9220       9230       9240       9250       9260       9270       9280       9290       9300
TTTCTATTAA GCTTACTGGG AAAAACAATC TATTCTCTCG ATCCAGAGGA ACTGCAGGTG CAGGTAAAAA CAGTAAAATC ACCCTCAATG ATATCCAATC 9310       9320       9330       9340       9350       9360       9370       9380       9390       9400
TATTTGGGAA TCAAACAAGT GGCAACCTAA TGTATCTTTA TGGCTTACAA TTAAATACCA AATGCGACAA CTTATAATGC ATCAAAGTTC TCGTCAGCCG 9410       9420       9430       9440       9450       9460       9470       9480       9490       9500
ACTGATTTAG TTCACATTGT TGACACACGA TCTGGTCTAA TAGTTATCAC CCCTGAAGTT GTTATTTGTT TTGATCGGTT AAATAGTGTT TTAATGTATT 9510       9520       9530       9540       9550       9560       9570       9580       9590       9600
TTACATTTGA GATGACTTTA ATGGTAAGTG ACATGTTTGA GGGAAGGATG AATGTCACCG CTCTCTGCAC TATTAGTCAT TACTTATCTC CACTAGGGCC 9610       9620       9630       9640       9650       9660       9670       9680       9690       9700
AAGGATAGAT AGATTGTTTT CCATTGTAGA TGAATTAGCA CAACTATTAG GTGACACTGT ATATAAAGTT ATTGCATCTC TTGAATCTTT AGTATATGGG 9710       9720       9730       9740       9750       9760       9770       9780       9790       9800
TGTCTACAAC TTAAAGATCC AGTAGTGGAA TTAGCAGGGT CATTTCATTC CTTTATTACA CAAGAGATTA TAGATATCCT AATTGGTTCA AAAGCCCTTG 9810       9820       9830       9840       9850       9860       9870       9880       9890       9900
ATAAGGATGA ATCAATAACT GTTACTACAC AATTGTTAGA TATATTTTCC AACCTTTCTC CAGATTTAAT TGCTGAGATG TTGTGTCTCA TGAGACTTTG 9910       9920       9930       9940       9950       9960       9970       9980       9990      10000
GGGTCATCCC ACTCTTACTG CTGCGCAAGC TGCAGGTAAA GTGAGAGAAT CTATGTGTGC AGGTAAGTTA CTTGATTTCC CTACAATAAT GAAAACTCTT 10010      10020      10030      10040      10050      10060      10070      10080      10090      10100
GCTTTTTTCC ACACAATTTT AATTAATGGT TACCGTAGAA AGAAAAATGG AATGTGGCCT CCACTTATAC TTCCTAAAAA TGCATCAAAA AGCTTAATAG 10110      10120      10130      10140      10150      10160      10170      10180      10190      10200
AATTTCAACA TGATAATGCT GAAATATCTT ACGAATATAC ACTCAAGCAT TGGAAAGAGA TCTCTCTCAT AGAATTTAGA AAGTGCTTTG ACTTTGATCC 10210      10220      10230      10240      10250      10260      10270      10280      10290      10300
TGGTGAGGAG CTAAGCATTT TTATGAAAGA CAAGGCAATA AGTGCTCCAA GAAGTGATTG GATGAGTGTA TTTCGTAGAA GTCTAATAAA ACAACGACAT 10310      10320      10330      10340      10350      10360      10370      10380      10390      10400
CAGAGACATC ATATTCCTAT GCCCAATCCA TTTAATAGAC GTCTATTACT CAATTTCTTA GAAGATGACA GTTTTGATCC AGTTGCCGAG CTTCAATATG 10410      10420      10430      10440      10450      10460      10470      10480      10490      10500
TTACCAGTGG TGAATATCTC CAAGATGACA CATTTGTGC ATCTTACTCA TTAAAAGAGA AAGAAATAAA ACCAGATGGA AGGATATTTG CTAAGCTTAC 10510      10520      10530      10540      10550      10560      10570      10580      10590      10600
TAATAGAATG CGGTCCTGTC AAGTAATTGC GGAAGCAATT CTCGCAAATC ATGCAGGTAC TCTAATGAAG GAAAACGGAG TTGTCTTGAA TCAATTATCA 10610      10620      10630      10640      10650      10660      10670      10680      10690      10700
CTGACTAAAT CATTGCTTAC TATGAGTCAA ATTGGCATAA TATCAGAAAA GGCGAAGAGA TATACGCGAG ATAACATCTC ATCCCAAGGT TTCCATACAA 10710      10720      10730      10740      10750      10760      10770      10780      10790      10800
TCAAGACTGA TTCTAAAAAT AAGAGGAAAA GCAAAACTGC ATCATCATAC CTCACAGATC CTGATGATAC ATTTGAACTT AGTGCATGTT TTATAACTAC 10810      10820      10830      10840      10850      10860      10870      10880      10890      10900
TGATCTTGCT AAAATACTGTC TTCAATGGAG ATATCAGACC ATAATCCATT TTGCTCGAAC ATTAAACAGA ATGTATGGAG TTCCACATTT ATTTGAATGG 10910      10920      10930      10940      10950      10960      10970      10980      10990      11000
ATTCATCTTC GTTTAATTAG ATCTACATTA TATGTTGGTG ATCCATTCAA TCCTCCTGCC GCAACTGATG CTTTCGATCT AGATAAAGTA TTAAATGGTG 11010      11020      11030      11040      11050      11060      11070      11080      11090      11100
ATATCTTTAT AGTCTCTCCC AAGGGAGGTA TTGAAGGCCT ATGTCAGAAA ATGTGGACAA TGATCTCTAT TTCTGTGATC ATCCTCTCTT CAGCCGAATC 11110      11120      11130      11140      11150      11160      11170      11180      11190      11200
CAAAACAAGA GTAATGAGCA TGGTTCAAGG AGATAATCAG GCGATTGCAG TTACAACAAG AGTTCCTAGA TCATTACCTA GTATTCAGAA AAAGGAGTTA 11210      11220      11230      11240      11250      11260      11270      11280      11290      11300
GCCTATGCAG CAAGCAAGTT ATTTTTTGAA AGACTTAGGG CAAATAATTA TGGGTTGGGT CATCAGCTAA AGGCTCAAGA AACTATAATA AGTTCCACGT 11310      11320      11330      11340      11350      11360      11370      11380      11390      11400
TCTTCATATA TAGTAAACGG GTATTTTATC AAGGACGTAT ACTAACACAG GCACTCAAAA ATGCTAGCAA GTTATGTCTT ACTGCAGATG TATTAGGTGA 11410      11420      11430      11440      11450      11460      11470      11480      11490      11500
ATGTACTCAA GCTTCCTGTT CAAATTCTGC TACTACCATC ATGAGATTAA CAGAAAATGG GGTTGAGAAA GATACATGTT ATAAGCTTAA TATTTATCAG 11510      11520      11530      11540      11550      11560      11570      11580      11590      11600
TCCATTCGTC AACTCACATA TGATCTAATA TTTCCCCAAT ACTCCATACC AGGTGAAACT ATAAGTGAGA TTTTCCTACA GCATCCAAGA CTAATCTCAC
```

FIGURE 11D

```
       11610      11620      11630      11640      11650      11660      11670      11680      11690      11700
   GTATTGTTCT GCTCCCTTCA CAGCTAGGTG GTCTTAATTA CCTCGCATGT AGCAGATTAT TTAACCGCAA TATCGGAGAT CCTCTTGGTA CAGCTGTGGC 11710      11720      11730      11740      11750      11760      11770      11780      11790      11800
   AGATCTCAAG AGGTTAATTA AATGTGGTGC TCTTGAATCA TGGATACTGT ATAATTTACT AGCAAGAAAA CCAGGGAAAG GTTCATGGGC AACTTTAGCA 11810      11820      11830      11840      11850      11860      11870      11880      11890      11900
   GCCGATCCAT ACTCATTGAA TCAAGAATAT CTTTATCCTC CTACTACTAT ACTTAAAAGA CATACTCAAA ATACTTTAAT GGAGATATGT CGGAATCCTA 11910      11920      11930      11940      11950      11960      11970      11980      11990      12000
   TGTTAAAGGG AGTTTTTACA GATAATGCAA AAGAGGAGGA AAATCTCCTT GCAAAATTTC TTCTTGATCG TGATATAGTA TTGCCAAGAG TTGCACACAT 12010      12020      12030      12040      12050      12060      12070      12080      12090      12100
   TATAATAGAT CAATCTAGCA TCGGAAGGAA GAAACAGATA CAAGGATTTT TTGACACCAC AAGGACCATA ATGAGACGAT CATTTGAAAT CAAACCACTC 12110      12120      12130      12140      12150      12160      12170      12180      12190      12200
   TCAACTAAGA AGACTCTTTC AGTCATAGAA TATAATACTA ATTACTTATC TTATAACTAC CCTGTCATAC TTAATCCTTT ACCTATTCCT GGATATTTAA 12210      12220      12230      12240      12250      12260      12270      12280      12290      12300
   ATTATATTAC TGACCAAACT TGCAGTATTG ATATATCTAG AAGTTTAAGA AAATTATCAT GGTCTTCTTT ATTGAATGGA AGAACTTTAG AAGGATTAGA 12310      12320      12330      12340      12350      12360      12370      12380      12390      12400
   AACTCCAGAT CCAATTGAAG TTGTCAATGG TTCCTTGATT GTAGGTACAG GAGATTGTGA TTTTTGTATG CAGGGTGACG ACAAATTTAC TTGGTTCTTT 12410      12420      12430      12440      12450      12460      12470      12480      12490      12500
   TTACCTATGG GGATAATTAT TGATGGAAAT CCTGAAACTA ATCCACCCAT CAGAGTTCCA TACATTGGGT CTAGAACAGA GGAAAGAAGA GTTGCATCAA 12510      12520      12530      12540      12550      12560      12570      12580      12590      12600
   TGGCATATAT TAAAGGTGCC ACACACAGTT TGAAGGCTGC TCTTAGAGGC GCAGGGGTAT ATATTTGGGC ATTCGGGGAT ACTGTAGTGA ACTGGAATGA 12610      12620      12630      12640      12650      12660      12670      12680      12690      12700
   TGCACTTGAT ATCGCAAATA CTAGGGTTAA GATATCCCTA GAGCAACTTC AGACCCTTAC ACCTCTTCCT ACATCTGCAA ACATTACACA CCGTTTAGAT 12710      12720      12730      12740      12750      12760      12770      12780      12790      12800
   GATGGAGCCA CAACACTTAA ATTCACTCCA GCTAGTTCCT ATGCATTTTC TAGTTATACT CATATATCAA ATGATCAACA ATATTTAGAA ATAGATCAGA 12810      12820      12830      12840      12850      12860      12870      12880      12890      12900
   GAGTAGTCGA TTCTAATATT ATTTATCAAC AATTAATGAT AACAGGACTT GGGATTATTG AGACCTACCA TAACCCACCT ATAAGGACTT CTACACAAGA 12910      12920      12930      12940      12950      12960      12970      12980      12990      13000
   AATCACTCTC CATTTGCACA CTAGCTCATC TTGTTGTGTT AGAAGTGTAG ATGGTTGCCT TATATGTGAG AGCAATGGAG AGGTTCCTCA GATCACTGTT 13010      13020      13030      13040      13050      13060      13070      13080      13090      13100
   CCCTATACTA ATACATTTGT ATATGATCCT GATCCACTAG CAGATTATGA GATTGCACAC CTAGATTATC TCTCCTACCA AGCTAAAATT GGAAGTACAG 13110      13120      13130      13140      13150      13160      13170      13180      13190      13200
   ATTACTACTC ACTCACTGAT AAAATTGACC TATTAGCACA TTTAACTGCA AAACAAATGA TAAACTCAAT AATTGGGTTA GATGAAACAG TATCAATTGT 13210      13220      13230      13240      13250      13260      13270      13280      13290      13300
   CAATGATGCG GTTATCCTAT CTGACTATAC TAATAACTGG ATTAGTGAAT GTTCTTATAC TAAGATAGAT TTAGTTTTTA AATTAATGGC ATGGAATTTC 13310      13320      13330      13340      13350      13360      13370      13380      13390      13400
   CTTCTTGAGC TTGCATTCCA GATGTACTAC TTAAGGATAT CATCTTGGAC AAATATATTT GACTATACTT ATATGACTTT ACGCAGGATA CCCGGAACTG 13410      13420      13430      13440      13450      13460      13470      13480      13490      13500
   CTCTAAATAA TATTGCAGCT ACTATTAGCC ATCCAAAATT ATTAAGACGT GCAATGAATC TTGATATTAT CACTCCTATA CATGCACCGT ATTTAGCTTC 13510      13520      13530      13540      13550      13560      13570      13580      13590      13600
   ATTAGATTAT GTCAAATTAA GTATTGATGC AATTCAGTGG GGAGTTAAAC AAGTTCTTGC TGATTTATCA AATGGAATTG ATCTTGAAAT CTTGATTCTT 13610      13620      13630      13640      13650      13660      13670      13680      13690      13700
   TCAGAGGATT CAATGGAAAT TAGTGATAGG GCAATGAATC TCATTGCTAG AAAACTAACT CTCCTTGCAC TTGTTAAAGG TGAGAACTAT ACTTTTCCAA 13710      13720      13730      13740      13750      13760      13770      13780      13790      13800
   AAATTAAAGG GATGCCACCA GAAGAAAAGT GTTTAGTCTT AACTGAATAT CTAGCAATGT GTTATCAAAA TACTCATCAC TTAGATCCAG ATCTTCAAAA 13810      13820      13830      13840      13850      13860      13870      13880      13890      13900
   GTATTTATAT AATCTAACTA ATCCAAAATT GACTGCATTT CCCAGTAACA ACTTCTACTT AACTAGAAAA ATCCTTAATC AAATTAGAGA ATCAGACGAA 13910      13920      13930      13940      13950      13960      13970      13980      13990      14000
   GGACAATATA TTATCACCTC ATATTATGAA TCCTTCGAAC AATTAGAAAC AGATATAATT CTTCACTCTA CTTTAACTGC TCCTTATGAT AATTCAGAAA 14010      14020      14030      14040      14050      14060      14070      14080      14090      14100
   CTCTAACAAA GTTCGATTTA TCCCTTGACA TCTTTCCACA TCCAGAATCT CTCGAGAAAT ATCCTCTTCC AGTTGATCAT GACTCTCGAT CTGCAATTTC 14110      14120      14130      14140      14150      14160      14170      14180      14190      14200
   AACACTAATT CCAGGCCCTC CTTCTCATCA TGTATTACGA CCACTAGGAG TGTCATCCAC AGCTTGGTAT AAAGGGATAA GTTATTGTAG ATACCTAGAA 14210      14220      14230      14240      14250      14260      14270      14280      14290      14300
   ACACAAAAGA TACAGACTGG TGATCATCTT TATTTAGCCG AAGGAAGCGG TGCTTCAATG TCACTTCTAG AACTCTTATT TCCAGGAGAT ACTGTCTATT 14310      14320      14330      14340      14350      14360      14370      14380      14390      14400
   ATAATAGTCT TTTTAGTAGT GGAGAGAATC CTCCACAGAG AAACTATGCC CCTCTTCCAA CTCAATTTGT ACAGAGTGTT CCATATAAAT TGTGGCAAGC 14410      14420      14430      14440      14450      14460      14470      14480      14490      14500
   TGATCTTGCT GATGATAGCA ATTTGATAAA AGATTTTGTC CCATTATGGA ATGGAAACGG TGCAGTTACA GACTTATCAA CAAAGGATGC AGTTGCATTC
```

FIGURE 11E

```
        14510      14520      14530      14540      14550      14560      14570      14580      14590      14600
   ATAATACATA AAGTAGGAGC AGAGAAAGCA TCCCTTGTCC ATATAGATCT CGAATCAACT GCTAATATAA ATCAGCAAAC TCTGTCCAGA TCCCAGATTC 14610      14620      14630      14640      14650      14660      14670      14680      14690      14700
   ATTCATTAAT TATAGCAACT ACTGTTCTTA AGAGGGGTGG GATATTAATT TATAAAACAT CATGGCTTCC GTTTTCTAGG TTTAGTCAAC TAGCAAGTCT 14710      14720      14730      14740      14750      14760      14770      14780      14790      14800
   ACTTTGGTGC TTCTTTGACC GGATCCATCT AATACGTAGT AGCTATTCTG ATCCTCACAG TCATGAGGTT TATCTTGTAT GTAGACTTGC CGCAGATTTT 14810      14820      14830      14840      14850      14860      14870      14880      14890      14900
   AGAACTATCG GTTTCAGTGC AGCTCTAGTA ACTGCTACTA CTCTTCACAA TGACGGATTC ACAACAATAC ATCCTGATGT TGTTTGTAGT TATTGGCAAC 14910      14920      14930      14940      14950      14960      14970      14980      14990      15000
   ACCATCTTGA AAATGTTGGG AGAGTCGGAA AAGTAATTGA TGAGATACTT GATGGTTTAG CCACCAACTT CTTCGCAGGA GATAATGGGC TTATTCTAAG 15010      15020      15030      15040      15050      15060      15070      15080      15090      15100
   ATGTGGAGGA ACTCCCAGCT CCAGAAAATG GTTAGAGATT GACCAGTTAG CATCATTTGA TTTGGTTCAA GATGCTCTGG TTACACTTAT CACTATACAC 15110      15120      15130      15140      15150      15160      15170      15180      15190      15200
   CTAAAGGAAA TTATAGAAGT GCAGTCATCA CATACAGAGG ATTATACATC TCTCCTCTTC ACACCTTATA ATATTGGTGC AGCAGGGAAA GTCAGAACTA 15210      15220      15230      15240      15250      15260      15270      15280      15290      15300
   TCATCAAATT AATTCTAGAA CGATCTTTAA TGTATACAGT CCGAAATTGG TTAGTTTTAC CCAGTTCCAT CCGGGATTCT GTACGACAAG ATTTAGAATT 15310      15320      15330      15340      15350      15360      15370      15380      15390      15400
   AGGGTCATTT AGATTAATGT CTATTTTAAG TGAACAGACA TTTCTTAAAA AGACACCCAC AAAAAAATAC TTACTTGATC AGCTTACAAG GACATATATA 15410      15420      15430      15440      15450      15460      15470      15480      15490      15500
   TCAACCTTCT TTAACTCTCA CTCAGTCCTT CCCCTCCACC GTCCATATCA AAAACAAATA TGGAAAGCCT TAGGTAGTGT AATATATTGT TCGGAGACAG 15510      15520      15530      15540      15550      15560      15570      15580      15590      15600
   TTGATATACC TCTAATTAAA GACATTCAGA TAGAAGATAT TAATGATTTT GAAGATATCG AGAGGGTAT CGATGGCGAA GAATTATGAC AACAATGATT 15610      15620      15630      15640      15650
   ATAAGAACTC ATGATAGTTT TATTTAAGAA AAACATATTG ATTTTCCCCT TGGT
```

FIGURE 11F

RECOVERY OF RECOMBINANT HUMAN PARAINFLUENZA VIRUS TYPE 2 (HPIV2) FROM CDNA AND USE OF RECOMBINANT HPIV2 IN IMMUNOGENIC COMPOSITIONS AND AS VECTORS TO ELICIT IMMUNE RESPONSES AGAINST PIV AND OTHER HUMAN PATHOGENS

BACKGROUND OF THE INVENTION

This application claims the benefit of U.S. Provisional Application No. 60/412,053, filed by Skiadopoulos et al. on Sep. 18, 2002, the disclosure of which is incorporated herein by reference.

BACKGROUND OF THE INVENTION

Human parainfluenza viruses (HPIVs) are important pathogens in human populations, causing severe lower respiratory tract infections in infants and young children. HPIV1 and HPIV2 are the principal etiologic agents of laryngotracheobronchitis (croup), and can also cause pneumonia and bronchiolitis (Chanock et al., Parainfluenza Viruses., p. 1341-1379, In D. M. Knipe, P. M. Howley, D. E. Griffin, R. A. Lamb, M. A. Martin, B. Roizman, and S. E. Straus (eds.) Fields Virology, 4th ed., Vol. 1, Lippincott Williams & Wilkins, Philadelphia, 2001). HPIV3 ranks second after respiratory syncytial virus (RSV) as a leading cause of hospitalization for viral lower respiratory tract disease in infants and young children (Collins et al., 3rd ed. In "Fields Virology," B. N. Fields, D. M. Knipe, P. M. Howley, R. M. Chanock, J. L. Melnick, T. P. Monath, B. Roizman, and S. E. Straus, Eds., Vol. 1, pp. 1205-1243. Lippincott-Raven Publishers, Philadelphia, 1996; Crowe et al., Vaccine 13:415-421, 1995; Marx et al., J. Infect. Dis. 176:1423-1427, 1997).

HPIVs are also important causes of respiratory tract disease in adults. Collectively, HPIV1, HPIV2, and HPIV3 have been identified through a 20 year study as responsible etiologic agents for approximately 18% of hospitalizations for pediatric respiratory tract disease (Murphy et al., Virus Res. 11:1-15, 1988). HPIVs have also been implicated in a significant proportion of cases of virally-induced middle ear effusions in children with otitis media (Heikkinen et al., N. Engl. J. Med. 340:260-4, 1999).

Despite considerable efforts to develop effective vaccines against HPIVs, no vaccines have yet been approved for any HPIV serotype, nor for ameliorating HPIV related illnesses. The most promising prospects to date are live attenuated vaccine viruses since these have been shown to be efficacious in non-human primates even in the presence of passively transferred antibodies, an experimental situation that simulates that present in the very young infant who possesses maternally acquired antibodies (Crowe et al., Vaccine 13:847-855, 1995; Durbin et al., J. Infect. Dis. 179:1345-1351, 1999). Two live attenuated HPIV3 vaccine candidates, a temperature-sensitive (ts) derivative of the wild type HPIV3 JS strain (designated HPIV3cp45) and a bovine PIV3 (BPIV3) strain, are undergoing clinical evaluation (Karron et al., Pediatr. Infect. Dis. J. 15:650-654, 1996; Karron et al., J. Infect. Dis. 171:1107-1114, 1995a; Karron et al., J. Infect. Dis. 172, 1445-1450, 1995b). The live attenuated PIV3cp45 vaccine candidate was derived from the JS strain of HPIV3 via serial passage in cell culture at low temperature and has been found to be protective against HPIV3 challenge in experimental animals and to be satisfactorily attenuated, genetically stable, and immunogenic in seronegative human infants and children (Belshe et al, J. Med. Virol. 10:235-242, 1982; Belshe et al., Infect. Immun. 37:160-5, 1982; Clements et al., J. Clin. Microbiol. 29:1175-82, 1991; Crookshanks et al., J. Med. Virol. 13:243-9, 1984; Hall et al., Virus Res. 22:173-184, 1992; Karron et al., J. Infect. Dis. 172:1445-1450, 1995b). Because these HPIV3 candidate vaccine viruses are biologically derived, there are no proven methods for adjusting the level of attenuation should this be found necessary from ongoing clinical trials.

To facilitate development of HPIV vaccines, recombinant DNA technology has recently made it possible to recover infectious negative-stranded RNA viruses from cDNA (for a review, see Conzelmann, J. Gen. Virol. 77:381-89, 1996). In this context, recombinant rescue of infectious virus has been reported for respiratory syncytial virus (RSV), rabies virus (RaV), canine distemper virus, mumps virus, infectious hematopoietic necrosis virus, simian virus 5 (SV5), rinderpest virus, Newcastle disease virus (NDV), vesicular stomatitis virus (VSV), measles virus (MeV), and Sendai virus (murine parainfluenza virus type 1 (MPIV1)) from cDNA-encoded genomic or antigenomic RNA in the presence of essential viral proteins (see, e.g., Garcin et al., EMBO J. 14:6087-6094, 1995; Lawson et al., Proc. Natl. Acad. Sci. U.S.A. 92:4477-81, 1995; Radecke et al., EMBO J. 14:5773-5784, 1995; Schnell et al., EMBO J. 13:4195-203, 1994; Whelan et al., Proc. Natl. Acad. Sci. U.S.A. 92:8388-92, 1995; Hoffman et al., J. Virol. 71:4272-4277, 1997; Kato et al., Genes to Cells 1:569-579, 1996, Roberts et al., Virology 247:1-6, 1998; Baron et al., J. Virol. 71:1265-1271, 1997; International Publication No. WO 97/06270; Collins et al., Proc. Natl. Acad. Sci. U.S.A. 92:11563-11567, 1995; Clarke et al., J. Virol. 74:4831-4838, 2000; Biacchesi et al., J. Virol. 74:11247-11253, 2000; Gassen et al., J. Virol. 74:10737-10744, 2000; U.S. patent application Ser. No. 08/892,403, filed Jul. 15, 1997 (corresponding to published International Application No. WO 98/02530 and priority U.S. Provisional Application Nos. 60/047,634, filed May 23, 1997, 60/046,141, filed May 9, 1997, and 60/021,773, filed Jul. 15, 1996); U.S. patent application Ser. No. 09/291,894, filed on Apr. 13, 1999; International Application No. PCT/US00/09695, filed Apr. 12, 2000 (which claims priority to U.S. Provisional Patent Application Ser. No. 60/129,006, filed Apr. 13, 1999); International Application No. PCT/US00/17755, filed Jun. 23, 2000 (which claims priority to U.S. Provisional Patent Application Ser. No. 60/143,132, filed by Buchholz et al. on Jul. 9, 1999); Juhasz et al., J. Virol. 71:5814-5819, 1997; He et al. Virology 237:249-260, 1997; Peters et al. J. Virol. 73:5001-5009, 1999; Baron et al. J. Virol. 71:1265-1271, 1997; Whitehead et al., Virology 247:232-9, 1998a; Whitehead et al., J. Virol. 72:4467-4471, 1998b; Jin et al. Virology 251:206-214, 1998; Buchholz et al. J. Virol. 73:251-259, 1999; and Whitehead et al., J. Virol. 73:3438-3442, 1999, each incorporated herein by reference in its entirety for all purposes).

Additional publications in the field of the invention report recovery of recombinant parainfluenza viruses (PIVs), specifically HPIV1, HPIV2, HPIV3, and BPIV3 (see, e.g., Durbin et al., Virology 235:323-332, 1997; Schmidt et al., J. Virol. 74:8922-8929, 2000; Kawano et al., Virology 284:99-112, 2001; U.S. patent application Ser. No. 09/083,793, filed May 22, 1998 (corresponding to U.S. Provisional Application No. 60/059,385, filed Sep. 19, 1997); U.S. Provisional Application No. 60/331,961, filed Nov. 21, 2001; and U.S. Provisional Application No. 60/047,575, filed May 23, 1997 (corresponding to International Publication No. WO 98/53078), each incorporated herein by reference). Some of these reports further address genetic manipulation of viral cDNA clones to determine the genetic basis of phenotypic changes in biological mutants, for example, which mutations in a biological mutant HPIV3 JS cp45 virus specify its ts, ca and att phenotypes, and which gene(s) or genome segment(s) of BPIV specify its attenuation phenotype. Additionally, certain of these reports and related publications discuss construction of novel PIV vaccine candidates having a wide range of different mutations, as well as methods for evaluating the level of attenuation, immunogenicity and phenotypic stability exhibited by such recombinant vaccine candidates (see also, U.S. application Ser. No. 09/586,479, filed Jun. 1, 2000 (corresponding to U.S. Provisional Patent Application Ser. No. 60/143,134, filed on Jul. 9, 1999); and U.S. patent application Ser. No. 09/350,821, filed by Durbin et al. on Jul. 9, 1999, each incorporated herein by reference).

Thus, infectious wild type recombinant PIVs, (r)PIVs, as well as a number of ts and otherwise modified derivatives, have now been recovered from cDNA. Reverse genetics systems have been used to generate infectious virus bearing defined mutations that specify attenuation and other desirable phenotypes, and to study the genetic basis of attenuation and other phenotypic changes in existing vaccine candidate viruses. For example, in HPIV3, the three amino acid substitutions found in the L gene of cp45, singularly or in combination, have been found to specify the ts and attenuation phenotypes. Additional ts and other attenuating mutations can be introduced in other regions of the HPIV3 genome.

In addition, a chimeric PIV1 vaccine candidate has been generated using the PIV3 cDNA rescue system by replacing the PIV3 HN and F open reading frames (ORFs) with those of PIV1 in a PIV3 full-length cDNA, that optionally contains selected attenuating mutations. Exemplary recombinant chimeric viruses derived from these cDNA-based methods include a HPIV3-1 recombinant bearing all three identified mutations in the L gene, rPIV3-1.cp45L (Skiadopoulos et al., *J. Virol.* 72:1762-8, 1998; Tao et al., *J. Virol.* 72:2955-2961, 1998; Tao et al., *Vaccine* 17:1100-1108, 1999, incorporated herein by reference). rHPIV3-1.cp45L was attenuated in hamsters and induced a high level of resistance to challenge with HPIV1. Yet another recombinant chimeric virus, designated rHPIV3-1cp45, has been produced that contains 12 of the 15 cp45 mutations, i.e., excluding the mutations that occur in HN and F. This recombinant vaccine candidate is highly attenuated in the upper and lower respiratory tract of hamsters and non-human primates and induces a high level of protection against HPIV1 infection (Skiadopoulos et al., *Vaccine* 18:503-510, 1999; Skiadopoulos et al., *Virology* 297:136-152, 2002, each incorporated herein by reference). However, for use against HPIV1, the infection and attendant immunogenicity of chimeric HPIV3-1 vaccine candidates against HPIV1 challenge is dampened in hosts that exhibit immune recognition of HPIV3.

Recently, a number of studies have focused on the possible use of viral vectors to express foreign antigens toward the goal of developing vaccines against a pathogen for which other vaccine alternatives have not yet proven successful. In this context, a number of reports suggest that foreign genes may be successfully inserted into a recombinant negative strand RNA virus genome or antigenome with varying effects (Bukreyev et al., *J. Virol.* 70:6634-41, 1996; Bukreyev et al., *Proc. Natl. Acad. Sci. U.S.A.* 96:2367-72, 1999; Finke et al. *J. Virol.* 71:7281-8, 1997; Hasan et al., *J. Gen. Virol.* 78:2813-20, 1997; He et al., *Virology* 237:249-60, 1997; Jin et al., *Virology* 251:206-14, 1998; Johnson et al., *J. Virol.* 71:5060-8, 1997; Kahn et al., *Virology* 254:81-91, 1999; Kretzschmar et al., *J. Virol.* 71:5982-9, 1997; Mebatsion et al., *Proc. Natl. Acad. Sci. U.S.A.* 93:7310-4, 1996; Moriya et al., *FEBS Lett.* 425:105-11, 1998; Roberts et al., *J. Virol.* 73:3723-32, 1999; Roberts et al., *J. Virol.* 72:4704-11, 1998; Roberts et al., *Virology* 247:1-6, 1998; Sakai et al., *FEBS Lett.* 456:221-226, 1999; Schnell et al., *Proc. Natl. Acad. Sci. U.S.A.* 93:11359-65, 1996a; Schnell et al., *J. Virol.* 70:2318-23, 1996b; Schnell et al., *Cell* 90:849-57, 1997; Singh et al., *J. Gen. Virol.* 80:101-6, 1999; Singh et al., *J. Virol.* 73:4823-8, 1999; Spielhofer et al., *J. Virol.* 72:2150-9, 1998; Yu et al., *Genes to Cells* 2:457-66 et al., 1999; Duprex et al., *J. Virol.* 74:7972-7979, 2000; Subash et al., *J. Virol.* 74:9039-9047, 2000; Krishnamurthy et al., *Virology* 278:168-182, 2000; Rose et al., *J. Virol.* 74:10903-10910, 2000; Tao et al., *J. Virol.* 74:6448-6458, 2000; McGettigan et al., *J. Virol.* 75:8724-8732, 2001; McGettigan et al., *J. Virol.* 75:4430-4434, 2001; Kahn et al., *J. Virol.* 75:11079-11087, 2001; Stope et al., *J. Virol.* 75:9367-9377, 2001; Huang et al., *J. Gen. Virol.* 82:1729-1736, 2001; Skiadopoulos et al., *J. Virol.* 75:10498-10504, 2001; Bukreyev et al., *J. Virol.* 75:12128-12140, 2001; U.S. patent application Ser. No. 09/614,285, filed Jul. 12, 2000 (corresponding to U.S. Provisional Patent Application Ser. No. 60/143,425, filed on Jul. 13, 1999), each incorporated herein by reference). When inserted into the viral genome under the control of viral transcription gene-start and gene-end signals, the foreign gene may be transcribed as a separate mRNA and yield significant protein expression. Surprisingly, in most cases the foreign sequence has been reported to be relatively stable and capable of expressing functional protein during numerous passages in vitro.

In order to successfully develop vectors for vaccine use, however, it is insufficient to simply demonstrate a high, stable level of protein expression. For example, this has been possible since the early-to-mid 1980s with recombinant vaccinia viruses and adenoviruses, and yet these vectors have proven to be disappointing tools for developing vaccines for human use. Similarly, most nonsegmented negative strand viruses that have been developed as vectors have not yet been shown to be amenable for human vaccine use. Examples in this context include vesicular stomatitis virus, an ungulate pathogen with no history of administration to humans except for a few laboratory accidents; Sendai virus, a mouse pathogen with no history of administration to humans; simian virus 5, a canine pathogen with no history of intentional administration to humans; and an attenuated strain of measles virus which must be administered systemically and would be neutralized by measles-specific antibodies present in nearly all humans due to maternal antibodies and widespread use of a licensed measles vaccine. Furthermore, some of these prior vector candidates have adverse effects, such as immunosuppression, which are directly inconsistent with their use as vectors. Thus, one must identify vectors whose growth characteristics, tropisms, and other biological properties make them appropriate as vectors for human use. It is further necessary to develop a viable immunization strategy, including efficacious timing and route of administration.

Proposed mononegaviruses for use as vaccine vectors include measles, mumps, VSV, and rabies viruses. However, measles virus has limitations relating to its potential use as a vaccine vector. For example, measles virus has been considered for use a vector for the protective antigen of hepatitis B virus (Singh et al., *J. Virol.* 73:4823-8, 1999). However, this combined measles virus-hepatitis B virus vaccine candidate could only be administered after nine months of age, on a schedule comparable to the indicated schedule for the licensed measles virus vaccine, whereas the current hepatitis B virus vaccine is recommended for use in early infancy. This is because the currently licensed measles vaccine is administered parenterally and is sensitive to neutralization and immunosuppression by maternal antibodies, and therefore is not effective if administered before 9-15 months of age. Thus, measles virus is a poor vector for antigens of pathogenic agents that cause disease in early infancy, such as RSV and the HPIVs.

The attenuated measles virus vaccine has been associated with altered immune responses and excess mortality when administered at increased dosages, which may be due at least in part to virus-induced immunosuppression that is a common feature of natural measles virus infection. This indicates that even an attenuated measles virus may not be suitable for vaccine vector use. Furthermore, the use of measles virus as a vector would be inconsistent with the global effort to eradicate this pathogen. Indeed, for these reasons it would be desirable to end the use of live measles virus and replace the present measles virus vaccine with a suitable non-measles vector that expresses measles virus protective antigens.

Rabies virus, a rare cause of infection of humans, has been considered for use as a vector (Mebatsion et al., *Proc. Natl. Acad. Sci. USA* 93:7310-4, 1996), but it is unlikely that a virus that is so highly fatal as rabies for humans could be developed for use as a live attenuated virus vector. Moreover, immunity to the rabies virus, which is not a ubiquitous human pathogen, is not needed for the general population. In addition, in some circumstances it may be desirable for the vector to be capable of eliciting a multispecific immune response against both the vector virus and the pathogen for which the vector is used as a carrier of antigenic determinants. While measles virus is less pathogenic than the rabies virus, infection by either of this vector candidate can yield undesirable results. Measles virus establishes a viremia with widespread infection and associated rash and the above-mentioned immunosuppression. Mild encephalitis during measles infection is not uncommon. Measles virus is also associated with a rare progressive fatal neurological disease called subacute sclerosing encephalitis.

In contrast to such vector candidates as rabies and measles, PIV infection and disease is typically more limited, in part by confinement of infection to the respiratory tract. Viremia and spread to secondary sites can occur in severely immunocompromised subjects, but this is not a typical effect of PIV infection. Acute respiratory tract disease is the only disease associated with PIVs. Thus, the use of PIVs as vectors will, on the basis of their biological characteristics, avoid complications such as interaction of virus with peripheral lymphocytes, leading to immunosuppression, or infection of secondary organs such as the testes or central nervous system, leading to other complications. These characteristics also render PIV a better vector candidate for successful immunization, which can be achieved more easily and effectively via alternate routes, such as direct administration to the respiratory tract, compared to immunization with vectors that require parental administration.

Among a host of human pathogens for which a vector-based vaccine approach may be desirable is the measles virus. A live attenuated vaccine has been available for more than three decades and has been largely successful in eradicating measles disease in the United States. However, the World Health Organization estimates that more than 45 million cases of measles still occur annually, particularly in developing countries, and the virus contributes to approximately one million deaths per year. One reason for the persistence of this disease is the inefficacy of current vaccine formulations to overcome maternal antibodies that inactivate the current vaccine.

Measles virus is a member of the *Morbillivirus* genus of the Paramyxoviridae family (Griffin et al., In *"Fields Virology"*, B. N. Fields, D. M. Knipe, P. M. Howley, R. M. Chanock, J. L. Melnick, T. P. Monath, B. Roizman, and S. E. Straus, Eds., Vol. 1, pp. 1267-1312. Lippincott-Raven Publishers, Philadelphia, 1996). It is one of the most contagious infectious agents known to man and is transmitted from person to person via the respiratory route (Griffin et al., In *"Fields Virology"*, B. N. Fields, D. M. Knipe, P. M. Howley, R. M. Chanock, J. L. Melnick, T. P. Monath, B. Roizman, and S. E. Straus, Eds., Vol. 1, pp. 1267-1312. Lippincott-Raven Publishers, Philadelphia, 1996). The measles virus has a complex pathogenesis, involving replication in both the respiratory tract and various systemic sites (Griffin et al., In *"Fields Virology"*, B. N. Fields, D. M. Knipe, P. M. Howley, R. M. Chanock, J. L. Melnick, T. P. Monath, B. Roizman, and S. E. Straus, Eds., Vol. 1, pp. 1267-1312. Lippincott-Raven Publishers, Philadelphia, 1996). Measles virus is discussed here as an exemplary pathogen for which a live attenuated vector vaccine is particularly desired. For reasons discussed in further detail herein below, a measles vaccine based on a recombinant HPIV2 vector system would satisfy a long-felt need in the art and fulfill an urgent need for additional effective vector systems to generate vaccines against other pathogens as well.

Although both mucosal IgA and serum IgG measles virus-specific antibodies can participate in the control of measles virus, the absence of measles virus disease in very young infants possessing maternally-acquired measles virus-specific antibodies identifies serum antibodies as a major mediator of resistance to disease (Griffin et al., In *"Fields Virology"*, B. N. Fields, D. M. Knipe, P. M. Howley, R. M. Chanock, J. L. Melnick, T. P. Monath, B. Roizman, and S. E. Straus, Eds., Vol. 1, pp. 1267-1312. Lippincott-Raven Publishers, Philadelphia, 1996). The two measles virus glycoproteins, the hemagglutinin (HA) and fusion (F) proteins, are the major neutralization and protective antigens (Griffin et al., In *"Fields Virology"*, B. N. Fields, D. M. Knipe, P. M. Howley, R. M. Chanock, J. L. Melnick, T. P. Monath, B. Roizman, and S. E. Straus, Eds., Vol. 1, pp. 1267-1312. Lippincott-Raven Publishers, Philadelphia, 1996).

The currently available live attenuated measles vaccine is administered by a parenteral route (Griffin et al., In *"Fields Virology"*, B. N. Fields, D. M. Knipe, P. M. Howley, R. M. Chanock, J. L. Melnick, T. P. Monath, B. Roizman, and S. E. Straus, Eds., Vol. 1, pp. 1267-1312. Lippincott-Raven Publishers, Philadelphia, 1996). Both the wild type measles virus and the vaccine virus are very readily neutralized by antibodies, and the measles virus vaccine is rendered non-infectious by even very low levels of maternally-acquired measles virus-specific neutralizing antibodies (Halsey et al., *N. Engl. J. Med.* 313:544-9, 1985; Osterhaus et al., *Vaccine* 16:1479-81, 1998). Thus, the vaccine virus is not given until the passively-acquired maternal antibodies have decreased to undetectable levels. In the United States, measles virus vaccine is not given until 12 to 15 months of age, a time when almost all children are readily infected with the measles virus vaccine.

Recent developments in the field of negative stranded RNA viral vaccines have involved the use of HPIV3-based vaccine vectors to deliver antigenic determinants of heterologous pathogens, including heterologous HPIVs. In particular, recombinant HPIV3 vaccine candidates have been disclosed that use a HPIV3 "vector" genome or antigenome combined with one or more heterologous genes of a different HPIV, or of a non-PIV pathogen to form a chimeric, bivalent or multivalent, HPIV3-based vaccine candidate (see, e.g., Durbin et al., *Virology* 235:323-332, 1997; Skiadopoulos et al., *J. Virol.* 72:1762-1768, 1998; Skiadopoulos et al., *J. Virol.* 73:1374-1381, 1999; Tao et al., *Vaccine* 19:3620-3631, 2001; Durbin et al., *J. Virol.* 74:6821-6831, 2000; U.S. patent application Ser. No. 09/083,793, filed May 22, 1998; U.S. patent application Ser. No. 09/458,813, filed Dec. 10, 1999; U.S. patent application Ser. No. 09/459,062, filed Dec. 10, 1999; U.S. Provisional Application No. 60/047,575, filed May 23, 1997 (corresponding to International Publication No. WO 98/53078), U.S. Provisional Application No. 60/059,385, filed Sep. 19, 1997; U.S. Provisional Application No. 60/170, 195 filed Dec. 10, 1999; U.S. patent application Ser. No. 09/733,692, filed Dec. 8, 2000 (corresponding to International Publication No. WO 01/42445A2), each incorporated herein by reference. The recombinant chimeric HPIV3 viruses are engineered to incorporate one or more heterologous donor sequences, typically supernumerary sequences, encoding one or more antigenic determinants of a different PIV or heterologous pathogen to produce an infectious, chimeric, bivalent or multivalent virus or subviral particle. In this manner, candidate HPIV3-based chimeric vaccine viruses can be made to elicit an immune response against one or more PIVs or a polyspecific response against a selected PIV and a non-PIV pathogen in a mammalian host susceptible to infection therefrom. Various modifications to chimeric HPIV3 vaccine candidates were reported to yield desired phenotypic effects, such as attenuation. Comparable disclosure has been provided for recombinant and chimeric recombinant HPIV1 vaccine candidates (see, U.S. Provisional Application No. 60/331,961, filed Nov. 21, 2001, incorporated herein by reference).

Although there have been numerous advances toward development of effective immunogenic compositions against HPIVs and other pathogens, including RSV and measles virus, there remains a clear need in the art for additional tools and methods to engineer safe and effective immunogenic compositions to alleviate the serious health problems attributable to these pathogens, particularly among young infants. Among the remaining challenges in this context is the need for additional tools to generate suitably attenuated, immunogenic and genetically candidates for use in diverse clinical settings against one or more pathogens. Additional challenges arise from the fact that HPIV1, HPIV2, and HPIV3 represent distinct viral serotypes, that do not elicit significant cross-immunity. Accordingly, there is an urgent need in the art for an effective immunogenic compositions to immunize against multiple HPIV serotypes. To facilitate these goals, existing methods for identifying and incorporating attenuating mutations into recombinant strains and for developing vector-based immunogenic compositions and methods must be expanded. In this context, it is particularly desirable to develop a method for recovery and genetic manipulation of HPIV2, to generate immunogenic compositions against this important human PIV, and to provide additional tools to generate novel vectors and immunization methods. Surprisingly, the present invention satisfies these needs and fulfills additional objects and advantages as described herein below.

SUMMARY OF THE INVENTION

The instant invention provides methods and compositions for recovering infectious, recombinant human parainfluenza virus type 2 (HPIV2). The invention also provides novel tools and methods for introducing defined, predetermined structural and phenotypic changes into an infectious HPIV2 candidate for use in immunogenic compositions and methods.

In one embodiment of the invention, methods are provided for producing an infectious, self-replicating, recombinant human parainfluenza virus type 2 (HPIV2) from one or more isolated polynucleotide molecules encoding the virus. The methods generally involve coexpressing in a cell or cell-free system one or more expression vector(s) comprising a polynucleotide molecule that encodes a partial or complete, recombinant HPIV2 genome or antigenome and one or more polynucleotide molecules encoding PIV N, P and L proteins, so as to produce an infectious HPIV2 particle.

Typically, the polynucleotide molecule that encodes the recombinant HPIV2 genome or antigenome is a cDNA. Thus, the invention is directed in more detailed aspects to such novel polynucleotides and their equivalents that encode a recombinant HPIV2, as disclosed herein. Likewise, the invention embraces expression vectors and constructs that incorporate a polynucleotide molecule encoding a recombinant HPIV2 genome or antigenome.

The HPIV2 genome or antigenome, and the N, P, and L proteins may all be produced from a single expression vector. More typically, the genome or antigenome is produced by a separate expression vector, and the N, P, and L proteins are produced by one, two, or three additional expression vector(s). In certain embodiments, one or more of the N, P and L proteins is supplied by expression of a recombinant HPIV genome or antigenome of the invention, or by coinfection with the same or different PIV. In alternate embodiments, one or more of the N, P and L proteins are from a heterologous PIV (e.g., HPIV1 or HPIV3).

The invention further embraces infectious, recombinant, self-replicating viral particles produced according to the foregoing methods, which particles include complete viruses as well as viruses that lack one or more non-essential protein(s) or non-essential portion(s) (e.g., a cytoplasmic, transmembrane or extracellular domain) of a viral protein. Viruses of the invention that lack one or more such non-essential component (e.g., a gene or genome segment from the PIV V open reading frame (ORF) or an intergenic or other non-coding or non-essential genome component) are referred to herein as incomplete viruses or "subviral particles." Exemplary subviral particles may lack any selected structural element, e.g., a gene, gene segment, protein, protein functional domain, etc. that is present in a complete virus (i.e., an assembled virion including a complete genome or antigenome, nucleocapsid and envelope). For example, a subviral particle of the invention may comprise an infectious nucleocapsid containing a genome or antigenome, and the products of N, P, and L genes. Other subviral particles are produced by partial or complete deletions or substitutions of non-essential genes and/or their products among other non-essential structural elements.

Complete viruses and subviral particles produced according to the methods of the invention are typically infectious and self-replicative through multiple rounds of replication in a mammalian host amenable to infection by PIV, including various in vitro mammalian cell populations, in vivo animal models widely known and accepted in the art as reasonably predictive of PIV activity in humans (including, mice, hamsters, cotton rats, non-human primates including African green monkeys and chimpanzees), and humans, including seronegative and seropositive infants, children, juveniles, and adults. However, viruses and subviral particles also can be designated that are highly defective for replication in vivo.

In certain detailed aspects of the invention, the polynucleotide molecule encoding the recombinant HPIV2 genome or antigenome encodes a sequence of a wild-type HPIV2. Alternatively, the genome or antigenome may bear one or more mutations from a biologically derived mutant HPIV2, or any combination of recombinantly-introduced mutation(s); including one or more polynucleotide insertions, deletions, substitutions, or rearrangements that is/are selected to yield desired phenotypic effect(s) in the recombinant virus.

Thus, the recombinant HPIV2 genome or antigenome may be engineered according to the methods of the invention to incorporate a recombinantly-introduced restriction site marker, or a translationally silent point mutation for handling or marking purposes. In other embodiments, the polynucleotide molecule encoding the recombinant HPIV2 genome or antigenome may incorporate one or more recombinantly-introduced attenuating mutations. In exemplary embodiments, the recombinant HPIV2 genome or antigenome incorporates one or more recombinantly-introduced, temperature sensitive (ts) or host range (hr) attenuating (att) mutations.

Often, the recombinant HPIV2 genome or antigenome will incorporate one or more attenuating mutation(s) identified in a heterologous mutant HPIV strain (such as HPIV1 or HPIV3), or in another mutant nonsegmented negative stranded RNA virus, for example RSV or murine PIV1 (MPIV1). For example, the recombinant HPIV2 genome or antigenome can be modified or constructed to incorporate one or more mutation(s) corresponding to mutation(s) identified in a HPIV2, or a heterologous PIV such as the well known candidate HPIV3 JS cp45. Useful mutations of HPIV3 JS cp45 or another mutant virus can specify a change in a HPIV2 protein selected from L, M, N, F, or HN or in a HPIV2 extragenic sequence selected from a 3' leader or N gene start sequence. Where the mutation relates to a particular amino acid residue, the recombinant HPIV2 genome or antigenome will often incorporate multiple nucleotide changes in a codon specifying the mutation to stabilize the modification against reversion.

In additional aspects of the invention, the recombinant HPIV2 genome or antigenome comprises an additional nucleotide modification specifying a phenotypic change selected from a change in growth characteristics, attenuation, temperature-sensitivity, cold-adaptation, plaque size, host-range restriction, or a change in immunogenicity. These additional modifications can alter one or more of the HPIV2 N, V, P, M, F, HN and/or L genes and/or a 3' leader, 5' trailer, a cis-acting sequence such as a gene start (GS) or gene end (GE) sequence, and/or intergenic region within the HPIV2 genome or antigenome. For example, one or more HPIV2 gene(s) can be deleted in whole or in part, or expression of the gene(s) can be reduced, ablated, or increased by a mutation in an RNA editing site, by a frameshift mutation, by a mutation that alters a translation start site, by introduction of one or more stop codons in an open reading frame (ORF) of the gene, or by a mutation in a transcription signal. In specific embodiments, the recombinant HPIV2 genome or antigenome is modified by a partial or complete deletion of the HPIV2 V gene, or one or more nucleotide change(s) that reduces or ablates expression of one or more HPIV2 genes yet yields a viable, replication competent, infectious viral construct. In other embodiments, the recombinant HPIV2 genome or antigenome is modified to encode a non-PIV molecule selected from a cytokine, a T-helper epitope, a restriction site marker, or a protein of a microbial pathogen capable of eliciting an immune response in a mammalian host.

In yet additional aspects of the invention, the recombinant HPIV2 genome or antigenome comprises a partial or complete HPIV2 "vector" genome or antigenome that is combined with one or more heterologous gene(s) or genome segment(s) encoding one or more antigenic determinant(s) of one or more heterologous pathogen(s) to form a chimeric HPIV2 genome or antigenome. The heterologous gene(s) or genome segment(s) encoding the antigenic determinant(s) can be added as supernumerary gene(s) or genome segment(s) adjacent to or within a noncoding region of the partial or complete HPIV2 vector genome or antigenome, or can be substituted for one or more counterpart gene(s) or genome segment(s) in a partial HPIV2 vector genome or antigenome. The heterologous gene(s) or genome segment(s) can include one or more heterologous coding sequences and/or one or more heterologous regulatory element(s) comprising an extragenic 3' leader or 5' trailer region, a gene-start signal, gene-end signal, editing region, intergenic region, or a 3' or 5' non-coding region.

In more detailed embodiments, the heterologous pathogen is one or more heterologous PIV(s) (e.g., HPIV1 and/or HPIV3) and the heterologous gene(s) or genome segment(s) encode(s) one or more PIV N, P, V, M, F, RN and/or L protein(s) or fragment(s) thereof. Thus, the antigenic determinant(s) may be selected from HPIV1 and HPIV3 HN and F glycoproteins, and antigenic domains, fragments and epitopes thereof, that is/are added to or substituted within the partial or complete HPIV2 genome or antigenome. In certain exemplary embodiments, genes encoding UN and F glycoproteins of HPIV3 or HPIV1 are substituted for counterpart HPIV2 UN and F genes in a partial HPIV2 vector genome or antigenome. In more detailed embodiments, the partial or complete HPIV2 genome or antigenome is modified to incorporate one or more gene(s) or genome segment(s) encoding one or more antigenic determinant(s) of HPIV1, and one or more gene(s) or genome segment(s) encoding one or more antigenic determinant(s) of HPIV3, to yield a chimeric HPIV2 capable of eliciting an immune response against HPIV1 and HPIV3 in a mammalian host. In this manner, a plurality of heterologous genes or genome segments encoding antigenic determinants of multiple heterologous PIVs can be added to or incorporated within the partial or complete HPIV vector genome or antigenome.

In related embodiments of the invention, chimeric HPIV2 viruses are provided wherein the vector genome is combined with one or more heterologous antigenic determinant(s) of a heterologous pathogen selected from measles virus, subgroup A and subgroup B respiratory syncytial viruses, mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses, human metapneumoviruses, and influenza viruses. In exemplary aspects, the heterologous antigenic determinant(s) is/are selected from measles virus HA and F proteins, subgroup A or subgroup B respiratory syncytial virus F, G, SH and M2 proteins, mumps virus HN and F proteins, human papilloma virus L1 protein, type 1 or type 2 human immunodeficiency virus gp160 protein, herpes simplex virus and cytomegalovirus gB, gC, gD, gE, gG, gH, gI, gJ, gK, gL, and gM proteins, rabies virus G protein, Epstein Barr Virus gp350 protein, filovirus G protein, bunyavirus G protein, flavivirus pre M, E, and NS1 proteins, human metapneuomovirus (HMPV) G and F protein, and alphavirus E protein, and antigenic domains, fragments and epitopes thereof. In certain specific embodiments, the heterologous pathogen is measles virus and the heterologous antigenic determinant(s) is/are selected from the measles virus HA and F proteins and antigenic domains, fragments and epitopes thereof. For example, a transcription unit comprising an open reading frame (ORF) of a measles virus HA gene can be added to or incorporated within a HPIV2 vector genome or antigenome to yield a chimeric candidate useful to immunize against measles and/or HPIV2 or another HPIV.

In additional embodiments, the partial or complete HPIV2 vector genome or antigenome is modified to incorporate one or more supernumerary heterologous gene(s) or genome segment(s) to form the chimeric HPIV2 genome or antigenome. Typically, the supernumerary gene(s) or genome segments(s) encode(s) one or more heterologous antigenic determinant(s), although non-coding inserts are also useful within recombinant, chimeric HPIV2 of the invention. In exemplary embodiments, one or more supernumerary heterologous gene(s) or genome segment(s) may be selected from HPIV1 HN, HPIV2 F, HPIV3 HN, HPIV3 F, measles HA and F, HMPV G and F proteins, and/or RSV subgroup A or B G and F proteins. These and other supernumerary heterologous gene(s) or genome segment(s) can be inserted at various sites within the recombinant genome or antigenome, for example at a position 3' to N, between the N/P, P/M, and/or HN/L genes, or at another intergenic junction or non-coding region of the HPIV2 vector genome or antigenome.

In more detailed embodiments, the chimeric HPIV2 genome or antigenome is engineered to encode antigens from one, two, three or four pathogens. For example, the genome or antigenome may encode antigenic determinants from one, two, three, four, or more different pathogens selected from a HPIV1, HPIV2, HPIV3, measles virus, respiratory syncytial virus, mumps virus, human papilloma virus, type 1 or type 2 human immunodeficiency virus, herpes simplex virus, cytomegalovirus, rabies virus, Epstein Barr Virus, filovirus, bunyavirus, flavivirus, alphavirus, human metapneumovirus, or influenza virus.

Where a gene or genome segment is added to or substituted within a recombinant HPIV2 genome or antigenome of the invention, it may be added or substituted at a position corresponding to a wild-type gene order position of a counterpart gene or genome segment within the partial or complete HPIV2 genome or antigenome, which is often the case when chimeric HPIV2 are generated by addition or substitution of a heterologous gene or genome segment into a partial or complete HPIV2 vector genome or antigenome. Alternatively, the added or substituted (e.g., heterologous) gene or genome segment can be located at a position that is more promoter-proximal or promoter-distal compared to a wild-type gene order position of a counterpart gene or genome segment within the partial or complete HPIV2 background genome or antigenome.

In additional aspects of the invention, chimeric HPIV2 candidates are provided wherein the HPIV2 vector genome or antigenome is modified to encode a chimeric glycoprotein incorporating one or more heterologous antigenic domains, fragments, or epitopes of a heterologous PIV, or of a non-PIV pathogen to form a chimeric genome or antigenome. In certain embodiments, the HPIV2 vector genome or antigenome is modified to encode a chimeric glycoprotein incorporating one or more antigenic domains, fragments, or epitopes from a second, antigenically distinct PIV to form the chimeric genome or antigenome. Additional embodiments include a chimeric HPIV2 wherein the genome or antigenome encodes a chimeric glycoprotein having antigenic domains, fragments, or epitopes from two or more HPIVs. In one example, the heterologous genome segment encodes a glycoprotein cytoplasmic, transmembrane or ectodomain which is substituted for a corresponding glycoprotein domain in the HPIV2 vector genome or antigenome. In more specific embodiments, one or more heterologous genome segment(s) of a second, antigenically distinct HPIV encoding one or more antigenic domains, fragments, or epitopes is/are substituted within a HPIV2 vector genome or antigenome to encode said chimeric glycoprotein. For example, the one or more heterologous genome segment(s) can be selected from ectodomains of HPIV1 and/or HPIV3 HN and/or F glycoproteins.

The chimeric HPIV2 candidates of the invention will typically be modified as described above for non-chimeric HPIV2 recombinants, e.g., by introduction of one or more attenuating mutations identified in a heterologous mutant PIV or other mutant nonsegmented negative stranded RNA virus. Thus, the HPIV2 genome or antigenome, or the chimeric HPIV2 genome or antigenome, can be modified to incorporate one or more point mutation(s), for example point mutations in one or more non-coding nucleotides or point mutations specifying an amino acid substitution, deletion or insertion, such as are identified in HPIV3 JS cp45.

In more detailed embodiments, the genome or antigenome of a chimeric or non-chimeric HPIV2 is modified to incorporate one or any combination of mutation(s) selected from mutations specifying previously identified amino acid substitution(s) in the L protein at a position corresponding to Tyr942, Leu992, and Thr1558 of HPIV3 JS cp45. Corresponding targets of wild-type (wt) HPIV2 L for incorporation of these exemplary mutations are Tyr948, Ala998, and Leu1566. In other embodiments, the recombinant HPIV2 genome or antigenome is modified to incorporate an attenuating mutation at an amino acid position corresponding to an amino acid position of an attenuating mutation identified in a heterologous, mutant nonsegmented negative stranded RNA virus, for example, respiratory syncytial virus (RSV).

In yet additional detailed embodiments, the recombinant HPIV2 genome or antigenome is further modified to incorporate an additional nucleotide modification specifying a phenotypic change selected from the following: a change in growth characteristics, attenuation, temperature-sensitivity, cold-adaptation, plaque size, host-range restriction, or immunogenicity. Such additional nucleotide modifications can alter one or more ORFs, including but not limited to the HPIV1 N, P, V, M, F, HN and/or L ORFs and/or a 3' leader, 5' trailer, and/or intergenic region within the HPIV2 genome or antigenome. In exemplary embodiments, the chimeric HPIV2 genome or antigenome is further modified such that one or more HPIV2 gene(s) is/are deleted in whole or in part or expression of the gene(s) is reduced, ablated, or increased by a mutation in an RNA editing site, by a frameshift mutation, by a mutation that alters a translation start site, by introduction of one or more stop codons in an open reading frame (ORF) of the gene, or by a mutation in a transcription signal. Often, the chimeric HPIV2 genome or antigenome will be engineered to incorporate a partial or complete deletion of the PIV V ORF or another non-essential gene or genome segment, or one or more nucleotide change(s) that reduces, ablates, or increases expression of one or more PIV genes. In other aspects, the chimeric HPIV2 genome or antigenome is modified to encode a non-PIV molecule selected from a cytokine, a T-helper epitope, a restriction site marker, or a protein of a microbial pathogen capable of eliciting an immune response in a mammalian host.

In still other aspects of the invention, the recombinant HPIV2 genome or antigenome is recombinantly modified to form a chimeric HPIV2 genome or antigenome incorporating one or more heterologous genes or genome segments from a non-human (e.g., bovine or SV5) PIV, to yield a human-non-human chimeric candidate having novel phenotypic properties, e.g., increased genetic stability, or altered attenuation, reactogenicity or growth in culture. Such recombinants may be produced by constructing a partial or complete HPIV2 vector genome or antigenome combined with one or more heterologous genes or genome segments from a non-human PIV. For example, the partial or complete HPIV2 vector genome or antigenome can be combined with one or more heterologous gene(s) or genome segment(s) of a N, P, L, V, or M gene of a BPIV3 to form a human-bovine chimeric genome or antigenome and produce novel candidates having a host-range (hr) attenuation phenotype. In more detailed embodiments, a bovine PIV type 3 (BPIV3) N, M, L, V, or P open reading frame (ORF) or a genome segment thereof is substituted for a counterpart HPIV2 N, M, L, V, or P ORF or genome segment to form the chimeric HPIV2-BPIV genome or antigenome. Alternatively, the PIV from which the heterologous gene(s) or genome segment(s) are donated to form the chimeric virus can be murine parainfluenza virus (MPIV), simian virus 5 (SV5), SV41, Newcastle disease virus (NDV), or other animal PIV.

In further aspects of the invention, the recombinant HPIV2 genome or antigenome incorporates a polynucleotide insertion of between 150 nucleotides (nts) and 4,000 nucleotides in length in a non-coding region (NCR) of the genome or antigenome or as a separate gene unit (GU). The recombinant HPIV2 candidates comprising NCR and GU inserts replicate efficiently in vitro and typically exhibit an attenuated phenotype in vivo. The polynucleotide insertion will typically lack a complete open reading frame (ORF) and will often specify an attenuated phenotype in the recombinant HPIV2. The polynucleotide insert can be introduced into the HPIV2 genome or antigenome in a reverse, non-sense orientation whereby the insert does not encode protein. In more specific embodiments, the polynucleotide insert is approximately 2,000 nts, 3,000 nts, or greater in length. In other embodiments, the polynucleotide insertion adds a total length of foreign sequence to the recombinant HPIV2 genome or antigenome of 30% to 50% or greater compared to the wild-type HPIV2 genome length of approximately 15,600 nt (e.g., 15,654 nt). In more detailed aspects, the polynucleotide insertion specifies an attenuation phenotype of the recombinant HPIV2 which exhibits at least a 10- to 100-fold decrease in replication in the upper and/or lower respiratory tract.

In other embodiments of the invention polynucleotide molecules that encode, or correspond, to a recombinant HPIV2 or chimeric HPIV2 genome or antigenome as described above are provided. In additional embodiments, polynucleotide expression vectors or constructs comprising a polynucleotide encoding a recombinant HPIV2 or chimeric HPIV2 genome or antigenome as described above and operably connected to expression regulatory sequences (e.g., promotor and terminator sequences) to direct expression of the vector in suitable host cell or cell-free expression system. In yet additional embodiments, a cell or cell-free expression system (e.g., a cell-free lysate) is provided which incorporates an expression vector comprising an isolated polynucleotide molecule encoding a recombinant HPIV2 genome or antigenome, as described above, and optionally including an expression vector comprising one or more isolated polynucleotide molecules encoding N, P, and L proteins of a PIV. One or more of the N, P, and L proteins may be expressed from HPIV2 or from a heterologous PIV. Upon expression, the genome or antigenome and N, P, and L proteins combine to produce an infectious HPIV particle, such as a viral or subviral particle. The isolated polynucleotide molecules encoding the HPIV2 genome or antigenome and the one or more isolated polynucleotide molecules encoding N, P, and L proteins of PIV can be expressed by a single vector. Alternatively, the genome and one or more of the N, P, and L proteins can be incorporated into two or more separate vectors.

The recombinant HPIV2 viruses of the invention are useful in various compositions to generate a desired immune response against one or more PIVs, or against PIV and one or more non-PIV pathogen(s), in a host susceptible to infection therefrom. Recombinant HPIV2 as disclosed herein are capable of eliciting a mono- or poly-specific immune response in an infected mammalian host, yet are sufficiently attenuated so as to not cause unacceptable symptoms of disease in the immunized host. The attenuated viruses, including subviral particles, may be present in a cell culture supernatant, isolated from the culture, or partially or completely purified. The virus may also be lyophilized, and can be combined with a variety of other components for storage or delivery to a host, as desired.

The invention further provides novel immunogenic compositions comprising a physiologically acceptable carrier and/or adjuvant and an isolated attenuated recombinant HPIV2 virus as described above. In preferred embodiments, the immunogenic composition is comprised of a recombinant HPIV2 having at least one, and preferably two or more attenuating mutations or other nucleotide modifications that specify a suitable balance of attenuation and immunogenicity, and optionally additional phenotypic characteristics. The immunogenic composition can be formulated in a dose of $10^3$ to $10^7$ PFU of attenuated virus. The immunogenic composition may comprise attenuated recombinant HPIV2 that elicits an immune response against a single PIV strain or against multiple PIV strains or serotypes or other pathogens such as RSV and/or HMPV. In this regard, recombinant HPIV2 can be combined in formulations with other PIV strains, or with other candidate viruses such as a live attenuated RSV.

In related aspects, the invention provides a method for stimulating the immune system of an individual to elicit an immune response against one or more PIVs, or against PIV and a non-PIV pathogen, in a mammalian subject. The method comprises administering a formulation of an immunologically sufficient amount a recombinant HPIV2 in a physiologically acceptable carrier and/or adjuvant. In one embodiment, the immunogenic composition is comprised of a recombinant HPIV2 having at least one, and preferably two or more attenuating mutations or other nucleotide modifications specifying a desired phenotype and/or level of attenuation as described above. The immunogenic composition can be formulated in a dose of $10^3$ to $10^7$ PFU of attenuated virus. The immunogenic composition may comprise a recombinant HPIV2 that elicits an immune response against a single PIV, against multiple PIVs, e.g., HPIV2 and HPIV3, or against one or more PIV(s) and a non-PIV pathogen such as measles or RSV.

In this context, recombinant HPIV2 viruses of the invention can elicit a monospecific immune response or a polyspecific immune response against multiple PIVs, or against one or more PIV(s) and a non-PIV pathogen. Alternatively, recombinant HPIV2 having different immunogenic characteristics can be combined in a mixture or administered separately in a coordinated treatment protocol to elicit more effective immune response against one PIV, against multiple PIVs, or against one or more PIV(s) and a non-PIV pathogen such as measles or RSV. Typically, the immunogenic compositions of the invention are administered to the upper respiratory tract, e.g., by spray, droplet or aerosol.

In other aspects of the invention, novel recombinant HPIV1 viruses and related compositions and methods are also provided. These HPIV1 recombinant viruses are useful in combination with the HPIV2 compositions and methods described herein, and provide additional exemplary mutations and other modifications for incorporation into recombinant HPIV1 and HPIV2 for use within immunogenic compositions and methods. As in the case of HPIV2, these embodiments of the invention are based on production of an infectious, self-replicating, recombinant human parainfluenza virus type 1 (HPIV1) from one or more isolated polynucleotide molecules encoding the virus. Foundational aspects of these embodiments are described, for example, in U.S. patent application Ser. No. 10/302,547, filed by Murphy et al. on Nov. 21, 2002 and in the corresponding PCT Publication Number WO 03/043587 A2, published on May 30, 2003 (each incorporated herein by reference).

In certain embodiments, the polynucleotide molecule encoding the recombinant HPIV1 genome or antigenome bears one or more mutations from a biologically derived mutant HPIV1, or any combination of recombinantly-introduced mutation(s); including one or more polynucleotide insertions, deletions, substitutions, or rearrangements that is/are selected to yield desired phenotypic effect(s) in the recombinant virus. In exemplary embodiments, the recombinant HPIV1 genome or antigenome incorporates one or more recombinantly-introduced, temperature sensitive (ts) or host range (hr) attenuating (att) mutations. Often, the recombinant HPIV1 genome or antigenome will incorporate one or more attenuating mutation(s) identified in a biologically derived mutant PIV strain, or in another mutant nonsegmented negative stranded RNA virus, for example RSV or murine PIV (MPIV). For example, the recombinant HPIV1 genome or antigenome can be modified or constructed to incorporate one or more mutation(s) corresponding to mutation(s) identified in a HPIV1, or a heterologous PIV such as the well known immunogenic composition candidate HPIV3 JS cp45. Useful mutations of HPIV3 JS cp45 or another mutant virus can specify a change in a HPIV1 protein selected from L, M, N, C, F, or HN or in a HPIV1 extragenic sequence selected from a 3' leader or N gene start sequence. Where the mutation relates to a particular amino acid residue, the recombinant HPIV1 genome or antigenome will often incorporate multiple nucleotide changes in a codon specifying the mutation to stabilize the modification against reversion.

In additional aspects of the invention, the recombinant HPIV1 genome or antigenome comprises an additional nucleotide modification specifying a phenotypic change selected from a change in growth characteristics, attenuation, temperature-sensitivity, cold-adaptation, plaque size, host-range restriction, or a change in immunogenicity. These additional modifications can alter one or more of the HPIV1 N, P, C, C', Y1, Y2, M, F, HN and/or L genes and/or a 3' leader, 5' trailer, a cis-acting sequence such as a gene start (GS) or gene end (GE) sequence, and/or intergenic region within the HPIV1 genome or antigenome. For example, one or more HPIV1 gene(s) can be deleted in whole or in part, or expression of the gene(s) can be reduced or ablated by a mutation in an RNA editing site, by a frameshift mutation, by a mutation that alters a translation start site, by introduction of one or more stop codons in an open reading frame (ORF) of the gene, or by a mutation in a transcription signal. In specific embodiments, the recombinant HPIV1 genome or antigenome is modified by a partial or complete deletion of one or more C, C', Y1, and/or Y2 ORF(s) or other auxiliary gene, or one or more nucleotide change(s) that reduces or ablates expression of one or more of the C, C', Y1, and/or Y2 ORF(s) or other auxiliary gene. In other embodiments, the recombinant HPIV1 genome or antigenome is modified to encode a non-PIV molecule selected from a cytokine, a T-helper epitope, a restriction site marker, or a protein of a microbial pathogen capable of eliciting an immune response in a mammalian host.

In yet additional aspects of the invention, the recombinant HPIV1 genome or antigenome comprises a partial or complete HPIV1 "vector" genome or antigenome that is combined with one or more heterologous gene(s) or genome segment(s) encoding one or more antigenic determinant(s) of one or more heterologous pathogen(s) to form a chimeric HPIV1 genome or antigenome. The heterologous gene(s) or genome segment(s) encoding the antigenic determinant(s) can be added as supernumerary gene(s) or genome segment (s)adjacent to or within a noncoding region of the partial or complete HPIV1 vector genome or antigenome, or can be substituted for one or more counterpart gene(s) or genome segment(s) in a partial HPIV1 vector genome or antigenome. The heterologous gene(s) or genome segment(s) can include one or more heterologous coding sequences and/or one or more heterologous regulatory element(s) comprising an extragenic 3' leader or 5' trailer region, a gene-start signal, gene-end signal, editing region, intergenic region, or a 3' or 5' non-coding region.

In related embodiments of the invention, chimeric HPIV1 viruses are provided wherein the vector genome is combined with one or more heterologous antigenic determinant(s) of a heterologous pathogen selected from measles virus, subgroup A and subgroup B respiratory syncytial viruses, mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses, human metapneumoviruses, and influenza viruses. In exemplary aspects, the heterologous antigenic determinant(s) is/are selected from measles virus HA and F proteins, subgroup A or subgroup B respiratory syncytial virus F, G, SH and M2 proteins, mumps virus HN and F proteins, human papilloma virus L1 protein, type 1 or type 2 human immunodeficiency virus gp160 protein, herpes simplex virus and cytomegalovirus gB, gC, gD, gE, gG, gH, gI, gJ, gK, gL, and gM proteins, rabies virus G protein, Epstein Barr Virus gp350 protein, filovirus G protein, bunyavirus G protein, flavivirus pre M, E, and NS1 proteins, human metapneuomovirus G and F protein, and alphavirus E protein, and antigenic domains, fragments and epitopes thereof.

Modifications useful within rHPIV1 viruses of the invention can be similarly incorporated into rHPIV2 viruses as described herein, and likewise modifications useful within rHPIV2 viruses of the invention can be incorporated into rHPIV1 for development of yet additional immunogenic compositions and methods.

BRIEF DESCRIPTION OF THE DRAWINGS

FIG. 1 (Panels A-E) illustrates various mutations identified in a heterologous negative stranded RNA virus that can be incorporated into recombinant HPIV2 candidates of the invention to yield attenuation or other desired phenotypic changes. Partial amino acid sequence alignments (SEQ ID NOS 1-16, respectively in order of appearance) are provided between HPIV2 wild-type (wt), HPIV3 wt, HPIV1 wt, or BPIV3 wt for regions of the indicated protein that contain known attenuating mutations. Based on these and similar comparisons, mutations are identified in a heterologous PIV or non-PIV virus for transfer into a recombinant HPIV2 of the invention. The amino acid position and substitution previously shown to confer a phenotypic change in the heterologous virus is indicated above each sequence alignment and wild type assignment is in bold font in the sequence alignment. The corresponding amino acid position in HPIV2 is indicated after the HPIV2 sequence. Amino acid positions that are conserved between all species of L protein in the alignment are underlined, representing additional targets for mutagenesis.

17). The sequence was modified from wild-type to contain a Not I restriction site (GCGGCCGC) one nucleotide prior to the translational start codon of the HPIV2 N gene (ATG, HPIV2/V94 nts 158-160). The Not I site was introduced by changing the HPIV2 sequence AGGTTCAA (HPIV2/V94 nts 149-156) to GCGGCCGC (Not I recognition sequence). The position of two potential N gene-start signals is indicated as shaded areas. The promoter element (open box) is a sequence that has been demonstrated to be important for viral replication and transcription in other Paramyxoviruses. Panel B: Insertion of the HPIV1 HN or RSV (subgroup A) G open reading frame as a supernumerary gene in the Not I site (SEQ ID NOS 18, 19, 17, 18, 20, and 17, respectively in order of appearance). A gene-start, intergenic, and gene-end sequence identical to that found between the HPIV2 N and P genes (HPIV2/V94 nts 1909-1938) is inserted after each supernumerary ORF. These signals serve to terminate transcription of the foreign ORF and start transcription of the downstream HPIV2 N gene, respectively. Each supernumerary gene cassette will be generated using PCR with a sense oligo that will include a Not I restriction site and an antisense oligo that contains gene-end (GE) and gene-start (GS) sequences that will be used to terminate transcription for the inserted gene and promote transcription for the HPIV2 N gene, respectively. A unique BstEII site is also included which will allow for the optional insertion of a second supernumerary ORF. The entire sequence is modified as necessary to conform to the rule of six by adjusting the length (n) of the sequence in the positions indicated by the arrow. The bottom section for each virus details the sequence of the HPIV2 backbone where the ORFs are to be inserted. This strategy can be used to engineer other unique restriction sites at any one of the gene junctions to allow for the insertion of multiple foreign genes.

Figure 3:
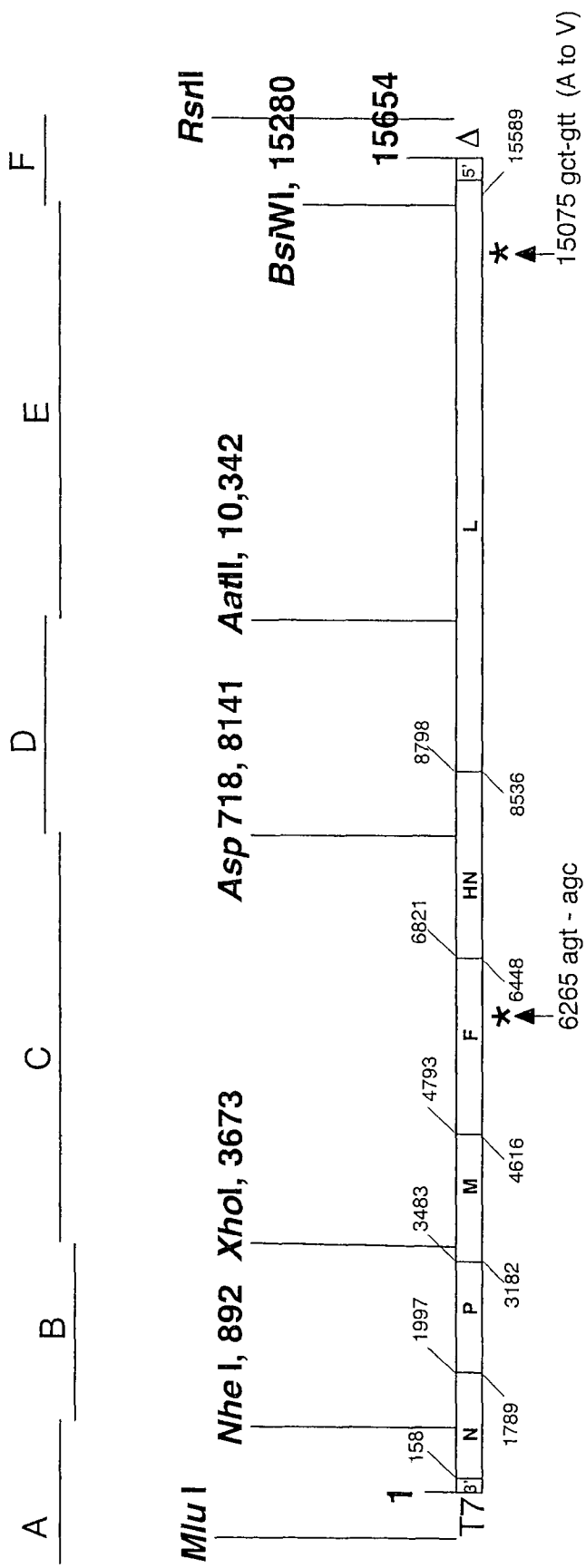

FIG. 3 provides a diagram (not to scale) of the assembled cDNA clone, pFLC HPIV2/V94, that yields the antigenomic RNA of HPIV2V94 when transcribed by T7 RNA polymerase. The 6 overlapping PCR fragments used to assemble the full-length antigenomic cDNA are shown (A-F). Restriction sites along with their nucleotide positions that were used to assemble the clone are shown above the boxed diagram of the viral genome. The T7 polymerase promoter (T7) and two non-viral G residues that enhance transcription flank the upstream end of the antigenome, and the hepatitis delta virus ribozyme sequence (Δ) flanks the downstream end. The relative position of each HPIV2 ORF is shown. The nucleotide changes from the consensus sequence of biologically derived HPIV2/94 are indicated (*) and the resulting amino acid change in the protein is shown.

FIG. 4 provides multi-step growth curves of HPIV2s. LLC-MK2 monolayers were infected in triplicate with the indicated HPIV2 at an m.o.i. of 0.01 at 32° C. Aliquots of the medium supernatants were harvested at 24-hour intervals and were assayed at 32° C. for virus titer. Virus titers are expressed as mean $\log_{10}$ TCID$_{50}$/ml±standard error. Panel A: Viruses were grown and titered in the absence of trypsin. Panel B: Viruses were grown with added porcine trypsin (5 ug/ml), and virus was quantified on LLC-MK2 cells with added trypsin.

Figure 5:
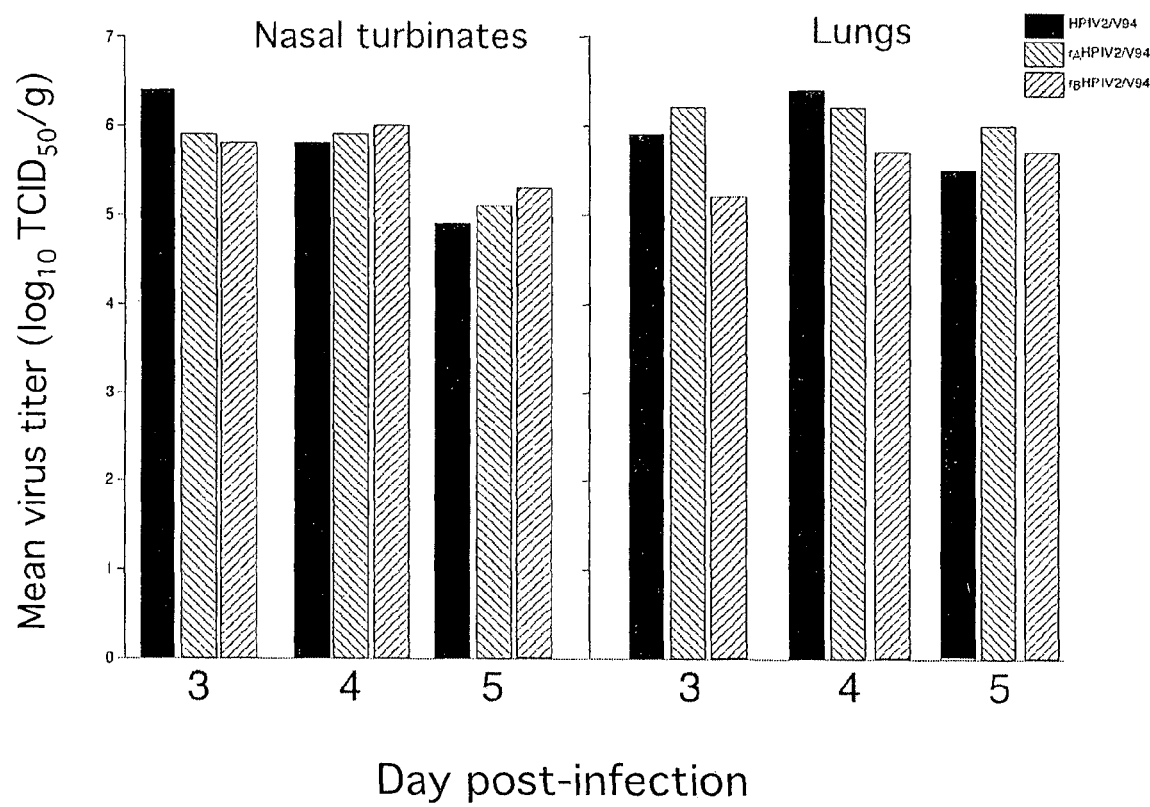

FIG. 5 illustrates in vivo characterization of rHPIV2/V94. Replication of the recombinant virus was studied in hamsters, an accepted animal model system for predicting growth and attenuation characteristics in human hosts. Hamsters were inoculated i.n. with $10^6$ TCID$_{50}$ of the indicated virus. Nasal tubinates and lung tissues from six animals from each group were harvested on days three, four, and five post-infection. Virus present in tissues was quantified by serial dilution on LLC-MK2 monolayers at 32° C. $r_A$HPIV2/V94 and $r_B$HPIV2/V94 are preparations of HPIV2 derived from separate transfections.

FIG. 6 provides a comparison of selected regions of the nucleotide sequence of the HPIV2 Toshiba and Greer strains (SEQ ID NOS 21-40, respectively in order of appearance). The Toshiba and Greer sequences were aligned using the BESTFIT alignment program (Wisconsin Package Version 10.2, Genetics Computer Group (GCG), Madison, Wis.). Missing nts are indicated by (.). Ten regions were identified (A-J) that likely represent sequence errors in the reported Toshiba strain sequence. These sequences (antigenomic sense) are found in (A), the Toshiba strain N gene start signal sequence missing 1-nt, (B) the Toshiba strain N ORF, missing codon-195 (Arg), (C) the Toshiba strain N gene end (containing 1 extra nt) and P gene start signals (missing 1-nt), (D) P ORF (missing 1 nt), (E) P ORF (containing 1 extra nt) resulting in missense of P aa 316-319 (changes GSDM (SEQ ID NO: 67) to QVIL (SEQ ID NO: 68)), (F) HN 3' NCR (missing 1 nt), (G) L ORF (missing codon-378 (Ala)), (H) L ORF (missing codon-741 (Pro)), (I-J) L ORF (containing 3 extra nts, resulting in missense of L polymerase aa 1735-1743 (changing TLTKFDLSL (SEQ ID NO: 69) to NSNKVRFIPF (SEQ ID NO: 70)).

FIG. 7 illustrates the structure of nucleotide inserts used to make HPIV2 antigenomic cDNAs that do not conform to the rule of six. Panel A. The wt nt sequence (SEQ ID NO: 41) around the EcoRV restriction site near the end of the L ORF is shown. Panel B. The sequences of the six antigenomic-sense oligonucleotides (SEQ ID NO: 42-47, respectively in order of appearance) inserted at the EcoRV restriction site spanning HPIV2 nt 15554-15559 is shown. Oligonucleotide duplexes were inserted between nt 15556 and 15557. Each oligonucleotide duplex contains a silent ATC to att mutation that destroys the EcoRV site and recreates the last 11 codons of the L ORF, and 12 HPIV2 nt including the TGA stop codon (bold) followed by 0-5 additional nt. The designation of the recombinant viruses generated from the cDNAs is indicated to the left: the virus designated rHPIV2N94(+6) corresponds to the rule of six, while the others contain the indicated number of additional nt (+1 to +5). The length of each oligonucleotide insert is shown on the right, with the rule of six length and the total length of the antigenomic cDNA indicated in parenthesis.

FIG. 8 illustrates nucleotide insertions and deletions detected in the genomic RNA of recombinant HPIV2s derived from cDNAs that do not conform to the rule of six (sequences are in antigenomic sense). Panel A. Four recombinant viruses were produced from cDNAs that did not conform to the rule of six, rHPIV2N94(+3), rHPIV2/V94(+4) (SEQ ID NO: 50), $r_A$HPIV2/V94(+5) (SEQ ID NO: 51), and $r_B$HPIV2N94(+5) (SEQ ID NO: 52), contained nt insertions that resulted in a polyhexameric genome length. Two insertions containing a total of 3 nt were identified in the FIN 5' and 3' noncoding regions (5' NCR (SEQ ID NO: 48) and 3' NCR (SEQ ID NO: 49)) of rHPIV2N94(+3). A 2-nt insertion within the intergenic (IG) region between the HN and L genes was identified in rHPIV2N94(+4). A 1-nt insertion was found in each clone of $r_A$HPIV2/V94(+5) and $r_B$HPIV2N94(+5), in one case at the end of the FIN GE signal and in the other in the HN 3' NCR. Panel B. Two recombinant viruses produced from cDNAs that did not conform to the rule of six, rHPIV2/V94(+2) (SEQ ID NO: 53) and rHPIV2N94(+1) (SEQ ID NO: 56), contained nt deletions that resulted in a polyhexameric genome length. rHPIV2N94(+2) was found to have a 2-nt deletion (underlined) within the IG region between the HN and L genes. rHPIV2N94(+1) was found to have a 1-nt deletion (underlined) near the end of the L polymerase ORF (SEQ ID NO: 54). This resulted in a frame shift in the L coding sequence that deleted the last 13 amino acids (SEQ ID NO: 55 of L and replaced them with an unrelated sequence of 21 amino acids (SEQ ID NO: 57, as shown. The nt sequence (antigenomic sense) in the region of the insertions is shown. The inserted nt are shown and the site of insertion is indicated by an arrow pointing downward. Deleted nt are shown and the location of the deletion is indicated by an arrow pointing upward. The FIN 5' or 3' non-coding region (NCR), transcription gene end (GE) and gene-start (GS) (in bold type) and intergenic regions (IG) between the HPIV2 HN and L ORFs are indicated. The L polymerase translation initiation codon (ATG) and translation termination codon (TGA) are underlined. The single letter amino acid designation is shown below the nt sequence for the wt and a mutant version of the HPIV2 L polymerase.

FIGS. 9A-F provide a nucleotide sequence for the HPIV2/V94 strain (SEQ ID NO: 58).

FIGS. 10A-F provide a nucleotide sequence for the HPIV2/V98 strain (SEQ ID NO: 59).

FIGS. 11A-F provide a nucleotide sequence for the HPIV2 Greer strain (SEQ ID NO: 60).

Figure 12:
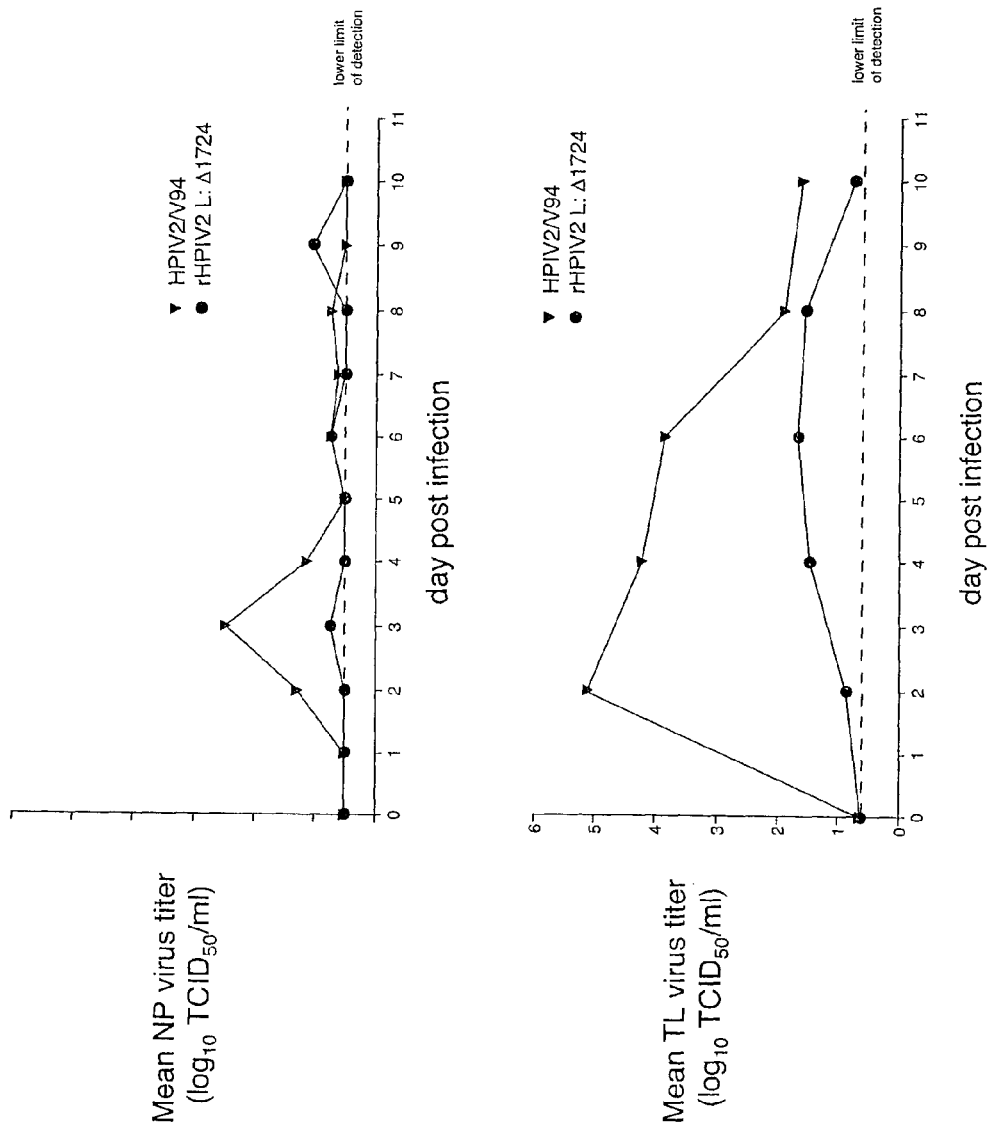

FIG. 12 illustrates the level of virus shedding in the upper and lower respiratory tract of African green monkeys infected with either the biologically derived HPIV2 or a recombinant HPIV2 containing a two amino acid deletion at positions 1764 and 1765 in the L polymerase protein. This "imported" mutation was initially identified in a recombinant human-bovine chimeric HPIV3 (designated rHPIV3-$L_B$), and the corresponding target site for the mutation in HPIV2 is at residue 1764. Substitutions and deletions at this target site are contemplated to generate attenuated HPIV2 constructs. In this example, a two residue deletion was engineered to delete the subject target residue along with a second residue to conform the cDNA construct to the "rule of six", although other 1764 deletion or substitution constructs can be readily generated without altering the 1765 residue. The lower limit of detection in the subject assay is indicated.

Figure 13:
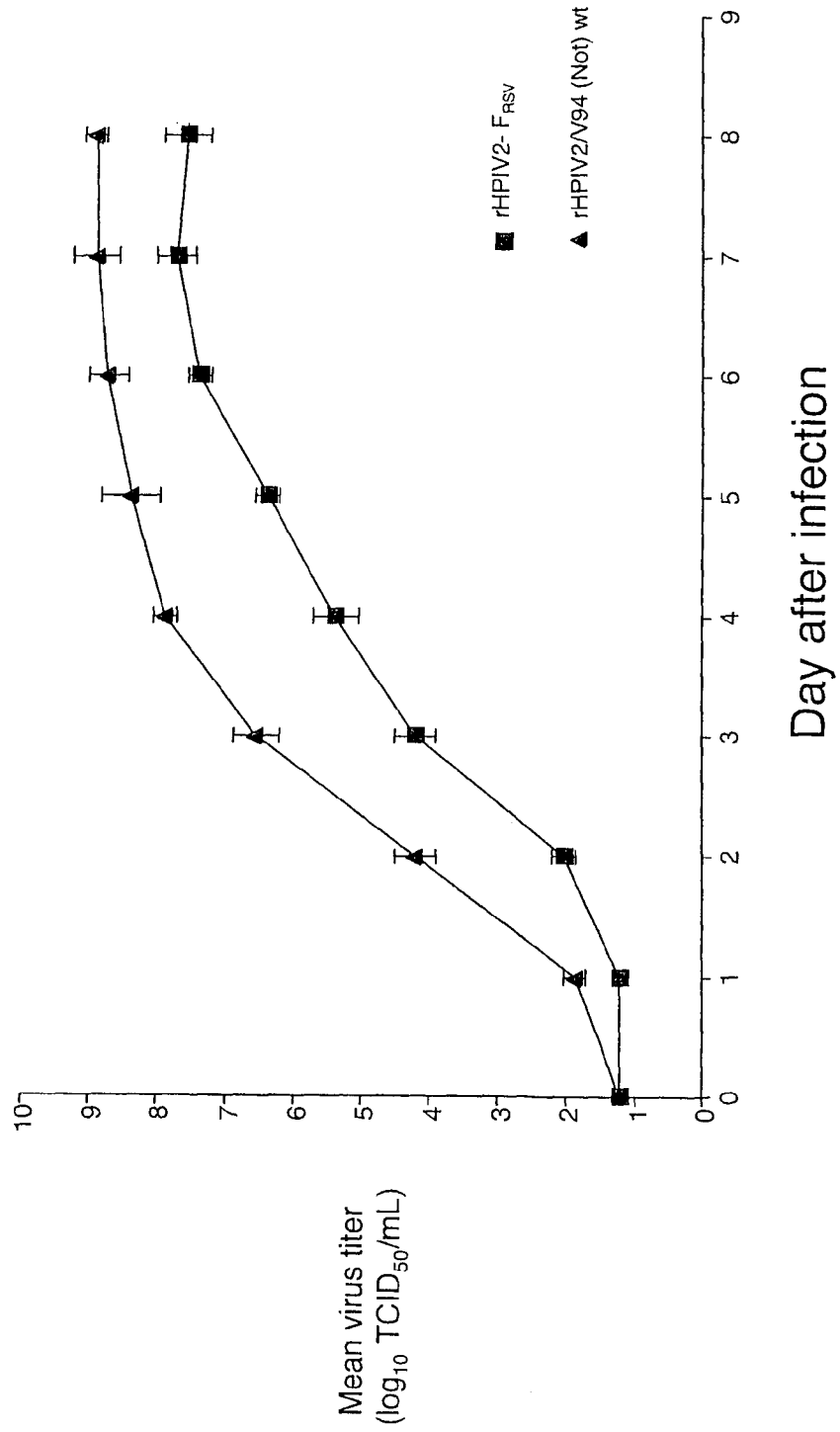

FIG. 13 illustrates multicycle replication of rHPIV2-FRSV and the recombinant parent virus, rHPIV2/V94, in simian LLC-MK2 cells. Triplicate monolayer cultures were infected at an input m.o.i. of 0.01 $TCID_{50}$ per cell with the wild type recombinant HPIV2 and the recombinant HPIV2 vector expressing the RSV fusion protein. The virus titers are shown as mean $log_{10}$ $TCID_{50}$/ml of triplicate samples.

Figure 14:
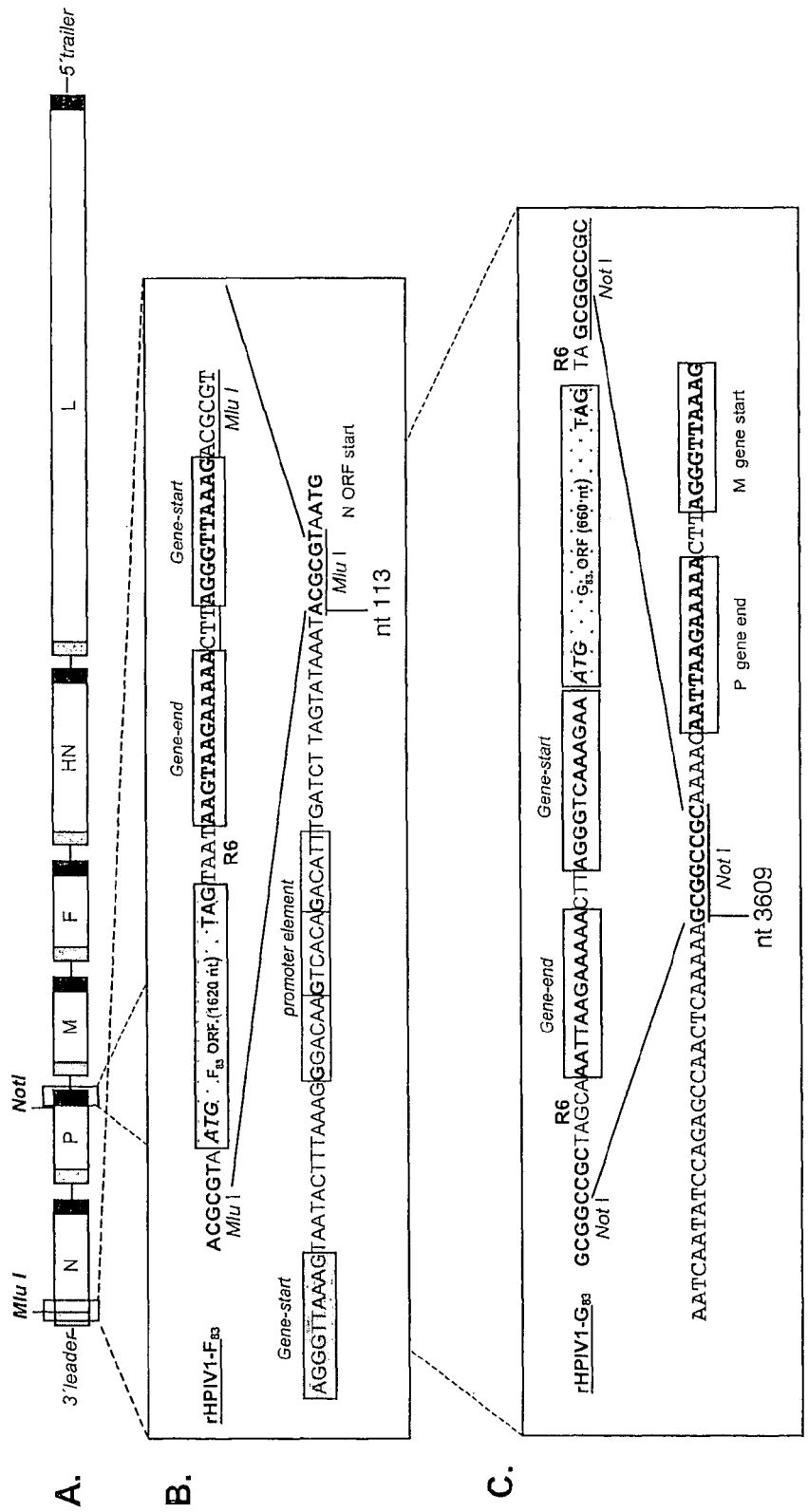

FIG. 14 illustrates modification of a recombinant HPIV1 of the invention for use as a vector for heterologous protective antigens of different PIV and non-PIV pathogens according to the invention. Panel A provides a diagram of the HPIV1 genome that has bee modified from wild-type to contain an Mlu I restriction site one nucleotide prior to the translational start codon of the N protein (starting at HPIV1 nt 113), or a Not I restriction site between the P and M ORFs, within the P gene 3' non-coding region (starting at HPIV1 nt 3609). Gene-start and gene-stop signals for each HPIV1 gene are shaded in gray and black, respectively. In panel B, the area enclosed by the rectangle around the Mlu I site is expanded and illustrates the insertion of the HMPV strain CAN83 F protein ORF (the complete F ORF is 1620 nt in length and encodes a 539 aa polypeptide. The length of the entire inserted supernumerary gene unit sequence is 1656 nt). For the recombinant virus that is illustrated in panel B, rHPIV1-$F_{83}$, the top sequence shows the insert that is generated using PCR with a sense oligo that includes an Mlu I restriction site (SEQ ID NO: 69) and an antisense oligo (SEQ ID NO: 62) that contains gene-stop and gene-start sequences that are used to terminate transcription for the inserted gene and promote transcription for the N gene, respectively. Additional nucleotides (indicated by R6) are inserted where necessary to conform the entire inserted sequence to the rule of six, and to maintain the HPIV1 gene start signal sequence phasing (Kolakofsky et al., *J. Virol.* 72: 891-899, 1998, incorporated herein by reference). The bottom section in the panel details the sequence of the HPIV1 backbone where the ORF is inserted (SEQ ID NO: 63). The naturally occurring gene-start sequence is boxed. The promoter element is a sequence that has been demonstrated to be important for viral replication and transcription. In panel C, the area enclosed by the rectangle around the Not I site is expanded and illustrates the insertion of the HMPV CAN83 strain G protein ORF from the CAN83 strain of HMPV (the complete G ORF is 660 nt in length and encodes a 179 aa polypeptide. The length of the entire inserted supernumerary gene unit sequence is 702 nt). For the recombinant virus that is illustrated in panel C, rHPIV1-$G_{83}$, the top sequence shows the insert that is generated using PCR with a sense oligo (SEQ ID NO: 64) that includes a Not I restriction site, gene-stop and gene-start sequences that are used to terminate transcription for the upstream P gene and promote transcription for the inserted supernumerary gene unit, respectively, and an anti-sense oligo that contains a NotI site (SEQ ID NO: 65). Additional nucleotides (indicated by R6) are inserted where necessary to conform the entire inserted sequence to the rule of six, and to maintain the HPIV1 gene start signal sequence phasing. The bottom section in the panel details the sequence of the HPIV1 backbone at the P-M junction where the ORF is inserted (SEQ ID NO: 66). The naturally occurring gene-end and gene start sequences are boxed. This strategy can be used to engineer other unique restriction sites at any one of the gene junctions or 3' or 5' portions of the genome or antigenome to allow for the insertion of foreign genes, as desired.

DESCRIPTION OF THE SPECIFIC EMBODIMENTS

The instant invention provides methods and compositions for the production and use of novel human parainfluenza virus type 2 (HPIV2) candidates. The recombinant HPIV2 viruses of the invention are infectious and immunogenic in humans and other mammals and are useful for generating immune responses against one or more PIVs, for example against one or more human PIVs (HPIVs). In additional embodiments, chimeric HPIV2 viruses are provided that elicit an immune response against a selected PIV and one or more additional pathogens, for example against multiple HPIVs or against a HPIV and a non-PIV virus such as respiratory syncytial virus (RSV), human metapneumovirus, or measles virus. The immune response elicited can involve either or both humoral and/or cell mediated responses. Preferably, recombinant HPIV2 viruses of the invention are attenuated to yield a desired balance of attenuation and immunogenicity. The invention thus provides novel methods for designing and producing attenuated, HPIV2 viruses that are useful as agents for eliciting a desired immune response against HPIV2 and other pathogens. An important feature of the invention is that it provides for the production, with high frequency, of recombinant PIVs having a defined genome sequence and predictable characteristics.

Exemplary recombinant HPIV2 viruses of the invention incorporate a recombinant HPIV2 genome or antigenome, as well as a PIV major nucleocapsid (N) protein, a nucleocapsid phosphoprotein (P), and a large polymerase protein (L). The N, P, and L proteins may be HPIV2 proteins, or one or more of the N, P, and L proteins may be of a different HPIV, for example HPIV1 or HPIV3. Additional PIV proteins may be included in various combinations to provide a range of infectious viruses, defined herein to include subviral particles lacking one or more non-essential viral components and complete viruses having all native viral components, as well as viruses containing supernumerary proteins, antigenic determinants or other additional components.

As set forth in the examples below, a complete consensus sequence was determined herein for the genomic RNA of a human parainfluenza virus type 2 (HPIV2) strain Vanderbilt/ 1994 (V94), a clinical isolate that was originally isolated from an infected, one year-old infant. The sequence thus identified was used to generate a full-length antigenomic cDNA and to recover a recombinant wild type HPIV2 (rHPIV2).

The replication of rHPIV2 in vitro and in the respiratory tract of hamsters was similar to that of its biologically derived parent virus. The biological properties of rHPIV2 in vitro and in vivo demonstrates that the rHPIV2 sequence corresponds to a wild type virus. This is a critical finding, since it demonstrates that the recombinant HPIV2 sequence is that of an authentic wild-type virus. This rHPIV2 therefore serves as a novel substrate for recombinant introduction of attenuating mutations for the generation of live-attenuated HPIV2 and other PIV candidates.

The Paramyxovirinae subfamily of the Paramyxoviridae family of viruses includes human parainfluenza virus types 1, 2, 3, 4A and 4B (HPIV1, HPIV2, HPIV3, HPIV4A, and HPIV4B, respectively). HPIV1, HPIV3, MPIV1, and bovine PIV3 (BPIV3) are classified together in the genus Respirovirus, whereas HPIV2 and HPIV4 are more distantly related and are classified in the genus Rubulavirus. MPIV1, simian virus 5 (SV5), and BPIV3 are animal counterparts of HPIV1, HPIV2, and HPIV3, respectively (Chanock et al., in *Parainfluenza Viruses*, Knipe et al. (Eds.), pp. 1341-1379, Lippincott Williams & Wilkins, Philadelphia, 2001, incorporated herein by reference).

The human PIVs have a similar genomic organization, although significant differences occur in the P gene (Chanock et al., in *Parainfluenza Viruses*, Knipe et al. (eds.), pp. 1341-1379, Lippincott Williams & Wilkins, Philadelphia, 2001; Lamb et al., in Paramyxoviridae: The viruses and their replication, Knipe et al. (eds.), pp. 1305-1340, Lippincott Williams & Wilkins, Philadelphia, 2001, each incorporated herein by reference). The 3' end of genomic RNA and its full-length, positive-sense replicative intermediate antigenomic RNA contain promoter elements that direct transcription and replication. The nucleocapsid-associated proteins are composed of the nucleocapsid protein (N), the phosphoprotein (P), and the large polymerase (L). The internal matrix protein (M) and the major antigenic determinants, the fusion glycoprotein (F) and hemagglutinin-neuraminidase glycoprotein (HN) are the envelope-associated proteins. The gene order is N, V/P, M, F, HN, and L.

With the exception of the P gene, each HPIV2 gene contains a single ORF and encodes a single viral protein. The P gene of the Paramyxovirinae subfamily variably encodes a number of proteins that are generated from alternative open reading frames (ORFs), by the use of alternative translational start sites within the same ORF, by an RNA polymerase editing mechanism, by ribosomal shunting, or through ribosomal frame shifting (Lamb et al., in Paramyxoviridae: The viruses and their replication, Knipe et al. (Eds.), pp. 1305-1340, Lippincott Williams & Wilkins, Philadelphia, 2001; Liston et al., *J Virol* 69:6742-6750, 1995; Latorre et al., *Mol. Cell. Biol.* 18:5021-5031, 1998, incorporated herein by reference). For example, the MPIV1 P gene expresses eight proteins. Four of these, C, C', Y1, and Y2, are expressed by translational initiation at four different codons within the C ORF that is present in a +1 reading frame relative to the P ORF (Curran et al., *Embo J.* 7:245-251, 1988, Dillon et al., *J. Virol.* 63:974-977, 1989; Curran et al., *Virology* 189:647-656, 1989, each, incorporated herein by reference). The HPIV2 P gene encodes the P protein and one additional protein, V. The V protein does not appear to be absolutely necessary for HPIV2 replication in cell culture. HPIV1 encodes a P protein but does not appear to encode a V protein, based on the lack of a homologous RNA editing site and the presence of a relict V coding sequence that is interrupted by 9-11 stop codons (Matsuoka et al., *J. Virol.* 65:3406-3410, 1991; Rochat et al., *Virus Res.* 24:137-144, 1992, incorporated herein by reference).

Infectious recombinant HPIV2 viruses according to the invention are produced by a recombinant coexpression system that permits introduction of defined changes into the recombinant HPIV2 and provides for the generation, with high frequency and fidelity, of HPIV2 having a defined genome sequence. These modifications are useful in a wide variety of applications, including the development of live attenuated viral strains bearing predetermined, defined attenuating mutations. Infectious PIV of the invention are typically produced by intracellular or cell-free coexpression of one or more isolated polynucleotide molecules that encode the HPIV2 genome or antigenome RNA, together with one or more polynucleotides encoding the viral proteins desired, or at least necessary, to generate a transcribing, replicating nucleocapsid.

cDNAs encoding a HPIV2 genome or antigenome are constructed for intracellular or in vitro coexpression with the selected viral proteins to form infectious PIV. By "HPIV2 antigenome" is meant an isolated positive-sense polynucleotide molecule which serves as a template for synthesis of progeny HPIV2 genome. Preferably a cDNA is constructed which is a positive-sense version of the HPIV2 genome corresponding to the replicative intermediate RNA, or antigenome, so as to minimize the possibility of hybridizing with positive-sense transcripts of complementing sequences encoding proteins necessary to generate a transcribing, replicating nucleocapsid.

In some embodiments of the invention the genome or antigenome of a recombinant HPIV2 (rHPIV2) need only contain those genes or portions thereof necessary to render the viral or subviral particles encoded thereby infectious. Further, the genes or portions thereof may be provided by more than one polynucleotide molecule, i.e., a gene may be provided by complementation or the like from a separate nucleotide molecule. In other embodiments, the PIV genome or antigenome encodes all functions necessary for viral growth, replication, and infection without the participation of a helper virus or viral function provided by a plasmid or helper cell line.

By "recombinant HPIV2" is meant a HPIV2 or HPIV2-like viral or subviral particle derived directly or indirectly from a recombinant expression system or propagated from virus or subviral particles produced therefrom. The recombinant expression system will employ a recombinant expression vector which comprises an operably linked transcriptional unit comprising an assembly of at least a genetic element or elements having a regulatory role in PIV gene expression, for example, a promoter, a structural or coding sequence which is transcribed into PIV RNA, and appropriate transcription initiation and termination sequences.

To produce infectious HPIV2 from a cDNA-expressed HPIV2 genome or antigenome, the genome or antigenome is coexpressed with those PIV (HPIV2 or heterologous PIV) proteins necessary to produce a nucleocapsid capable of RNA replication, and render progeny nucleocapsids competent for both RNA replication and transcription. Transcription by the genome nucleocapsid provides the other PIV proteins and initiates a productive infection. Alternatively, additional PIV proteins needed for a productive infection can be supplied by coexpression.

In certain embodiments of the invention, complementing sequences encoding proteins necessary to generate a transcribing, replicating HPIV2 nucleocapsid are provided by one or more helper viruses. Such helper viruses can be wild type or mutant. Preferably, the helper virus can be distinguished phenotypically from the virus encoded by the HPIV2 cDNA. For example, it may be desirable to provide monoclonal antibodies that react immunologically with the helper virus but not the virus encoded by the HPIV2 cDNA. Such antibodies can be neutralizing antibodies. In some embodiments, the antibodies can be used in affinity chromatography to separate the helper virus from the recombinant virus. To aid the procurement of such antibodies, mutations can be introduced into the HPIV2 cDNA to provide antigenic diversity from the helper virus, such as in the HN or F glycoprotein genes.

Expression of the HPIV2 genome or antigenome and proteins from transfected plasmids can be achieved, for example, by each cDNA being under the control of a selected promoter (e.g., for T7 RNA polymerase), which in turn is supplied by infection, transfection or transduction with a suitable expression system (e.g., for the T7 RNA polymerase, such as a vaccinia virus MVA strain recombinant which expresses the T7 RNA polymerase, as described by Wyatt et al., *Virology* 210:202-205, 1995, incorporated herein by reference). The viral proteins, and/or T7 RNA polymerase, can also be provided by transformed mammalian cells or by transfection of preformed mRNA or protein.

A HPIV2 genome or antigenome may be constructed for use in the present invention by, e.g., assembling cloned cDNA segments, representing in aggregate the complete genome or antigenome, by polymerase chain reaction or the like (PCR; described in, e.g., U.S. Pat. Nos. 4,683,195 and 4,683,202, and PCR Protocols: A Guide to Methods and Applications, Innis et al., eds., Academic Press, San Diego, 1990, each incorporated herein by reference) of reverse-transcribed copies of HPIV2 mRNA or genome RNA. For example, a first construct may be generated which comprises cDNAs containing the left hand end of the antigenome, spanning from an appropriate promoter (e.g., T7 RNA polymerase promoter) and assembled in an appropriate expression vector, such as a plasmid, cosmid, phage, or DNA virus vector. The vector may be modified by mutagenesis and/or insertion of a synthetic polylinker containing unique restriction sites designed to facilitate assembly. For ease of preparation the N, P, L and other desired PIV proteins can be assembled in one or more separate vectors. The right hand end of the antigenome plasmid may contain additional sequences as desired, such as a flanking ribozyme and single or tandem T7 transcriptional terminators. The ribozyme can be hammerhead type, which would yield a 3' end containing a single nonviral nucleotide, or can be any of the other suitable ribozymes such as that of hepatitis delta virus (Perrotta et al., *Nature* 350:434-436, 1991, incorporated herein by reference) that would yield a 3' end free of non-PIV nucleotides.

Alternative means to construct cDNA encoding the HPIV2 genome or antigenome include reverse transcription-PCR using improved PCR conditions (e.g., as described in Cheng et al., *Proc. Natl. Acad. Sci. USA* 91:5695-5699, 1994, incorporated herein by reference) to reduce the number of subunit cDNA components to as few as one or two pieces. In other embodiments different promoters can be used (e.g., T3, SPQ or different ribozymes, such as that of a hammerhead variety. Different DNA vectors (e.g., cosmids) can be used for propagation to better accommodate the larger size genome or antigenome.

By "infectious clone" or "infectious cDNA" of HPIV2 is meant cDNA or its product, synthetic or otherwise, as well as RNA capable of being directly incorporated into infectious virions which can be transcribed into genomic or antigenomic HPIV2 RNA capable of serving as a template to produce the genome of infectious HPIV2 viral or subviral particles. As noted above, defined mutations can be introduced into an infectious HPIV2 clone by a variety of conventional techniques (e.g., site-directed mutagenesis) into a cDNA copy of the genome or antigenome. The use of genomic or antigenomic cDNA subfragments to assemble a complete genome or antigenome cDNA as described herein has the advantage that each region can be manipulated separately, where small cDNA constructs provide for better ease of manipulation than large cDNA constructs, and then readily assembled into a complete cDNA.

Isolated polynucleotides (e.g., cDNA) encoding the HPIV2 genome or antigenome may be inserted into appropriate host cells by transfection, electroporation, mechanical insertion, transduction or the like, into cells which are capable of supporting a productive HPIV2 infection, e.g., HEp-2, FRhL-DBS2, LLC-MK2, MRC-5, and Vero cells. Transfection of isolated polynucleotide sequences may be introduced into cultured cells by, for example, calcium phosphate-mediated transfection (Wigler et al., *Cell* 14:725, 1978; Corsaro et al., *Somatic Cell Genetics* 7:603, 1981; Graham et al., *Virology* 52:456, 1973, electroporation (Neumann et al., *EMBO J.* 1:841-845, 1982), DEAE-dextran mediated transfection (Ausubel et al., (ed.) Current Protocols in Molecular Biology, John Wiley and Sons, Inc., NY, 1987), cationic lipid-mediated transfection (Hawley-Nelson et al., *Focus* 15:73-79, 1993) or a commercially available transfection regent, e.g., Lipofectamine-2000 (Invitrogen, Carlsbad, Calif.) or the like (each of the foregoing references are incorporated herein by reference in its entirety).

By providing infectious clones of HPIV2, the invention permits a wide range of alterations to be recombinantly produced within the HPIV2 genome (or antigenome), yielding defined mutations that specify desired phenotypic changes. The compositions and methods of the invention for producing recombinant HPIV2 permit ready detailed analysis and manipulation of HPIV2 molecular biology and pathogenic mechanisms using, e.g., defined mutations to alter the function or expression of selected HPIV2 proteins. Using these methods and compositions, one can readily distinguish mutations responsible for desired phenotypic changes from silent incidental mutations, and select phenotype-specific mutations for incorporation into a recombinant HPIV2 genome or antigenome. In this context, a variety of nucleotide insertions, deletions, substitutions, and rearrangements can be made in the HPIV2 genome or antigenome during or after construction of the cDNA. For example, specific desired nucleotide sequences can be synthesized and inserted at appropriate regions in the cDNA using convenient restriction enzyme sites. Alternatively, such techniques as site-specific mutagenesis, alanine scanning, PCR mutagenesis, or other such techniques well known in the art can be used to introduce mutations into the cDNA.

Recombinant modifications of HPIV2 provided within the invention are directed toward the production of improved candidate viruses, e.g., to enhance viral attenuation and immunogenicity, to ablate epitopes associated with undesirable immunopathology, to accommodate antigenic drift, etc. To achieve these and other objectives, the compositions and methods of the invention allow for a wide variety of modifications to be introduced into a HPIV2 genome or antigenome for incorporation into infectious, recombinant HPIV2. For example, foreign genes or gene segments encoding antigenic determinants (e.g., protective antigens or immunogenic epitopes) may be added within a HPIV2 clone to generate recombinant HPIV2 viruses capable of inducing immunity to both HPIV2 and another virus or pathogenic agent from which the antigenic determinant(s) was/were derived. Alternatively, foreign genes may be inserted, in whole or in part, encoding modulators of the immune system, such as cytokines, to enhance immunogenicity of a candidate virus. Other mutations that may be included within HPIV2 clones of the invention include, for example, substitution of heterologous genes or gene segments (e.g., a gene segment encoding a cytoplasmic tail of a glycoprotein gene) with a counterpart gene or gene segment in a PIV clone. Alternatively, the relative order of genes within a HPIV2 clone can be changed, a HPIV2 genome promoter or other regulatory element can be replaced with its antigenome counterpart, or selected HPIV2 gene(s) rendered non-functional (e.g., by functional ablation involving introduction of a stop codon to prevent expression of the gene). Other modifications in a HPIV2 clone can be made to facilitate manipulations, such as the insertion of unique restriction sites in various non-coding or coding regions of the HPIV2 genome or antigenome. In addition, nontranslated gene sequences can be removed to increase capacity for inserting foreign sequences.

As noted above, it is often desirable to adjust the phenotype of recombinant HPIV2 viruses for use by introducing additional mutations that increase or decrease attenuation or otherwise alter the phenotype of the recombinant virus. Detailed descriptions of the materials and methods for producing recombinant PIV from cDNA, and for making and testing various mutations and nucleotide modifications set forth herein as supplemental aspects of the present invention are provided in, e.g., Durbin et al., *Virology* 235:323-332, 1997; U.S. patent application Ser. No. 09/083,793, filed May 22, 1998; U.S. patent application Ser. No. 09/458,813, filed Dec. 10, 1999; U.S. patent application Ser. No. 09/459,062, filed Dec. 10, 1999; U.S. Provisional Application No. 60/047,575, filed May 23, 1997 (corresponding to International Publication No. WO 98/53078), and U.S. Provisional Application No. 60/059,385, filed Sep. 19, 1997, each incorporated herein by reference.

In particular, these incorporated references describe methods and procedures for mutagenizing, isolating and characterizing PIV to obtain attenuated mutant strains (e.g., temperature sensitive (ts), cold passaged (cp) cold-adapted (ca), small plaque (sp) and host-range restricted (hr) mutant strains) and for identifying the genetic changes that specify the attenuated phenotype. In conjunction with these methods, the foregoing incorporated references detail procedures for determining replication, immunogenicity, genetic stability and immunogenic efficacy of biologically derived and recombinantly produced attenuated HPIVs in accepted model systems reasonably correlative of human activity, including hamster or rodent and non-human primate model systems. In addition, these references describe general methods for developing and testing immunogenic compositions, including monovalent and bivalent immunogenic compositions against HPIV. Methods for producing infectious recombinant HPIV3 by construction and expression of cDNA encoding a PIV genome or antigenome coexpressed with essential PIV proteins are also described in the above-incorporated references, which include description of the following exemplary plasmids that may be employed to produce infectious HPIV3 clones: p3/7(131) (ATCC 97990); p3/7(131)2G (ATCC 97889); and p218(131) (ATCC 97991); each deposited under the terms of the Budapest Treaty with the American Type Culture Collection (ATCC) of 10801 University Boulevard, Manassas, Va. 20110-2209, U.S.A., and granted the above identified accession numbers (deposits incorporated herein by reference). Methods for producing infectious recombinant HPIV1 by construction and expression of cDNA encoding a HPIV1 recombinant or chimeric genome or antigenome coexpressed with essential PIV proteins are similarly described in U.S. Provisional Application No. 60/331,961, filed Nov. 21, 2001, and in Newman et al., *Virus Genes* 24:77-92, 2002, each incorporated herein by reference.

Also disclosed in the above-incorporated references are methods for constructing and evaluating infectious recombinant HPIV that are modified to incorporate phenotype-specific mutations identified in biologically derived PIV mutants, e.g., cold passaged (cp), cold adapted (ca), host range restricted (hr), small plaque (sp), and/or temperature sensitive (ts) mutants, for example the HPIV3 JS cp45 mutant strain. The HPIV3 JS cp45 strain has been deposited under the terms of the Budapest Treaty with the American Type Culture Collection (ATCC) of 10801 University Boulevard, Manassas, Va. 20110-2209, U.S.A. under Patent Deposit Designation PTA-2419 (deposit incorporated herein by reference). Mutations identified in this and other heterologous mutants viruses can be readily incorporated into recombinant HPIV2 of the instant invention, as described herein below.

As exemplified in FIG. 1 (Panels A-E) various mutations identified in a heterologous negative stranded RNA virus can be incorporated into recombinant HPIV2 candidates of the invention to yield attenuation or other desired phenotypic changes. The figure provides exemplary sequence alignments between HPIV2 wild-type (wt), HPIV3 wt, HPIV1 wt, or BPIV3 wt identifying regions containing known attenuating mutations in the heterologous virus. Based on these and similar comparisons, mutations previously identified in a heterologous PIV or non-PIV virus are mapped to a corresponding position in HPIV2 for "transfer" (i.e., introduction of an identical, conservative or non-conservative mutation, potentially including a substitution, deletion or insertion, at a homologous or corresponding position identified by the alignment) into recombinant HPIV2 of the invention. A large assemblage of such mutations are available (see, e.g., Newman et al., *Virus Genes* 24:77-92, 2002; Feller et al., *Virology* 276:190-201, 2000; Skiadopoulos et al., *Virology* 260:125-35, 1999; and Durbin et al., *Virology* 261:319-30, 1999, each incorporated herein by reference) for incorporation into recombinant HPIV2 and chimeric HPIV2 candidates of the invention. As depicted in FIG. 1, a corresponding amino acid position previously shown to confer a phenotypic change in a heterologous virus (when the indicated wild-type residue is altered, e.g., by substitution) is identified by conventional sequence alignment. The corresponding amino acid position in HPIV2 is thereby identified as a target site for mutation in a recombinant HPIV2 to yield attenuation or other desired phenotypic changes.

In certain detailed embodiments, the HPIV2 genome or antigenome is recombinantly modified to incorporate one or any combination of mutation(s) selected from mutations specifying previously identified amino acid substitution(s) in the L protein at a position corresponding to Tyr942, Leu992, and/or Thr1558 of HPIV3 JS cp45. Corresponding targets of wild-type (wt) HPIV2 L for incorporation of these exemplary mutations are Tyr948, Ala998, and Leu1566. In other embodiments, the recombinant HPIV2 genome or antigenome is modified to incorporate an attenuating mutation at an amino acid position corresponding to an amino acid position of an attenuating mutation identified in a heterologous, mutant nonsegmented negative stranded RNA virus, for example, another HPIV, a non-human PIV such as a bovine PIV3 (BPIV3) or murine PIV1 (MPIV1), or a non-PIV virus such as respiratory syncytial virus (RSV). In exemplary embodiments, an attenuating mutation identified in a BPIV3 virus L protein, at amino acid position Thr 1711, is incorporated in a recombinant HPIV2 of the invention at the corresponding position (Ser1724), as identified by conventional alignment methods (FIG. 1, Panels A-E).

In more specific embodiments, the HPIV2 genome or antigenome incorporates one or any combination of mutation(s) selected from mutations specifying amino acid substitution(s) in the L protein of Tyr948His, Ala998Phe, Leu1566Ile, and/or Ser1724Ile of HPIV2 L, (FIG. 1, Panels B-E). Other mutations, including substitutions and deletions, at the indicated target site for mutation, particularly those that are conservative to the foregoing exemplary mutations, are useful to achieve desired attenuation in recombinant HPIV2 candidates.

Considering, for example, mutations in non-human PIV viruses for use within the invention, the Kansas strain of BPIV3 was studied herein based on its known restriction in replication in the respiratory tract of humans and other primates. To identify the genetic determinants of the host-range attenuation phenotype of BPIV3 in primates, the antigenomic cDNA of HPIV3 was modified to contain the N, P, M, or L ORF of BPIV3 in place of the analogous HPIV3 ORF. In addition, the F and HN genes were transferred together as a pair to replace their HPIV3 counterparts, as described previously (Schmidt et al., *J. Virol.* 74:8922-9, 2000, incorporated herein by reference). Each of the chimeric bovine-human PIV3s containing the N, P, M, F and HN, or L was recovered from cDNA. The recombinant chimeric viruses were biologically cloned by plaque isolation and vRNA was isolated from the cloned virus and was used as a template to generate RT-PCR products. The structure of the genome flanking the substituted ORF was confirmed for each recombinant virus by sequencing and restriction enzyme analysis.

Two recombinant viruses, rHPIV3-$L_{BT1711I}$ and rHPIV3-$L_B$, bearing the BPIV3 L ORF were generated. rHPIV3-$L_{BT1711I}$ was generated first, but after it was found to be highly temperature sensitive in its replication in vitro, it was sequenced and was found to contain two point mutations in the L ORF that resulted in an Ala-425 to Val (A425V) and a Thr-1711 to Ile substitution (T1711I). The latter mutation was present in the antigenomic cDNA, but the former was a spontaneous mutation occurring following transfection of this cDNA. Another recombinant was generated (rHPIV3 $L_B$) that had the authentic BPIV3 L ORF sequence.

The kinetics of replication of each chimeric rHPIV3 in vitro was compared to that of their wild type rHPIV3 and BPIV3 parent viruses by infecting LLC-MK2 cells at an m.o.i. of 0.01 and measuring virus yield at 24 hour intervals. Except for rHPIV3-$L_{BT1711I}$, all of the chimeric rHPIV3s bearing BPIV3 ORF substitutions grew at a rate similar to that of their parent viruses, and all of the chimeric viruses grew to over $10^7$ TCID$_{50}$/ml by day 5 post-infection. This confirmed that each of the substituted wild type BPIV3 proteins exhibited a high degree of compatibility with the proteins and cis-acting signals of the HPIV3 backbone. In contrast, the restricted replication of rHPIV3-$L_{B\ T1711I}$ in vitro indicates one or both of the amino acid substitutions in its BPIV3 L polymerase protein are attenuating in vitro.

Considering these results, it was of interest to further characterize the restricted replication exhibited by the mutant rHPIV3-$L_{B\ T1711I}$ virus. To determine if the ORF substitutions in each rHPIV3 altered the ability of these viruses to grow at elevated temperatures, the level of temperature sensitivity of replication of each chimeric rHPIV3 was compared to that of the parent viruses and that of rHPIV3cp45, which is a well characterized ts and attenuated candidate HPIV3 vaccine that was previously shown to be appropriately attenuated and immunogenic in humans and non-human primates. The wild type and chimeric rHPIV3s were evaluated for their ability to grow on LLC-MK2 cells at the permissive temperature of 32° C. and at a range of higher temperatures. Surprisingly, both rHPIV3-$L_B$ and rHPIV3-$L_{B\ T1711I}$ were highly ts, with rHPIV3-$L_{B\ T1711I}$ being more ts than either rHPIV3-$L_B$ or rHPIV3cp45. As noted above, the BPIV3 L ORF present in the rHPIV3-$L_{B\ T1711I}$ virus contained two amino acid coding changes relative to wild type BPIV3 and it was of interest to determine which one, or both, was responsible for the increased ts phenotype of rHPIV3-$L_{B\ T1711I}$ compared to rHPIV3-$L_B$. An alternative viral clone of rHPIV3-$L_{B\ T1711}$I was identified that contained the T1711I substitution but not the A425V mutation. This virus had the same shut-off temperature as rHPIV3-$L_{B\ T1711I}$, indicating that the T1711I mutation alone is responsible for the increased level of temperature sensitivity of rHPIV3-$L_{B\ T1711I}$.

Each of the above-noted BPIV3 ORFs conferred restriction of replication in the upper or lower respiratory tract of rhesus monkeys when substituted for the analogous ORF in HPIV3, demonstrating that the host-range attenuation phenotype of BPIV3 is polygenic. Comparing the mean peak titer of virus replication in the upper respiratory tract, the chimeric rHPIV3s fell into three groups: (i) viruses bearing the BPIV3 M or L ORF or the F and HN genes were restricted approximately 16 to 32-fold; (ii) viruses bearing the BPIV3 N or $L_{T1711I}$ ORF exhibited a 40-100 fold restriction of replication; and (iii) the chimeric HPIV3 with the BPIV3 P ORF substitution exhibited a 1000-fold restriction in replication, suggesting that the BPIV3 P ORF is the major contributor to the attenuation phenotype. The level of replication of rHPIV3-$P_B$ was even lower than its BPIV3 parent virus in the upper respiratory tract, suggesting that some of its restricted replication in vivo may also be due to a gene incompatibility effect that was not evident in vitro. A similar pattern of host range restriction for the panel of chimeric viruses was observed in the lower respiratory tract. Because rHPIV3-$L_{B\ T1711I}$ was attenuated for replication in vitro and was highly ts, the level of attenuation of this virus observed in vivo likely is due to a combination of restricted replication specified by host-range sequences and that specified by its high level of temperature sensitivity (the body temperature of rhesus monkeys is about 39° C.).

To evaluate the immunogenicity of the rHPIV3s, serum samples were collected prior to infection and on day 28 or 31 following infection with the chimeric rHPIV3s or their parent viruses, and the level of serum HAI antibodies to HPIV3 was determined. Each of the chimeric recombinants bearing the HPIV3 F and HN glycoproteins induced a high level of HAI antibodies to HPIV3, whereas rHPIV3-$F_B HN_B$ and the BPIV3 parent virus bearing the BPIV3 glycoproteins induced 8 to 16-fold less HAI antibody reactive with the human virus. rHPIV3 $L_{B\ T1711I}$, rHPIV3-$N_B$, and rHPIV3-$P_B$ replicated approximately 2 to 10-fold less efficiently in the respiratory tract of rhesus monkeys compared to BPIV3, yet they induced approximately 4 to 32-fold more HPIV3 HAI antibodies, likely because they bear the homologous HPIV3 glycoproteins.

To evaluate the protective efficacy of the chimeric rHPIV3s, monkeys were challenged IN and IT with $10^6$ TCID$_{50}$ of wild type HPIV3. NP and TL samples were collected at 2-day intervals for 10 days post-challenge, and the virus present in the samples was quantified on LLC-MK2 cells. Each of the chimeric recombinants tested afforded a high level of protection against HPIV3 replication, including the highly attenuated rHPIV3-P$_B$ and rHPIV3 L$_{B\ T1711I}$ Analysis of serum samples collected following the challenge showed that each of the groups developed a similar, high titer of HAI antibodies to HPIV3, indicating that all the monkeys had indeed been infected.

The high level of attenuation of rHPIV3-L$_{B\ T1711I}$ in rhesus monkeys reflects the additivity of the restriction of replication specified by host-range sequences of its L gene and one or both of the T1711I and A425V point mutations. The T1711I mutation was shown to confer the ts phenotype in vitro and thus likely also is responsible for the attenuation phenotype in vivo, although a contribution by the A425V mutation cannot be excluded at this time. The increased attenuation of rHPIV3-L$_{B\ T1711I}$ versus rHPIV3-L$_B$ illustrates that ts and host range determinants of attenuation can be combined to fine-tune the level of attenuation of a candidate HPIV2 virus of the invention.

In certain other detailed embodiments of the invention, the recombinant HPIV2 genome or antigenome incorporates a recombinant modification that specifies an attenuating mutation at an amino acid position corresponding to an amino acid position of an attenuating mutation identified in a non-PIV, heterologous, mutant nonsegmented negative stranded RNA virus. In exemplary embodiments, the heterologous, mutant nonsegmented negative stranded RNA virus is respiratory syncytial virus (RSV). In one specific embodiment, the attenuating mutation identified in RSV comprises an amino acid substitution of phenylalanine at position 521 of the RSV L protein, which aligns with a conserved position in the HPIV2, HPIV3, and HPIV1 L proteins. In HPIV2, the conserved target site for mutation corresponds to the Phe460 of the HPIV2 L protein (FIG. 1, Panel A). In one exemplary embodiment, Phe460 of the HPIV2 L protein is substituted to a Leu residue or, alternatively, to another amino acid.

Many of the foregoing exemplary mutations which can be engineered in a recombinant HPIV2 candidate of the invention have been successfully engineered and recovered in recombinant HPIV3 based candidates (Durbin et al., *Virology* 235:323-332, 1997; Skiadopoulos et al., *J. Virol.* 72:1762-1768, 1998; Skiadopoulos et al., *J. Virol.* 73:1374-1381, 1999; U.S. patent application Ser. No. 09/083,793, filed May 22, 1998; U.S. patent application Ser. No. 09/458,813, filed Dec. 10, 1999; U.S. patent application Ser. No. 09/459,062, filed Dec. 10, 1999; U.S. Provisional Application No. 60/047, 575, filed May 23, 1997 (corresponding to International Publication No. WO 98/53078), and U.S. Provisional Application No. 60/059,385, filed Sep. 19, 1997, each incorporated herein by reference). In addition, the above-incorporated references describe construction of chimeric PIV recombinants, e.g., having the HN and F genes of HPIV1 substituted into a partial HPIV3 background genome or antigenome, which is further modified to bear one or more of the attenuating mutations identified in HPIV3 JS cp45. One such chimeric recombinant incorporates all of the attenuating mutations identified in the L gene of cp45. It has since been shown that all of the cp45 mutations outside of the heterologous (HPIV1) HN and F genes can be incorporated in a HPIV3-1 recombinant to yield an attenuated, chimeric candidate.

Yet additional mutations that may be incorporated in recombinant HPIV2 of the invention are mutations, e.g., attenuating mutations, identified in non-PIV pathogens, particularly other nonsegmented negative stranded RNA viruses besides PIV. In each of these contexts, attenuating and other desired mutations identified in one negative stranded RNA virus may be "transferred", e.g., copied, to a corresponding position within the genome or antigenome of a recombinant HPIV2 of the invention. Briefly, desired mutations in one heterologous negative stranded RNA virus are transferred to the recombinant HPIV2 recipient (either in a "vector" HPIV2 genome or antigenome or in the heterologous "donor" gene or genome segment). This involves mapping the mutation in the heterologous mutant virus, identifying by routine sequence alignment the corresponding site in the recipient, recombinant HPIV2, and mutating the native sequence in the recombinant HPIV2, typically to correspond to an identical or conservative mutation to the heterologous mutant genotype, as described in International Application No. PCT/US00/09695, filed Apr. 12, 2000, published as WO 00/61737 on Oct. 19, 2000 corresponding to U.S. National Phase application Ser. No. 09/958,292, filed on Jan. 8, 2002, and claiming priority to U.S. Provisional Patent Application Ser. No. 60/129,006, filed on Apr. 13, 1999, each incorporated herein by reference. Additional description pertaining to this aspect of the invention is provided in Newman et al., *Virus Genes* 24:77-92, 2002; Feller et al., *Virology* 10; 276:190-201, 2000; Skiadopoulos et al., *Virology* 260:125-35, 1999; and Durbin et al., *Virology* 261:319-30, 1999, each incorporated herein by reference.

It is often desired to modify the recipient recombinant HPIV2 genome or antigenome to encode an alteration at the subject site of mutation that corresponds conservatively to the alteration identified in the heterologous mutant virus. For example, if an amino acid substitution marks a site of mutation in the mutant virus compared to the corresponding wild-type sequence, then a similar substitution can be engineered at the corresponding residue(s) in the recombinant HPIV2. Preferably the substitution will specify an identical or conservative amino acid to the substitute residue present in the mutant viral protein. However, it is also possible to alter the native amino acid residue at the site of mutation non-conservatively with respect to the substitute residue in the mutant protein (e.g., by using any other amino acid to disrupt or impair the function of the wild-type residue). Negative stranded RNA viruses from which exemplary mutations are identified and transferred into a recombinant HPIV2 of the invention include other PIVs (e.g., HPIV1, HPIV3, BPIV3 and MPIV1), RSV, Newcastle disease virus (NDV), simian virus 5 (SV5), measles virus (MeV), rinderpest virus, canine distemper virus (CDV), rabies virus (RaV) and vesicular stomatitis virus (VSV), among others.

Attenuating mutations in biologically derived PIV and other nonsegmented negative stranded RNA viruses for incorporation within recombinant HPIV2 of the invention may occur naturally or may be introduced into wild-type PIV strains and thereafter identified and characterized by well known mutagenesis and analytic procedures. For example, incompletely attenuated parental PIV or other heterologous viral mutant strains can be produced by chemical mutagenesis during virus growth in cell cultures to which a chemical mutagen has been added, by selection of virus that has been subjected to passage at suboptimal temperatures in order to introduce growth restriction mutations, or by selection of a mutagenized virus that produces small plaques (sp) in cell culture, as described in the above incorporated references.

By "biologically derived" is meant any virus not produced by recombinant means. Thus, biologically derived PIV include all naturally occurring PIV, including, e.g., naturally occurring PIV having a wild-type genomic sequence and PIV having allelic or mutant genomic variations from a reference wild-type PIV sequence, e.g., PIV having a mutation specifying an attenuated phenotype. Likewise, biologically derived PIV include PIV mutants derived from a parental PIV by, inter alia, artificial mutagenesis and selection procedures not involving direct recombinant DNA manipulation.

As noted above, production of a sufficiently attenuated biologically derived PIV or other viral mutant can be accomplished by several known methods. One such procedure involves subjecting a partially attenuated virus to passage in cell culture at progressively lower, attenuating temperatures. For example, partially attenuated mutants are produced by passage in cell cultures at suboptimal temperatures. Thus, a cold-adapted (ca) mutant or other partially attenuated PIV strain is adapted to efficient growth at a lower temperature by passage in culture. This selection of mutant PIV during cold-passage substantially reduces any residual virulence in the derivative strains as compared to the partially attenuated parent. Alternatively, specific mutations can be introduced into biologically derived PIV by subjecting a partially attenuated parent virus to chemical mutagenesis, e.g., to introduce ts mutations or, in the case of viruses which are already ts, additional ts mutations sufficient to confer increased attenuation and/or stability of the ts phenotype of the attenuated derivative. Means for the introduction of ts mutations into PIV include replication of the virus in the presence of a mutagen such as 5-fluorouridine according to generally known procedures. Other chemical mutagens can also be used. Attenuation can result from a ts mutation in almost any PIV gene, although a particularly amenable target for this purpose has been found to be the polymerase (L) gene. The level of temperature sensitivity of replication in exemplary attenuated PIV for use within the invention is determined by comparing its replication at a permissive temperature with that at several restrictive temperatures. The lowest temperature at which the replication of the virus is reduced 100-fold or more in comparison with its replication at the permissive temperature is termed the shutoff temperature. In experimental animals and humans, both the replication and virulence of PIV correlate with the mutant's shutoff temperature.

From biologically derived PIV and other nonsegmented negative stranded RNA viruses, a large "menu" of attenuating mutations is identifiable by the teachings herein, each of which can be combined with any other mutation(s) for adjusting the level of attenuation, immunogenicity and genetic stability in recombinant HPIV2 of the invention. In this context, many recombinant HPIV2 candidates will include one or more, and preferably two or more, mutations from a biologically derived PIV or other heterologous viral mutant, e.g., any one or combination of mutations identified above from HPIV3 JS cp45, BPIV3, and RSV. Preferred recombinant HPIV2 viruses within the invention will incorporate a plurality of mutations thus identified. Often, these mutations are stabilized against reversion in recombinant HPIV2 by multiple nucleotide substitutions in a codon specifying each mutation.

Mutations compiled into a "menu" as described above are introduced as desired, singly or in combination, to adjust recombinant HPIV2 of the invention to an appropriate level of attenuation, immunogenicity, genetic resistance to reversion from an attenuated phenotype, etc. In accordance with the foregoing description, the ability to produce infectious recombinant HPIV2 from cDNA permits introduction of specific engineered changes within the recombinant HPIV2. In particular, infectious, recombinant HPIV2 viruses can be employed for further identification of specific mutation(s) in biologically derived, attenuated HPIV2 strains, for example mutations that specify ts, ca, att and other phenotypes. Desired mutations identified by this and other methods are introduced into recombinant HPIV2 candidate strains. The capability of producing virus from cDNA allows for routine incorporation of these mutations, individually or in various selected combinations, into a full-length cDNA clone, where after the phenotypes of rescued recombinant viruses containing the introduced mutations to be readily determined.

By identifying and incorporating specific mutations associated with desired phenotypes, e.g., a ca or ts phenotype, into infectious recombinant HPIV2, the invention provides for other, site-specific modifications at, or within close proximity to, the identified mutation. Whereas most attenuating mutations produced in biologically derived PIVs are single nucleotide changes, other "site specific" mutations can also be incorporated by recombinant techniques into a recombinant HPIV2. As used herein, site-specific mutations include insertions, substitutions, deletions or rearrangements of from 1 to 3, up to about 5-15 or more altered nucleotides (e.g., altered from a wild-type PIV sequence, from a sequence of a selected mutant PIV strain, or from a parent recombinant PIV clone subjected to mutagenesis). Such site-specific mutations may be incorporated at, or within the region of, a selected, biologically derived point mutation. Alternatively, the mutations can be introduced in various other contexts within a recombinant HPIV2 clone, for example at or near a cis-acting regulatory sequence or nucleotide sequence encoding a protein active site, binding site, immunogenic epitope, etc.

Site-specific recombinant HPIV2 mutants typically retain a desired attenuating phenotype, but may additionally exhibit altered phenotypic characteristics unrelated to attenuation, e.g., enhanced or broadened immunogenicity, and/or improved growth. Further examples of desired, site-specific mutants include recombinant HPIV2 mutants engineered to incorporate additional, stabilizing nucleotide mutations in a codon specifying an attenuating point mutation. Where possible, two or more nucleotide substitutions are introduced at codons that specify attenuating amino acid changes in a parent mutant or recombinant HPIV2 clone, yielding a recombinant HPIV2 with greater genetic resistance to reversion from an attenuated phenotype. In other embodiments, site-specific nucleotide substitutions, additions, deletions or rearrangements are introduced upstream or downstream, e.g., from 1 to 3, 5-10 and up to 15 nucleotides or more 5' or 3', relative to a targeted nucleotide position, e.g., to construct or ablate an existing cis-acting regulatory element.

In addition to single and multiple point mutations and site-specific mutations, changes to the recombinant HPIV2 disclosed herein include deletions, insertions, substitutions or rearrangements of one or more gene(s) or genome segment(s). Particularly useful are deletions involving one or more gene(s) or genome segment(s), which deletions have been shown to yield additional desired phenotypic effects (see, e.g., U.S. patent application Ser. No. 09/350,821, filed by Durbin et al. on Jul. 9, 1999, incorporated herein by reference). For example, in HPIV1, expression of one or more of the C, C', Y1, and/or Y2 open reading frame(s) (ORF(s) or other auxiliary gene) can be reduced or ablated by modifying the recombinant HPIV1 genome or antigenome, e.g., to incorporate a mutation that alters the coding assignment of an initiation codon or mutation(s) that introduce one or one or more stop codon(s). Alternatively, one or more of the C, C', Y1, and/or Y2 ORF(s) or other auxiliary gene can be deleted in whole or in part to render the corresponding protein(s) partially or entirely non-functional or to disrupt protein expression altogether. Recombinant HPIV2, which lack the C, C', Y1, and/or Y2 ORF(s), can be modified in a similar fashion to delete or reduce expression of a gene, typically by deleting or modifying an auxiliary gene or genome segment, such as the V ORF, and these recombinants will possess highly desirable phenotypic characteristics for development of immunogenic compositions. For example, these modifications may specify one or more desired phenotypic changes including (i) altered growth properties in cell culture, (ii) attenuation in the upper and/or lower respiratory tract of mammals, (iii) a change in viral plaque size, (iv) a change in cytopathic effect, and (v) a change in immunogenicity.

Thus, in more detailed aspects of the instant invention, a recombinant HPIV2 incorporates one or more partial or complete gene deletions, knock out mutations, or mutations that simply reduce or increase expression of an HPIV2 gene. This can be achieved, e.g., by introducing a frame shift mutation or termination codon within a selected coding sequence, altering translational start sites, changing the position of a gene or introducing an upstream start codon to alter its rate of expression, changing GS and/or GE transcription signals to alter phenotype, or modifying an RNA editing site (e.g., growth, temperature restrictions on transcription, etc.). In more detailed aspects of the invention, recombinant HPIV2 viruses are provided in which expression of one or more gene(s), e.g., a V ORF, is ablated at the translational or transcriptional level without deletion of the gene or of a segment thereof, by, e.g., introducing multiple translational termination codons into a translational open reading frame, altering an initiation codon, or modifying an editing site. These forms of knock-out virus will often exhibit reduced growth rates and small plaque sizes in tissue culture. Thus, these methods provide yet additional, novel types of attenuating mutations which ablate expression of a viral gene that is not one of the major viral protective antigens. In this context, knock-out virus phenotypes produced without deletion of a gene or genome segment can be alternatively produced by deletion mutagenesis, as described, to effectively preclude correcting mutations that may restore synthesis of a target protein. Other gene knock-outs can be made using alternate designs and methods that are well known in the art (as described, for example, in (Kretschmer et al., *Virology* 216:309-316, 1996; Radecke et al., *Virology* 217:418-421, 1996; Kato et al., *EMBO J.* 16:578-587, 1987; and Schneider et al., *Virology* 277:314-322, 1996, each incorporated herein by reference).

Nucleotide modifications that may be introduced into recombinant HPIV2 constructs of the invention may alter small numbers of bases (e.g., from 15-30 bases, up to 35-50 bases or more), large blocks of nucleotides (e.g., 50-100, 100-300, 300-500, 500-1,000 bases), or nearly complete or complete genes (e.g., 1,000-1,500 nucleotides, 1,500-2,500 nucleotides, 2,500-5,000, nucleotides, 5,000-6,0000 nucleotides or more) in the vector genome or antigenome or heterologous, donor gene or genome segment, depending upon the nature of the change (i.e., a small number of bases may be changed to insert or ablate an immunogenic epitope or change a small genome segment, whereas large block(s) of bases are involved when genes or large genome segments are added, substituted, deleted or rearranged.

In related aspects, the invention provides for supplementation of mutations adopted into a recombinant HPIV2 clone from biologically derived PIV, e.g., ca and ts mutations, with additional types of mutations involving the same or different genes in a further modified recombinant HPIV2. Each of the HPIV2 genes can be selectively altered in terms of expression levels, or can be added, deleted, substituted or rearranged, in whole or in part, alone or in combination with other desired modifications, to yield a recombinant HPIV2 exhibiting novel characteristics. Thus, in addition to or in combination with attenuating mutations adopted from biologically derived PIV and/or non-PIV mutants, the present invention also provides a range of additional methods for attenuating or otherwise modifying the phenotype of a recombinant HPIV2 based on recombinant engineering of infectious PIV clones. A variety of alterations can be produced in an isolated polynucleotide sequence encoding a targeted gene or genome segment, including a donor or recipient gene or genome segment in a recombinant HPIV2 genome or antigenome for incorporation into infectious clones. More specifically, to achieve desired structural and phenotypic changes in recombinant HPIV2, the invention allows for introduction of modifications which delete, substitute, introduce, or rearrange a selected nucleotide or nucleotide sequence from a parent genome or antigenome, as well as mutations which delete, substitute, introduce or rearrange whole gene(s) or genome segment(s), within a recombinant HPIV2.

Thus provided are modifications in recombinant HPIV2 of the invention which simply alter or ablate expression of a selected gene, e.g., by introducing a termination codon within a selected PIV coding sequence or altering its translational start site or RNA editing site, changing the position of a PIV gene relative to an operably linked promoter, introducing an upstream start codon to alter rates of expression, modifying (e.g., by changing position, altering an existing sequence, or substituting an existing sequence with a heterologous sequence) GS and/or GE transcription signals to alter phenotype (e.g., growth, temperature restrictions on transcription, etc.), and various other deletions, substitutions, additions and rearrangements that specify quantitative or qualitative changes in viral replication, transcription of selected gene(s), or translation of selected protein(s). In this context, any PIV gene or genome segment which is not essential for growth can be ablated or otherwise modified in a recombinant PIV to yield desired effects on virulence, pathogenesis, immunogenicity and other phenotypic characters. In addition to coding sequences, noncoding, leader, trailer and intergenic regions can be similarly deleted, substituted or modified and their phenotypic effects readily analyzed, e.g., by the use of minireplicons, and the recombinant HPIV2 described herein.

In addition to these changes, the order of genes in a recombinant HPIV2 construct can be changed, a PIV genome promoter replaced with its antigenome counterpart or vice versa, portions of genes removed or substituted, and even entire genes deleted. Different or additional modifications in the sequence can be made to facilitate manipulations, such as the insertion of unique restriction sites in various intergenic regions or elsewhere. Nontranslated gene sequences can be removed to increase capacity for inserting foreign sequences.

Other mutations for incorporation into recombinant HPIV2 constructs of the invention include mutations directed toward cis-acting signals, which can be readily identified, e.g., by mutational analysis of PIV minigenomes. For example, insertional and deletional analysis of the leader, trailer and/or flanking sequences identifies viral promoters and transcription signals and provides a series of mutations associated with varying degrees of reduction of RNA replication or transcription. Saturation mutagenesis (whereby each position in turn is modified to each of the nucleotide alternatives) of these cis-acting signals also can be employed to identify many mutations that affect RNA replication or transcription. Any of these mutations can be inserted into a chimeric PIV antigenome or genome as described herein. Evaluation and manipulation of trans-acting proteins and cis-acting RNA sequences using the complete antigenome cDNA is assisted by the use of PIV minigenomes as described in the above-incorporated references.

Additional mutations within recombinant HPIV2 viruses of the invention may also include replacement of the 3' end of genome with its counterpart from antigenome or vice versa, which is associated with changes in RNA replication and transcription. In one exemplary embodiment, the level of expression of specific PIV proteins, such as the protective HN and/or F antigens, can be increased by substituting the natural sequences with ones which have been made synthetically and designed to be consistent with efficient translation. In this context, it has been shown that codon usage can be a major factor in the level of translation of mammalian viral proteins (Haas et al., *Current Biol.* 6:315-324, 1996, incorporated herein by reference). Optimization by recombinant methods of the codon usage of the mRNAs encoding the HN and F proteins of recombinant HPIV2 will provide improved expression for these genes.

In another exemplary embodiment, a sequence surrounding a translational start site (preferably including a nucleotide in the −3 position relative to the AUG start site) of a selected HPIV2 gene or donor gene incorporated in an HPIV2 vector is modified, alone or in combination with introduction of an upstream start codon, to modulate gene expression by specifying up- or down-regulation of translation. Alternatively, or in combination with other recombinant modifications disclosed herein, gene expression of a recombinant HPIV2 can be modulated by altering a transcriptional GS or GE signal of any selected gene(s) of the virus. In alternative embodiments, levels of gene expression in a recombinant HPIV2 candidate are modified at the level of transcription. In one aspect, the position of a selected gene in the PIV gene map can be changed to a more promoter-proximal or promoter-distal position, whereby the gene will be expressed more or less efficiently, respectively. According to this aspect, modulation of expression for specific genes can be achieved yielding reductions or increases of gene expression from two-fold, more typically four-fold, up to ten-fold or more compared to wild-type levels often attended by a commensurate decrease in expression levels for reciprocally, positionally substituted genes. These and other transpositioning changes yield novel recombinant HPIV2 viruses having attenuated phenotypes, for example due to decreased expression of selected viral proteins involved in RNA replication, or having other desirable properties such as increased antigen expression.

In other embodiments, recombinant HPIV2 viruses useful in immunogenic compositions can be conveniently modified to accommodate antigenic drift in circulating virus. Typically the modification will be in the HN and/or F proteins. An entire HN or F gene, or a genome segment encoding a particular immunogenic region thereof, from one PIV (HPIV2 or another HPIV) strain or group is incorporated into a recombinant HPIV2 genome or antigenome cDNA by replacement of a corresponding region in a recipient clone of a different PIV strain or group, or by adding one or more copies of the gene, such that multiple antigenic forms are represented. Progeny virus produced from the modified recombinant HPIV2 can then be used in immunization protocols against emerging PIV strains.

In certain aspects of the invention, replacement of a HPIV2 coding sequence or non-coding sequence (e.g., a promoter, gene-end, gene-start, intergenic or other cis-acting element) with a heterologous (e.g., non-HPIV2) counterpart yields chimeric HPIV2 having a variety of possible attenuating and other phenotypic effects. For example, host range and other desired effects can be engineered by importing a bovine PIV3 (BPIV3) or murine PIV1 (MPIV 1) protein, SV5, SV41, NDV, protein domain, gene or genome segment into a recombinant HPIV2 "background" genome or antigenome, wherein the bovine or murine gene does not function efficiently in a human cell, e.g., from incompatibility of the heterologous sequence or protein with a biologically interactive HPIV sequence or protein (i.e., a sequence or protein that ordinarily cooperates with the substituted sequence or protein for viral transcription, translation, assembly, etc.) or, more typically in a host range restriction, with a cellular protein or some other aspect of the cellular milieu which is different between the permissive and less permissive host. In exemplary embodiments, bovine PIV sequences are selected for introduction into HPIV2 based on known aspects of bovine and heterologous human PIV structure and function.

In more detailed aspects, the invention provides methods for attenuating recombinant HPIV2 candidates based on the construction of chimeras between HPIV2 and a non-human PIV, for example MPIV1 (Sendai virus), BPIV3, SV5, SV41, and NDV (e.g., as disclosed in U.S. patent application Ser. No. 09/586,479, filed Jun. 1, 2000 by Schmidt et al. (corresponding to PCT Publication WO 01/04320); Schmidt et al., *J. Virol.* 74:8922-9, 2000, each incorporated herein by reference). This method of attenuation is based on host range effects due to the introduction of one or more gene(s) or genome segment(s) of the non-human PIV into a human PIV vector-based chimeric virus. For example, there are numerous nucleotide and amino acid sequence differences between BPIV and HPIVs, which are reflected in host range differences. Between HPIV3 and BPIV3 the percent amino acid identity for each of the following proteins is: N (86%), P (65%), M (93%), F (83%), HN (77%), and L (91%). The host range difference is exemplified by the highly permissive growth of HPIV3 in rhesus monkeys, compared to the restricted replication of two different strains of BPIV3 in the same animal (van Wyke Coelingh et al., *J. Infect. Dis.* 157: 655-662, 1988, incorporated herein by reference). Although the basis of the host range differences between HPIV3 and BPIV3 remains to be fully elucidated, it has been shown to involve multiple gene and multiple amino acid differences. The involvement of multiple genes and possibly cis-acting regulatory sequences, each involving multiple amino acid or nucleotide differences, gives a broad basis for attenuation, one which is highly stable to reversion. This is in contrast to the situation with other live attenuated HPIV3 viruses that are attenuated by one or several point mutations. In this case, reversion of any individual mutation may yield a significant reacquisition of virulence or, in a case where only a single residue specified attenuation, complete reacquisition of virulence. In exemplary embodiments of the invention, the recombinant HPIV2 genome or antigenome is combined with a heterologous gene or genome segment, such as an N, P, M, or L, ORF derived from a BPIV3, or another animal paramyxoviruses.

The above-incorporated references disclose that HPIV3/BPIV3 chimeric recombinants involving both bovine PIV3 strains Kansas (Ka) and shipping fever (SF) are viable and replicate as efficiently in cell culture as either HPIV3 or BPIV3 parent—indicating that the chimeric recombinants did not exhibit gene incompatibilities that restricted replication in vitro. This property of efficient replication in vitro is important since it permits efficient manufacture of this biological. Also, the Ka and the SF HPIV3/BPIV3 chimeric recombinants (termed cKa and cSF), bearing only one bovine gene, are nearly equivalent to their BPIV3 parents in the degree of host range restriction in the respiratory tract of the rhesus monkey. In particular, the cKa and cSF viruses exhibit approximately a 60-fold or 30-fold reduction, respectively, in replication in the upper respiratory tract of rhesus monkeys compared to replication of HPIV3. Based on this finding, it is expected that other BPIV3 genes will also confer desired levels of host range restriction within chimeric HPIV2 candidates of the invention. Thus, according to the methods herein, a list of attenuating determinants will be readily identified in heterologous genes and genome segments of BPIV3 and other non-human PIVs that will confer, in appropriate combination, a desired level of host range restriction and immunogenicity on recombinant HPIV2 viruses.

Chimeric human-bovine or human-murine recombinant HPIV2 are therefore provided herein that include a partial or complete "background" HPIV2 genome or antigenome derived from or patterned after HPIV2 combined with one or more heterologous gene(s) or genome segment(s) of a non-human PIV to form the chimeric PIV genome or antigenome. In preferred aspects of the invention, chimeric HPIV2 of this type incorporate a partial or complete HPIV2 background genome or antigenome combined with one or more heterologous gene(s) or genome segment(s), e.g., from a bovine PIV. The partial or complete background genome or antigenome typically acts as a recipient backbone into which the heterologous genes or genome segments of the counterpart, non-human PIV are incorporated. Heterologous genes or genome segments from the counterpart PIV represent "donor" genes or polynucleotides that are combined with, or substituted within, the background genome or antigenome to yield a chimeric HPIV2 that exhibits novel phenotypic characteristics compared to one or both of the contributing PIVs. For example, addition or substitution of heterologous genes or genome segments within a selected recipient HPIV2 strain may result in an increase or decrease in attenuation, growth changes, altered immunogenicity, or other desired phenotypic changes as compared with a corresponding phenotype(s) of the unmodified recipient and/or donor (U.S. patent application Ser. No. 09/586,479, filed Jun. 1, 2000 by Schmidt et al.; Schmidt et al., J. Virol. 74:8922-9, 2000, each incorporated herein by reference).

Genes and genome segments that may be selected for use as heterologous substitutions or additions within chimeric PIV vectors include genes or genome segments encoding a PIV N, V, P, M, F, HN and/or L protein(s) or portion(s) thereof. In addition, genes and genome segments encoding proteins found in other PIV viruses, as well as non-PIV proteins (e.g., an SH protein as found in mumps, RSV, and SV5 viruses), may be incorporated within additional chimeric HPIV2 recombinants of the invention. Regulatory regions, such as the extragenic 3' leader or 5' trailer regions, and gene-start, gene-end, intergenic regions, or 3' or 5' non-coding regions, are also useful as heterologous substitutions or additions. In exemplary aspects, chimeric HPIV2 bearing one or more bovine or murine PIV gene(s) or genome segment(s) exhibit a high degree of host range restriction, e.g., in the respiratory tract of mammalian models of human PIV infection such as hamsters and non-human primates. In more detailed embodiments HPIV2 is attenuated by the addition or substitution of one or more bovine PIV3 gene(s) or genome segment(s) selected from N, M, L, V, and P genes and genome segments to a partial or complete HPIV2 background genome or antigenome.

Preferably, the degree of host range restriction exhibited by human-bovine and other chimeric HPIV2 for use as candidates of the invention is comparable to the degree of host range restriction exhibited by the respective non-human PIV or other "donor" strain. Preferably, the restriction should have a true host range phenotype, i.e., it should be specific to the host in question and should not restrict replication in vitro in a suitable cell line. In addition, chimeric HPIV2 bearing one or more bovine or murine PIV gene(s) or genome segment(s) elicit a desired immunogenic response in hosts susceptible to HPIV2 infection. Thus, the invention provides a new basis for attenuating a live HPIV2 virus vector for developing immunogenic compositions against HPIV2 and other pathogens based on host range effects.

In combination with the host range phenotypic effects provided in the human-non-human chimeric HPIV2 of the invention, it is often desirable to adjust the attenuation phenotype by introducing additional mutations that increase or decrease attenuation of the chimeric virus. Thus, in additional aspects of the invention, attenuated, human-bovine or human-murine chimeric HPIV2 are produced in which the chimeric genome or antigenome is further modified by introducing one or more attenuating mutations specifying an attenuating phenotype in the resultant virus or subviral particle. These can include mutations generated de novo and tested for attenuating effects according to a rational design mutagenesis strategy. Alternatively, the attenuating mutations may be identified in existing biologically derived mutant PIV and non-PIV viruses and thereafter incorporated into a human-bovine or human-murine chimeric HPIV2 of the invention. Exemplary mutations specify lesions in RNA regulatory sequences or in encoded proteins.

In preferred chimeric HPIV2 candidates of the invention, attenuation marked by replication in the lower and/or upper respiratory tract in an accepted animal model that is reasonably correlated with PIV replication and immunogenic activity in humans (e.g., hamsters, rhesus monkeys or chimpanzees), is reduced by at least about two-fold, more often about 5-fold, 10-fold, or 20-fold, and preferably 50-100-fold and up to 1,000-fold or greater overall (e.g., as measured between 3-8 days following infection) compared to growth of the corresponding wild-type or mutant parental PIV strain.

Figure 2:
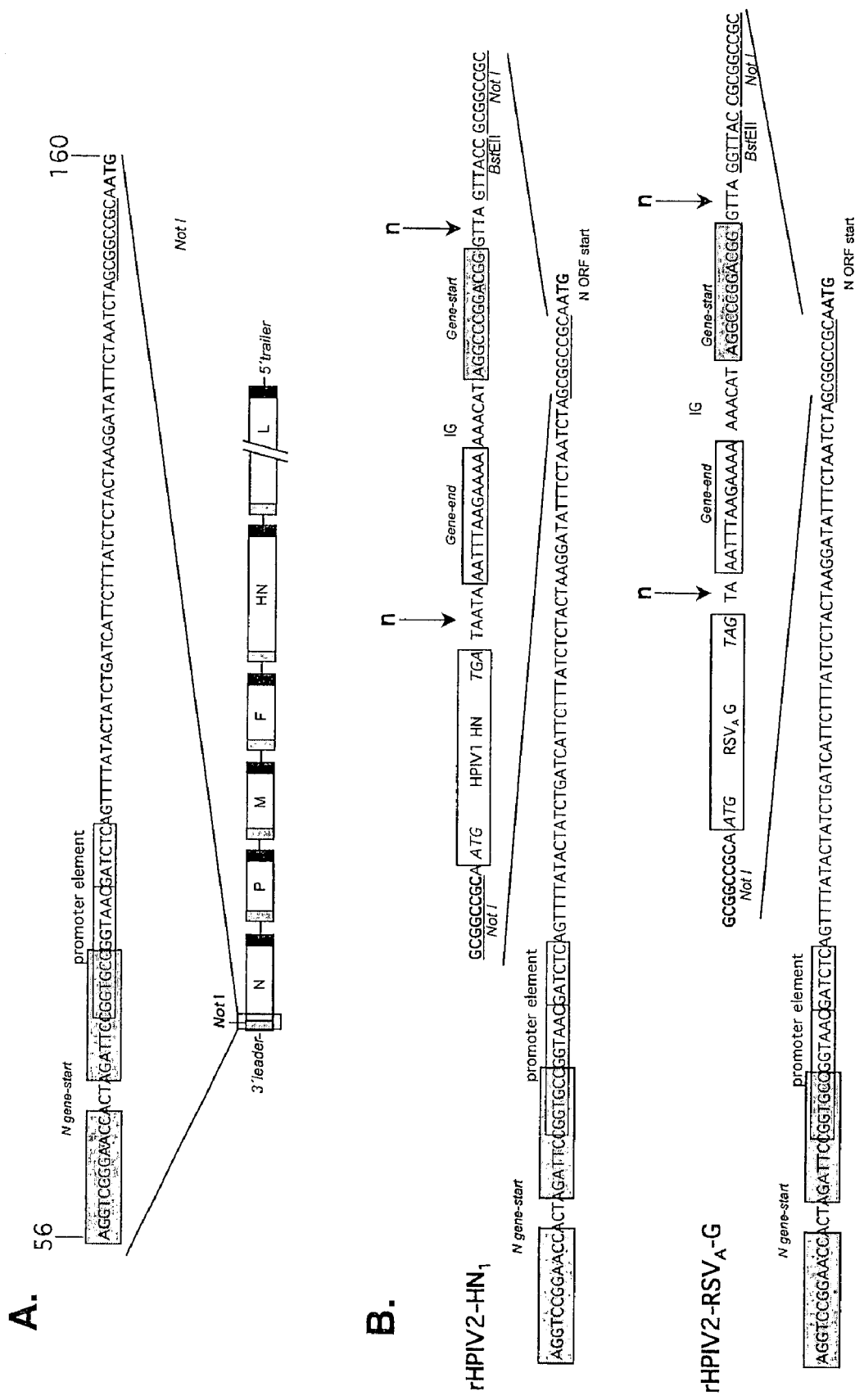
FIG. 2 illustrates modification of HPIV2 for use as a vector of other viral antigens. Panel A: Diagram (not to scale) of the HPIV2 genome illustrating the placement of a unique promoter-proximal Not I restriction site. The location of HPIV2/V94 nts 56-160 in the complete genome diagram is indicated with a box, and the sequence is shown above (SEQ ID NO.

Within the methods of the invention, additional genes or genome segments may be inserted into or proximate to a recombinant or chimeric HPIV2 genome or antigenome. For example, various supernumerary heterologous gene(s) or genome segment(s) can be inserted at any of a variety of sites within the recombinant genome or antigenome, for example at a position 3' to N, between the N/P, P/M, and/or HN/L genes, or at another intergenic junction or non-coding region of the HPIV2 vector genome or antigenome. Exemplary gene insertion details are illustrated in FIG. 2. The inserted genes may be under common control with recipient genes, or may be under the control of an independent set of transcription signals. Genes of interest in this context include genes encoding cytokines, for example, an interleukin (IL-2 through IL-18, e.g., interleukin 2 (IL-2), interleukin 4 (IL-4), interleukin 5 (IL-5), interleukin 6 (IL6), interleukin 18 (IL-18), tumor necrosis factor alpha (TNFα), interferon gamma (IFNγ), or granulocyte-macrophage colony stimulating factor (GM-CSF), as well as (see, e.g., U.S. application Ser. No. 09/614,285, filed Jul. 12, 2000 and priority U.S. Provisional Application Ser. No. 60/143,425 filed Jul. 13, 1999, each incorporated herein by reference). Coexpression of these additional proteins provides the ability to modify and improve immune responses against recombinant HPIV2 of the invention quantitatively and/or qualitatively.

In other aspects of the invention, insertion of heterologous nucleotide sequences into recombinant HPIV2 candidates are employed separately to modulate the level of attenuation of candidate recombinants, e.g., for the upper respiratory tract.

Thus, it is possible to insert nucleotide sequences into a recombinant HPIV2 that both direct the expression of a foreign protein and that attenuate the virus in an animal host, or to use nucleotide insertions separately to attenuate candidate viruses. To define some of the rules that govern the effect of gene insertion on attenuation, gene units of varying lengths may be inserted into a wild type HPIV2 backbone and the effects of gene unit length on attenuation examined. Novel gene unit insertions are contemplated in this regard that do not contain a significant ORF, permitting identification of the effect of gene unit length independently of an effect of the expressed protein of that gene. These heterologous sequences may be inserted as an extra gene unit of various sizes, e.g., from about 150 or more nts in length up to 3,000 nts or more in length. As demonstrated herein, gene insertions or extensions larger than about 3,000 nts in length.

Gene unit (GU) insertions of about 1,000 or 2,000 nts in length will substantially attenuate rHPIV2 candidates for the upper respiratory tract of mammalian subjects. In addition, gene unit insertions can have the dual effect of both attenuating a candidate virus and inducing an immunogenic response against a second virus. Alternately, gene extensions in the 3'-noncoding region (NCR) of a HPIV2 gene, which cannot express additional proteins, can also be attenuating in and of themselves. Within these methods of the invention, gene insertion length is a determinant of attenuation.

GU and NCR insertions within recombinant HPIV2 of the invention produce an attenuation phenotype characterized by efficient replication in vitro and decreased replication in vivo, a phenotype not previously described for other paramyxovirus insertions. The mechanism of attenuation resulting from a GU insertion may result from one or more of the following factors acting predominantly in vivo. The addition of an extra gene unit may decrease the level of transcription of downstream genes since there is a transcriptional gradient in which more promoter-proximal genes are transcribed at a higher rate than the more promoter-distal genes. The decreased expression of the downstream gene products resulting from the decreased abundance of their mRNAs could result in attenuation if their gene product is limiting or if a specific ratio of gene products that is required for efficient replication is altered. It is thought that the transcription gradient is a consequence of the transcriptase complex falling off the template during transcription as well as during the transfer across gene junctions. Alternatively, the increase in the overall length of the genome and the extra mRNAs transcribed may increase the level of viral double stranded RNA made which in turn may induce a higher level of the antiviral activity of the interferon system. Finally, the overall level of genome replication may be reduced due to the increase in length of the genome and the antigenome. This may result from a disengagement of replicase complexes from the template during replication of the genomic RNA or antigenomic RNA. The decreased amount of genome available for packaging into virions may result in a decrease in virus yield that results in attenuation.

The mechanism of attenuation resulting from a NCR insertion may result from one or more of the following factors. The extra length of the 3'-end of HN mRNA resulting from the NCR insertion may contribute to the instability of the mRNA and lead to a decrease in the expression of the HN protein. Alternatively, the increase in the overall length of the genome and the extra length of the HN mRNA may increase the level of viral double stranded RNA made that can induce a higher level of the antiviral activity of the interferon system. Alternatively or additionally, the overall level of genome replication may be reduced due to the increase in length of the genome and the antigenome. This may result from a disengagement of replicase complexes from the template during replication of the genomic RNA or antigenomic RNA. The decreased amount of genome available for packaging into virions could result in a decrease in virus yield that results in attenuation. Finally, the addition of extra nucleotides to the 3' end of the HN gene could decrease the level of transcription of downstream genes since the transcriptase complex could fall off the template during transcription of the extra nucleotides at the 3' end of the HN gene.

Deletions, insertions, substitutions and other mutations involving changes of whole viral genes or genome segments within rHPIV2 of the invention yield highly stable candidates, which are particularly important in the case of immunosuppressed individuals. Many of these changes will result in attenuation of resultant strains, whereas others will specify different types of desired phenotypic changes. For example, accessory (i.e., not essential for in vitro growth) genes are excellent candidates to encode proteins that specifically interfere with host immunity (see, e.g., Kato et al., *EMBO. J.* 16:578-87, 1997, incorporated herein by reference). Ablation of such genes in candidate viruses is expected to reduce virulence and pathogenesis and/or improve immunogenicity.

In more detailed embodiments of the invention, chimeric HPIV2 viruses are constructed using a HPIV2 "vector" genome or antigenome that is recombinantly modified to incorporate one or more antigenic determinants of a heterologous pathogen. The vector genome or antigenome is comprised of a partial or complete HPIV2 genome or antigenome, which may itself incorporate nucleotide modifications such as attenuating mutations. The vector genome or antigenome is modified to form a chimeric structure through incorporation of a heterologous gene or genome segment. More specifically, chimeric HPIV2 viruses of the invention are constructed through a cDNA-based virus recovery system that yields recombinant viruses that incorporate a partial or complete vector or "background" HPIV2 genome or antigenome combined with one or more "donor" nucleotide sequences encoding the heterologous antigenic determinant(s). In exemplary embodiments a HPIV2 vector genome or antigenome is modified to incorporate one or more genes or genome segments that encode antigenic determinant(s) of one or more heterologous PIVs (e.g., HPIV1 and/or HPIV3), and/or a non-PIV pathogen (e.g., RSV, human metapneumovirus, or measles virus). Thus constructed, chimeric HPIV2 viruses of the invention may elicit an immune response against a specific PIV, e.g., HPIV1, HPIV2, and/or HPIV3, or against a non-PIV pathogen. Alternatively, compositions and methods are provided employing a HPIV2-based chimeric virus to elicit a polyspecific immune response against multiple PIVs, e.g., HPIV2 and HPIV3, or against one or more HPIVs and a non-PIV pathogen such as measles virus. Exemplary construction of a chimeric, vector HPIV2 candidate virus is illustrated in FIG. 2.

In preferred aspects of the invention, a chimeric HPIV2 in this context incorporates a partial or complete human HPIV2 incorporating one or more heterologous polynucleotide(s) encoding one or more antigenic determinants of the heterologous pathogen, which polynucleotides may be added to or substituted within the HPIV2 vector genome or antigenome to yield the chimeric HPIV2 recombinant. The chimeric HPIV2 virus thus acquires the ability to elicit an immune response in a selected host against the heterologous pathogen. In addition, the chimeric virus may exhibit other novel phenotypic characteristics compared to one or both of the vector PIV and heterologous pathogens.

The partial or complete vector genome or antigenome generally acts as a backbone into which heterologous genes or genome segments of a different pathogen are incorporated. Often, the heterologous pathogen is a different PIV from which one or more gene(s) or genome segment(s) is/are combined with, or substituted within, the vector genome or antigenome. In addition to providing novel immunogenic characteristics, the addition or substitution of heterologous genes or genome segments within the vector HPIV2 strain may confer an increase or decrease in attenuation, growth changes, or other desired phenotypic changes as compared with the corresponding phenotype(s) of the unmodified vector and donor viruses.

Heterologous genes or genome segments of one PIV or non-PIV virus may be added as a supernumerary genomic element to a partial or complete genome or antigenome of HPIV2. Alternatively, one or more heterologous gene(s) or genome segment(s) of one PIV may be substituted at a position corresponding to a wild-type gene order position of a counterpart gene(s) or genome segment(s) that is deleted within the HPIV2 vector genome or antigenome. In yet additional embodiments, the heterologous gene or genome segment is added or substituted at a position that is more promoter-proximal or promotor-distal compared to a wild-type gene order position of the counterpart gene or genome segment within the vector genome or antigenome to enhance or reduce, respectively, expression of the heterologous gene or genome segment.

The introduction of heterologous immunogenic proteins, protein domains and immunogenic epitopes to produce chimeric HPIV2 is particularly useful to generate novel immune responses in an immunized host. Addition or substitution of an immunogenic gene or genome segment from one, donor pathogen within a recipient HPIV2 vector genome or antigenome can generate an immune response directed against the donor pathogen, the HPIV2 vector, or against both the donor pathogen and vector.

General methods and compositions useful for engineering chimeric PIV viruses have been developed for HPIV3 (Durbin et al., *Virology* 235:323-332, 1997; Skiadopoulos et al., *J. Virol.* 72:1762-1768, 1998; Tao et al., *J Virol* 72:2955-2961, 1998; Skiadopoulos et al., *J. Virol.* 73:1374-1381, 1999; Skiadopoulos et al., *Vaccine* 18:503-510, 1999; Tao et al., *Vaccine* 17:1100-1108, 1999; Tao et al., *Vaccine* 18:1359-1366, 2000; U.S. patent application Ser. No. 09/083,793, filed May 22, 1998; U.S. patent application Ser. No. 09/458,813, filed Dec. 10, 1999; U.S. patent application Ser. No. 09/459,062, filed Dec. 10, 1999; U.S. Provisional Application No. 60/047,575, filed May 23, 1997 (corresponding to International Publication No. WO 98/53078), and U.S. Provisional Application No. 60/059,385, filed Sep. 19, 1997, each incorporated herein by reference). In particular, the above-incorporated references describe construction of chimeric PIV recombinants, e.g., having the HN and F genes of HPIV1 substituted into a partial HPIV3 background genome or antigenome, which is further modified to bear one or more of the attenuating mutations identified in HPIV3 JS cp45. One such chimeric recombinant incorporates all of the attenuating mutations identified in the L gene of cp45 outside of the heterologous (HPIV1) HN and F genes, yielding an attenuated, chimeric candidate.

However, it has been reported that prior infection with HPIV3 partially restricts both the immunogenicity of HPIV3-1 recombinant viruses and the efficacy of such viruses against subsequent HPIV1 challenge. This restriction appears to be due to an immune response against the HPIV3 internal proteins that are shared by the two viruses (Tao et al., *Vaccine* 17:1100-1108, 1999; Tao et al., *Vaccine* 18:1359-1366, 2000, each incorporated herein by reference). The immune response against the internal HPIV3 proteins was short-lived and did not appear to contribute to long-term efficacy, but it might be sufficient to interfere with sequential immunizations spaced at relatively short intervals such as two months, as is envisioned for the live-attenuated RSV and PIV immunogenic compositions (see Introduction). The HPIV2 reverse genetics system described here resolves this problem by providing live-attenuated HPIV2 that will be infectious and immunogenic in infants that have been previously exposed to HPIV3, as well as other viruses such as RSV.

Chimeric HPIV2 of the invention may also be constructed that express a chimeric protein, for example an immunogenic glycoprotein having a cytoplasmic tail and/or transmembrane domain specific to a HPIV2 vector fused to a heterologous ectodomain of a different PIV or non-PIV pathogen to provide a fusion protein that elicits an immune response against the heterologous pathogen. For example, a heterologous genome segment encoding a glycoprotein ectodomain from a HPIV1 or HPIV3 HN or F glycoprotein may be joined with a genome segment encoding the corresponding HPIV2 HN or F glycoprotein cytoplasmic and transmembrane domains to form a HPIV2-1 or HPIV2-3 chimeric glycoprotein that elicits an immune response against HPIV1 or HPIV3.

Briefly, HPIV2 of the invention expressing a chimeric glycoprotein comprise a major nucleocapsid (N) protein, a nucleocapsid phosphoprotein (P), a large polymerase protein (L), and a HPIV2 vector genome or antigenome that is modified to encode a chimeric glycoprotein. The chimeric glycoprotein incorporates one or more heterologous antigenic domains, fragments, or epitopes of a second, antigenically distinct HPIV. Preferably, this is achieved by substitution within the HPIV2 vector genome or antigenome of one or more heterologous genome segments of the second HPIV that encode one or more antigenic domains, fragments, or epitopes, whereby the genome or antigenome encodes the chimeric glycoprotein that is antigenically distinct from the parent, vector virus.

In more detailed aspects, the heterologous genome segment or segments preferably encode a glycoprotein ectodomain or immunogenic portion or epitope thereof, and optionally include other portions of the heterologous or "donor" glycoprotein, for example both an ectodomain and transmembrane region that are substituted for counterpart glycoprotein ecto- and transmembrane domains in the vector genome or antigenome. Preferred chimeric glycoproteins in this context may be selected from HPIV HN and/or F glycoproteins, and the vector genome or antigenome may be modified to encode multiple chimeric glycoproteins. In preferred embodiments, the HPIV2 vector genome or antigenome is a partial genome or antigenome and the second, antigenically distinct HPIV is either HPIV1 or HPIV3. In one exemplary embodiment, both glycoprotein ectodomain(s) of HPIV1 or HPIV3 HN and F glycoproteins are substituted for corresponding HN and F glycoprotein ectodomains in the HPIV2 vector genome or antigenome. In another exemplary embodiment, HPIV1 or HPIV3 ectodomain and transmembrane regions of one or both HN and/or F glycoproteins are fused to one or more corresponding HPIV2 cytoplasmic tail region(s) to form the chimeric glycoprotein. Further details concerning these aspects of the invention are provided in U.S. patent application Ser. No. 09/459,062, filed on Dec. 10, 1999 by Tao et al., incorporated herein by reference.

As used herein, the term "gene" generally refers to a portion of a subject genome, e.g., a HPIV2 genome, encoding an mRNA and typically begins at the upstream end with a gene-start (GS) signal and ends at the downstream end with the gene-end (GE) signal. The term gene is also interchangeable with the term "translational open reading frame", or ORF, particularly in the case where a protein, such as the C protein, is expressed from an additional ORF rather than from a unique mRNA. The viral genome of all PIVs also contains extragenic leader and trailer regions, possessing part of the promoters required for viral replication and transcription, as well as non-coding and intergenic regions. Transcription initiates at the 3' end and proceeds by a sequential stop-start mechanism that is guided by short conserved motifs found at the gene boundaries. The upstream end of each gene contains a gene-start (GS) signal, that directs initiation of its respective mRNA. The downstream terminus of each gene contains a gene-end (GE) motif that directs polyadenylation and termination.

To construct chimeric HPIV2 viruses of the invention, one or more PIV gene(s) or genome segment(s) may be deleted, inserted or substituted in whole or in part. This means that partial or complete deletions, insertions and substitutions may include open reading frames and/or cis-acting regulatory sequences of any one or more of the PIV genes or genome segments. By "genome segment" is meant any length of continuous nucleotides from the PIV genome, which might be part of an ORF, a gene, or an extragenic region, or a combination thereof. When a subject genome segment encodes an antigenic determinant, the genome segment encodes at least one immunogenic epitope capable of eliciting a humoral or cell mediated immune response in a mammalian host. The genome segment may also encode an immunogenic fragment or protein domain. In other aspects, the donor genome segment may encode multiple immunogenic domains or epitopes, including recombinantly synthesized sequences that comprise multiple, repeating or different, immunogenic domains or epitopes.

Exemplary genome sequences of heterologous viruses for use within these aspects of the invention have been described for the human PIV3 strains JS (GenBank accession number Z11575, incorporated herein by reference) and Washington (Galinski M. S. In Kingsbury, D. W. (Ed.), *The Paramyxoviruses*, pp. 537-568, Plenum Press, New York, 1991, incorporated herein by reference); for HPIV1/Wash64 (GenBank accession number AF457102, incorporated herein by reference); for the bovine PIV3 (BPIV3) strain 910N (GenBank accession number D80487, incorporated herein by reference); for BPIV3 Kansas (GenBank accession number AF178654, incorporated herein by reference); for BPIV Shipping fever (GenBank accession number AF178655, incorporated herein by reference); for RSV A2 (GenBank accession number AF035006, incorporated herein by reference); and for hMPV (GenBank accession number AF371337, incorporated herein by reference).

In preferred embodiments of the invention, the chimeric HPIV2 bears one or more major antigenic determinants of a human PIV, or multiple human PIVs, including HPIV1, HPIV2 and/or HPIV3. These preferred candidates elicit an effective immune response in humans against one or more selected HPIVs. As noted above, the antigenic determinant(s) that elicit(s) an immune response against HPIV may be encoded by the HPIV2 vector genome or antigenome, or may be inserted within or joined to the PIV vector genome or antigenome as a heterologous gene or gene segment. The major protective antigens of human PIVs are their HN and F glycoproteins. However, all PIV genes are candidates for encoding antigenic determinants of interest, including internal protein genes that may encode such determinants as, for example, CTL epitopes.

Preferred chimeric HPIV2 candidate viruses of the invention bear one or more major antigenic determinants from each of a plurality of HPIVs or from a HPIV and a non-PIV pathogen. Chimeric HPIV2 viruses thus constructed include one or more heterologous gene(s) or genome segment(s) encoding antigenic determinant(s) of the same or a heterologous (for example HPIV1 or HPIV3) PIV. These and other constructs yield chimeric PIVs that elicit either a mono- or poly-specific immune response in humans to one or more HPIVs. Further detailed aspects of the invention are provided in U.S. patent application Ser. No. 09/083,793, filed May 22, 1998; U.S. patent application Ser. No. 09/458,813, filed Dec. 10, 1999; U.S. patent application Ser. No. 09/459,062, filed Dec. 10, 1999; U.S. Provisional Application No. 60/047,575, filed May 23, 1997 (corresponding to International Publication No. WO 98/53078), U.S. Provisional Application No. 60/059,385, filed Sep. 19, 1997; U.S. Provisional Application No. 60/170,195 filed Dec. 10, 1999; and U.S. patent application Ser. No. 09/733,692, filed Dec. 8, 2000 (corresponding to International Publication No. WO 01/42445A2), each incorporated herein by reference.

In other exemplary aspects of the invention, chimeric HPIV2 incorporate a HPIV2 vector genome or antigenome modified to express one or more major antigenic determinants of non-PIV pathogen, for example measles virus. The methods of the invention are generally adaptable for incorporation of antigenic determinants from a wide range of additional pathogens within chimeric HPIV2 candidates. In this regard the invention also provides for development of candidates against subgroup A and subgroup B respiratory syncytial viruses (RSV), HMPV, measles virus, human metapneumoviruses, mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses and influenza viruses, among other pathogens. Pathogens that may be targeted for development of immunogenic compositions according to the methods of the invention include viral and bacterial pathogens, as well as protozoans and multicellular pathogens. Useful antigenic determinants from many important human pathogens in this context are known or readily identified for incorporation within chimeric HPIV2 of the invention. Thus, major antigens have been identified for the foregoing exemplary pathogens, including the measles virus HA and F proteins; the F, G, SH and M2 proteins of RSV, mumps virus HN and F proteins, human papilloma virus L1 protein, type 1 or type 2 human immunodeficiency virus gp160 protein, herpes simplex virus and cytomegalovirus gB, gC, gD, gE, gG, gH, gI, gJ, gK, gL, and gM proteins, rabies virus G protein, human metapneuomovirus F and G proteins, Epstein Barr Virus gp350 protein; filovirus G protein, bunyavirus G protein, flavivirus E and NS1 proteins, and alphavirus E protein. These major antigens, as well as other antigens known in the art for the enumerated pathogens and others, are well characterized to the extent that many of their antigenic determinants, including the full length proteins and their constituent antigenic domains, fragments and epitopes, are identified, mapped and characterized for their respective immunogenic activities.

Among the numerous, exemplary mapping studies that identify and characterize major antigens of diverse pathogens for use within the invention are epitope mapping studies directed to the hemagglutinin-neuraminidase (HN) gene of HPIV3 (van Wyke Coelingh et al., *J. Virol.* 61:1473-1477, 1987, incorporated herein by reference). This report provides detailed antigenic structural analyses for 16 antigenic variants of HPIV3 variants selected by using monoclonal antibodies (MAbs) to the HN protein that inhibit neuraminidase, hemagglutination, or both activities. Each variant possessed a single-point mutation in the HN gene, coding for a single amino acid substitution in the HN protein. Operational and topographic maps of the HN protein correlated well with the relative positions of the substitutions. Computer-assisted analysis of the HN protein predicted a secondary structure composed primarily of hydrophobic β sheets interconnected by random hydrophilic coil structures. The HN epitopes were located in predicted coil regions. Epitopes recognized by MAbs which inhibit neuraminidase activity of the virus were located in a region which appears to be structurally conserved among several paramyxovirus HN proteins and which may represent the sialic acid-binding site of the HN molecule.

This exemplary work, employing conventional antigenic mapping methods, identified single amino acids that are important for the integrity of HN epitopes. Most of these epitopes are located in the C-terminal half of the molecule, as expected for a protein anchored at its N terminus (Elango et al., *J. Virol.* 57:481-489, 1986). Previously published operational and topographic maps of the PIV3 HN indicated that the MAbs employed recognized six distinct groups of epitopes (I to VI) organized into two topographically separate sites (A and B), which are partially bridged by a third site (C). These groups of epitopes represent useful candidates for antigenic determinants that may be incorporated, alone or in various combinations, within chimeric HPIV2 viruses of the invention. (See, also, Coelingh et al., *Virology* 143:569-582, 1985; Coelingh et al., *Virology* 162:137-143, 1988; Ray et al., *Virology* 148:232-236, 1986; Rydbeck et al., *J. Gen. Virol.* 67:1531-1542, 1986, each incorporated herein by reference).

Additional studies by van Wyke Coelingh et al. (*J. Virol.* 63:375-382, 1989) provide further information relating to selection of PIV antigenic determinants for use within the invention. In this study, twenty-six monoclonal antibodies (MAbs) (14 neutralizing and 12 nonneutralizing) were used to examine the antigenic structure, biological properties, and natural variation of the fusion (F) glycoprotein of HPIV3. Analysis of laboratory-selected antigenic variants and of PIV3 clinical isolates indicated that the panel of MAbs recognizes at least 20 epitopes, 14 of which participate in neutralization. Competitive binding assays confirmed that the 14 neutralization epitopes are organized into three nonoverlapping principal antigenic regions (A, B, and C) and one bridge site (AB), and that the 6 nonneutralization epitopes form four sites (D, E, F, and G). Most of the neutralizing MAbs were involved in nonreciprocal competitive binding reactions, suggesting that they induce conformational changes in other neutralization epitopes.

Other antigenic determinants for use within the invention have been identified and characterized for respiratory syncytial virus (RSV). For example, Beeler et al., *J. Virol.* 63:2941-2950, 1989, incorporated herein by reference, employed eighteen neutralizing monoclonal antibodies (MAbs) specific for the fusion glycoprotein of the A2 strain of RSV to construct a detailed topological and operational map of epitopes involved in RSV neutralization and fusion. Competitive binding assays identified three nonoverlapping antigenic regions (A, B, and C) and one bridge site (AB). Thirteen MAb-resistant mutants (MARMs) were selected, and the neutralization patterns of the MAbs with either MARMs or RSV clinical strains identified a minimum of 16 epitopes. MARMs selected with antibodies to six of the site A and AB epitopes displayed a small-plaque phenotype, which is consistent with an alteration in a biologically active region of the F molecule. Analysis of MARMs also indicated that these neutralization epitopes occupy topographically distinct but conformationally interdependent regions with unique biological and immunological properties. Antigenic variation in F epitopes was then examined by using 23 clinical isolates (18 subgroup A and 5 subgroup B) in cross-neutralization assays with the 18 anti-F MAbs. This analysis identified constant, variable, and hypervariable regions on the molecule and indicated that antigenic variation in the neutralization epitopes of the RSV F glycoprotein is the result of a noncumulative genetic heterogeneity. Of the 16 epitopes, 8 were conserved on all or all but 1 of 23 subgroup A or subgroup B clinical isolates. These antigenic determinants, including the full length proteins and their constituent antigenic domains, fragments and epitopes, all represent useful candidates for integration within chimeric PIV of the invention to elicit novel immune responses as described above. (See also, Anderson et al., *J. Infect. Dis.* 151:626-633, 1985; Coelingh et al., *J. Virol.* 63:375-382, 1989; Fenner et al., *Scand. J. Immunol.* 24:335-340, 1986; Fernie et al., *Proc. Soc. Exp. Biol. Med.* 171:266-271, 1982; Sato et al., *J. Gen. Virol.* 66:1397-1409, 1985; Walsh et al., *J. Gen. Virol.* 67:505-513, 1986, and Olmsted et al., *J. Virol.* 63:411-420, 1989, each incorporated herein by reference).

To express antigenic determinants of heterologous PIVs and non-PIV pathogens, the invention provides numerous methods and constructs. In certain detailed embodiments, a transcription unit comprising an open reading frame (ORF) of a gene encoding an antigenic protein (e.g., the measles virus HA gene) is added to a HPIV2 vector genome or antigenome at various positions, yielding exemplary chimeric PIV1/measles candidates. In exemplary embodiments, chimeric HPIV2 viruses are engineered that incorporate heterologous nucleotide sequences encoding protective antigens from respiratory syncytial virus (RSV) to produce infectious, attenuated candidates. The cloning of RSV cDNA and other disclosure pertaining to aspects of the invention set forth herein is provided in U.S. patent application Ser. No. 08/720,132, filed Sep. 27, 1996, corresponding to International Publication WO 97/12032 published Apr. 3, 1997, and priority U.S. Provisional Patent Application No. 60/007,083, filed Sep. 27, 1995; U.S. Provisional Patent Application No. 60/021,773, filed Jul. 15, 1996; U.S. Provisional Patent Application No. 60/046,141, filed May 9, 1997; U.S. Provisional Patent Application No. 60/047,634, filed May 23, 1997; U.S. patent application Ser. No. 08/892,403, filed Jul. 15, 1997 corresponding to International Publication No. WO 98/02530 published on Jan. 22, 1998; U.S. patent application Ser. No. 09/291,894, filed on Apr. 13, 1999 corresponding to International Publication No. WO 00/61611 published Oct. 19, 2000, and priority U.S. Provisional Patent Application Ser. No. 60/129,006, filed on Apr. 13, 1999; U.S. patent application Ser. No. 09/602,212, filed Jun. 23, 2000 and corresponding International Publication No. WO 01/04335 published on Jan. 18, 2001, and priority U.S. Provisional Patent Application Nos. 60/129,006, filed Apr. 13, 1999, 60/143,097, filed Jul. 9, 1999, and 60/143,132, filed Jul. 9, 1999; International Publication No. WO 00/61737 published on Oct. 19, 2000; Collins et al., *Proc Nat. Acad. Sci. U.S.A.* 92:11563-11567, 1995; Bukreyev et al., *J. Virol.* 70:6634-41, 1996, Juhasz et al., *J. Virol.* 71:5814-5819, 1997; Durbin et al., *Virology* 235:323-332, 1997; He et al. *Virology* 237:249-260, 1997; Baron et al. *J. Virol.* 71:1265-1271, 1997; Whitehead et al., *Virology* 247:232-9, 1998a; Whitehead et al., *J. Virol.* 72:4467-4471, 1998b; Jin et al. *Virology* 251:206-214, 1998; and Whitehead et al., *J. Virol.* 73:3438-3442, 1999, and Bukreyev et al., *Proc. Nat. Acad. Sci. U.S.A.* 96:2367-72, 1999, each incorporated herein by reference in its entirety for all purposes). Other reports and discussion incorporated or set forth herein identify and characterize RSV antigenic determinants that are useful within the invention.

PIV chimeras incorporating one or more RSV antigenic determinants, preferably comprise a HPIV2 vector genome or antigenome combined with a heterologous gene or genome segment encoding an antigenic RSV glycoprotein, protein domain (e.g., a glycoprotein ectodomain) or one or more immunogenic epitopes. In one embodiment, one or more genes or genome segments from RSV F and/or G genes is/are combined with the vector genome or antigenome to form the chimeric HPIV2 candidate. Certain of these constructs will express chimeric proteins, for example fusion proteins having a cytoplasmic tail and/or transmembrane domain of HPIV2 fused to an ectodomain of RSV to yield a novel attenuated virus that optionally elicits a multivalent immune response against both HPIV2 and RSV.

Considering the epidemiology of RSV and HPIV1, HPIV2, and HPIV3, it may be desired to administer immunogenic compositions of the invention in a predetermined, sequential schedule. RSV and HPIV3 cause significant illness within the first four months of life whereas most of the illness caused by HPIV1 and HPIV2 occur after six months of age (Chanock et al., in *Parainfluenza Viruses*, Knipe et al. (Eds.), pp. 1341-1379, Lippincott Williams & Wilkins, Philadelphia, 2001; Collins et al., *In Fields Virology*, Vol. 1, pp. 1205-1243, Lippincott-Raven Publishers, Philadelphia, 1996; Reed et al., *J. Infect. Dis.* 175:807-13, 1997, each incorporated herein by reference). Accordingly, certain sequential immunization protocols of the invention may involve administration of a immunogenic composition as described herein that elicits an immune response against HPIV3 and/or RSV (e.g., as a combined immunogenic composition) two or more times early in life, with the first dose administered at or before one month of age, followed by an immunogenic composition against HPIV1 and/or HPIV2 at about four and six months of age.

The invention therefore provides novel combinatorial immunogenic compositions and coordinate immunization protocols for multiple pathogenic agents, including multiple PIVs and/or PIV and a non-PIV pathogen. These methods and formulations effectively target early immunization against RSV and PIV3. One preferred immunization sequence employs one or more live attenuated immunogenic compositions against RSV and PIV3 as early as one month of age (e.g., at one and two months of age) followed by a bivalent PIV1 and PIV2 immunogenic composition at four and six months of age. It is thus desirable to employ the methods of the invention to administer multiple PIV immunogenic compositions, including one or more chimeric PIV candidates, coordinately, e.g., simultaneously in a mixture or separately in a defined temporal sequence (e.g., in a daily or weekly sequence), wherein each virus preferably expresses a different heterologous protective antigen. Such a coordinate/sequential immunization strategy, which is able to induce secondary antibody responses to multiple viral respiratory pathogens, provides a highly powerful and extremely flexible immunization regimen that is driven by the need to immunize against each of the three PIV viruses and other pathogens in early infancy.

Other sequential immunizations according to the invention permit the induction of a high titer of antibody targeted to a heterologous pathogen, such as measles. In one embodiment, young infants (e.g. 2-4 month old infants) are immunized with an attenuated HPIV3 or a chimeric HPIV2-3 (incorporating HPIV3 antigenic determinant(s)s) and/or HPIV3 virus that elicits an immune response against HPIV3 and/or a heterologous pathogen (for example a chimeric HPIV2 or HPIV3 virus expressing the measles virus HA protein and also adapted to elicit an immune response against HPIV3). Subsequently, e.g., at four months of age the infant is again immunized but with a different, secondary vector construct, such as a recombinant HPIV2 virus expressing the measles virus HA gene and the HPIV2 antigenic determinants as functional, obligate glycoproteins of the vector. Following the first immunization, the recipient will elicit a primary antibody response to both the PIV3 HN and F proteins and to the measles virus HA protein, but not to the PIV2 HN and F protein. Upon secondary immunization with the rHPIV2 expressing the measles virus HA, the recipient will be readily infected with the immunogenic composition because of the absence of antibody to the PIV2 HN and F proteins and will develop both a primary antibody response to the PIV2 HN and F protective antigens and a high titered secondary antibody response to the heterologous measles virus HA protein. A similar sequential immunization schedule can be developed where immunity is sequentially elicited against HPIV3 and then HPIV2 by one or more of the chimeric viruses disclosed herein, simultaneous with stimulation of an initial and then secondary, high titer immunogenic response against measles or another non-PIV pathogen. This sequential immunization strategy, preferably employing different serotypes of PIV as primary and secondary vectors, effectively circumvents immunity that is induced to the primary vector, a factor ultimately limiting the usefulness of vectors with only one serotype. The success of sequential immunization with rHPIV3 and rHPIV3-1 virus candidates as described above has been reported (Tao et al., *Vaccine* 17:1100-8, 1999, incorporated herein by reference), but with the limitation of decreased immunogenicity of rHPIV3-1 against HPIV1 challenge. The present invention, in which the backbone of the booster virus is antigenically unrelated to the primary virus or vector, overcomes this important limitation.

Further in accordance with these aspects of the invention, exemplary coordinate immunization protocols may incorporate two, three, four and up to six or more separate HPIV viruses administered simultaneously (e.g., in a polyspecific mixture) in a primary immunization step, e.g., at one, two or four months of age. For example, two or more HPIV2-based viruses can be administered that separately express one or more antigenic determinants (i.e., whole antigens, immunogenic domains, or epitopes) selected from the G protein of RSV subgroup A, the F protein of RSV subgroup A, the G protein of RSV subgroup B, the F protein of RSV subgroup B, the G protein of HMPV, the F protein of HMPV, the HA protein of measles virus, and/or the F protein of measles virus. Coordinate booster administration of these same HPIV2-based constructs can be repeated at two months of age. Subsequently, e.g., at four months of age, a separate panel of 2-6 or more antigenically distinct (referring to vector antigenic specificity) live attenuated HPIV2-based viruses can be administered in a secondary immunization step. For example, secondary immunization may involve concurrent administration of a mixture or multiple formulations that contain(s) multiple HPIV2 constructs that collectively express RSV G from subgroup A, RSV F from subgroup A, RSV F from subgroup B, RSV G from subgroup B, measles virus HA, and/or measles virus F, or antigenic determinants from any combination of these proteins. This secondary immunization provides a boost in immunity to each of the heterologous RSV and measles virus proteins or antigenic determinant(s) thereof. At six months of age, a tertiary immunization step involving administration of one to six or more separate live attenuated HPIV2-1 or HPIV2-3 vector-based recombinants can be coordinately administered that separately or collectively express RSV G from subgroup A, RSV F from subgroup A, RSV G from subgroup B, RSV F from subgroup B, the G protein of HMPV, the F protein of HMPV, measles virus HA, and/or measles virus F, or antigenic determinant(s) thereof. Optionally at this step in the immunization protocol, rHPIV3 and rHPIV2 immunogenic compositions may be administered in booster formulations. In this way, the strong immunity characteristic of secondary antibody to HPIV1, HPIV2, HPIV3, RSV A, RSV B, HMPV, and measles viruses are all induced within the first six months of infancy. Such a coordinate/sequential immunization strategy, which is able to induce secondary antibody responses to multiple viral respiratory pathogens, provides a highly powerful and extremely flexible immunization regimen that is driven by the need to immunize against each of the three PIV viruses and other pathogens in early infancy.

The present invention thus overcomes the difficulties inherent in prior approaches to the development of vector based immunogenic compositions and provides unique opportunities for immunization of infants during the first year of life against a variety of human pathogens. Previous studies in developing live-attenuated PIV immunogenic compositions indicate that, unexpectedly, rPIVs and their attenuated and chimeric derivatives have properties that make them uniquely suited among the nonsegmented negative strand RNA viruses as vectors to express foreign proteins as immunogenic compositions against a variety of human pathogens. The skilled artisan would not have predicted that the human PIVs, which tend to grow substantially less well than the model nonsegmented negative strand viruses and which typically have been underrepresented with regard to molecular studies, would prove to have characteristics which are highly favorable as vectors. It is also surprising that the intranasal route of administration of these immunogenic compositions has proven a very efficient means to stimulate a robust local and systemic immune response against both the vector and the expressed heterologous antigen. Furthermore, this route provides additional advantages for immunization against heterologous pathogens that infect the respiratory tract or elsewhere.

The present invention provides major advantages over previous attempts to immunize young infants against measles virus and other microbial pathogens. First, the HPIV2 recombinant vector into which the protective antigen or antigens of heterologous pathogens such as measles virus are inserted can be attenuated in a finely adjusted manner by incorporation of one or more attenuating mutations or other modifications to attenuate the virus for the respiratory tract of the very young, seronegative or seropositive human infant. An extensive history of prior clinical evaluation and practice (see, e.g., Karron et al., *Pediatr. Infect. Dis. J.* 15:650-654, 1996; Karron et al., *J. Infect. Dis.* 171:1107-1114, 1995a; Karron et al., *J. Infect. Dis.* 172:1445-1450, 1995, each incorporated herein by reference) greatly facilitates evaluation of derivatives of these recombinants bearing foreign protective antigens in the very young human infant.

Yet another advantage of the invention is that chimeric HPIV2 bearing heterologous sequences will replicate efficiently in vitro to enable large-scale production of immunogenic compositions. This is in contrast to the replication of some single-stranded, negative-sense RNA viruses that can be inhibited in vitro by the insertion of a foreign gene (Bukreyev et al., *J. Virol.* 70:6634-41, 1996). Also, the presence of three antigenic serotypes of HPIV, each of which causes significant disease in humans and hence can serve simultaneously as vector and to elicit an immune response, presents a unique opportunity to sequentially immunize the infant with antigenically distinct variants of HPIV each bearing the same foreign protein. In this manner the sequential immunization permits the development of a primary immune response to the foreign protein which can be boosted during subsequent infections with the antigenically distinct HPIV also bearing the same or a different foreign protein or proteins, i.e., the protective antigen of measles virus or of another microbial pathogen. It is also likely that readministration of homologous HPIV vectors will also boost the response to both HPIV and the foreign antigen since the ability to cause multiple reinfections in humans is an unusual but characteristic attribute of the HPIVs (Chanock et al., Parainfluenza Viruses., p. 1341-1379, In D. M. Knipe, P. M. Howley, D. E. Griffin, R. A. Lamb, M. A. Martin, B. Roizman, and S. E. Straus (eds.) *Fields Virology,* 4th ed., Vol. 1, Lippincott Williams & Wilkins, Philadelphia, 2001, incorporated herein by reference).

Yet another advantage of the invention is that the introduction of a gene unit into a HPIV2 vector has several highly desirable effects for the production of attenuated viruses. First, the insertion of gene units expressing, for example, the HA of measles virus or the HN of HPIV1 or HPIV3 can specify a host range phenotype on the HPIV2 vector, where the resulting HPIV2 vector replicates efficiently in vitro but is restricted in replication in vivo in both the upper and lower respiratory tracts. Thus, the insertion of a gene unit expressing a viral protective antigen as an attenuating factor for the HPIV2 vector is a desirable property in live attenuated virus of the invention.

The HPIV2 vector system has unique advantages over other members of the single-stranded, negative-sense viruses of the Order Mononegavirales. First, most other mononegaviruses that have been used as vectors are not derived from human pathogens (e.g., murine PIV1 (Sendai virus) (Sakai et al., *FEBS Lett.* 456:221-6, 1999), vesicular stomatitis virus (VSV) which is a bovine pathogen (Roberts et al., *J. Virol.* 72:4704-11, 1998), and canine PIV2 (SV5) He et al., *Virology* 237:249-60, 1997)). For these nonhuman viruses, little or only weak immunity would be conferred against any human virus by antigens present in the vector backbone. Thus, a nonhuman virus vector expressing a supernumerary gene for a human pathogen would induce resistance only against that single human pathogen. In addition, use of viruses such as SV5, rabies, or Sendai virus as vector would expose subjects to viruses that they likely would not otherwise encounter during life.

An important and specific advantage of the HPIV2 vector system is that its preferred, intranasal route of administration, mimicking natural infection, will induce both mucosal and systemic immunity and reduces the neutralizing and immunosuppressive effects of maternally-derived serum IgG that is present in infants. While these same advantages theoretically are possible for using RSV as a vector, for example, we have found that RSV replication is strongly inhibited by inserts of greater than approximately 500 bp (Bukreyev et al., *Proc. Natl. Acad. Sci. USA* 96:2367-72, 1999). In contrast, as described herein, HPIV2 will often accommodate several large gene inserts. The finding that recombinant RSV is unsuitable for bearing large inserts, whereas recombinant PIVs are highly suitable, represents unexpected results.

It might be proposed that some other viral vector could be given intranasally to obtain similar benefits as shown for PIV vectors, but this has not been successful to date. For example, the MVA strain of vaccinia virus expressing the protective antigens of HPIV3 was evaluated as a live attenuated intranasal immunogenic composition against HPIV3. Although this vector appeared to be a very efficient expression system in cell culture, it was inexplicably inefficient in inducing resistance in the upper respiratory tract of primates (Durbin et al., *Vaccine* 16:1324-30, 1998, incorporated herein by reference) and was inexplicably inefficient in inducing an effective immune response in the presence of passive serum antibodies (Durbin et al., *J. Infect. Dis.* 179:1345-51, 1999, incorporated herein by reference). In contrast, PIV3 and RSV candidates have been found to be protective in the upper and lower respiratory tract of non-human primates, even in the presence of passive serum antibodies (Crowe et al., *Vaccine* 13:847-855, 1995; Durbin et al., *J. Infect. Dis.* 179:1345-51, 1999, each incorporated herein by reference).

As noted above, the invention permits a wide range of alterations to be recombinantly produced within the HPIV2 genome or antigenome, yielding defined mutations that specify desired phenotypic changes. As also noted above, defined mutations can be introduced by a variety of conventional techniques (e.g., site-directed mutagenesis) into a cDNA copy of the genome or antigenome. The use of genomic or antigenomic cDNA subfragments to assemble a complete genome or antigenome cDNA as described herein has the advantage that each region can be manipulated separately, where small cDNA constructs provide for better ease of manipulation than large cDNA constructs, and then readily assembled into a complete cDNA. Thus, the complete antigenome or genome cDNA, or a selected subfragment thereof, can be used as a template for oligonucleotide-directed mutagenesis. This can be through the intermediate of a single-stranded phagemid form, such as using the MUTA-gen®V kit of Bio-Rad Laboratories (Richmond, Calif.), or a method using the double-stranded plasmid directly as a template such as the Chameleon® mutagenesis kit of Strategene (La Jolla, Calif.), or by the polymerase chain reaction employing either an oligonucleotide primer or a template which contains the mutation(s) of interest. A mutated subfragment can then be assembled into the complete antigenome or genome cDNA. A variety of other mutagenesis techniques are known and can be routinely adapted for use in producing the mutations of interest in a PIV antigenome or genome cDNA of the invention.

Thus, in one illustrative embodiment mutations are introduced by using the MUTA-gene® phagemid in vitro mutagenesis kit available from Bio-Rad Laboratories. In brief, cDNA encoding a PIV genome or antigenome is cloned into the plasmid pTZ18U, and used to transform CJ236 cells (Life Technologies). Phagemid preparations are prepared as recommended by the manufacturer. Oligonucleotides are designed for mutagenesis by introduction of an altered nucleotide at the desired position of the genome or antigenome. The plasmid containing the genetically altered genome or antigenome is then amplified.

Mutations can vary from single nucleotide changes to the introduction, deletion or replacement of large cDNA segments containing one or more genes or genome segments. Genome segments can correspond to structural and/or functional domains, e.g., cytoplasmic, transmembrane or ectodomains of proteins, active sites such as sites that mediate binding or other biochemical interactions with different proteins, epitopic sites, e.g., sites that stimulate antibody binding and/or humoral or cell mediated immune responses, etc. Useful genome segments in this regard range from about 15-35 nucleotides in the case of genome segments encoding small functional domains of proteins, e.g., epitopic sites, to about 50, 75, 100, 200-500, and 500-1,500 or more nucleotides.

The ability to introduce defined mutations into infectious recombinant HPIV2 has many applications, including the manipulation of PIV pathogenic and immunogenic mechanisms. For example, the functions of HPIV2 proteins, including the N, P, M, F, HN, and L proteins and products of the V ORF, can be manipulated by introducing mutations which ablate or reduce the level of protein expression, or which yield mutant protein. Various genome RNA structural features, such as promoters, intergenic regions, and transcription signals, can also be routinely manipulated within the methods and compositions of the invention. The effects of trans-acting proteins and cis-acting RNA sequences can be readily determined, for example, using a complete antigenome cDNA in parallel assays employing PIV minigenomes (Dimock et al., *J. Virol.* 67:2772-8, 1993, incorporated herein by reference in its entirety), whose rescue-dependent status is useful in characterizing those mutants that may be too inhibitory to be recovered in replication-independent infectious virus.

Certain substitutions, insertions, deletions or rearrangements of genes or genome segments within recombinant HPIV2 of the invention (e.g., substitutions of a genome segment encoding a selected protein or protein region, for instance a cytoplasmic tail, transmembrane domain or ectodomain, an epitopic site or region, a binding site or region, an active site or region containing an active site, etc.) are made in structural or functional relation to an existing, "counterpart" gene or genome segment from the same or different PIV or other source. Such modifications yield novel recombinants having desired phenotypic changes compared to wild-type or parental PIV or other viral strains. For example, recombinants of this type may express a chimeric protein having a cytoplasmic tail and/or transmembrane domain of one PIV fused to an ectodomain of another PIV. Other exemplary recombinants of this type express duplicate protein regions, such as duplicate immunogenic regions.

As used herein, "counterpart" genes, genome segments, proteins or protein regions, are typically from heterologous sources (e.g., from different PIV genes, or representing the same (i.e., homologous or allelic) gene or genome segment in different PfV types or strains). Typical counterparts selected in this context share gross structural features, e.g., each counterpart may encode a comparable protein or protein structural domain, such as a cytoplasmic domain, transmembrane domain, ectodomain, binding site or region, epitopic site or region, etc. Counterpart domains and their encoding genome segments embrace an assemblage of species having a range of size and sequence variations defined by a common biological activity among the domain or genome segment variants.

Counterpart genes and genome segments, as well as other polynucleotides disclosed herein for producing recombinant PIV within the invention, often share substantial sequence identity with a selected polynucleotide "reference sequence," e.g., with another selected counterpart sequence. As used herein, a "reference sequence" is a defined sequence used as a basis for sequence comparison, for example, a segment of a full-length cDNA or gene, or a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith & Waterman, (*Adv. Appl. Math.* 2:482, 1981), by the homology alignment algorithm of Needleman & Wunsch, (*J. Mol. Biol.* 48:443, 1970), by the search for similarity method of Pearson & Lipman, (*Proc. Natl. Acad. Sci. U.S.A.* 85:2444, 1988) (each incorporated herein by reference), by computerized implementations of these algorithms (GAP, BESTFIT, FASTA, and TFASTA in the Wisconsin Genetics Software Package Release 7.0, Genetics Computer Group, 575 Science Dr., Madison, Wis., incorporated herein by reference), or by inspection, and the best alignment (i.e., resulting in the highest percentage of sequence similarity over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

In addition to these polynucleotide sequence relationships, proteins and protein regions encoded by recombinant HPIV2 of the invention are also typically selected to have conservative relationships, i.e. to have substantial sequence identity or sequence similarity, with selected reference polypeptides. As applied to polypeptides, the term "sequence identity" means peptides share identical amino acids at corresponding positions. The term "sequence similarity" means peptides have identical or similar amino acids (i.e., conservative substitutions) at corresponding positions. The term "substantial sequence identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). The term "substantial similarity" means that two peptide sequences share corresponding percentages of sequence similarity. Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. Abbreviations for the twenty naturally occurring amino acids used herein follow conventional usage (*Immunology—A Synthesis,* 2nd ed., E. S. Golub & D. R. Gren, eds., Sinauer Associates, Sunderland, Mass., 1991, incorporated herein by reference). Stereoisomers (e.g., D-amino acids) of the twenty conventional amino acids, unnatural amino acids such as α, α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). Moreover, amino acids may be modified by glycosylation, phosphorylation and the like.

To select candidate viruses according to the invention, the criteria of viability, attenuation and immunogenicity are determined according to well-known methods. Viruses that will be most desired in immunogenic compositions of the invention must maintain viability, have a stable attenuation phenotype, exhibit replication in an immunized host (albeit at lower levels), and effectively elicit production of an immune response in a recipient sufficient to elicit a desired immune response. The recombinant HPIV2 viruses of the invention are not only viable and appropriately attenuated, they are more stable genetically in vivo—retaining the ability to stimulate an immune response and in some instances to expand the immune response elicited by multiple modifications, e.g., induce an immune response against different viral strains or subgroups, or to stimulate a response mediated by a different immunologic basis, e.g., secretory versus serum immunoglobulins, cellular immunity, and the like.

Recombinant HPIV2 viruses of the invention can be tested in various well-known and generally accepted in vitro and in vivo models to confirm adequate attenuation, resistance to phenotypic reversion, and immunogenicity. In in vitro assays, the modified virus (e.g., a multiply attenuated, biologically derived or recombinant PIV) is tested, e.g., for temperature sensitivity of virus replication, i.e. ts phenotype, and for the small plaque or other desired phenotype. Modified viruses are further tested in animal models of PIV infection. A variety of animal models have been described and are summarized in various references incorporated herein. PIV model systems, including rodents and non-human primates, for evaluating attenuation and immunogenic activity of PIV candidates are widely accepted in the art, and the data obtained therefrom correlate well with PIV infection, attenuation and immunogenicity in humans.

In accordance with the foregoing description, the invention also provides isolated, infectious recombinant HPIV2 for use in immunogenic compositions. The attenuated virus which is a component of an immunogenic composition is in an isolated and typically purified form. By isolated is meant to refer to PIV which is in other than a native environment of a wild-type virus, such as the nasopharynx of an infected individual.

More generally, isolated is meant to include the attenuated virus as a component of a cell culture or other artificial medium where it can be propagated and characterized in a controlled setting. For example, attenuated HPIV2 of the invention may be produced by an infected cell culture, separated from the cell culture and added to a stabilizer.

For use in immunogenic compositions, recombinant HPIV2 produced according to the present invention can be used directly in formulations, or lyophilized, as desired, using lyophilization protocols well known to the artisan. Lyophilized virus will typically be maintained at about 4° C. When ready for use the lyophilized virus is reconstituted in a stabilizing solution, e.g., saline or comprising SPG, $Mg^{++}$ and HEPES, with or without adjuvant, as further described below.

HPIV2-based immunogenic compositions of the invention contain as an active ingredient an immunogenically effective amount of a recombinant HPIV2 produced as described herein. The modified virus may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. Acceptable adjuvants include incomplete Freund's adjuvant, MPL™ (3-O-deacylated monophosphoryl lipid A; Corixa, Hamilton Ind.) and IL-12 (Genetics Institute, Cambridge Mass.), among many other suitable adjuvants well known in the art.

Upon immunization with a recombinant HPIV2 composition as described herein, via aerosol, droplet, oral, topical or other route, the immune system of the host responds to the immunogenic composition by producing antibodies specific for PIV proteins, e.g., F and HN glycoproteins. As a result of the immunization with an immunogenically effective amount of a recombinant HPIV2 produced as described herein, the host becomes at least partially or completely immune to infection by the targeted PIV or non-PIV pathogen, or resistant to developing moderate or severe infection therefrom, particularly of the lower respiratory tract.

The host to which the immunogenic compositions are administered can be any mammal which is susceptible to infection by PIV or a selected non-PIV pathogen and which host is capable of generating an immune response to the antigens of the immunizing strain. Accordingly, the invention provides methods for creating immunogenic compositions for a variety of human and veterinary uses.

The compositions containing the recombinant HPIV2 of the invention are administered to a host susceptible to or otherwise at risk for PIV infection to enhance the host's own immune response capabilities. Such an amount is defined to be a "immunogenically effective dose." In this use, the precise amount of recombinant HPIV2 to be administered within an effective dose will depend on the host's state of health and weight, the mode of administration, the nature of the formulation, etc., but will generally range from about $10^3$ to about $10^7$ plaque forming units (PFU) or more of virus per host, more commonly from about $10^4$ to $10^6$ PFU virus per host. In any event, the formulations should provide a quantity of modified PIV of the invention sufficient to elicit a detectable immune response in the host patient against the subject pathogen(s).

The recombinant HPIV2 produced in accordance with the present invention can be combined with viruses of other PIV serotypes or strains to elicit a desired immune response against multiple PIV serotypes or strains. Alternatively, an immune response against multiple PIV serotypes or strains can be achieved by combining protective epitopes of multiple serotypes or strains engineered into one virus, as described herein. Typically when different viruses are administered they will be in admixture and administered simultaneously, but they may also be administered separately. Immunization with one strain may immunize against different strains of the same or different serotype.

In some instances it may be desirable to combine the recombinant HPIV2 immunogenic compositions of the invention with immunogenic compositions that induce immune responses to other agents, particularly other childhood viruses. In another aspect of the invention the recombinant HPIV2 can be employed as a vector for protective antigens of other pathogens, such as respiratory syncytial virus (RSV) or measles virus, by incorporating the sequences encoding those protective antigens into the recombinant HPIV2 genome or antigenome that is used to produce infectious virus, as described herein.

In all subjects, the precise amount of recombinant HPIV2 administered, and the timing and repetition of administration, will be determined using conventional methods based on the patient's state of health and weight, the mode of administration, the nature of the formulation, etc. Dosages will generally range from about $10^3$ to about $10^7$ plaque forming units (PFU) or more of virus per patient, more commonly from about $10^4$ to $10^6$ PFU virus per patient. In any event, the formulations should provide a quantity of attenuated recombinant HPIV2 sufficient to effectively stimulate or induce an anti-PIV or other anti-pathogenic immune response, e.g., as can be determined by hemagglutination inhibition, complement fixation, plaque neutralization, and/or enzyme-linked immunosorbent assay, among other methods. In this regard, individuals are also monitored for signs and symptoms of upper respiratory illness. As with administration to chimpanzees, the attenuated virus of grows in the nasopharynx of recipients at levels approximately 10-fold or more lower than wild-type virus, or approximately 10-fold or more lower when compared to levels of incompletely attenuated virus.

In neonates and infants, multiple administrations may be required to elicit sufficient levels of immunity. Administration should begin within the first month of life, and at intervals throughout childhood, such as at two months, six months, one year and two years, as necessary to maintain an immune response against native (wild-type) PIV infection. Similarly, adults who are particularly susceptible to repeated or serious PIV infection, such as, for example, health care workers, day care workers, family members of young children, the elderly, individuals with compromised cardiopulmonary function, may require multiple immunizations to establish and/or maintain immune responses. Levels of induced immunity can be monitored by measuring amounts of neutralizing secretory and serum antibodies, and dosages adjusted or immunizations repeated as necessary to maintain desired levels of immune response. Further, different candidate viruses may be indicated for administration to different recipient groups. For example, an engineered HPIV2 expressing a cytokine or an additional protein rich in T cell epitopes may be particularly advantageous for adults rather than for infants.

HPIV2-based immunogenic compositions produced in accordance with the present invention can be combined with viruses expressing antigens of another subgroup or strain of PIV to elicit an immune response against multiple PIV subgroups or strains. Alternatively, the candidate virus may incorporate protective epitopes of multiple PIV strains or subgroups engineered into one PIV clone, as described herein.

The recombinant HPIV2 immunogenic compositions of the invention elicit production of an immune response that reduces or alleviates serious lower respiratory tract disease, such as pneumonia and bronchiolitis when the individual is subsequently infected with wild-type PIV. While the naturally circulating virus is still capable of causing infection, particularly in the upper respiratory tract, there is a very greatly reduced possibility of rhinitis as a result of the immunization. Boosting of resistance by subsequent infection by wild-type virus can occur. Following immunization, there are detectable levels of host engendered serum and secretory antibodies which are capable of neutralizing homologous (of the same subgroup) wild-type virus in vitro and in vivo.

Preferred recombinant HPIV2 candidates of the invention exhibit a very substantial diminution of virulence when compared to wild-type virus that naturally infects humans. The virus is sufficiently attenuated so that symptoms of infection will not occur in most immunized individuals. In some instances the attenuated virus may still be capable of dissemination to unimmunized individuals. However, its virulence is sufficiently abrogated such that severe lower respiratory tract infections in the immunized host do not occur.

The level of attenuation of recombinant HPIV2 candidates may be determined by, for example, quantifying the amount of virus present in the respiratory tract of an immunized host and comparing the amount to that produced by wild-type PIV or other attenuated PIV which have been evaluated as candidate strains. For example, the attenuated virus of the invention will have a greater degree of restriction of replication in the upper respiratory tract of a highly susceptible host, such as a chimpanzee, compared to the levels of replication of wild-type virus, e.g., 10- to 1000-fold less. In order to further reduce the development of rhinorrhea, which is associated with the replication of virus in the upper respiratory tract, a useful candidate virus should exhibit a restricted level of replication in both the upper and lower respiratory tract. However, the attenuated viruses of the invention must be sufficiently infectious and immunogenic in humans to elicit a desired immune response in immunized individuals. Methods for determining levels of PIV in the nasopharynx of an infected host are well known in the literature.

Levels of induced immunity provided by the immunogenic compositions of the invention can also be monitored by measuring amounts of neutralizing secretory and serum antibodies. Based on these measurements, dosages can be adjusted or immunizations repeated as necessary to maintain desired levels of immune response. Further, different candidate viruses may be advantageous for different recipient groups. For example, an engineered recombinant HPIV2 strain expressing an additional protein rich in T cell epitopes may be particularly advantageous for adults rather than for infants.

In yet another aspect of the invention the recombinant HPIV2 is employed as a vector for transient gene therapy of the respiratory tract. According to this embodiment the recombinant HPIV2 genome or antigenome incorporates a sequence that is capable of encoding a gene product of interest. The gene product of interest is under control of the same or a different promoter from that which controls PIV expression. The infectious recombinant HPIV2 produced by coexpressing the recombinant HPIV2 genome or antigenome with the N, P, L and other desired PIV proteins, and containing a sequence encoding the gene product of interest, is administered to a patient. Administration is typically by aerosol, nebulizer, or other topical application to the respiratory tract of the patient being treated. Recombinant HPIV2 is administered in an amount sufficient to result in the expression of therapeutic or prophylactic levels of the desired gene product. Representative gene products that may be administered within this method are preferably suitable for transient expression, including, for example, interleukin-2, interleukin-4, gamma-interferon, GM-CSF, G-CSF, erythropoietin, and other cytokines, glucocerebrosidase, phenylalanine hydroxylase, cystic fibrosis transmembrane conductance regulator (CFTR), hypoxanthine-guanine phosphoribosyl transferase, cytotoxins, tumor suppressor genes, antisense RNAs, and other candidate antigens.

The following examples are provided by way of illustration, not limitation. These examples describe the development of a novel reverse genetics system for the recovery of HPIV2 from cDNA, and the use of this system for construction of novel recombinant HPIV2 candidates. Briefly, the examples below detail investigations leading to the complete sequence of a clinical isolate of HPIV2. Also described is the construction of a complete antigenomic cDNA, rescue of infectious, recombinant HPIV2 virus, and investigations to characterize the phenotype of recombinant HPIV2 candidates of the invention in vitro and in vivo

EXAMPLE I

Sequence Determination of Human Parainfluenza Virus Type 2 (HPIV2) and Generation of a Recombinant Wild Type HPIV2 from Cloned DNA The present Example demonstrates complete genomic sequence determination of a human parainfluenza virus type 2 (HPIV2) virus that can be directly recovered, without modification into recombinantly derived HPIV2. The subject viral strain for this analysis is Vanderbilt/1994 (V94), which was originally isolated in 1994 from an infected 13 month-old infant. The HPIV2/V94 genome is shown herein to be 15,654 nucleotides in length and, therefore, to conform to the "rule of six". This rule relates to the observation that efficient RNA replication by members of subfamily Paramyxovirinae, family Paramyxoviridae, requires a genome nucleotide length that is evenly divisible by six (Kolakofsky et al., J. Virol. 72:891-9, 1998, incorporated herein by reference).

The determination of a complete wt HPIV2 sequence disclosed herein allows the generation of cDNAs that can be used to produce HPIV2 of defined sequence and growth characteristics. In the present example, a wt rHPIV2/V94 cDNA is described that can be used as a substrate for systematically introducing attenuating mutations to derive live-attenuated HPIV2 candidates, whose genome length and sequence are well defined. In addition, genes encoding foreign protective antigens can be introduced into the rHPIV2/V94 genome to produce live-attenuated candidates able to elicit an immune response against HPIV2 and other pathogens. These attenuated HPIV2 vectors will typically be designed to have genome lengths that conform to the rule of six.

Cell Lines and Viruses

HEp-2 (ATCC CCL 23) and LLC-MK2 (ATCC CCL 7.1) cells were maintained in OptiMEM I (Life Technologies, Gaithersburg, Md.) supplemented with 5% FBS and gentamicin sulfate (50 ug/mL). Recombinant and biologically derived HPIV2s were propagated in LLC-MK2 cells and were quantified by limiting dilution with virus-infected cultures identified by hemadsorption with guinea pig erythrocytes, as described previously (Hall et al., *Virus Res.* 22:173-184, 1992, incorporated herein by reference).

Virion RNA Isolation

Confluent monolayers of LLC-MK2 cells were infected with HPIV2/V94 at a multiplicity of infection (m.o.i.) of approximately one $TCID_{50}$ per cell. At 4-6 days post-infection, clarified supernatants were harvested and virus was precipitated by incubation in 7.5% (w/v) PEG-8000 on ice for 2 hr followed by centrifugation at 10,845×g for 1 hr. Virion RNA (vRNA) was isolated by extraction of the pellet with TRIzol reagent (Invitrogen, Inc., Carlsbad, Calif.) and chloroform. vRNA was precipitated with an equal volume of isopropanol. The vRNA pellet was washed in 70% ethanol and resuspended in diethyl pyrocarbonate (DEPC) treated $H_2O$.

Reverse Transcription (RT), Polymerase Chain Reaction (PCR), and Nucleotide Sequencing vRNA was reverse transcribed using the Thermoscript RT-PCR System (Invitrogen, Inc.) and random hexamer primers. PCR was carried out on the reverse transcribed cDNA product using the Herculase Enhanced Polymerase Blend (Stratagene, LaJolla, Calif.). The antigenomic HPIV2 cDNA was generated from the RT and RACE products (see below) in six overlapping PCR fragments using primers homologous to fragments from previously published strains of HPIV2, or primers based on HPIV2/V94 sequence obtained during the course of the experiments. The nucleotide sequences of cDNA products were determined by direct sequence analysis of the RT-PCR products using a Perkin-Elmer ABI 3100 sequencer with the dRhodamine sequencing kit (Perkin-Elmer Applied Biosystems, Warrington, UK). The sequence was assembled from the six overlapping RT-PCR fragments using the Autoassembler (Perkin-Elmer Applied Biosystems) program.

The 3' terminal genomic sequence of HPIV2 was converted to cDNA using the 3' RACE System for Rapid Amplification of cDNA Ends (Invitrogen, Inc.) as specified by the manufacturer. Briefly, vRNA was polyadenylated at its 3'-end using poly A polymerase (Invitrogen. Inc.) followed by first-strand cDNA synthesis primed with oligo (dT) and PCR using an HPIV2 specific reverse primer and a forward AUAP primer supplied with the kit. RACE products were sequenced directly as described above. To determine the sequence for the 3'-end, two independently derived RACE products were sequenced and were found to be identical.

The 5' genomic terminus of HPIV2 was amplified from vRNA following first-strand cDNA synthesis, terminal transferase tailing, and PCR amplification as specified by the 5' RACE System for Rapid Amplification of cDNA 5' end Version 2.0 (Invitrogen, Inc.). The amplified cDNA RACE products were sequenced directly. The sequence for the 5'-end was determined with multiple sequencing reactions of two independently derived 5' RACE products, and the sequences were found to be identical.

Assembly of a Full-Length rHPIV2 cDNA Antigenomic Clone

A full-length cDNA clone encoding the HPIV2 antigenomic RNA was constructed from six cloned overlapping RT-PCR and RACE products using the following restriction sites in the HPIV2 genome: Nhe I (nt 892 position in the complete antigenomic sequence), Xho I (nt 3673), Asp 718 (nt 8141), Aat II (nt 10342), and Bsi WI (nt 15280) (FIG. 3).

Briefly, the first fragment was generated using the 3' RACE system (Invitrogen, Inc.) and the Herculase Enhanced Polymerase Blend (Stratagene, La Jolla, Calif.) with specific HPIV2 primers and a primer containing an Mlu I site followed by a T7 promoter, two non-viral G residues, and the antigenomic cDNA corresponding to 3'-end of the viral genome. The next four fragments (FIG. 3) were reverse transcribed using the Thermoscript RT-PCR System (Invitrogen, Inc.) and PCR amplified with the Herculase Enhanced Polymerase Blend (Stratagene). The final fragment containing the 5'-end was reverse transcribed using the 5' RACE System (Invitrogen, Inc.) and amplified with the Herculase Enhanced Polymerase Blend (Stratagene). The individual PCR products were cloned into a pUC19 plasmid modified to contain restriction enzyme sites to accept the PCR fragments, and were sequenced using a Perkin-Elmer ABI 3100 sequencer with the BigDye sequencing kit (Perkin-Elmer Applied Biosystems), and compared to the consensus sequence of HPIV2/V94 prior to assembly.

All six PCR products were assembled into a pUC19 vector modified to contain Mlu I, BspEI, Xho I, Asp 718, Aat II, Bsi WI, Cla I and Rsr II restriction sites to generate pUC-HPIV2/94. The infectious full-length cDNA plasmid, designated pFLC-HPIV2/V94, was generated by subcloning the Mlu I to Rsr II HPIV2/V94 cDNA fragment from pUC-HPIV2/V94 into a modified pBlueScript (Schmidt et al., *J. Virol.* 74:8922-9, 2000, incorporated herein by reference), and contains the following elements: a T7 promoter followed by two nonviral guanosine residues, the complete antigenomic 15654 nt sequence of HPIV2/V94, a hepatitis delta virus ribozyme, and a T7 polymerase transcriptional terminator as previously described for the generation of recombinant HPIV3, BPIV3, and HPIV1 (Durbin et al., *Virology* 235:323-332, 1997; Schmidt et al., *J. Virol.* 74:8922-9, 2000, each incorporated herein by reference). The sequence of the full-length cDNA was verified by DNA sequence analysis. Two point mutations were identified in the F and L ORFs of the full-length cDNA that had not been present in the consensus sequence occurred during the assembly of the clone at positions 6265 (agt to agc; silent) and 15075 (gct to gtt; Ala-2093 to Val). These mutations were used as markers to distinguish the recombinant HPIV2 from the biologically derived HPIV2/V94 parent.

HPIV2 N, P, and L Support Plasmids for the Recovery of HPIV2/V94 from cDNA

A support plasmid encoding the N protein of HPIV2/V94 (pTM-$N_2$) was derived from vRNA using the Thermoscript RT-PCR System (Invitrogen, Inc.) and the Advantage-HF PCR kit (Clontech) using a antigenomic sense oligonucleotide that contained an Afl III site spanning the N ORF ATG translation initiation codon site and an anti-sense oligo containing an EcoRI site. The PCR product was digested with Afl III and EcoRI and cloned into pTM1 (Durbin et al., *Virology* 235:323-332, 1997; Durbin et al., *Virology* 234:74-83, 1997; Elroy-Stein et al., *Proc. Natl. Acad. Sci. USA*. 86:6126-30, 1989, each incorporated herein by reference) that was digested with Nco I and EcoRI.

The HPIV2V94 P protein expression plasmid (pTM-$P_2$) was generated from two overlapping PCR fragments (Moeller et al., *J. Virol.* 75:7612-20, 2001, incorporated herein by reference) and was engineered to contain a two guanosine nt insertion within the HPIV2 P gene editing site (nt 2481-2487), to generate the complete P ORF (as distinguished thereby from the V ORF), which was subcloned into pTM1 as an Nco I to EcoRI fragment.

An HPIV2 L polymerase expression plasmid (pTM-$L_2$) was made by PCR amplification with a sense oligo containing an Nco I site spanning the L gene ATG translation initiation codon, and an antisense oligo downstream of a unique Aat II site (nt 10342) in the L ORF. The remainder of the L ORF was derived from a subclone used to construct the HPIV2 full-length clone. The PCR product was digested with Asp718 and Aat II and was cloned into a pUC19 plasmid containing the HPIV2 nts 10342 to 15654 followed by the unique extragenomic Rsr II site. The complete HPIV2/V94 L ORF was then subcloned into a modified pTM1 as an Nco I to Rsr II fragment.

Recovery of Viruses from CDNA and Sequencing of Viral RNA (vRNA)

Recombinant HPIV2/V94 was recovered from two independent clones of the full length HPIV2/V94 antigenomic cDNA transfected into HEp-2 cells, as described previously (Skiadopoulos et al., *Virology* 272:225-34, 2000, incorporated herein by reference). Briefly, HEp-2 cells in 6-well plates (Costar, Corning, Inc., Corning, N.Y.) were co-transfected with a full-length HPIV2/V94 cDNA plasmid and the three HPIV2 support plasmids (pTM $N_2$, pTM $P_2$, pTM $L_2$), using Lipofectamine-2000 reagent (Invitrogen, Inc.). The HEp-2 cells were simultaneously infected with MVA-T7 as described previously (Durbin et al., *Virology* 235:323-332, 1997; Schmidt et al., *J. Virol.* 74:8922-9, 2000, each incorporated herein by reference). Supernatant was harvested on day three or four post-transfection and was passaged two times on LLC-MK2 monolayers. To confirm that viruses were derived from cDNA rather than representing contamination by biologically derived virus, RT was performed and segments of the viral genome were amplified by PCR. Sequence analysis of the PCR products revealed the presence of the two point mutations that are present in the F and L genes of the recombinant virus, designated rHPIV2/V94, but that are not present in the wild type parental virus. As a control, PCR was performed without the prior RT step: this did not yield a detectable product, showing that the template was RNA rather than containing DNA. Each rHPIV2/V94 was then biologically-cloned by plaque to plaque purification on LLC-MK2 monolayers and was further propagated on LLC-MK2 cells, as previously described (Skiadopoulos et al., *Virology* 260:125-35, 1999, incorporated herein by reference) to generate two pools of HPIV2/V94 (designated $r_A$HPIV2/V94 and $r_B$HPIV2/V94) derived from two independent transfections.

vRNA was isolated from the biologically cloned $r_A$HPIV2/V94 as described previously (Skiadopoulos et al., *Virology* 260:125-35, 1999, incorporated herein by reference) and was used as the template for reverse transcription and polymerase chain reaction (RT-PCR) using oligonucleotide primers. The amplified products were analyzed by DNA sequencing to determine the complete genomic sequence of $r_A$HPIV2/V94.

Results

The complete genomic sequence of HPIV2 strain Vanderbilt 1994 (HPIV2/V94) (sequence provided in FIGS. 9A-F; GenBank accession no. AF533010, incorporated herein by reference) was determined from RT-PCR products amplified from purified vRNA. The sequence analysis was performed directly on RT-PCR products without a cloning step, and thus yielded a reliable consensus sequence. The HPIV2 genome was determined to be 15,654 bp in length, and thus the sequence provided herein conforms to the rule of six.

A complete HPIV2 antigenomic cDNA, designated pFLC-HPIV2/V94, was constructed from six overlapping RT-PCR and RACE products and contained two nucleotide changes in the F and L genes, respectively, as markers (FIG. 3). The antigenomic cDNA was transfected into HEp-2 cells and virus was recovered using the support HPIV2/V94 N, P, and L protein expression plasmids and co-infection with MVA-T7. Virus was readily recovered after only a single passage of the HEp-2 transfection supernatant onto LLC-MK2 monkey kidney cell monolayers, and the presence of the nucleotide markers present in the HPIV2 F and L genes was confirmed by RT-PCR of vRNA and sequence analysis. Amplification of RT-PCR products was dependent on the addition of RT, indicating that the template was indeed viral RNA and not contaminating DNA.

The complete sequence of $r_A$HPIV2/V94 was determined from RT-PCR products of vRNA isolated from recombinant virus that had been biologically cloned by sequential plaque to plaque purification. Specifically, the isolated genomic sequence of the recovered virus was identical to that of the biologically derived HPIV2 strain V94 parent except for two incidental, single-nt substitution mutations that were present in the antigenomic cDNA and serve as markers for recombinant HPIV2. The first mutation at position 6265 (T to C) in the F gene is translationally silent. The second mutation at nt 15075 (C to T) results in an alanine-2093 to valine substitution in the L gene. This amino acid position is not conserved between other parainfluenza viruses and lies outside of the six domains that are conserved between Paramyxoviruses. These point mutations serve as markers for a virus derived from cDNA. A third translationally silent nt substitution at nt 13786 (T to C) that arose during propagation of the virus in cell culture was also identified. The incidental mutations did not alter growth in vitro (see below). Partial sequence analysis of $r_B$HPIV2 showed that this incidental mutation was not present, consistent with the idea that it is an inconsequential mutation acquired during virus growth.

EXAMPLE II

Replication of Recombinant HPIV2 In vitro

The mean peak titer of recombinant and biologically derived HPIV2 was determined by multi-cycle growth titrations. Each HPIV2 tested was inoculated in triplicate into LLC-MK2 monolayers in 6-well plates at a multiplicity of infection (m.o.i.) of 0.01, and cultures were incubated at 32° C. with and without porcine derived trypsin added to the culture medium, as described previously (16). 0.5 ml of medium from each well was harvested and replaced with 0.5 ml of fresh medium at 0 hr and at 1 to 7 days post-infection. Virus present in the samples was quantified by titration on LLC-MK2 monolayers in 96-well plates that were incubated for seven days at 32° C. Virus was detected by hemadsorption and is reported as $\log_{10}$ TCID$_{50}$/ml (50% tissue culture infectious dose/ml).

The growth properties in cell culture of rHPIV2/V94 recovered from cDNA were indistinguishable from that of the biologically derived HPIV2/V94 (FIG. 4), and growth in vitro did not require the addition of trypsin to the culture medium (compare FIG. 4, panels A and B). Growth at 32° C., 39° C. and 40° C. was also examined, and the rHPIV2V/94 and biologically derived viruses were not ts at the higher temperatures. Thus, the incidental nt substitutions in rHPIV2/V94 did not alter growth properties in vitro.

EXAMPLE III

Replication of rHPIV2/V94 and Biologically Derived Wild type HPIV2/V94 in Hamsters 4 week-old Golden Syrian hamsters (Charles River Laboratories, NY), in groups of 6 were inoculated intranasally (IN) with 0.1 ml of L15 medium containing $10^{6.0}$ $TCID_{50}$ of virus. On day 3, 4 or 5 post-infection, the lungs and nasal turbinates were harvested, and the virus was quantified by serial dilution of tissue homogenates on LLC-MK2 monolayers, as previously described (Skiadopoulos et al., *J. Virol.* 72:1762-8, 1998, incorporated herein by reference). The mean virus titer was calculated for each group of hamsters and is expressed as $\log_{10}$ $TCID_{50}$/gram of tissue.

The replication of rHPIV2/V94 in the respiratory tract of hamsters was compared to that of the biologically derived HPIV2/V94 to determine whether the recovered rHPIV2/V94 retained the replicative properties of its biological parent in vivo. In this regard, hamsters are accepted in the art as a useful animal model of HPIV infection in humans that provides reasonably correlative findings for such activities as attenuation and immunogenicity between the model and humans, wherein the model is understood to be a less permissive host than humans.

The two pools of the recombinant rHPIV2/V94, which were derived from two different cDNA clones, were studied in parallel to assess the variability in replication between two separate preparations of the same virus. These were compared with the biologically derived preparation of HPIV2/V94. Groups of 18 hamsters were separately inoculated intranasally (IN) with $10^{6.0}$ $TCID_{50}$ of each HPIV2. On days three, four, or five, the lungs and nasal turbinates were harvested from six hamsters from each group, and the level of replication of each virus was determined (FIG. 5). The level of replication of the two preparations of rHPIV2 was similar to that of the biologically derived HPIV2 on all of the days tested, demonstrating that the recombinant HPIV2/V94 had similar replication properties in vivo as its biologically derived counterpart, and therefore, represents an authentic recombinant wt HPIV2/V94. Clearly, the incidental amino acid substitution at position 2093 of the L polymerase did not affect the level of replication of rHPIV2/V94 in vivo. In addition to these studies, a full-length antigenomic cDNA encoding an alanine at position 2093 of the L protein, as occurs in the biologically derived HPIV2/V94, was also generated, and this modified HPIV2/V94 cDNA which now would be identical in a sequence to the consensus sequence for biologically derived HPIV2/V94, was also used to recover recombinant HPIV2/V94 in vitro.

EXAMPLE IV

Determination of the Complete Genomic Sequences of Three Strains of HPIV2

Members of the Respirovirus and Morbillivirus genera of the Paramyxovirinae subfamily of paramyxoviruses reportedly have been considered to have a general requirement that the nucleotide length of the genome be an even multiple of six in order for efficient RNA replication, and hence virus replication, to occur (Calain et al., *J. Virol.* 67:4822-30, 1993; Chanock et al. Parainfluenza Viruses. 4th ed. In "Fields Virology", 4$^{th}$ ed., Knipe et al., Eds., Vol. 1, pp. 1341-1379, Lippincott Williams&Wilkins, Philadelphia, 2001; Hausmann et al., *RNA* 2:1033-45, 1996; Kolakofsky et al. *J. Virol.* 72:891-9, 1998; Peeters et al., *Arch. Virol.* 145(9), 1829-45, 2000, each incorporated herein by reference). This "rule of six" was demonstrated in studies with mini-replicons and is consistent with the observation that the complete genomic sequences for these viruses are even multiples of six nucleotides. More recently, studies with parainfluenza virus type 3 provided evidence that this "rule of six" operates at the level of complete infectious virus (Skiadopoulos et al., *Virology* 297:136-152, 2002). This rule is thought to be a consequence of each N protein subunit interacting with exactly six nucleotides in the vRNA-nucleoprotein complex.

However, it has remained unclear whether the rule of six applies to the Rubulavirus genus of the paramyxoviruses. For example, studies with mini-replicons of simian virus type 5 suggested that there was considerable flexibility with regard to this rule (Murphy et al., *Virology* 232:145-57, 1997, incorporated herein by reference). Also, the complete genome sequence determined for the Toshiba strain of HPIV2 was not an even multiple of six, whereas that of HPIV2/V94 did conform to the rule of six, and recombinant Toshiba strain HPIV2 was recovered from cDNA-encoded antigenomic RNA that did not conform to the rule of six (Kawano et al., *Virology* 284:99-112, 2001, incorporated herein by reference).

Initial investigations herein focused on whether the natural genome length of HPIV2 conformed to the rule of six. As noted above, the biologically derived HPIV2 strain Vanderbilt 9412-6 (HPIV2/V94) was obtained in 1994 from a 13 month old infant presenting with upper and lower respiratory tract infection, high fever and otitis media, and therefore represents a recent, low passaged isolate of HPIV2. The complete genomic sequence of HPIV2/V94 was determined from RT-PCR products amplified from purified vRNA. The sequence analysis was performed directly on RT-PCR products without a cloning step, and thus yields a consensus sequence. The HPIV2/V94 genome was found to be 15,654 nt in length and thus conforms to the rule of six (Calain et al., *J. Virol.* 67:4822-30, 1993; Kolakofsky et al. *J. Virol.* 72:891-9, 1998, each incorporated herein by reference). Two additional HPIV2 strains were also sequenced. The prototype HPIV2 Greer strain was originally isolated in 1955 from an infected 11-month old infant (Chanock, *J. Exp. Med.* 104:555-76, 1956, incorporated herein by reference), and the HPIV2 Vanderbilt 9811-18 (V98) strain was isolated in 1998 from an infected 20-month old infant. The sequences for the V98 and Greer strains are provided in FIGS. 10A-F and 11A-F, respectively, and by respective reference GenBank accession no.s AF533011, AF533012 (each incorporated herein by reference). The genome sizes for HPIV2/Greer and HPIV2/V98 were both determined to be 15,654 nt, the same as HPIV2/V94. Thus, three strains of HPIV2, isolated over 40 years apart, have identical polyhexameric genome lengths.

Sequence Comparison of the HPIV2 Strains

The nucleotide sequence of the Greer, V94 and V98 strains were compared by the Gap sequence alignment program (Genetics Computer Group (GCG), Madison, Wis.) The percent identity among the three strains was 95.0% for the V94 and V98 strains; 97.4% for the V98 and Greer strains; and 96.2% for the Greer and V94 strains. Thus, the recent V94 and V98 isolates of HPIV2 are highly related to the 1955 Greer isolate. The cis-acting transcription gene start (GS) and gene end (GE) signal sequences were highly conserved. Furthermore, the haxamer phasing of all known cis-actin genomic sequences was exactly conserved among each of these viruses. Hexamer phasing refers to the position of any particular sequence motif within the respective genome hexamer(s). Correct hexamer phasing of cis-acting signals may be important for their optimal functioning (Kolalofsky et al. 1998) and is another ramification of the rule of six. The predicted HPIV2/V94 N, P, V, M, F, HN and L polypeptide sequences were compared to Greer, V98 and several other members of the Rubulaviruses (including SV5W3A strain, GenBank accession no. AF052755; SV41 strain Toshiba/Chanock, GenBank accession no. X64275; and mumps virus isolate 88-1961, GenBank accession no. AF467767, each incorporated herein by reference) and the percent identity is shown in Table 1. The predicted polypeptide sequences are almost completely conserved between the three HPIV2 strains, with the highest degree of divergence occurring in the HN glycoprotein.

TABLE 1

Amino acid sequence identity between the proteins of HPIV2/V94 and the analogous proteins of HPIV2 Greer and V98 strains, SV41, SV5 and mumps virus

| | Percent identity of HPIV2/V94[a] with: | | | | |
|---|---|---|---|---|---|
| | HPIV2 | | | | Mumps |
| Protein | Greer | V98 | SV41 | SV5 | virus |
| N (543)[b] | 97.8 | 98.0 | 71.1 | 53.6 | 47.3 |
| P (395) | 99.0 | 98.0 | 66.8 | 42.0 | 34.5 |
| V (225) | 99.6 | 97.3 | 68.9 | 42.6 | 32.2 |
| M (377) | 98.7 | 98.9 | 71.7 | 50.1 | 40.9 |
| F (551) | 99.1 | 98.0 | 59.6 | 45.9 | 37.4 |
| HN (571) | 96.1 | 94.9 | 60.8 | 45.8 | 39.0 |
| L (2263) | 99.7 | 99.2 | 77.8 | 62.1 | 59.0 |

[a]Percent identity between HPIV2/V94 and the analogous protein of the indicated virus was determined by the Pileup program of the Wisconsin Package Version 10.2 (Genetics Computer Group (GCG), Madison, Wisc.).
[b]Number in parenthesis is the predicted amino acid length of the indicated HPIV2/V94 protein.

The HPIV2 Toshiba strain (Genbank ascension number X57559; NC 003443, incorporated herein by reference) and the Greer strain were compared by BESTFIT sequence alignment (Wisconsin Package Version 10.2, Genetics Computer Group (GCG), Madison, Wis., incorporated herein by reference) and were found to have 99.8% sequence identity. Thus, the Toshiba and Greer strains have a total of 34 nucleotide differences. Ten major sequence discrepancies between the Toshiba and Greer strains were identified (FIG. 6). These included 13 nucleotides present in the Greer strain that were missing from the reported Toshiba strain sequence, and 5 additional nucleotides reported for the Toshiba sequence that were not present in the Greer strain. These included a 1-nt deletion in the N and P transcription gene start signal sequences, respectively, a 1-nt insertion within the N gene end signal sequence, a 1-nt deletion in the HN gene 3' NCR, and nt deletions or insertions in the N, P and L ORFs that resulted in coding changes in those ORFs (FIG. 6). Correction for these 18 errors in the Toshiba strain would yield a genome length of 15654, the same size as reported here for the V94, V98 and Greer strains of HPIV2.

Remarkably, nearly one half of the differences between the Toshiba and Greer strains involved apparent insertions or deletions. By far the most common nucleotide differences between closely related paramyxoviruses involve nucleotide substitutions. Deletions and insertions are much more rare. The percentage of changes that involved cis-acting RNA signals or resulted in amino acid coding changes also was unusually high. The high frequency of deletions and insertions in particular suggested that many of the differences in the Toshiba strain represented errors in CDNA synthesis, cloning or sequence analysis rather than true differences in nature, and suggested that the observed non-compliance with the rule of six also might be due to error. This point, however, could not be resolved by sequence inspection alone.

EXAMPLE V

Recombinant Mutant HPIV2s can be Generated from Full-Length Antigenomic HPIV2 cDNAs that do not Conform to the Rule of Six As noted above, the genome length of the Toshiba strain of HPIV2 was reported to be 15646 nt (6n+4) (Genbank accession number X57559; NC 003443) (Kawano et al., *Virology* 178:289-92, 1990a; Kawano et al., *Virology* 179:857-61, 1990b; Kawano et al., *Virology* 174:308-13, 1990c; Kawano et al., *Virology* 284:99-112, 2001; Kawano et al., *Nucleic Acids Res.* 19:2739-46, 1991, each incorporated herein by reference). This reported length is 4 nt longer than a length that would conform the genome to be an even multiple of six and by convention its hexamer length is designated 6n+4. In addition to these reports, an HPIV2 Toshiba strain cDNA that did not conform to the rule of six (15665 nts; 6n+5) was reportedly successfully used to recover a recombinant HPIV2 in cell culture (Kawano et al., *Virology* 284:99-112, 2001). Based on this information, it was previously thought that HPIV2, unlike other members of the Paramyxovirinae (Chanock et al. Parainfluenza Viruses. 4th ed. In "Fields Virology", 4[th] ed., Knipe et al., Eds., Vol. 1, pp. 1341-1379, Lippincott Williams&Wilkins, Philadelphia, 2001) did not have a strict requirement for its genome length to conform to the rule of six (Kawano et al., *Virology* 284:99-112, 2001. Recently it was reported that mutant recombinant HPIV3s can be derived from cDNAs that do not conform to the rule of six (Skiadopoulos et al., *Virology* 297:136-152, 2002), although HPIV3 has a requirement for a polyhexameric genome length, as demonstrated with minigenome replication assays and sequencing of two wt HPIV3 genomes Durbin et al., *Virology* 235:323-332, 1997a; Durbin et al., *Virology* 234:74-83, 1997b; Galinski, In "The Paramyxoviruses", D. W. Kingsbury, Ed., pp. 537-568. Plenum Press, New York, 1991; Stokes et al., *Virus Res.* 25:91-103, 1992—published erratum appears in *Virus Res.* 27:96, 1993, each incorporated herein by reference). Sequence analysis of HPIV3 recombinants derived from cDNAs that did not conform to the rule of six indicated that they contained nucleotide insertions that corrected the length of the viral genome so that it conformed to the rule of six (Skiadopoulos et al., *Virology* 297:136-152, 2002). This showed that a) the complete infectious HPIV3 conforms to the rule of six, confirming the minigenomes studies, and b) that when HPIV3 is recovered from antigenomic cDNA that does not conform to the rule of six, there apparently is an efficient mechanism that modifies by mutation the antigenome of genome length to bring it into strict compliance with the rule of six.

The requirement for a polyhexameric genome length had not been directly examined for HPIV2, and it is not clear if HPIV2 requires a polyhexameric genome for efficient replication. To determine whether HPIV2/V94 can be recovered from full-length cDNAs that do not conform to the rule of six and to establish if these recovered viruses contain genome length correction mutations, full-length antigenomic cDNAs of HPIV2/V94 were generated that were modified to each contain an oligonucleotide insert (FIG. 7) at an EcoRV restriction site near the end of the L polymerase gene. This site was chosen so as to not interfere with the hexamer phasing of the upstream cis-acting gene start (GS) signal sequences, which may be important for efficient expression of paramyxovirus mRNAs (Kawano et al., *Virology* 284:99-112, 2001, inch). Also, this region does not contain any known cis-acting sequences. The insertions served to maintain the L polymerase ORF sequence, but modified the genome length such that the antigenomic HPIV2 cDNA length was increased by 42 nt (6n with respect to hexamer spacing and conforms to the rule of six), 43 nt (6n+1), 44 nt (6n+2), 45 nt (6n+3), 46 nt (6n+4), or 47 nt (6n+5) (FIG. 7). These cDNAs were transfected into HEp-2 cells along with HPIV2 support plasmids, as described above. The supernatants were harvested after 3 or 4 days and were passaged twice on LLC-MK2 monolayer cultures. Surprisingly, virus was readily recovered from every cDNA tested, indicating that, although HPIV2 genomes are polyhexameric, recombinant HPIV2 can be generated from a cDNA that does not conform to the rule of six.

Recombinant HPIV2s recovered from cDNAs that did not conform to the rule of six (rHPIV2/V94 (+1), rHPIV2/V94 (+2), rHPIV2/V94 (+3), rHPIV2/V94 (+4), and rHPIV2/V94 (+5)) were biologically cloned by plaque purification on LLC-MK2 monolayer cultures and were further amplified by passage on LLC-MK2 cells, as described above. rHPIV2/V94 (+1), rHPIV2/V94 (+2), rHPIV2/V94(+3), rHPIV2/V94 (+4), and rHPIV2/V94(+5) were derived from cDNAs that were 15,697, 15,698, 15,699, 15,700 nts, or 15,701 nts in length, respectively, which is 1, 2, 3, 4, or 5 more than that required to conform to the rule of six (6n+1, 6n+2, 6n+3, 6n+4 or 6n+5, respectively). vRNA was isolated from each of these recovered recombinant viral isolates and was used to perform RT-PCR and RACE. The PCR products were sequenced directly without cloning and a complete consensus sequence of each viral genome was generated, as described above. This analysis showed that the genome length of viruses generated from cDNAs that did not conform to the rule of six was modified in each case by nt insertions or deletions such that each recovered virus conformed to the rule of six (FIG. 8).

Complete genome sequencing of the rHPIV2/V94 (+3) vRNA RT-PCR products revealed that this virus had acquired a 2-nt (AA, antigenome sense) insertion in the HN gene 5' non-coding region (NCR) and a 1-nt (T, antigenome sense) insertion within a poly-T tract in the HN gene 3' NCR (FIG. 8A). The genome size of rHPIV2/V94 (+3) was 15,702 nts, i.e. three nts longer than the HPIV2 cDNA from which it was derived. Thus, the 3-nt insertion served to modify the viral genome length so that it conforms to the rule of six. Complete sequencing of the rHPIV2/V94 (+4) genome also showed that this virus had sustained a 2-nt insertion (AT, antigenome sense) at the end of the intergenic region between the HN and L genes and immediately upstream of the L gene GS signal sequence (FIG. 8A). The genome size of rHPIV2/V94 (+4) was 15,702 nts, i.e. two nts longer than the 6n+ 4 HPIV2 cDNA from which it was derived. Thus, the 2-nt insertion served to generate a polyhexameric genome length. Two independently derived, and biologically cloned rHPIV2s generated from a full-length antigenomic cDNA that was 15,701 nt (6n+5; $r_A$HPIV2/V94(+5) and $r_B$HPIV2/V94(+5)). $r_B$HPIV2/V94(+5) was completely sequenced and was found to have a single nt insertion in HN 3' untranslated region. The other ($r_A$HPIV2/V94(+5)) was partially sequenced and was found to contain a single nucleotide insertion in the HN GE signal sequence that could serve to correct the genome length so that it conforms to the rule of six (FIG. 8A). rHPIV2/V94 (+1) and rHPIV2/V94(+2) were completely sequenced and were found to have 1 and 2 nt deletions, respectively, that served to generate a polyhexameric genome (FIG. 8B). The 2 nt deletion that was found in rHPIV2/V94(+2) occurred within the intergenic sequence between the HN and L genes. Interestingly, the single nt deletion in rHPIV2/V94(+1) occurred near the end of the coding region for the L polymerase and changed the 13 amino acids encoded after codon 2250. Thus, the majority of genome length corrections occurred at sites in non-coding regions but one mutant contained an alteration in the downstream end of an ORF.

In summary, the foregoing examples provide a detailed demonstration that HPIV2 conforms to the rule of six, a demonstration that is particularly relevant because it was correlated with recovery of a complete, infectious recombinant virus. This discovery involved determination of complete genomic sequences for three strains of HPIV2, namely the prototype Greer strain and two recent HPIV2 isolates, V94 and V98. Each of these strains had a polyhexameric 15,654 nt genome length, demonstrating that the HPIV2 genome length is conserved and conforms to the rule of six. A polyhexameric antigenomic HPIV2/V94 cDNA was used to recover a recombinant HPIV2/V94 and the length of the recovered virus was also 15,654. Full-length antigenomic HPIV2 cDNAs that deviated from the rule of six by 1 to 5 nts yielded viruses that contained non-templated nt insertions or deletions which served to generate polyhexameric genomes. These findings demonstrate that an HPIV2 polyhexameric genome can be generated from a cDNA that does not conform to the rule of six, and that virus recovery in this context involves spontaneous mutations that correct the length of the genome to conform to the rule of six. This demonstrates that HPIV2 requires a polyhexameric genome for successful recovery, and is consistent with the findings that the genomes of the HPIV2 Greer, V98 and V94 strains conform to the rule of six. Thus, the requirement for a polyhexameric genome has now been demonstrated for members of the Rubulavirus and Respirovirus genera of the Paramyxovirinae subfamily, and suggests that conformation to the rule of six and the ability to correct defects that deviate the genome length from the rule of six may be universal for all members of this paramyxovirus subfamily.

Comparison of the HPIV2 Toshiba strain and the Greer strain genome sequences reveals that these strains share 99.8% sequence identity. The Toshiba and Greer strains exhibit a total of 34 nucleotide differences. Several sequence discrepancies between the Toshiba and Greer strains were noted. These included 13 nucleotides present in the Greer strain that were missing from the reported Toshiba strain sequence, and 5 additional nucleotides reported for the Toshiba sequence that were not present in the Greer strain. The high frequency of apparent deletions and insertions in particular suggests that many of the differences in the Toshiba strain represented errors in CDNA cloning, synthesis or sequence analysis—rather than true differences in nature, and also suggests that the previously reported non-compliance with the rule of six might be due to sequencing error. Correction for these 18 errors in the Toshiba strain would yield a genome length of 15,654, the same size as reported here for the V94, V98 and Greer strains of HPIV2. Based on these findings, it is likely that the recombinant Toshiba strain that was recovered previously from a cDNA that did not conform to the rule of six (Kawano et al., *Virology* 284:99-112, 2001, incorporated herein by reference) similarly sustained one or more nucleotide insertions or, potentially, deletions that would correct the genome to comply with the rule of six.

The mechanism for the genome length correction observed here for HPIV2 and previously for HPIV3 (Skiadopoulos et al., *Virology* 297:136-152, 2002) derived from cDNAs that did not follow the rule of six is not known, but two possibilities can be considered. First, nt insertions or deletions may occur during the first step of the recovery of virus from cDNA, during the (during the) synthesis of the initial antigenome RNA from the transfected antigenomic plasmid by the T7 RNA polymerase. The bacteriophage T7 polymerase has been shown to insert or delete nts after homopolymeric A or T runs, at a rate of up to 1 in 1×4.5×10$^7$ nt (Kroutil et al., *Biochemistry* 35:1046-1053, 1996, incorporated herein by reference).

The second possibility is that the nt modifications are generated by the HPIV2 polymerase. This could occur either by random nt insertions/deletions that might arise during replication of the genome or antigenome, or by a mechanism whereby the nucleoprotein replication complex somehow detects a deviation in the genome length and adds or deletes the appropriate number of nts to correct the defect and to generate a polyhexameric length. Random insertion/deletion misincorporations by either the T7 polymerase or the viral polymerase complex would be expected to occur at equal frequency at any position throughout the genome. Corrections occurring early within an open reading frame would likely be lethal for virus replication and generally only genomes with insertions in non-coding regions would be viable. The finding that the majority of the insertions or deletions reported here that modified the length of rHPIV2/V94 occurred between the HN and L genes suggests that the genome length corrections did not occur by a random insertion/deletion mechanism. Furthermore, viruses such as rHPIV2/V94 (+3) contained multiple insertion sites. Insertions at multiple sites would be expected to occur at an even much lower frequency than single-site insertions, again suggesting that random insertion is not the mechanism by which polyhexameric genome lengths are generated from cDNAs that do not conform to the rule of six.

Previously, we found that recombinant HPIV3 derived from cDNAs that did not conform to the rule of six also contained nt insertions that served to modify the genome length to conform to the rule of six. These insertions (A or U) occurred either within a polyadenylation signal sequence (poly-U), or within a poly-A or poly-U tract of a foreign gene insert contained within the HPIV3 genome. In the present study we also demonstrated a preference for homopolymeric A or U tracts as sites for insertion, suggesting that the nt insertions may be the result of polymerase stuttering. The only exception was the AU insertion and an AU deletion that occurred at an AUAU sequence in the IG region between the HN and L genes of rHPIV2/V94 (+4) and rHPIV2/V94 (+2), respectively, however these modifications may also be a result of polymerase slippage and stuttering. Interestingly, we have not observed any G or C insertions or deletions in any of the HPIV2 or HPIV3 constructs that have been sequenced. It was previously shown that Sendai virus minigenomes whose lengths did not conform to the rule of six and which contained the P gene editing site (a poly-G stretch) underwent in vitro nt insertions or deletions within the editing site that served to generate polyhexameric genome lengths (Hausmann et al., *RNA* 2:1033-45, 1996). DI genomes of SV5, a prototype virus of the Rubulavirus genus, were also shown to undergo in vitro genome length modification by nt insertions, and SV5 DI genomes whose length conformed to the rule of six replicated more efficiently than uncorrected genomes (Murphy et al., *Virology* 232:145-157, 1997, incorporated herein by reference). Other negative-stranded RNA viruses have also been shown to generate modified genomes that contain nt insertions. VSV, which is a member of the Rhabdoviridae family and has a similar genomic organization as paramyxoviruses but does not follow the rule of six, has been shown to accumulate many nt insertions in the 3' NCR of the glycoprotein gene during the natural evolution of the virus (Bilsel et al., *J. Virol.* 64:4873-83, 1990, incorporated herein by reference).

The nt insertions identified included homopolymeric stretches of U and/or As and it was suggested that these occurred by polymerase stuttering. RSV, a paramyxovirus that does not follow the rule of six, is able to generate neutralization resistant mutants by inserting or deleting As within a homopolymeric A stretch in the G protein gene (Garcia-Barreno et al., *J. Virol.* 68:5460-68, 1994; Garcia-Barreno et al., *EMBO J.* 9:4181-87, 1990).

It is not clear from the present study if the ability to correct deviations in genome length is an intrinsic property of the viral replication machinery that is used during the natural evolution of the virus to maintain proper genome length, or is an artifact of the reverse genetics system. The conservation of the length of the HPIV2 genome in strains isolated over 40 years apart, the numerous examples of negative-stranded RNA viruses that have the ability to modify their genome length, and the ease with which recombinant parainfluenza viruses can be derived from cDNAs that do not conform to the rule of six suggests that the former may be the case.

Summarizing the foregoing Examples, an authentic wild type (wt) rHPIV2/V94 was recovered from HEp-2 cells transfected with a full-length antigenomic HPIV2 cDNA and support plasmids expressing the HPIV2/V94 N, P and L proteins. The in vitro and in vivo growth characteristics of the recombinant HPIV2/V94 were generally indistinguishable to those of its biologically derived parent. Importantly, sequence analysis showed that the genome sequence of the recovered rHPIV2 was exactly consistent with the antigenomic cDNA from which it was derived with the exception of a single nt sub situation. This substitution was not present in a second isolate of recovered rHPIV2, indicating that it was an incidental point mutation such as is commonly observed in RNA viruses. Thus apart from the occasional incidental mutations characteristic of RNA virus growth, it is possible to derive rHPIV3 in which the genome sequence is exactly as designed. One requirement for success is conforming with the rule of six, which had previously been thought not to apply to HPIV2.

As discussed above, a reported HPIV2 strain (Toshiba) was previously sequenced and its genome length (Genbank ascension number X57559) was disclosed to be 15,646 nt in length. Notably, this reported sequence is 2 nt shorter or 4 Nt longer than the length shown here to be required for conformation to the rule of six, and 8 nt shorter than the correct sequence reported here for HPIV2/V94. Accordingly, this reported sequence exceeds an even multiple of six by 4 nt (6n+4) (Kawano et al., *Virology* 178:289-92, 1990a; Kawano et al., *Virology* 179:857-61, 1990b; Kawano et al., *Virology* 174: 308-13, 1990c; Kawano et al., *Virology* 284:99-112, 2001; Kawano et al., *Nucleic Acids Res.* 19:2739-46, 1991, each incorporated herein by reference). In addition, an HPIV2 Toshiba strain cDNA that did not conform to the rule of six was reported to yield successful recovery of a recombinant HPIV2 in cell culture (Kawano et al., 2001, supra). These observations provided strong support that HPIV2 does not have a requirement for its genome length to conform to the rule of six (Id.) On the basis of these reports, previous researchers considered that HPIV2 did not have a strict requirement for its genome length to conform to the rule of six.

The rule of six was originally proposed for murine parainfluenza virus type 1 (MPIV1), also called Sendai virus, based on (1) the observation that the nt length of the MPIV1 genome is an even multiple of six, and (2) studies with MPIV 1 minireplicons, which showed that efficient RNA replication was achieved only when the nt length of the minireplicon was an even multiple of six (Calain et al. *J. Virol.* 67:4822-4831, 1993, incorporated herein by reference). Other reports propose that members of the Respirovirus and Morbillivirus genera of Paramyxoviridae generally follow the rule of six, based on the nt lengths of naturally occurring genomes and on minigenome studies with a few representative viruses (Durbin et al., *Virology* 234:74-83, 1997b; Pelet et al., *Virology* 224:405-141, 1996; Sidhu et al., *Virology* 208:800-71, 1995, each incorporated herein by reference). This requirement for polyhexameric length is thought to be a consequence of each N protein subunit interacting with exactly six nucleotides in the vRNA-nucleoprotein complex (Kolakofsky et al., *J. Virol.* 72:891-899, 1998; Vulliemoz et al., *J. Virol.* 75:4506-18, 2001, each incorporated herein by reference). It should be noted that the rule of six not been previously been rigorously tested by systematic manipulation of complete infectious virus, which is the dispositive setting for determining the relevance and significance of the rule to virus biology. Rather, available experimental evidence was based primarily on incomplete, helper-dependent, non-infectious minireplicons assayed in vitro.

The rule of six does not appear to apply to numerous other nonsegmented negative strand RNA viruses, such as members of the Rhabdoviridae and Filoviridae families. The rule also does not apply to the Pneumovirus genus of Paramyxoviridae (Samal et al., *J. Virol.* 70:5075-5082, 1996, incorporated herein by reference), represented by human RSV, and probably also does not apply to the Metapneumovirus genus of Paramyxoviridae (van den Hoogen et al. *Virology* 295:119-132, 2002, incorporated herein by reference). Thus, most nonsegmented negative strand viruses do not conform to the rule of six, and a similar requirement that the genome nt length be a multiple of a specific integer does not exist in any other type of virus.

The remaining genus of Paramyxoviridae, Rubulavirus, also did not appear to follow the rule of six. For example, minireplicon studies with SV5, a prototype Rubulavirus, indicated that a polyhexameric was not required for efficient RNA replication. (Murphy et al., *Virology* 232:145-157, 1997, incorporated herein by reference).

Other previous observations were consistent with the idea that Rublaviruses, as exemplified by HPIV2, did not follow the rule of six. For example, in members of Respirovirus and Morbillivirus, which do conform to the rule of six, the positions of the first nt of the gene start (GS) signals of the various genes are largely conserved with regard to the hexameric phasing, suggesting that correct hexamer phasing of cis-acting signals is important for optimal functioning (Kolakofsky et al., 1998). Also, the members of these two genera have highly conserved trinucleotide intergenic regions, whose precise and invariant length also would be consistent with maintaining hexameric phasing of cis-acting sequences. In contrast, the Rubulaviruses have a low degree of conservation of the phasing of the GS signals (Kolakofsky et al., *J. Virol.* 72:891-899, 1998, incorporated herein by reference). Also, Rubulaviruses have highly variable intergenic regions: in the case of HPIV2, these vary in length from 4 nt up to 45 nt. These findings suggest that hexameric phasing of cis-acting signals is not important for HPIV2.

It has, therefore, become generally accepted in the field that the rule of six was limited to two genera of Paramyxoviridae: Respirovirus and Morbillivirus. Also, as noted above, this rule was based largely on in vitro studies with minireplicon systems, and its importance to complete infectious virus and viral biology had not been clearly established. In any case, this rule was thought to not apply to Rublaviruses. This was view was strongly supported by the teachings of Kawano et al., 2001, supra, who disclosed the genome length of HPIV2 to be non-polyhexameric, and who further reported that a non-polyhexameric recombinant antigenomic cDNA produced infectious HPIV2. This report concerning HPIV2 was particularly compelling, because the underlying studies involved the reported recovery of complete infectious virus, as opposed to simple minireplicon RNA replication studies. The recovery of infectious virus from an antigenomic cDNA clone typically is relatively inefficient, such that a well of $1.5 \times 10^6$ transfected cells might yield virus from 10 or fewer cells. Furthermore, any defect that reduced the replication efficiency of infectious virus by even a small margin would quickly become apparent during multi-cycle virus growth. Hence, the reported ability to recover infectious virus was considered to provide a very stringent test that the cDNA-encoded antigenomic RNA was highly functional. Therefore, the previous recovery of recombinant Toshiba strain HPIV2 from a non-polyhexameric antigenomic cDNA seemingly provided convincing evidence that the rule of six did not apply to this virus.

One of the key advantages of a cDNA based reverse genetics system for the generation of viral variants is the ability to reproducibly recover recombinant viruses that contain a defined sequence. The goal of producing defined viral strains for development of useful immunogenic compositions is possible only if an engineered antigenomic sequence can be faithfully recovered in infectious virus. The reliable recovery of defined recombinant viruses is essential for studies to systematically adjust the level of viral attenuation and immunogenicity.

Unexpectedly, the present invention shows that the consensus sequences determined for three additional strains of HPIV2, including two clinical isolates of low passage history, conform to the rule of six. Comparison with the published Toshiba sequence provides evidence that the latter contains numerous unpredictable nucleotide (nt) deletions and insertions. While the origin and significance of these insertions/deletions are not known, such mutations are not characteristic of natural drift in this type of virus but rather are hallmarks of cloning or sequencing errors. Given the previous report that recombinant Toshiba strain HPIV2 was recovered from a non-polyhexameric antigenomic cDNA (Kawano et al., 2001, supra), it was undertaken herein to systematically investigate the possibility of recovering infectious virus from a panel of antigenomic cDNAs specifically engineered to span the full range of non-compliance with polyhexamer phasing. Remarkably, recombinant virus was recovered readily from each cDNA. These results would generally have been construed to validate the results reported by Kawano et al., as summarized above. However, detailed description and analysis of complete consensus genomic sequences presented herein demonstrate that each recovered virus did not contain a faithful genomic copy of its respective antigenomic cDNA. Instead, each contained one or more nt insertions or deletions that served to confer a polyhexameric genomic length. This demonstrates that there is a for rapid emergence of polyhexameric genomes in recombinant HPIV2 viruses derived from non-polyhexameric antigenomes.

These findings have important implications for the development of defined mutant HPIV2 viruses and vectored immunogenic compositions by reverse genetics. Specifically, while virus can readily be recovered from a HPIV2 cDNA that is not of polyhexameric length, the present invention shows that such virus will contain one or more unpredictable insertions or deletions. The locations of these mutations cannot be clearly forecast, and the potential of these mutations to alter the properties of the virus or vector with regard to growth, immunogenicity, expression of a supernumerary gene insert, pathogenicity, and other properties is equally unpredictable. Thus, the use of a non-polyhexameric antigenomic HPIV3 cDNA would generally be viewed to specifically preclude the production of recombinant virus with a genome of known sequence, since the recovered virus will have one or more unpredictable insertions or deletions.

The discovery that natural isolates of HPIV2 have polyhexameric length genomes, that HPIV2 strictly follows the rule of six at the level of infectious virus, and that non-polyhexameric antigenomic cDNAs readily generate mutated virus and must be avoided, was unanticipated and provides the basis for the generation of recombinant HPIV2-based immunogenic compositions and viral vectors of defined sequence by reverse genetics.

In the present disclosure, recovery of virus from a HPIV2 cDNA that does not conform to the rule of six, and the demonstration that such virus has undergone length adjustments to conform to the rule of six, clarifies the requirement of HPIV2 to conform to the rule of six, and further evinces that the mechanism for this conformity is self-correction. In this context, previous understanding in the art concerning HPIV2, which contemplated that this virus does not conform to the rule of six, leads to a situation that would greatly complicate, and in the majority of cases preclude, the production of viruses of defined sequence. This is because a recovered virus that is not compliant with the rule of six would be under a strong selective pressure to self-correct to conform to the rule of six, since this would confer more efficient replication and allow the corrected virus to quickly outgrow the starting virus. Such self-correction would involve nt insertions or deletions to make the genome an even multiple of six. Indeed in the examples in the present invention all viruses recovered from antigenomes that did not comply to the rule of six contained mutations.

Furthermore, it is not possible to reliably predict where in the HPIV2 genome such corrective changes might occur. For example, instances of correction in the above-mentioned PIV3 system have been found both within and outside of open reading frames, and within cis-acting signals. Similarly, it is not possible to reliably predict what the phenotypic consequences of such changes might be. For example, there are numerous instances of mutations that have minimal effect on growth in vitro but are very deleterious on replication in vivo. This is especially problematic for use of rHPIV2 as a vector, since a supernumerary foreign protective antigen, which is not required for replication of the virus, would be a preferential target for the random insertions/deletions that would serve to correct the genome. The insertion or deletion of nts would disrupt the reading frame or cis-acting regulatory sequences and potentially ablate expression of the foreign protective antigen. Thus, a recovery system that is not compliant with the rule of six cannot reliably produce viruses of defined sequences and, indeed, would preferentially produce mutant viruses that have sustained length correction by Nt deletion or insertion within the genome with potentially altered properties. It therefore would not be a desirable substrate for the generation of live-attenuated candidate HPIV2 immunogenic compositions.

The recovery of virus from a cDNA not in compliance with the rule of six has the highly unpredictable effect of forcing mutations to occur. A principal adverse consequence of this phenomenon is that one cannot reliably forecast where such length corrections might occur, nor is it possible to cannot control the location(s) of such correction(s). In addition, such corrections almost always affect gene start phasing. Accordingly, the demonstration here of the dependence of HPIV2 on the rule of six, and adherence to this rule by virus strains so recovered, is important for the production of virus of predetermined sequence. Conversely, the failure to recognize and adhere to this rule heretofore precluded recovery of virus having a defined, reproducible sequence, as opposed to a recombinant virus having mutations whose location, and phenotypic significance, could not have been clearly forecast.

The foregoing studies suggest that, when a virus is recovered from cDNA that does not conform to the rule of six, two possible explanations can be considered: (1) that the rule of six does not apply, or (2) length correction occurred. The second possibility previously seemed unlikely, because for paramyxoviruses insertions and deletions tend to be much less frequent than nucleotide substitutions, and because it is difficult to imagine how such a length correction might occur with sufficient frequency to account for the efficient recovery that was observed for non-compliant cDNAs. Accordingly, previous reports rendered a strong conclusion that HPIV2 does not strictly obey the 'rule of six'.

The present discoveries are therefore remarkable and unpredictable, because they show that length correction indeed does occur, and apparently occurs at an inexplicably high frequency. Previously, the facile recovery of virus from non-compliant cDNAs was interpreted to mean that the rule of six does not apply strictly to HPIV2. From this accepted model, artisans would have proceeded to unknowingly develop recombinant viruses containing undisclosed mutations conferring unknown phenotypic properties. The present invention provides unexpected information that will avoid this critical obstacle to the development of viruses and vectors from recombinant HPIV2.

EXAMPLE VI

Importation of Mutations Identified in Heterologous Paromyxoviruses into the L Protein of HPIV2

Within other aspects of the present invention, various attenuating mutations identified in heterologous paramyxoviruses can be introduced into a recombinant HPIV2, singly or in combination, to obtain a suitable degree of attenuation or other desired phenotypic effects. For example, specific mutations that confer the attenuation phenotype of HPIV3 cp45 can be introduced at a corresponding target site in rHPIV2. Additional attenuating mutations have been developed by "importing" attenuating point mutations from RSV and BPIV3 into a recombinant HPIV. In certain embodiments, point mutations are introduced into recombinant viruses of the invention using two or three nucleotide changes at a codon specifying the mutation, rather than one, which will stabilize the mutation against reversion to wild type.

Since attenuating mutations have not been previously described or available for HPIV2, the use of heterologous mutations is particularly desired to attenuate rHPIV2 of the invention. Using sequence alignments as a guide, several mutations identified in the L protein of HPIV3cp45, and in a novel attenuated chimeric bovine-human recombinant designated rHPIV3-$L_B$, were used as exemplary mutations to produce live-attenuated HPIV2 for use in immunogenic compositions. These included recombinants bearing mutations at positions 460, 948, 1565, and amino acids 1724-1725 ($\Delta$1724) of the L polymerase. Recombinants recovered from HPIV2 cDNA were biologically cloned and were confirmed to contain the appropriate mutation specified by the cDNA using RT-PCR of purified vRNA as described previously. Each of the four mutant recombinants bearing HPIV2 L mutations grew to high titer ($\geqq$27.8 $\log_{10}$ TCID$_{50}$/ml) indicating that replication was not restricted at permissive temperature (32° C.). Unexpectedly, one mutant, rHPIV2: Δ1724, containing a 2 amino acid deletion in the L protein (note that two codons were deleted in this mutant to conform to the rule of six, although the corresponding target site of interest for importing the mutation is residue 1724) grew to almost $10^9$ TCID$_{50}$/ml—indicating that its growth in vitro was also unaffected by the mutation in the L protein. These exemplary mutations and other mutations identified in heterologous paramyxoviruse can be introduced into a rHPIV having other nucleotide modifications, for example chimeric and vector HPIV2 constructs as described herein.

Replication of Mutant rHPIV2s in LLC-MK2 Cells at Permissive and Restrictive Temperatures The ts phenotype for each of the four exemplary mutant rHPIV2 viruses was determined by comparing its level of replication to that of rHPIV2 wild type at 32° C. and 38° C. and 39° C. as described previously (Skiadopoulos et al., Vaccine 18:503-510, 1999, incorporated herein by reference). Briefly, each virus was serially diluted 10-fold in 96-well LLC-MK2 monolayer cultures in L-15 media (Quality Biologicals or Gibco-Invitrogen, Inc.) and antibiotics. Replicate plates were incubated at the temperatures indicated above for six days, and virus infected cultures were detected by hemadsorption with guinea pig erythrocytes. Virus titer at each temperature was determined in two to six separate experiments and is expressed as the $\log_{10}$ 50 percent tissue culture infectious doses per milliliter (TCID$_{50}$/ml). The reduction in titer at elevated temperature was compared to the titer at 32° C., and a mean reduction in titer was determined. The shut-off temperature of a rHPIV2 mutant is defined as the lowest temperature at which the reduction in virus titer compared to its titer at 32° C. was 100-fold greater than that of wild type rHPIV2 at the same temperature. A mutant is defined as temperature sensitive if its reduction in replication at 39° C., i.e., the titer at 32° C. minus that at 39° C., is 100-fold or greater than that of wild type rHPIV2.

As a reference in some experiments, a recombinant HPIV1 L protein mutant, rHPIV1 L: Y942Hcp45, was concurrently tested as described above except trypsin was added to the growth medium. The four exemplary rHPIV2 viruses bearing mutations imported from RSV, HPIV3 or rHPIV3-L$_B$ were tested for their ability to replicate at permissive temperature (32° C.) versus a range of higher temperatures (38-39° C.) by titration on LLC-MK2 monolayers (Table 2). Interestingly none of the ts and att mutations imported from RSV or HPIV3cp45 specified a ts phenotype in rHPIV2. However, the mutation targeting residue 1724 of the L protein specified a ts phenotype with a shutoff temperature of 39° C.

TABLE 2

Replication of biologically derived and recombinant HPIV2 at permissive and restrictive temperatures

| | Titer[a] at indicated temperature (° C.) ($\log_{10}$ TCID$_{50}$/ml) | | |
|---|---|---|---|
| Virus | 32 | 38 | 39 |
| rHPIV2/V94 (Not) wt | 8.1 | 8.5 | 7.3 |
| rHPIV1 L: Y942H$_{cp45}$ | 8.1 | 2.6 | 2.5 |
| rHPIV2 L: F460L | 8.6 | 8.0 | 7.7 |
| rHPIV2 L: Y948H | 8.6 | 8.2 | 7.1 |

TABLE 2-continued

Replication of biologically derived and recombinant HPIV2 at permissive and restrictive temperatures

| | Titer[a] at indicated temperature (° C.) ($\log_{10}$ TCID$_{50}$/ml) | | |
|---|---|---|---|
| Virus | 32 | 38 | 39 |
| rHPIV2 L: L1565I | 8.0 | 7.7 | 7.1 |
| rHPIV2 L: Δ1724 | 7.8 | 6.3 | 4.5 |

[a]Values in bold type are at or below the shut-off temperature, which is defined as a 100-fold or more reduction in titer compared to the titer at 32° C. while correcting for the loss of wild type titer.

Replication of Biologically Derived and rHPIV2 Mutant Viruses in the Respiratory Tract of Hamsters The ability of these exemplary mutant HPIV2 strains to replicate in the respiratory tract of hamsters was evaluated as follows. Four to five week-old Golden Syrian hamsters were inoculated intranasally with 0.1 ml of L-15 medium containing $10^{6.0}$ TCID$_{50}$ of a wild type or mutant HPIV2. Lungs and nasal turbinates were harvested on day four post-infection, and the titer of virus was determined as previously described (Skiadopoulos et al., Vaccine 18:503-510, 1999). The mean $\log_{10}$ TCID$_{50}$/g was calculated for each group of six hamsters. Each of the wild type, biologically derived strains of HPIV2 replicated to high titer in the upper and lower respiratory tract of hamsters. The level of replication of the recombinant HPIV2 was similar to that of its biologically derived parent virus. The ability of the four rHPIV2 mutants containing a mutation imported from RSV, HPIV3cp45, or rHPIV3-LB to replicate in the upper and lower respiratory tract of hamsters was examined. The level of replication of the rHPIV2 mutants in the upper (nasal turbinates) and lower (lungs) respiratory tract of infected hamsters was compared to that of wild type recombinant HPIV2 (Table 3). Among the single amino acid mutations, recombinant HPIV2 bearing the F460L or L1565I mutations in the L protein exhibited a 100-fold or greater reduction in replication in the lower respiratory tract of hamsters compared to the recombinant rHPIV2/V94 (Not) parent virus. These results demonstrate that the two subject mutations specify an in vivo attenuation phenotype for rHPIV2.

TABLE 3

Replication of biologically derived strains of HPIV2 and recombinant wild type or mutant HPIV2/V94 in the respiratory tract of hamsters

| | | Mean virus titer ($\log_{10}$ TCID$_{50}$/g ± S.E.) | |
|---|---|---|---|
| Virus[a] | No. of animals | Nasal Turbinates | Lungs |
| HPIV2/Greer wild type | 4 | 6.1 ± 0.1 | 5.8 ± 0.1 |
| HPIV2/V98 wild type | 6 | 5.4 ± 0.2 | 4.8 ± 0.4 |
| HPIV2/V94 wild type | 6 | 4.9 ± 0.2 | 5.2 ± 0.8 |
| rHPIV2/V94 (Not) | 6 | 5.2 ± 0.1 | 5.5 ± 0.3 |
| rHPIV2 L: F460L | 6 | 5.0 ± 0.1 | 3.1 ± 0.3 |
| rHPIV2 L: Y948H | 6 | 5.6 ± 0.1 | 4.5 ± 0.4 |
| rHPIV2 L: L1565I | 6 | 4.6 ± 0.4 | 3.1 ± 0.5 |
| rHPIV2-F$_{RSV}$ | 6 | 4.1 ± 0.3 | 2.1 ± 0.4 |

[a]Hamsters in groups of 6 or 4 were inoculated IN with $10^6$ TCID$_{50}$ of the indicated virus. Nasal turbinates and lung tissues were harvested on day 4 post-infection, and virus present in the tissues was quantified by serial dilution on LLC-MK2 monolayers incubated at 32° C. The mean virus titer ± standard error (S.E.) is shown.
Values in bold show a 100-fold or more reduction in titer compared to the titer of rHPIV2/V94.

Attenuation of rHPIV2 in Non-Human Primates

The replication of the rHPIV2-L: Δ1724 recombinant was compared to that of the wild type HPIV2/V94 in an accepted non-human primate model for evaluating attenuation of recombinant HPIVs for use in immunogenic compositions in humans (African green monkeys seronegative for HPIV2). The monkeys were inoculated intranasally (IN) and intratracheally (IT) with one milliliter of L15 medium containing $10^6$ TCID$_{50}$ of virus suspension, as described previously (Durbin et al., *Vaccine* 16:1324-30, 1998). Nasopharyngeal swab samples were collected on days 1 through 10 post immunization, and tracheal lavage samples were collected on days 2, 4, 6, 8, and 10 post-immunization. Virus present in the collected samples was quantified by serial dilution on LLC-MK2 monolayer cultures at 32° C. and is expressed as $\log_{10}$ TCID$_{50}$/ml (Table 4). The biologically derived virus replicated to a high level in the lower respiratory tract and to a lower level in the upper respiratory tract (FIG. 12). The rHPIV2-L:Δ1764 mutant was attenuated for replication in both the upper and lower respiratory tracts relative to its biologically derived parent virus. This identified the L:Δ1724 mutation as one that confers a high level of attenuation to rHPIV2 in primates. Because this mutation is a two amino acid deletion, the subject recombinant virus will be highly stable following replication in vivo—a highly desired characteristic for a candidate virus for use in immunogenic compositions and methods.

TABLE 4

Level of virus replication of biologically derived and recombinant HPIV2 in African green monkeys

| Virus administered[a] | Mean peak virus titer[b] ± S.E. ($\log_{10}$TCID$_{50}$/ml) in: | |
| --- | --- | --- |
| | NP swab | TL |
| HPIV2/Greer wild type | 2.7 ± 0.6 | 3.7 ± 0.5 |
| HPIV2/V98 wild type | 2.6 ± 0.6 | 4.6 ± 0.5 |
| HPIV2/V94 wild type | 2.5 ± 0.6 | 5.2 ± 0.3 |
| rHPIV2/V94 (Not) wt | 1.9 ± 0.5 | 3.4 ± 0.2 |
| rHPIV2 L: Δ1724 | 1.3 ± 0.5 | 2.0 ± 0.2 |

[a]Animals were infected IN and IT with $10^6$ TCID$_{50}$ of the indicated virus.
[b]Nasopharyngeal (NP) swab samples were collected on days 1 to 10 post-infection. Tracheal lavage (TL) samples were collected on days 2, 4, 6, 8 and 10 post-infection. Mean of the peak virus titer for each animal in its group irrespective of sampling day.
S.E. = standard error.
The lower limit of detection of virus titer is 10 TCID$_{50}$/ml.

EXAMPLE VII

Use of the Wild type rHPIV2/V94 as a Vector to Express Protective Antigens of Heterologous Pathogens In other aspects of the invention, compositions and methods are provided that employ various recombinant HPIV2 constructs as vectors to express one or more protective antigen(s) of a heterologous pathogen, for example as a substitute or supernumerary gene or genome segment. Heterologous pathogens of interest in these aspects of the invention include, for example, heterologous PIVs, measles virus, human metapneumovirus (HMPV), and RSV.

As noted above, HPIV1, 2 and 3 represent different serotypes that do not naturally provide cross protection, and hence effective immunogenic compositions must be designed specifically against each serotype virus. In addition, recombinant HPIV2 viruses of the invention have properties that make them particularly useful as vectors to express the protective antigens of other microbial pathogens, including other HPIVs.

The major protective antigens of HPIVs and of certain other mononegavirus pathogens, such as measles virus and respiratory syncytial virus (RSV), are the two major surface proteins that mediate attachment and penetration of the host cell. These are the HN and F glycoproteins of the PIVs, the HA and F glycoproteins of measles virus, and the G and F proteins of RSV. Importantly, for each of these viruses, either glycoprotein expressed alone functions as a neutralization and protective antigen. In contrast, "internal" proteins of these viruses can induce protective immunity that appears to be mediated by CD8+ cytotoxic T cells, but this protective effect wanes within a matter of months and does not appear to be a significant component of long lived resistance to reinfection (Connors et al., *J Virol* 65:1634-71991; Kulkarni et al., *J Virol* 67:1044-9, 1993; Tao et al., *Vaccine* 17:1100-1108, 1999). Numerous studies have shown that expression of even a single mononegavirus protective glycoprotein antigen can elicit a high level immune response in mammalian subjects, which may include both local and systemic immunity—despite neutralizing and immunosuppressive effects of maternal antibodies present in infants and young children. Unexpectedly, HPIV2 vectors of the invention are particularly well suited as vectors for immunization against a number of pathogens, especially for pediatric populations.

While several members of the Paramyxovirus family have been shown to be suitable as expression vectors, a recombinant HPIV2 expression vector has not been previously described. Modification of a single recombinant virus to induce immunity against multiple pathogens has several advantages. It is more feasible and expeditious to develop a single attenuated chimeric viral "backbone" construct expressing antigens that elicit a polyspecific immune response against multiple pathogens, than it is to develop separate attenuated viruses for each pathogen. Each pathogen offers different challenges for manipulation, attenuation and demonstration of safety and efficacy, and it would be a daunting task to develop an attenuated version of each of a series of pathogens. It is considerably more efficient to develop, prepare, handle, and administer a single immunogenic virus than it is to administer several attenuated viruses. Reducing the number of immunizing viruses also will simplify the crowded schedule of pediatric immunizations. Several attenuated viruses can be administered as a mixture, but this complicates development of clinically applicable immunogenic compositions, since each component must be shown to be safe separately, and then shown to be safe and efficacious as a mixture. One particular problem with the administration of mixtures of viruses is the common phenomenon of viral interference, in which one or more of the viruses in the mixture interferes with the replication of one or more of the other components. This may result in reduced replication and immunogenicity for one or more components, which is obviated by the use of a single vector backbone. Also, since some viruses such as measles virus have particular safety concerns, as described below, it is safer to use a single comparatively benign virus such as HPIV2 as a vector bearing multiple supernumerary antigens, as opposed to a mixture of separately-attenuated viruses, each of which must be developed and validated separately.

The HPIV2 vector system has unique advantages over other members of the single-stranded, negative-sense viruses of the Order Mononegavirales. First, most other mononegaviruses that have been used as vectors are not derived from human pathogens e.g. murine HPIV1 (Sendai virus) (Sakai et al., *FEBS Lett* 456: 221-61999), vesicular stomatitis virus (VSV) which is a bovine pathogen (Roberts et al., 1998), and canine PIV2 (SV5) (He et al., *Virology* 237:249-60, 1997). For these nonhuman viruses, little or only weak immunity is conferred against any human virus by antigens present in the vector backbone. Thus, a nonhuman virus vector expressing a supernumerary gene for a human pathogen will generally only elicit an effective immune response against that single human pathogen. In addition, use of non-human viruses such as VSV, SV5, rabies, or Sendai virus as vector requires exposure of subjects to viruses that they likely would not otherwise encounter during life. Infection with, and immune responses against, such nonhuman viruses poses additional safety concerns because there is little experience of infection with these viruses in humans.

Three human mononegaviruses that have been proposed for use as vectors, measles, mumps, and rabies viruses, have additional limitations that make them poor candidates for this purpose. For example, measles virus has been considered for use a vector for the protective antigen of hepatitis B virus (Singh et al., *J Virol* 73: 4823-8, 1999). However, this combined measles virus-hepatitis B virus vaccine could only be given, like the licensed measles virus vaccine, after nine months of age, whereas the current hepatitis B virus vaccine is recommended for use in early infancy. This is because the currently licensed measles virus vaccine is administered parenterally and is very sensitive to neutralization and immunosuppression by maternal antibodies, and therefore is not effective if administered before 9-15 months of age. Thus, it could not be used to vector antigens that cause disease in early infancy and therefore would not be useful for eliciting effective immune responses in these subjects against RSV and HPIVs. Another well known, characteristic effect of measles virus infection is virus-mediated immunosuppression, which can last several months and is not a desirable feature for a vector. The attenuated measles virus vaccine was associated with altered immune responses and excess mortality when administered at increased dose, which might be due at least in part to virus-induced immunosuppression and indicates that even an attenuated measles virus might not be appropriate as a vector. Furthermore, the use of measles virus as a vector would be inconsistent with the global effort to eradicate this pathogen. Indeed, for these reasons it would be desirable to end the use of live measles virus and replace the present measles virus vaccine with a PIV vector that expresses measles virus protective antigens, as described herein.

Rabies virus, a rare cause of infection of humans, has been also considered for use as a vector (Mebatsion et al., *Proc. Natl. Acad. Sci. U.S.A.* 93:7310-4, 1996), but it is unlikely that a vector that is 100% fatal for humans would be developed for use as a live attenuated virus vector, especially since immunity to the rabies virus, which is not a ubiquitous human pathogen, is not needed for the general population. While mumps and measles viruses are less pathogenic, infection by either virus can involve undesirable features. Mumps virus infects the parotid gland and can spread to the testes, sometimes resulting in sterility. Measles virus establishes a viremia, and the widespread nature of its infection is exemplified by the associated widespread rash. Mild encephalitis during mumps and measles infection is not uncommon. Measles virus also is associated with a rare progressive fatal neurological disease called subacute sclerosing encephalitis.

In contrast, PIV infection and disease in normal individuals is limited to the respiratory tract, a site that is much more advantageous for immunization than the parenteral route. Viremia and spread to secondary sites can occur in severely immunocompromised experimental animals and humans, but this is not a characteristic of typical PIV infection. Acute respiratory tract disease is the only disease associated with PIVs. Thus, use of PIVs as vectors will, on the basis of their biological characteristics, avoid complications such as interaction of virus with peripheral lymphocytes, leading to immunosuppression, or infection of secondary organs such as the testes or central nervous system, leading to other complications.

An important and specific feature of PIV vector systems is that they may be administered intranasally, mimicking natural infection and inducing both mucosal and systemic immune responses. PIV vector systems will also reduce neutralizing and immunosuppressive effects of maternally-derived serum IgG that is present in infants. In addition to these advantages, conditions have been established to obtain high titers of PIV3 in microcarrier culture that are 10 to 1000 times greater than can be achieved with viruses such as RSV and measles virus. Additional advantages of a PIV vector system relate to ease of propagation, transport, storage and handling compared to other contemplated vector systems.

The recombinant HPIV2 viruses described here can be used as vectors for expressing the protective antigens of heterologous human pathogens, for example by inserting a supernumerary gene encoding one or more antigenic determinants of a different pathogen, such as another Paramyxovirus. For example, the F and/or HN protein(s) of HPIV1 or HPIV3, or the F and/or G glycoprotein(s) of respiratory syncytial virus (RSV) (or one or more antigenic domains, segments, or epitopes thereof) can be substituted or inserted as a supernumerary gene or genome segment into a recombinant HPIV2 backbone or vector. Exemplary design of such a chimeric rHPIV2 is illustrated in FIG. 2. In this example, a unique restriction enzyme endonuclease recognition sequence (Not I) is introduced by PCR mutagenesis immediately upstream of the translation initiation codon (AUG) of the HPIV2 N gene (nts 158-160). This can then be used to insert an operable coding sequence corresponding to an antigen or antigenic determinant of a heterologous virus. In exemplary embodiments an open reading frame (ORF) encoding a heterologous antigen is placed under HPIV2 cis-acting transcription control elements and is transcribed as an additional mRNA.

Use of Recombinant HPIV2 as an Expression Vector for Supernumerary Foreign Genes Including the RSV F Glycoprotein and Green Fluorescent Protein (GFP).

Thus, in one exemplary aspect of the invention, the superior characteristics of rHPIV2 vectors provide for development of immunogenic compositions effective to elicit an immune response against RSV. In the present example, HPIV2 cDNAs were constructed containing gene units expressing the RSV subtype A fusion protein (F) ORF or a green fluorescent protein (GFP) ORF inserted upstream of the N coding sequence and under the control of the cis-acting HPIV2 transcription signals. From these cDNA constructs, recombinant HPIV2 vector viruses expressing the RSV F protein or GFP were recovered. Recombinants were biologically cloned and high titer pools were generated ($\geq 7.0 \log_{10}$ $TCID_{50}$/ml). Expression of the GFP was confirmed by fluorescent microscopy, indicating that supernumerary genes inserted upstream of the HPIV2 N gene are well tolerated. Unexpectedly, the recombinant containing an additional gene encoding the RSV F protein (rHPIV2-FRSV) was moderately attenuated for replication in vitro (FIG. 13). This virus grew to $10^{7.6}$ $TCID_{50}$ in cell culture. However, its rate of growth was reduced compared to wild type HPIV2. Expression of the RSV fusion protein was confirmed by indirect immunofluorescence using monoclonal antibodies to the RSV fusion protein as described previously (Skiadopoulos et al., *J Virol* 70:1117-24, 1996; Skiadopoulos et al., *Virology* 297: 136-52, 2002; Schmidt et al., *J Virol* 75: 4594-603, 2001)). Thus this recombinant expresses the protective antigens of two human pathogens, RSV and HPIV2.

The level of replication of rHPIV2-FRSV in hamsters was determined by inoculating groups of 6 hamsters IN with $10^6$ $TCID_{50}$ of rHPIV2-FRSV or rHPIV2 wt and determining the level of replication of each virus in the lungs and nasal turbinates on day 4 post-infection. As shown in Table 3, the rHPIV2-FRSV was 10-fold reduced for replication in the upper respiratory tract, and 2500-fold reduced for replication in the lower respiratory tract. This level of attenuation was unexpected because similar chimeric bovine-human PIV3 and HPIV1 recombinants bearing the RSV F gene in the first transcriptional position were not attenuated in vitro or in vivo. This identifies rHPIV2-FRSV as a novel class of HPIV2 mutant; an HPIV2 expression vector attenuated by virtue of a single gene unit insertion upstream of the N gene.

EXAMPLE VIII

Additional Analyses of Attenuating Mutations in rHPIV1 for Development of Immunogenic Compositions and Methods As noted above, the instant invention also provides novel recombinant HPIV1 viruses and related compositions and methods that are useful alone and/or in combination with the HPIV2 compositions and methods described herein. For economy of description, foundational aspects of these embodiments are described, for example, in U.S. patent application Ser. No. 10/302,547, filed by Murphy et al. on Nov. 21, 2002 and in the corresponding PCT Publication Number WO 03/043587 A2, published on May 30, 2003 (each incorporated herein by reference). Mutations and other modifications identified and characterized for rHPIV1 viruses of the invention can be readily incorporated and evaluated in rHPIV2 viruses described herein, and vice versa.

In exemplary embodiments, the recombinant HPIV1 genome or antigenome incorporates one or more recombinantly-introduced, temperature sensitive (ts) or host range (hr) mutations. Often, the recombinant HPIV1 genome or antigenome will incorporate one or more attenuating mutation(s) identified in a biologically derived mutant PIV strain, or in another mutant nonsegmented negative stranded RNA virus, for example RSV or murine PIV (MPIV). For example, the recombinant HPIV1 genome or antigenome can be modified or constructed to incorporate one or more mutation(s) corresponding to mutation(s) identified in a HPIV1, or a heterologous PIV such as the well known immunogenic composition candidate HPIV3 JS cp45. Useful mutations of HPIV3 JS cp45 or another mutant virus can specify a change in a HPIV1 protein selected from L, M, N, C, F, or HN or in a HPIV1 extragenic sequence selected from a 3' leader or N gene start sequence. Where the mutation relates to a particular amino acid residue, the recombinant HPIV1 genome or antigenome will often incorporate multiple nucleotide changes in a codon specifying the mutation to stabilize the modification against reversion.

The large polymerase protein (L) is highly conserved at the amino acid level between human parainfluenza virus type 1 and type 3 (HPIV1 and HPIV3). The Y942H and L992F temperature sensitive (ts) and attenuating amino acid substitution mutations, previously identified in the L polymerase of the HPIV3-cp45 vaccine candidate, were introduced into homologous positions of the L polymerase of recombinant HPIV1 (rHPIV1). In rHPIV1, the Y942H mutation specified the ts phenotype in vitro and the attenuation (att) phenotype in hamsters, whereas the L992F mutation specified neither phenotype. Each of these two mutations in both HPIV3-cp45 and rHPIV1 was generated by a single nucleotide substitution and, therefore, had the potential to readily revert to a codon specifying the wild type amino acid residue. In the present Example, the effects of introducing alternative amino acid assignments at either codon was evaluated as a strategy to increase genetic stability and to explore the range of possible attenuation phenotypes for rHPIVs of the invention.

An HPIV1 antigenomic cDNA was molecularly engineered to specify each of the other 18 amino acids at position 942 of the L protein or 17 of the 18 other amino acids at position 992. Thirteen rHPIV1 codon substitution mutants with alternative amino acid substitutions at position 942 and 10 mutants at position 992 were shown to be viable. At position 942, a number of mutants with a similar level of temperature sensitivity and attenuation as the Y942H virus were identified, several of which differed by three nucleotides from either of the two codons encoding the wild type assignment of Tyr. One such mutant, the Y942A virus, was directly confirmed to possess a high level of genetic and phenotypic stability upon serial passage in vitro at successively elevated restrictive temperatures compared to the Y942H virus involving a single nucleotide substitution, which was relatively unstable. At position 992, three substitution mutants, L992V, L992C and L992N, were obtained that, in contrast to the L992F virus, possessed the ts and att phenotypes. These findings identify codon substitution mutations that specify increased genetic stability and/or increased attenuation, properties that are highly desirable for mutations in a live attenuated HPIV1 or HPIV2.

In the HPIV3 backbone, the Y942H and L992F mutations each specify the ts phenotype in vitro and the att phenotype in hamsters. One objective in the present Example was to determine the effect of each mutation in the HPIV1 backbone, and to validate a general strategy for increase the genetic and phenotypic stability of ts and att amino acid point mutations in live attenuated HPIVs. The high mutation rate for RNA viruses in general renders single-nucleotide changes susceptible to genetic and phenotypic instability. Since one mechanism of loss of the ts phenotype is reversion of the nucleotide substitution to the wild type assignment, we sought to modify the rHPIV1 codons such that two or three nucleotide changes would be required to restore the wild type amino acid coding assignment. This strategy has been previously employed to generate a set of attenuated recombinant Sindbis viruses bearing codon substitution mutations at several sties in the E2 virion protein. (Polo et al., *J Virol* 65:6358-61, 1991; Schoepp et al., *Virology* 193:149-59, 1993). These recombinant viruses exhibited different levels of attenuation in vivo, but their phenotypic stability in vitro or in vivo was not explored. Thus, we used mutagenesis at rHPIV1 codons 942 and 992 to explore the range of viable amino acid coding assignments at each position and recovered 13 rHPIV1 viruses each with a different amino acid at position 942 and 10 viruses each with a substitution at position 992. These codon substitution mutants were assayed for temperature sensitivity of replication in vitro and for their ability to replicate in the respiratory tract of hamsters. rHPIV1 viruses with increased attenuation or genetic stability were identified in both codons. These mutations will be useful as attenuating mutations in rHPIV1 and rHPIV2 for development of effective immunogenic compositions and methods.

Viruses and Cells

LLC-MK2 cells (ATCC CCL 7.1) and HEp-2 cells (ATCC CCL 23) were maintained in Opti-MEM I (Gibco-Invitrogen, Inc. Grand Island, N.Y.) supplemented with 5% FBS, gentamicin sulfate (50 µg/ml), and 2 mM glutamine (Gibco-Invitrogen, Inc.) The recombinant HPIV1 (rHPIV1) and rHPIV1 mutants were grown in LLC-MK2 cells as described previously. (Newman et al., *Virus Genes* 24:77-92, 2002).

Construction of point mutations in the antigenomic HPIV1 cDNA. The mutations were introduced into the appropriate rHPIV1 subgenomic clones (Newman et al., *Virus Genes* 24:77-92, 2002) using a modified PCR mutagenesis protocol described elsewhere (Moeller et al., *J Virol* 75:7612-20, 2001) with the Advantage-HF PCR Kit (Clontech Laboratories, Palo Alto, Calif.). The subgenomic clone containing the mutation was then sequenced for the entirety of the region that was PCR-amplified using a Perkin-Elmer ABI 3100 sequencer with the BigDye sequencing kit (Perkin-Elmer Applied Biosystems, Warrington, UK) to confirm that the subclone contained the introduced mutation but did not contain any adventitious mutations introduced during PCR amplification. Full-length HPIV1 cDNA clones (FLCs) containing the mutations were assembled using standard molecular cloning techniques (Newman et al., *Virus Genes* 24:77-92, 2002), and the region containing the introduced mutation in each FLC was sequenced as described above to ensure that the FLC contained the introduced mutation.

Recovery of rHPIV1 Mutant Viruses

Recovery of rHPIV1 mutants was performed as described previously (Newman et al., *Virus Genes* 24:77-92, 2002). To confirm that viruses contained the appropriate mutations, viral RNA (vRNA) was isolated from infected cell supernatant fluids using the Qiaquick vRNA kit (Qiagen Inc., Valencia Calif.), and the appropriate region in each was amplified by RT-PCR as described previously (Newman et al., *Virus Genes* 24:77-92, 2002) and analyzed by sequencing. All of the sequence analysis of viral RNA in this study involved direct analysis of uncloned RT-PCR products. Control RT-PCR reactions were performed in which the RT enzyme was omitted to confirm that the RT-PCR products were generated from RNA rather than contaminating DNA. For FLCs containing a codon substitution mutation, initial virus recovery attempts were made as described above using the pTM(L1) support plasmid that contained the HPIV1 wild type L protein sequence (Newman et al., *Virus Genes* 24:77-92, 2002). In several instances involving the 942 or 992 codon the virus recovered contained the wild type L coding protein coding sequence, indicating that recombination had occurred between the pTM(L1) support plasmid and the mutant FLC (11). Therefore, subsequent recovery attempts were performed in which the wild type pTM(L1) support plasmid was replaced with one containing the appropriate L mutation present in the FLC being rescued. The recovered rHPIV1 viruses were biologically cloned by two successive rounds of terminal dilution using LLC-MK2 monolayers in 96-well plates (Costar, Corning Inc.) The presence of the introduced mutation in each biologically cloned virus was confirmed by sequence analysis of the RT-PCR product.

Replication of rHPIV1 mutants in LLC-MK2 cells at permissive and restrictive temperatures. The ts phenotype for each of the rHPIV1 mutant viruses was determined by comparing their replication levels to that of rHPIV1 wild type virus at 32° C., 35° C., 36° C., 37° C., 38° C., and 39° C. as described previously (34). Virus titer, which is expressed as a mean $log_{10}$ 50 percent tissue culture infectious dose per milliliter ($log_{10}$ $TCID_{50}$/ml), was determined in one to three separate experiments. The reduction in titer (log) at each restrictive temperature, determined by comparison to the titer at permissive temperature of 32° C., was recorded for each experiment and the mean reduction was calculated. The ts phenotype was defined as a 100-fold or greater reduction in titer compared to the wild type virus.

Replication of rHPIV1 Mutant Viruses in the Respiratory Tract of Hamsters

Four-week-old Golden Syrian hamsters were inoculated intranasally with 0.1 ml L-15 (Invitrogen Corp., Grand Island, N.Y.) containing $10^{6.0}$ $TCID_{50}$ of a wild type or mutant HPIV1. Four days later, the nasal turbinates and lungs were collected as previously described (Newman et al., *Virus Genes* 24:77-92, 2002). Virus present in the samples was quantified by titration on LLC-MK2 monolayers at 32° C. Infected cells were detected on day six post-infection by hemadsorption with guinea pig erythrocytes. The mean titer ($log_{10}$ $TCID_{50}$/g) was calculated for each group of six hamsters. The att phenotype was defined as a 100-fold or greater reduction in virus titer in either or both anatomical locations compared to wild type.

Determination of the genetic and phenotypic stability of rHPIV1-Y942H and rHPIV1-Y942A in LLC-MK2 cells by passage at restrictive temperatures. rHPIV1 mutants with the original Y942H mutation or with the Y942A mutation were grown on LLC-MK2 monolayers at 32° C. with an input inoculum of approximately 0.01 $TCID_{50}$ per cell until cytopathology was visible (approximately 5-7 days). The virus in the supernatant was diluted 1/1000 and was passed again on LLC-MK2 monolayers at 32° C. This was repeated for a total of 10 passages. Alternatively, the two viruses were also passaged at increasingly restrictive temperatures as follows: two passages (as described above) at 32° C., two at 35° C., two at 36° C., and two at 37° C., after which undiluted supernatant from the second 37° C. passage harvest was passed to LLC-MK2 monolayers at 38° C., and then passed once at 39° C., for a total of 10 passages.

At each passage level aliquots were frozen for phenotypic and genotypic analysis. The level of replication and temperature sensitivity of both rHPIV1-Y942H and rHPIV1-Y942A were determined and compared to rHPIV1 as described above. Sequence analysis of each virus was performed as described above.

Results

Recovery of rHPIV1 Bearing Codon Substitution Mutations at Amino Acid Position 942 in the L Protein The Y942H mutation in the L protein of the attenuated HPIV3-cp45 virus was introduced by reverse genetics into the homologous position in rHPIV1, resulting in a viable virus designated rHPIV1-Y942H (Table 5). This mutation in rHPIV1, as in the original HPIV3-cp45 virus, involved a single nucleotide substitution (TAC to CAC, substitution underlined). Given the sequences of the possible codons for Tyr (TAT and TAC) and His (CAT and CAC), this amino acid substitution could not be designed to involve more than a single nucleotide change. To evaluate the full range of possible phenotypes involving this amino acid locus, we prepared additional mutant cDNAs in which position 942 was changed to each of the 18 other possible amino acid assignments. Whenever possible, codons were chosen so as to maximize the number of nucleotide differences compared to the two possible codons for the wild type Tyr assignment (Table 5).

TABLE 5

Recovery of rHPIV1 bearing codon substitution mutations at amino acid position 942 in the L protein

| Virus | Codon[a] | No. of nucleotide changes needed to restore wt amino acid | rHPIV1 mutant recovered? | Adventitious coding mutations in L ORF |
|---|---|---|---|---|
| rHPIV1 wild type | TAT, TAC | 0 | + | nd[b] |
| rHPIV1-Y942H | CAC | 1 | + | none |
| rHPIV1-Y942C[c] | TGC | 1 | + | none |
| rHPIV1-Y942F | TTT | 1 | + | none |
| rHPIV1-Y942N[c] | AAC | 1 | + | none |
| rHPIV1-Y942D[c] | GAC | 1 | + | none |
| rHPIV1-Y942S | AGC | 2 | + | none |
| rHPIV1-Y942W | TGG | 2 | + | none |
| rHPIV1-Y942Q | CAG | 2 | + | S1302N |
| rHPIV1-Y942K | AAA | 2 | −[d] | nd |
| rHPIV1-Y942I | ATC | 2 | − | nd |
| rHPIV1-Y942E | GAG | 2 | − | nd |
| rHPIV1-Y942M[c] | ATG | 3 | + | L1367S |
| rHPIV1-Y942A | GCG | 3 | + | none |
| rHPIV1-Y942T[c] | ACA | 3 | + | none |
| rHPIV1-Y942G | GGG | 3 | + | none |
| rHPIV1-Y942V[c] | GTG | 3 | + | G1755Q |
| rHPIV1-Y942L[c] | CTG | 3 | + | none |
| rHPIV1-Y942R | CGG | 3 | − | nd |
| rHPIV1-Y942P | CCG | 3 | − | nd |

[a]In the case of wild type, the two possible codons yielding the wild type amino acid for tyrosine (Y) are shown; for each mutant the codon chosen for introduction into rHPIV1 is shown.
[b]nd, not done: the L gene sequence was not confirmed either because the virus is the previously-sequenced wild type, or the virus was not recovered.
[c]Virus was recovered with pTML containing the indicated codon substitution. The other viruses were recovered using wild type pTML.
[d]−, not recovered.

Of these 18 additional codon substitution mutants, 13 were recovered in infectious virus. If the desired rHPIV1 recombinant was not recovered after three to five attempts, we considered the mutant to be nonviable. Each of the recovered viruses was biologically cloned and the complete L gene was sequenced, confirming in each case the presence of the introduced mutation. Of the 14 recovered rHPIV1 codon substitution mutants, including the original Y942H mutant, three were found to each have one additional adventitious coding mutation in L (Table 5). It is not unusual to find adventitious mutations, often phenotypically silent, in cloned biologically-derived or recombinant virus when the extra expedient is taken to perform the extensive sequence analysis involved. The possible contribution of these adventitious mutations to phenotypes exhibited by these three mutants was not further studied because the 11 mutants lacking adventitious mutations in the L ORF were more than sufficient for analysis for the purposes of this study. Each of the 14 rHPIV1-942 codon substitution mutants replicated efficiently in vitro at 32° C. and achieved titers of at least 107 TCID50/ml (Table 6).

TABLE 6

Temperature sensitivity and attenuation phenotype of rHPIV1 L protein codon-942 substitution mutants

| Virus | No. of nucleotide changes needed to restore wild type amino acid | Virus titer at 32° C. ($\log_{10}$ $TCID_{50}$/ml) | Mean $\log_{10}$ reduction in virus titer at indicated temperature (° C.)[a] | | | | | Replication of virus in hamsters | | |
|---|---|---|---|---|---|---|---|---|---|---|
| | | | 35 | 36 | 37 | 38 | 39 | No. of animals | Nasal Turbinates | Lungs |
| rHPIV1 wild type | 0 | 7.8 | 0.1 | 0.4 | 0.8 | 1.5 | 1.8 | 30 | 4.2 ± 0.2 | 3.9 ± 0.4 |
| rHPIV1-Y942Hcp45 | 1 | 8.0 | — | 1.4 | 3.1 | 5.1 | 5.8 | 18 | ≤1.5 ± 0.0 | ≤1.5 ± 0.0 |
| rHPIV1-Y942C | 1 | 8.0 | 1.8 | 2.1 | 2.3 | 4.8 | 6.5 | 6 | 4.4 ± 0.2 | 3.4 ± 0.4 |
| rHPIV1-Y942F | 1 | 8.1 | 0.3 | 1.3 | 1.9 | 3.4 | 5.4 | 6 | 3.8 ± 0.1 | 3.9 ± 0.2 |
| rHPIV1-Y942N | 1 | 9.0 | 1.0 | 2.1 | 3.7 | 4.3 | 7.0 | 6 | 2.0 ± 0.2 | 1.6 ± 0.1 |
| rHPIV1-Y942D | 1 | 7.9 | 3.3 | 5.3 | >6.6 | >6.7 | >6.9 | 6 | 1.6 ± 0.1 | 1.8 ± 0.3 |
| rHPIV1-Y942S | 2 | 8.3 | 0.6 | 1.2 | 3.6 | 5.2 | >6.4 | 6 | 3.2 ± 0.1 | 1.8 ± 0.2 |
| rHPIV1-Y942W | 2 | 8.4 | 0.8 | 1.5 | 3.0 | 4.2 | >6.4 | 12 | 1.8 ± 0.2 | 1.6 ± 0.1 |
| rHPIV1-Y942Q | 2 | 7.0 | 1.4 | 3.6 | >4.7 | >5.8 | >5.9 | 12 | 1.5 ± 0.1 | 1.7 ± 0.2 |
| rHPIV1-Y942M | 3 | 7.3 | 3.0 | 5.3 | >6.0 | >5.8 | >6.2 | 6 | ≤1.5 ± 0.0 | ≤1.5 ± 0.0 |
| rHPIV1-Y942A | 3 | 8.1 | 3.5 | 3.5 | >5.1 | >6.4 | >6.8 | 6 | ≤1.5 ± 0.0 | ≤1.5 ± 0.0 |
| rHPIV1-Y942T | 3 | 8.0 | 1.8 | 3.0 | >5.0 | >6.8 | >6.9 | 6 | ≤1.5 ± 0.0 | ≤1.5 ± 0.0 |
| rHPIV1-Y942G | 3 | 8.1 | 1.0 | 3.1 | >4.1 | >5.8 | >7.3 | 6 | ≤1.5 ± 0.0 | ≤1.5 ± 0.0 |

TABLE 6-continued

Temperature sensitivity and attenuation phenotype of rHPIV1 L protein codon-942 substitution mutants

| | No. of nucleotide changes needed to restore wild type amino acid | Virus titer at 32° C. (log$_{10}$ TCID$_{50}$/ml) | Mean log$_{10}$ reduction in virus titer at indicated temperature (° C.)[a] | | | | | Replication of virus in hamsters | | |
|---|---|---|---|---|---|---|---|---|---|---|
| | | | | | | | | | Mean titer of virus (log$_{10}$ TCID$_{50}$/g ± S.E.) | |
| Virus | | | 35 | 36 | 37 | 38 | 39 | No. of animals | Nasal Turbinates | Lungs |
| rHPIV1-Y942V | 3 | 7.0 | 2.6 | 5.0 | >5.7 | >5.8 | >6.1 | 12 | ≤1.5 ± 0.0 | <u>1.6 ± 0.1</u> |
| rHPIV1-Y942L | 3 | 7.0 | 2.8 | 5.0 | 5.5 | 5.5 | >5.8 | 6 | ≤1.5 ± 0.0 | ≤1.5 ± 0.0 |

[a]Reduction is compared to titer at 32° C. Values represent average of 3 experiments.
[b]Values in bold are the temperatures at which the virus titer was reduced 100-fold or more than that of rHPIV1.
[c]Underlined values represent greater than 100 fold reduction compared to rHPIV1.

Temperature Sensitivity and Attenuation Phenotype of rHPIV1 Codon 942 Substitution Mutants The rHPIV1 virus bearing the Y942H mutation transferred from HPIV3-cp45 was strongly ts in vitro, exhibiting a 2.6 log10 reduction in virus yield at 35° C. relative to 32° C. (Table 6). This demonstrates that this "imported" mutation functions efficiently as a ts mutation in the rHPIV1 backbone. Remarkably, each of the 13 other recovered rHPIV1 mutants also was ts, and a spectrum of temperature sensitivity was seen amongst the mutants. Five rHPIV1 mutants, namely those with the Y942D, Y942M, Y942A, Y942V, or Y942L mutation, were found to be as ts as rHPIV1-Y942H, and the latter four involved codons which would each require three nucleotide changes to restore a Tyr at position 942. Thus, a virus with a ts phenotype comparable to that of rHPIV1-Y942H can be readily generated according to the teachings herein that requires three nucleotide changes at position 942 to restore the wild type Tyr residue.

The ability of the codon substitution viruses to replicate in the upper (nasal turbinates) and lower (lungs) respiratory tract of infected hamsters was compared to that of wild type rHPIV1 (Table 6). The rHPIV1 bearing the Y942H mutation transferred from HPIV3-cp45 was highly attenuated in both the upper and lower respiratory tract of hamsters compared to its rHPIV1 parent virus (Table 6). This demonstrates that this HPIV3-derived mutation functions efficiently as an att mutation in the HPIV1 backbone. Eleven of the 13 rHPIV1 mutants were attenuated in hamsters, as defined by exhibiting 100-fold or greater decrease in virus titer in either the upper or lower respiratory tract compared to HPIV1 wild type (underlined values in Table 6). Each of the six rHPIV1 mutants that would require three nucleotide changes in codon 942 to restore the wild type amino acid (Y942M, Y942A, Y942T, Y942G, Y942V and Y942L) was as attenuated as rHPIV1-Y942H. Thus, a virus with a comparable att phenotype as the rHPIV1-Y942H can be produced according to the invention that requires three nucleotide changes at position 942 to restore the wild type Tyr.

Passage of rHPIV1 Mutants with the Original Y942H Mutation or the "Stabilized" Y942A Codon at Restrictive Temperatures For ts viruses, passage of the virus at restrictive temperature has been an effective method to determine the level of stability of the ts phenotype (Belshe et al., *J Virol* 24:8-12, 1977; Richardson et al., Arch Virol 54:53-60, 1977; Treanor et al, *J Virol* 68:7684-8, 1994). Therefore, this procedure was employed to compare the stability of the ts phenotype of the original mutant (rHPIV1-Y942H), containing a single nucleotide substitution at codon 942, with that of rHPIV1-Y942A, containing three nucleotide substitutions in this codon. The two viruses were (i) passaged 10 times at the permissive temperature of 32° C., or (ii) passaged at increasingly restrictive temperatures as follows: twice at 32° C., twice at 35° C., twice at 36° C., twice at 37° C., once at 38° C. and once at 39° C., for a total of 10 passages. Aliquots of virus from various passage levels were analyzed for ts phenotype and were subjected to partial or complete sequence analysis of the L gene (Table 7).

TABLE 7

Temperature sensitivity and sequence analysis of rHPIV1 mutants with the L protein Y942H mutation (single nucleotide substitution) or the Y942A mutation (three nucleotide substitutions) following passage at restrictive temperatures

| Virus | Passage series[a] | Passage level analyzed[b] (° C.) | Mean titer (log$_{10}$ pfu/ml) at 32° C. | Mean log$_{10}$ reduction in virus titer at indicated temperature | | Sequence of L gene and protein[c] | | |
|---|---|---|---|---|---|---|---|---|
| | | | | 38° C. | 39° C. | codon 942 (amino acid assignment) | Extent of sequencing[d] | Second-site Mutations |
| rHPIV1 wild type | | | 8.0 | 1.2 | 3.4 | TAT (Tyr) | F | None |

TABLE 7-continued

Temperature sensitivity and sequence analysis of rHPIV1 mutants with the L protein Y942H mutation (single nucleotide substitution) or the Y942A mutation (three nucleotide substitutions) following passage at restrictive temperatures

| Virus | Passage series[a] | Passage level analyzed[b] (° C.) | Mean titer (log$_{10}$ pfu/ml) at 32° C. | Mean log$_{10}$ reduction in virus titer at indicated temperature | | Sequence of L gene and protein[c] | | |
|---|---|---|---|---|---|---|---|---|
| | | | | 38° C. | 39° C. | codon 942 (amino acid assignment) | Extent of sequencing[d] | Second-site Mutations |
| rHPIV1-Y942H | | unpassaged | 6.7 | 3.7[e] | >5.2[f] | CAC (His) | C | None |
| rHPIV1-Y942H | 1 | p10-32 | 7.7 | 3.5 | 5.5 | CAC (His) | C | None |
| rHPIV1-Y942H | 2 | p4-35 | 7.5 | 3.3 | 5.3 | CAC (His) | C | None |
| rHPIV1-Y942H | 2 | p6-36 | 7.2 | 2.0 | 4.0 | TAC (Tyr) | C | None |
| rHPIV1-Y942H | 2 | p8-37 | 7.0 | 0.3 | 3.5 | TAC (Tyr) | C | None |
| rHPIV1-Y942H | 2 | p9-38 | 6.5 | 1.0 | 3.3 | TAC (Tyr) | F | None |
| rHPIV1-Y942H | 2 | p10-39 | 5.2 | 1.0 | 3.0 | TAC (Tyr) | F | None |
| rHPIV1-Y942A | | unpassaged | 6.5 | 4.8 | >5.0[f] | GCG (Ala) | P | None |
| rHPIV1-Y942A | 3 | p10-32 | 7.5 | 4.0 | 4.5 | GCG (Ala) | P | None |
| rHPIV1-Y942A | 4 | p4-35 | 7.0 | 4.3 | >5.5[f] | GCG (Ala) | P | None |
| rHPIV1-Y942A | 4 | p6-36 | 7.0 | 4.0 | 4.8 | GCG (Ala) | P | V1016L |
| rHPIV1-Y942A | 4 | p8-37 | 6.7 | 3.5 | >5.2[f] | GCG (Ala) | P | V1016L/N1125D[g] |
| rHPIV1-Y942A | 4 | p9-38 | 6.2 | 3.5 | >4.7[f] | GCG (Ala) | F | V1016L/N1125D |
| rHPIV1-Y942A | 5 | p10-39 | 5.2 | 3.0 | >3.7[f] | GCG (Ala) | F | S1328P |

Series 1 and 2 involve the Y942H mutant at the permissive and restrictive temperature regimens, respectively (Materials and Methods). Series 3 involves the Y942A mutant at the permissive regimen, while 4 and 5 are independent parallel series at the restrictive regimen.
Samples were analyzed from various passage levels within series 1 to 5: each passage level is identified by its number (p1 to p10) and its temperature (32 to 39, representing 32° C. to 39° C.).
Consensus sequence determined from uncloned RT-PCR products.
The amount of the L gene sequenced was: F (full), the entire L gene ORF; P, partial, nucleotides 10,000-13,300, C, codon-proximal, the region immediately surrounding codon 942.
Value in bold is the temperature at which the virus titer was reduced 100-fold or more than that of rHPIV1 wild type virus.
No detectable virus.
Electropherogram indicated 50% of each nucleotide (A or G) at nucleotide 12143 in codon 1125.

The ts phenotype of each of the two mutant viruses, rHPIV1-Y942H and rHPIV1-Y942A, was unchanged by 10 passages at 32° C. (passage series 1 and 3, respectively, in Table 7), and sequence analysis of each L gene indicated that the respective mutant codon was unchanged, and no additional mutations were detected. In contrast, analysis of aliquots from the passage of the rHPIV1-Y942H mutant (passage series 2 in Table 7) at restrictive temperature showed that by passage level p6-36 (36° C.) the virus had lost its ts phenotype and the consensus sequence at codon 942 had reverted directly back to that of the wild type assignment of Tyr (CAC to TAC). This single nucleotide change restored the ability of Y942H-p6 to replicate at restrictive temperatures rendering it indistinguishable from the rHPIV1 wild type virus in this regard. There were no other mutations in the L gene of this virus even following additional passage at increasingly restrictive temperatures, as confirmed by sequence analysis of the complete L gene of virus from passage levels p9-38 and p10-39 (38° C. and 39° C., respectively, passage series 2, Table 3).

In two independent series of passages, the Y942A mutant did not revert at codon 942 even at the highly restrictive temperatures of 38° C. or 39° C. (Table 7, passage series 4 and 5), i.e., the sequence at codon 942 remained GCG in all passages sequenced. The level of temperature sensitivity of virus from passage levels p8-37 and p9-38 (37° C. and 38° C., respectively, Table 7, passage series 4) remained highly ts at both 38° C. and 39° C. However, there was a partial loss of the ts phenotype, such that the replication of these isolates was increased about 20-fold at 38° C. (Table 3, passage series 4) compared to the original Y942A mutant. This shift in ts phenotype was associated with the acquisition of two second-site amino acid point mutations in the L protein, V1016L and N1125D. Nonetheless, the p8-37 and p9-38 viruses remained 200-fold more restricted in their replication at 38° C. than wild type rHPIV1, and both viruses failed to replicate at 39° C. in the ts assay. This suggested that the acquisition of the two second-site mutations in L partially suppressed the level of temperature sensitivity specified by the Y942A mutation. Since the complete Y942A p9-38 genome was not sequenced, it also is possible that one or more extragenic suppressor mutations also were present. Similarly, the virus from the p10-39 (39° C.) passage level of an independent passage series (Table 7, passage series 5) manifested an intermediate level of temperature sensitivity at 38° C. between that of the wild type rHPIV1 and the starting Y942A virus, but remained sufficiently ts that it failed to replicate at 39° C. (Table 7). This partial loss of temperature sensitivity was associated with the development of a third second-site mutation in L, namely, S1328P. Thus, a ts mutation involving a single nucleotide substitution readily reverted to the wild type assignment and rapidly became the predominant viral species during passage at restrictive temperatures. In contrast, reversion was not observed involving a codon that differed from wild type by three nucleotides, but a partial loss of the ts phenotype was observed after 8 passages at increasingly restrictive temperatures, and putative second-site intragenic suppressor mutations were detected.

Recovery of rHPIV1 Bearing Codon Substitution Mutations at Amino Acid Position 992 in the L Protein A second L protein mutation from HPIV3-cp45 L, L992F, was introduced into the homologous position in rHPIV1 by reverse genetics, resulting in a viable virus designated rHPIV1-L992F (Table 8). Additional mutants were constructed in which position 992 was changed into 17 of the 18 other possible amino acid assignments (lacking only Ser, Table 8). Codons were chosen to maximize the number of nucleotide differences compared to the possible codons for the wild type assignment of Leu, but this was made difficult by the existence of six different codons for Leu. Nonetheless, nine of the substitution mutations could be designed to involve two nucleotide differences compared to any Leu codon (Table 8). Of these 17 additional mutations, 10 recombinant viruses bearing the appropriate mutation were recovered and were readily propagated in vitro and were biologically cloned. Of the seven remaining rHPIV1 mutants, three (L992R, L992P, and L992Q) were recovered in the transfection harvest but reverted to wild type during biological cloning, two others (L992E and L992D) were recovered in the transfection harvest but replicated very inefficiently and could not be propagated. Two others (L992G and L992T) recombined with the wt pTM(L1) and were not further studied. The L gene was sequenced around the site of the mutation in each of the recovered, stable mutant viruses, and the presence of each introduced mutation was confirmed. Each of the recovered codon 992 substitution mutants replicated efficiently in vitro at 32° C. and achieved titers of $\geq 10^7$ TCID50/ml (Table 9).

TABLE 8

Recovery of rHPIV1 bearing codon substitution mutations at amino acid position 992 in the L protein

| Virus | Codon[a] | No. of nucleotide changes needed to restore wild type amino acid | rHPIV1 mutant recovered? |
|---|---|---|---|
| rHPIV1 wild type | TTA, TTG, CTT, CTC, CTA, CTG | 0 | + |
| rHPIV1 L992F cp45 | TTT | 1 | + |
| rHPIV1 L992M | ATG | 1 | + |

TABLE 8-continued

Recovery of rHPIV1 bearing codon substitution mutations at amino acid position 992 in the L protein

| Virus | Codon[a] | No. of nucleotide changes needed to restore wild type amino acid | rHPIV1 mutant recovered? |
|---|---|---|---|
| rHPIV1 L992H | CAC | 1 | + |
| rHPIV1 L992I | ATC | 1 | + |
| rHPIV1 L992W | TGG | 1 | + |
| rHPIV1 L992R | CGG | 1 | −[b] |
| rHPIV1 L992V | GTC | 1 | + |
| rHPIV1 L992Q | CAG | 1 | −[b,c] |
| rHPIV1 L992E | GAG | 1 | −[d] |
| rHPIV1 L992P | CCG | 1 | −[b] |
| rHPIV1 L992A | GCG | 2 | + |
| rHPIV1 L992Y | TAC | 2 | + |
| rHPIV1 L992C | TGC | 2 | + |
| rHPIV1 L992N | AAC | 2 | + |
| rHPIV1 L992D | GAC | 2 | −[d] |
| rHPIV1 L992T | ACC | 2 | −[c] |
| rHPIV1 L992G | GGG | 2 | −[c] |
| rHPIV1 L992K | AAG | 2 | + |

[a]In the case of wild type, the six possible codons yielding the wild type amino acid for leucine (L) are shown; for each mutant the codon chosen for introduction into rHPIV1 is shown. A cDNA bearing an L992S mutation was not constructed.
[b]Mutant was recovered but reverted to wild type during passage at 32° C. and was not further studied.
[c]Mutant recombined with wild type pTML1 and was not further studied.
[d]Virus was recovered from transfection, but titer was low and virus was lost on subsequent passage.

TABLE 9

Temperature sensitivity and attenuation phenotype of rHPIV1 L protein codon-992 substitution mutants

| Virus | No. of nucleotide changes needed to restore wild type amino acid | Virus titer at 32° C. ($\log_{10}$ TCID$_{50}$/ml)[b] | Mean $\log_{10}$ reduction[a] in virus titer at indicated temp (° C.) | | | | Replication of virus in hamsters | | |
|---|---|---|---|---|---|---|---|---|---|
| | | | 35 | 36 | 37 | 38 | 39 | No. of animals | Mean titer of virus ($\log_{10}$ TCID$_{50}$/g ± S.E.) |
| | | | | | | | | | Nasal Turbinates | Lungs |
| rHPIV1-wild type | 0 | 7.5 | 0.1 | 0.1 | 0.5 | 0.6 | 1.2 | 30 | 4.2 ± 0.2 | 3.9 ± 0.4 |
| rHPIV1 L992F cp45 | 1 | 8.1 | 0.2 | 0.3 | 1.3 | 0.9 | 2.4 | 12 | 4.4 ± 0.3 | 3.0 ± 0.2 |
| rHPIV1 L992M | 1 | 8.4 | 0.2 | 0.2 | 0.4 | 0.7 | 2.7 | 6 | 4.7 ± 0.3 | 3.2 ± 0.4 |
| rHPIV1 L992I | 1 | 8.2 | 0.3 | 0.5 | 0.5 | 2.7 | 4.3[b] | 6 | 4.1 ± 0.2 | 2.6 ± 0.3 |
| rHPIV1 L992W | 1 | 8.5 | 0.0 | 0.5 | 0.8 | 3.7 | 3.8 | 6 | 4.0 ± 0.2 | 3.3 ± 0.1 |
| rHPIV1 L992H | 1 | 8.1 | 0.3 | 1.3 | 1.3 | 1.8 | 4.9 | 6 | 3.3 ± 0.2 | 3.4 ± 0.1 |
| rHPIV1 L992V | 1 | 6.2[d] | 0.7 | 0.5 | 1.5 | 2.5 | 4.0 | 6 | ≤1.5 ± 0.0[c] | 1.7 ± 0.2 |
| rHPIV1 L992N | 2 | 7.8 | 0.6 | 0.3 | 0.6 | 2.0 | 3.3 | 6 | 2.7 ± 0.2 | ≤1.5 ± 0.0 |
| rHPIV1 L992Y | 2 | 8.5 | 0.0 | 0.2 | 0.5 | 1.4 | 2.9 | 6 | 4.5 ± 0.2 | 3.3 ± 0.4 |
| rHPIV1 L992K | 2 | 8.6 | 0.0 | 1.2 | 0.2 | 1.8 | 3.0 | 6 | 4.1 ± 0.3 | 3.1 ± 0.4 |
| rHPIV1 L992A | 2 | 7.9 | 0.5 | 0.3 | 1.2 | 3.0 | 4.5 | 6 | 3.6 ± 0.2 | 3.2 ± 0.3 |
| rHPIV1 L992C | 2 | 7.3 | 0.7 | 2.2 | 2.9 | 4.0 | >4.9 | 6 | 3.2 ± 0.2 | 1.7 ± 0.1 |

[a]Reduction is compared to titer at 32° C. Values represent average of 2-3 experiments.
[b]Values in bold are the temperatures at which the virus titer was reduced 100-fold or more than that of rHPIV1.
[c]Underlined values represent greater than 100-fold reduction compared to rHPIV1 in the same pulmonary compartment.
[d]Other preparations of this virus had titers of $\geq 10^7$, indicating efficient growth at permissive temperature.

Temperature Sensitivity and Attenuation Phenotype of rHPIV1 Codon 992 Substitution Mutants The rHPIV1 virus bearing the L992F mutation transferred from HPIV3-cp45 was not ts in vitro (Table 9). Six of the 10 additional rHPIV1 mutants that were recovered were ts, and a spectrum of temperature sensitivity was seen amongst the mutants. One virus, rHPIV1-L992C, exhibited the greatest level of temperature sensitivity, with a 100-fold reduction of replication at 36° C. Thus, a rHPIV1 codon 992 substitution mutant was generated according to the teachings herein that, in contrast to the original non-ts rHPIV1-L992F mutant, was substantially ts.

The level of replication of the codon 992 substitution mutants in the upper and lower respiratory tract of hamsters was compared with that of rHPIV1 (Table 9). The rHPIV1-L992F virus was not attenuated in hamsters: thus, the L992F mutation is attenuating in HPIV3 (Skiadopoulos et al., *J Virol* 72:1762-8. 1998) but not HPIV1. However, three of the 10 other recovered codon 992 substitution mutants (L992V, L992N, and L992C) were reduced in replication 100-fold or more compared to wild type virus. Thus, several rHPIV1 codon 992 substitution mutants were provided according to the teachings herein with an att phenotype. Interestingly, the rHPIV1-L992V mutant was only slightly ts, suggesting that the L992V mutation confers a predominantly non-ts attenuation phenotype.

The ability to recover recombinant negative strand RNA viruses from cDNA makes it possible to develop live attenuated virus candidates for use in immunogenic compositions by the planned introduction of attenuating mutations to a wild type virus. This can be done in a sequential manner in response to ongoing pre-clinical and clinical evaluation until a desired balance between attenuation and immunogenicity is achieved (Collins et al., *Virology* 296:204-11, 2002; Murphy et al., *J Clin Invest* 110:21-7, 2002). Within the present invention, genetic stability of rHPIV1 and rHPIV2 can be achieved by the accumulation of a sufficient number of attenuating mutations to make loss of the attenuation phenotype unlikely during manufacture and during the brief period of replication of these respiratory viruses in humans (Collins et al., *Virology* 296:204-11, 2002; Murphy et al., *J Clin Invest* 110:21-7, 2002). In addition, attenuating mutations can be designed that have improved stability, such as the deletion of entire genes or, as in the present study, the "stabilization" of point mutations. The addition of point mutations that specify the ts and att phenotype to partially attenuated viruses is useful in the incremental attenuation of viruses such as respiratory syncytial virus and HPIV3 (Collins et al., *Virology* 296:204-11, 2002; Skiadopoulos et al., *Virology* 260:125-35, 1999). However, as indicated above, the att phenotype specified by these mutations can be subject to modification by direct reversion or other mutation during replication in vivo (Tolpin et al., *Virology* 112:505-517, 1981; Wright et al., *J Infect Dis* 182: 1331-1342, 2000). Since molecular engineering makes it possible to alter codons that specify the ts and att phenotypes, the present study was useful to elucidate whether the choice of alternative codons at a given locus can be used to enhance the genetic stability of a ts-att mutation and to augment the level of attenuation.

The introduction of the Y942H mutation of the L gene of HPIV3-cp45 into the corresponding position of rHPIV1 yielded a virus that possessed the ts and att phenotypes. However, these phenotypes were the result of a single nucleotide substitution in codon 942 and thus might be subject to instability. Thirteen additional viable rHPIV1 mutants were generated that contained various alternative amino acid assignments at codon 942, and all were ts. The noted failure to recover 5 amino acid substitution mutants indicates that mutations that specify these amino acids in codon 942 are dead-end mutations, i.e., they would be non-viable. Nonetheless, eleven of the 13 recovered, viable mutants were successfully demonstrated to be attenuated for replication in the respiratory tract of hamsters. Six highly attenuated mutants (those with a Met, Ala, Thr, Gly, Val, or Leu substitution at position 942) were identified that would require three nucleotide changes to occur to generate a codon that specified the wild type Tyr residue at codon 942. However, two other mutants (those with a Cys or Phe at position 942) out of the 13 recovered rHPIV1 mutants replicated in hamsters as efficiently as wild type HPIV1. Thus, the naturally-occurring Tyr-942 assignment was not the only one that conferred a wild type-like phenotype: Cys-942 and Phe-942 did as well.

Therefore, the present invention provides additional direction and guidance to choose a 942 assignment that (i) specifies an appropriate level of attenuation, and (ii) differs by two, or preferably three, nucleotides from all possible codons for Tyr, Cys and Phe. For four of the six highly attenuated viruses (those with a Met, Gly, Val, or Leu substitution), it would take only two nucleotide substitutions in their codons to give rise to a virus with a Tyr, Cys, or Phe at position 942. The remaining two highly attenuated viruses (with Ala or Thr assignments) would take three nucleotide substitutions to generate a codon for Tyr, Cys, or Phe. Thus, in this systematic examination of the ts and att phenotypes of 13 viable codon 942 substitution mutations, the Y942A and the Y942T mutations were identified as codon 942 substitutions that were highly attenuated and would require three nucleotide changes to occur to yield a virus with a wild type-like phenotype. Fortunately, both of these viruses were among the 11 mutants that were recovered without adventitious mutations in the L gene, and thus these findings are unambiguous.

The genetic and phenotypic stability of one of these two rHPIV1 viruses, the Y942A virus, was examined following replication at restrictive temperatures. This was done in parallel with the original Y942H virus, which differed from wild type by only a single nucleotide. The Y942H virus readily reverted to wild type phenotype after only four passages at 35-36° C., whereas the "codon stabilized" Y942A virus exhibited only a partial loss of the ts phenotype even after eight passages at elevated temperatures. The phenotypic instability of the Y942H virus was accompanied by a direct reversion to the wild type sequence at codon 942. This change occurred only following replication at elevated temperature, demonstrating the important role that elevated temperature played in selecting for the ts rHPIV1-Y942H revertant.

Sequence analysis confirmed that the "stabilized" Y942A virus retained the GCG Ala codon throughout its passages at elevated temperatures. However, the partial loss of the ts phenotype noted above was associated with the acquisition of one or two second-site amino acid substitutions involving three different positions in L. This suggests that these are intracistronic suppressor mutations that partially restored the ability of rHPIV1-Y942A to replicate at 38° C. It also is possible that an extracistronic suppressor mutation, e.g., in P or N, could have developed that contributed to the partial restoration of replication of the mutant at elevated temperature (Mucke et al., *Virology* 158:112-7, 1987; Treanor et al, *J Virol* 68:7684-8, 1994). The finding that the "stabilized" Y942A virus retained a high degree of temperature sensitivity even following passage at highly restrictive temperatures suggests that it also would be more phenotypically stable in vitro and in vivo than the "non-stabilized" Y942H virus. This analysis of the codon substitutions at residue 942 of the HPIV1 L protein provides an example of how to identify mutations that exhibit a set of properties including both attenuation and phenotypic/genetic stability desirable for inclusion in a live attenuated virus. This particular example turned out to have several advantages that facilitated the selection of a "stabilized" mutant assignment: (i) the wild type assignment of Tyr has only two possible codons, and (ii) among the mutants with alternative amino acid assignments, only two were not highly attenuated, and (iii) these two assignments each has only two possible codons.

It was previously reported that the introduction of the HPIV3-cp45 L992F L protein mutation into a wild type HPIV3 backbone conferred the ts phenotype in vitro and the att phenotype in hamsters (30), identifying L992F as an independent ts att mutation. However, the introduction of this mutation into the homologous position in the HPIV1 background in the present study did not confer either phenotype. When alternative amino acid assignments were introduced at codon 992, only 10 of 17 mutants were recovered, indicating that this site is indeed sensitive to mutation. Three codon substitution mutants were identified, rHPIV1-L992V, rHPIV1-L992N, and rHPIV1-L992C, that were 10- to 100-fold restricted in replication in the upper or lower respiratory tract of hamsters compared to rHPIV1 wild type virus. Thus, these findings exemplify a second use of codon substitution mutations, i.e., to generate mutants with an enhanced level of attenuation in vivo. It was of interest to find that each of the three attenuated recombinants (rHPIV1-L992C, rHPIV1-L992V and rHPIV1-L992N) also was temperature sensitive. However, there was a dissociation between the level of temperature sensitivity and the level of attenuation. For example the L992C mutation restricted replication in vitro at 36-37° C. and was attenuating primarily in the lower respiratory tract, whereas the L992V mutation restricted replication in vitro only at 39° C. but was highly attenuating in both the upper and lower respiratory tract. Thus, the L992V mutation is predominantly of the non-ts type. This is in contrast to the situation with the codon 942 substitution mutations examined in the present study, where there generally was a strong association between the level of temperature sensitivity in vitro and the level of attenuation in vivo.

Live attenuated viruses that contain ts attenuating mutations can be stabilized by the addition of non-ts attenuating mutations (Murphy et al., *Vaccine* 15:1372-1378 1997). Also, ts mutations exert their attenuating effect more prominently in the lower, warmer region of the respiratory tract, whereas non-ts mutations would attenuate irrespective of this temperature gradient. Hence, a mixture of both types of mutations would be optimal to achieve the dual goals of preventing serious lower respiratory tract disease and reducing upper respiratory tract congestion. The ts and non-ts codon substitution mutations identified in this report are now being combined with additional non-ts attenuating mutations to generate rHPIV1 viruse that are satisfactorily attenuated, efficacious in immunogenic compositions, and genetically stable.

EXAMPLE IX

Production and Characterization of Recombinant HPIV1 P/C Gene Deletion Mutants

In additional aspects of the invention, the recombinant HPIV1 or HPIV2 genome or antigenome comprises an additional nucleotide modification specifying a phenotypic change selected from a change in growth characteristics, attenuation, temperature-sensitivity, cold-adaptation, plaque size, host-range restriction, or a change in immunogenicity. For example, in HPIV1 these additional modifications can alter one or more of the N, P, C, C', Y1, Y2, M, F, HN and/or L genes and/or a 3' leader, 5' trailer, a cis-acting sequence such as a gene start (GS) or gene end (GE) sequence, and/or intergenic region within the HPIV1 genome or antigenome. For example, one or more HPIV1 gene(s) can be deleted in whole or in part, or expression of the gene(s) can be reduced or ablated by a mutation in an RNA editing site, by a frameshift mutation, by a mutation that alters a translation start site, by introduction of one or more stop codons in an open reading frame (ORF) of the gene, or by a mutation in a transcription signal. In specific embodiments, the recombinant HPIV1 genome or antigenome is modified by a partial or complete deletion of one or more C, C', Y1, and/or Y2 ORF(s) or other auxiliary gene, or one or more nucleotide change(s) that reduces or ablates expression of one or more of the C, C', Y1, and/or Y2 ORF(s) or other auxiliary gene. In other embodiments, the recombinant HPIV1 genome or antigenome is modified to encode a non-PIV molecule selected from a cytokine, a T-helper epitope, a restriction site marker, or a protein of a microbial pathogen capable of eliciting an immune response in a mammalian host.

Interferons, which are host cell proteins elaborated in response to infection with viruses, induce an antiviral state in cells that restricts replication of virus in the interferon treated cells. Since this is a powerful component of the host's innate immunity, it is not surprising that many viruses have developed elaborate strategies to counteract the antiviral activity of the interferons (Garcia-Sastre, *Virology* 279:375-384, 2001; Goodbourn et al., *J. Gen. Virol.* 81:2341-2364, 2000; Samuel, *Clin. Microbiol. Rev.* 14:778-809, 2001). The C and V proteins of many paramyxoviruses, which are encoded by alternative translational open reading frames (ORFs) in the P gene of the paramyxoviruses (Chanock et al., *In Fields Virology* 1:1341-1379, 2001), are involved in inhibition of the host-cell response to both Type 1 and Type 2 interferons. Mutations that affect the C or V ORFs of PIV1 or PIV2 viruses often result in ablation of this anti-interferon activity (Didcock et al., *J. Virol.* 1999; Garcin et al., *J. Virol.* 75:6800-6807, 2001; Garcin et al., *Virology* 295:256-265, 2002; Parisien et al., *Virology* 283:230-239, 2001), and viruses with such mutations become sensitive to antiviral actions of interferon and exhibit reduced replication in vitro in interferon competent cells and in vivo in interferon competent animals (Garcia-Sastre, *Virology* 279:375-384, 2001). Viruses with such mutations have been considered for use as live attenuated virus vaccines (Garcia-Sastre, *Virology* 279:375-384, 2001), since they can readily be prepared in vitro in known interferon-negative cells. The V and C proteins have functions other than just putative interferon function (Chanock et al., *In Fields Virology* 1:1341-1379, 2001); Lamb et al., *In Fields Virology* 1:1305-1340, 2001), therefore, introduced mutations could affect one or more of the functions of the accessory proteins. Since the complete set of the functions of the accessory proteins have not been defined, mutations in the accessory proteins that attenuate the virus might do so by a mechanism that is not related to its anti-interferon properties. Thus, a goal in developing immunogenic compositions of the invention includes production of live attenuated HPIV1 whose attenuation is based solely, or in part, on the presence of mutations that render the virus fully susceptible to the host's interferon response.

Since HPIV1 lacks a V ORF (Newman et al., *Virus Genes* 24:1, 77-92, 2002), the anti-interferon protein of this virus may be one or more of the C proteins (including the set of C, C', Y1, and Y2 proteins). Mutations in the C protein of Sendai virus, a murine PIV1 highly related to HPIV1, that interfere with the antiviral activity of interferon and that attenuate the replication of this virus for mice have been described (Garcin et al., *J. Virol.* 75:6800-6807, 2001; Garcin et al., *Virology* 295:256-265, 2002). Single-nucleotide substitution mutations that affect the C protein, but not the P protein, in recombinant HPIV3 have been reported (Durbin et al., *Virology* 261:319-330, 1999; Skiadopoulos et al., *J. Virol.* 73:1374-1381, 1999a). HPIV3 recombinants bearing the HPIV3cp45 C mutation (196T) or the F 170S mutation were reportedly restricted for replication in vivo but not in vitro and, similarly, rHPIV1 bearing the F170S$_{MPIV1}$ mutation in C was reportedly attenuated in hamsters. These mutants were not ts and replicated efficiently in vitro. These types of non-ts attenuating mutations are an important element in the production of phenotypically stable live-attenuated viruses of the invention, as outlined herein. However, only a single-nucleotide substitution specifies the F170S mutation, and such mutations would therefore require only a single nucleotide substitution to revert to a wild type virulence phenotype. The findings summarized in the present Example present a method to produce live attenuated rHPIV1 subviral particles that contain functional deletions in the C protein, which will exhibit greater stability of the attenuation phenotype in vivo. Also described is the recovery of rHPIV1 viruses bearing these deletion mutations.

To generate live-attenuated HPIV1 recombinants whose likelihood to revert to wt is highly diminished, deletion mutations were introduced within the P/C gene of HPIV1 in the region of the overlap of the P and C ORFs. A region located in the N-terminal end of the HPIV1 C protein that may interact with and abrogate the cell's interferon response (Garcin et al., *J. Virol.* 75:6800-6807, 2001) pathway was mutagenized. Mutations were introduced in this area by PCR mutagenesis that deleted codons 10-15 of the C ORF. This mutation also deleted codons 13-19 of the P ORF. A subset of mutations deleting C ORF codons 10-11, 12-13, and 14-15 were also generated by PCR mutagenesis (see FIG. 13 of U.S. patent application Ser. No. 10/302,547, filed by Murphy et al. on Nov. 21, 2002; and corresponding PCT Publication Number WO 03/043587 A2, published on May 30, 2003, each incorporated herein by reference). Preferable mutants are ones in which C function is altered without affecting P function, since the latter is an essential protein required for viable HPIV1. Therefore, we first evaluated the ability of a P gene containing these mutations to support the recovery of rHPIV1 from a full-length rHPIV1 antigenomic cDNA in transfected cells. This is an appropriate assay for P function, since a functional P support plasmid is an essential component of the set of three support plasmids used in the recovery of infectious viruses from transfected infectious parainfluenza virus cDNAs. Each of the five deletion mutations indicated were introduced into the pTM-($P_1$) support plasmid. HEp-2 cells were transfected with pTM ($N_1$), pTM ($L_1$), full-length wild type HPIV1 antigenomic cDNA, and each of the pTM ($P_1$) containing the deletions indicated and were coinfected with MVA-T7, as described above. Surprisingly, each of the P deletion mutants supported the recovery of rHPIV1 from cDNA. Importantly, infectious rHPIV1 was not recovered from control transfection reactions lacking a P support plasmid, indicating that the pTM ($P_1$) containing the deletions were functional.

A P/C gene deletion mutation specifying deletion of amino acids 10-15 in the N-terminal end, or at amino acids 168-170 of the C proteins were introduced into the full-length antigenomic HPIV1 cDNA, and these cDNAs were used to recover mutant recombinant HPIV1 containing P/C gene deletions. Two viruses have been recovered to date, and they grew to high titer in cell culture indicating that the introduced mutations were not attenuating in vitro. rHPIV1 C: Δ10-15($F_{RSV}$), a recombinant HPIV1 expressing the RSV F protein from a supernumerary gene inserted upstream of the HPIV1 N ORF and encoding a deletion of C protein amino acids 10-15 grew to 7.0 $\log_{10}$ TCID$_{50}$/ml in LLC-MK2 cells. Thus, this rHPIV1 replicates efficiently in tissue culture despite a six amino acid deletion in P, a six amino acid deletion in C, and a six amino acid deletion in C'. The attenuation of rHPIV1 viruses bearing this mutation, which we have shown to be viable and capable of efficient replication in tissue culture cells, can now be readily determined in hamsters and African Green monkeys. If rHPIV1 viruses bearing this mutation are appropriately attenuated and immunogenic, this mutation can be introduced into any rHPIV1 alone or along with other ts and non-ts attenuating mutations to generate phenotypically stable live-attenuated rHPIVs.

An additional 2-codon deletion mutation was introduced in the middle of the P/C gene. This mutation spans amino acid F170, whose substitution at amino acid residues 168-170 of the rHPIV1 C protein has been shown to confer a non-ts attenuation phenotype. The mutation was also introduced into pTM ($P_1$) and this support plasmid was functional in the rescue assay described above (FIG. 15, Panel B), indicating that the function of the P protein is not adversely affected. A rHPIV1 virus bearing the deletion in the P/C gene, designated rHPIV1 C:ΔF170, was recovered from transfected cells as described previously. This deletion mutation modifies each of the 5 known P/C gene proteins (P, C, C', Y1, and Y2) including deletion of amino acid 172 and 173 in the P protein, and 168-170 in the C protein. Although this mutant encoded 5 protein with deletion, it replicated well in cell culture. Satisfactorily attenuated and phenotypically stable rHPIV viruses can be generated bearing this deletion mutation alone or in combination with other attenuating mutations for use in immunogenic compositions and methods of the invention.

Characterization of the Level of Replication and Efficacy Against Wild Type HPIV1 Challenge of a Recombinant HPIV1 C Protein Deletion Mutant in Hamsters and Non-Human Primates The in vivo growth characteristics of rHPIV1 C:F170S bearing the single C protein amino acid substitution at F170 and rHPIV1 C:ΔF170 containing the P/C gene deletion mutation described above was examined in animal models generally accepted as predictive of HPIV replicative potential and immunogenic activity in humans, namely Golden syrian hamsters (*Mesocritus Auratus*) and African green monkeys (*Cercopithecus aethiops*). The level of replication of rHPIV1 C:F170S and rHPIV1 C:ΔF170 in the upper and lower respiratory tract of infected hamsters was compared to that of unmodified biologically derived (HPIV1$_{LLC1}$) and recombinant HPIV1 (rHPIV1$_{LLC4}$) control viruses. As shown in Table 10, the level of replication of rHPIV1-ΔF170 was highly restricted in both the upper and lower respiratory tract of hamsters and was nearly identical to that of the rHPIV1 C: F 170S bearing the F 170S substitution mutation, indicating that deletion of the F 170 amino acid results in a similar attenuation phenotype as the F170 to serine substitution mutation. This attenuation phenotype is characterized by a similar level of restriction of replication in both the upper and lower respiratory tracts, a highly desirable phenotype that should result in abrogation of the upper (rhinitis and otitis media) and lower respiratory tract disease (croup) caused by this virus in humans. Since rHPIV1 C:F170S, rHPIV1 C:ΔF170, and rHPIV1 C: Δ10-15($F_{RSV}$) each contain the R84G amino acid substitution in the C protein and the T553A substitution in the HN protein that confer a host range attenuation phenotype on rHPIV1$_{LLC4}$, the present observations indicate that the substitution and deletion mutations at C protein residue 170 and at residues 10-15 of C are compatible for viability with the host range attenuating mutations, namely, the R84G amino acid substitution in the C protein and the T553A substitution in the HN protein other. Thus the attenuation phenotype of the rHPIV1 mutants containing these sets of attenuating mutations should be highly phenotypically stable in vitro.

TABLE 10

Replication of rHPIV1 wt and mutant viruses in hamsters

| Immunizing Virus[b] | No. of Nucleotides Required for Reversion to WT | No. animals | Mean virus titer (log$_{10}$ TCID$_{50}$/ g ± S.E.[a]) in: Nasal Turbinates | Lungs |
|---|---|---|---|---|
| HPIV1$_{LLC1}$ | 0 | 6 | 5.1 ± 0.1 | 4.5 ± 0.5 |
| rHPIV1$_{LLC4}$ | 0 | 6 | 4.0 ± 0.1 | 3.6 ± 0.3 |
| rHPIV1 C: Δ☐170 | 3+ | 6 | 2.5 ± 0.1[c] | 2.6 ± 0.2[c] |
| rHPIV1 C: F170S | 1 | 12 | 2.5 ± 0.1[c] | 2.5 ± 0.1[c] |

[a]S.E. Standard error
[b]Hamsters were inoculated IN with 10$^6$ TCID$_{50}$ of the indicated virus. Nasal turbinates and lung tissues from six animals for each group were harvested on day 4. Virus present in the tissues was quantified by serial dilution on LLC-MK2 monolayers at 32° C. and infected cultures were detected by hemadsorption with guinea pig erythrocytes after 6 days.
[c]Values in bold show an approximately 100-fold or more reduction in titer compared to the titer of wild type HPIV1$_{LLC1}$.

The level of replication of the rHPIV1 C:ΔF170 recombinant was also compared to the biologically-derived (rHPIV1$_{LLC1}$) and recombinant HPIV1 (rHPIV1$_{LLC4}$) in HPIV1 seronegative African green monkeys by the intranasal (IN) and intratracheal (IT) administration of 10$^6$ TCID$_{50}$ of virus at each site, as described previously. As shown in Table 11, the mean peak virus titer of the mutant rHPIV1 with the ΔF170 or the F170S C protein mutation was approximately 100-fold and 40-fold attenuated for replication in the upper and lower respiratory tract of infected monkeys, respectively, compared to the replication of wild type HPIV1$_{LLC1}$ virus. The daily mean virus titer for the C protein mutants was also reduced compared to that of the wild type HPIV1$_{LLC1}$ virus and to rHPIV1$_{LLC4}$ (FIG. 16). The recombinants containing a ΔF170 or a F170S mutation in the C protein were also more attenuated for replication in the lower respiratory tract compared to the parent rHPIV1$_{LLC4}$ virus, indicating that the attenuation specified by the mutations at residue 170 in the C protein are additive to the attenuation specified by the mutations found in the C or HN protein of rHPIV1$_{LLC4}$ for the lower respiratory tract of African Green monkeys. Thus, both the deletion and substitution mutation in the HPIV1 anti-interferon C protein confer an attenuation of replication phenotype in the respiratory tract of African green monkeys. Despite this attenuation, both viruses induced a high level of protection against wild type virus (Table 11). Importantly, the ΔF170 mutation would require an insertion of 6 nucleotides to revert to a wild type HPIV1 sequence. Because this recombinant mutant virus was designed to conform to the rule of six, correcting insertions into mutant PIVs such as these P gene deletion mutants are predicted to be extremely unlikely to occur. Furthermore, C protein deletion mutations such as the one described here will very likely impart an exceptionally stable attenuation phenotype following replication in vitro and in vivo, an important consideration for the safety of the immunizing virus in the target infant population, and for the large scale manufacture of immunogenic compositions. If necessary, the various attenuating mutations identified in the C protein can be combined with each other or with attenuating mutations identified in other parts of the genome to modify the level of attenuation of recombinant HPIVs of the invention.

TABLE 11

Level of virus replication in seronegative African green monkeys infected with biologically derived or recombinant HPIV1

| Virus administered[a] | Number of animals | Mean peak virus titer ± S.E.[b] (log$_{10}$ TCID$_{50}$/ml) in: NP swab[c] | TL[d] | Mean peak challenge virus titer[e] (log$_{10}$ TCID$_{50}$/ml) in: NP swab | TL |
|---|---|---|---|---|---|
| HPIV1$_{LLC1}$ | 4 | 4.2 ± 0.3 | 5.1 ± 0.7 | 0.8 ± 0.3 | 0.5 ± 0.0 |
| rHPIV1$_{LLC4}$ | 10 | 2.4 ± 0.3 | 5.0 ± 0.3 | 0.6 ± 0.1 | 0.6 ± 0.1 |
| rHPIV1 C: F170S | 4 | 2.0 ± 0.1 | 3.5 ± 0.6 | 1.1 ± 0.4 | 0.5 ± 0.0 |
| rHPIV1 C: ΔF170 | 4 | 2.1 ± 1.0 | 3.6 ± 0.6 | 0.8 ± 0.1 | 1.2 ± 0.4 |
| None | 4 | nd | nd | 4.7 ± 0.5 | 6.2 ± 0.7 |

[a]Monkeys were inoculated intranasally and intratracheally with 10$^6$ TCID$_{50}$ of the indicated virus. Data was compiled from three studies.
[b]Mean of the peak virus titers for the animals in each group irrespective of sampling day. SE, standard error. Virus titrations were performed on LLC-MK2 cells at 32° C., and infected cultures were detected after 7 days by hemadsorption with guinea pig erythrocytes. The limit of detection was 1.0 log$_{10}$ TCID$_{50}$/ml.
[c]Nasopharyngeal samples were collected on days 0 to 10 postinfection. The titers on day 0 were ≦0.5 log$_{10}$ TCID$_{50}$/ml.
[d]Tracheal lavage samples were collected on days 2, 4, 6, 8, and 10 postinfection. The titers on day 0 were ≦0.5 log$_{10}$ TCID$_{50}$/ml.
[e]Each animal was challenged with the wild type Wash/64 strain, HPIV1$_{LLC1}$. NP and TL samples were collected on days 2, 4, 6, and 8. The titer of virus present in the samples was determined as described above.

EXAMPLE X

Use of Recombinant HPIV1 as an Expression Vector for Supernumerary Foreign Genes In yet additional aspects of the invention, the recombinant HPIV1 genome or antigenome comprises a partial or complete HPIV1 "vector" genome or antigenome that is combined with one or more heterologous gene(s) or genome segment(s) encoding one or more antigenic determinant(s) of one or more heterologous pathogen(s) to form a chimeric HPIV1 genome or antigenome. The heterologous gene(s) or genome segment(s) encoding the antigenic determinant(s) can be added as supernumerary gene(s) or genome segment(s) adjacent to or within a noncoding region of the partial or complete HPIV1 vector genome or antigenome, or can be substituted for one or more counterpart gene(s) or genome segment(s) in a partial HPIV1 vector genome or antigenome. The heterologous gene(s) or genome segment(s) can include one or more heterologous coding sequences and/ or one or more heterologous regulatory element(s) comprising an extragenic 3' leader or 5' trailer region, a gene-start signal, gene-end signal, editing region, intergenic region, or a 3' or 5' non-coding region.

In related embodiments of the invention, chimeric HPIV1 viruses are provided wherein the vector genome is combined with one or more heterologous antigenic determinant(s) of a heterologous pathogen selected from measles virus, subgroup A and subgroup B respiratory syncytial viruses, mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses, human metapneumoviruses, and influenza viruses. In exemplary aspects, the heterologous antigenic determinant(s) is/are selected from measles virus HA and F proteins, subgroup A or subgroup B respiratory syncytial virus F, G, SH and M2 proteins, mumps virus HN and F proteins, human papilloma virus L1 protein, type 1 or type 2 human immunodeficiency virus gp160 protein, herpes simplex virus and cytomegalovirus gB, gC, gD, gE, gG, gH, gI, gJ, gK, gL, and gM proteins, rabies virus G protein, Epstein Barr Virus gp350 protein, filovirus G protein, bunyavirus G protein, flavivirus pre M, E, and NS1 proteins, human metapneuomovirus G and F protein, and alphavirus E protein, and antigenic domains, fragments and epitopes thereof.

The complete genomic sequence of a biologically derived HPIV1/Wash/64 strain that had been passaged four times in LLC-MK2 cells and had acquired two putative host-range amino acid substitutions in the C and HN proteins was determined (GenBank Accession No. AF457102), and a full-length antigenomic HPIV1 cDNA was generated. A recombinant virus (rHPIV1$_{LLC4}$) that was derived from this cDNA was attenuated for replication compared to a biologically derived HPIV1 that had been passaged once in LLC-MK2 cells (HPIV1$_{LLC1}$). This antigenomic cDNA encoding a C protein R84G substitution and an HN protein T553A substitution was used to derive the recombinant viruses described below.

To generate an antigenomic HPIV1 cDNA that could be used as a vector, a unique Mlu I restriction site was introduced immediately upstream of the HPIV1 N gene translation initiation codon in the full-length antigenomic HPIV1 cDNA (nts 113-118) by PCR mutagenesis, as described previously (U.S. patent application Ser. No. 10/302,547, filed by Murphy et al. on Nov. 21, 2002; and corresponding PCT Publication Number WO 03/043587 A2, published on May 30, 2003, each incorporated herein by reference). The supernumerary gene insertion site in the vector was designed so that it did not disrupt any of the postulated HPIV1 replication and transcription cis-acting elements predicted by analogy to heterologous paramyxoviruses. The present example describes insertion of an additional transcriptional unit into the MluI site (nts 113-118) upstream of the N protein ORF (FIG. 14). However, based on the successful results described herein, alternative unique restriction sites can also be used, and these can also be introduced at other gene junctions, such as the N-P, P-M or HN-L junction. For example, a unique Not I site was also introduced into the antigenomic HPIV1 cDNA in the P-M junction and this was used to introduce a gene unit expressing the HMPV CAN83 strain G protein.

To generate the HPIV1 based HMPV glycoprotein expression vector, the HMPV CAN83 strain (GenBank Accession No. AY297749 incorporated herein by reference) F glycoprotein ORF was modified for insertion into the Mlu I site of rHPIV1 described previously (U.S. patent application Ser. No. 10/302,547; PCT Publication Number WO 03/043587). The strategy was to express the heterologous ORF as an additional, separate mRNA, and hence it was important that it be introduced into the rHPIV1 genome so that it was preceded by a functional HPIV1 gene start signal and followed by a functional HPIV1 gene end signal. The cDNA was designed so that the entire inserted gene unit conformed to the "rule of six" and the phasing of the HPIV1 gene start signals were maintained. The MluI insertion site followed the putative gene start signal of the N gene. Hence, for insertion at this site, the HMPV F ORF needed to be modified by insertion of an Mlu I site at its upstream end and addition of a HPIV1 gene end signal, intergenic region, gene start signal, and a MluI site at its downstream end (FIG. 14). The inserted sequence was 1656 nucleotides in length and thus the length of the modified HPIV1 antigenomic cDNA conformed to the rule of six, which holds for other members of Genus Respirovirus (Chanock et al., In Fields Virology 1:1341-1379, 2001) and also appears to apply to HPIV1.

Recombinant virus (rHPIV1-F$_{83}$) was readily recovered from transfected HEp-2 cells using the HPIV1 N, P and L protein expression plasmids and MVA-T7 infection. The virus supernatant was then passaged several times on LLC-MK2 cells grown at 32° C. vRNA isolated from LLC-MK2 cells infected with rHPIV1-F$_{83}$ was used to generate a RT-PCR product flanking the supernumerary gene, and sequence analysis confirmed that the sequence of the supernumerary gene present in rHPIV1-F$_{83}$ was as designed. Thus, an additional gene encoding a foreign antigen can be readily inserted into recombinant HPIV1 using the putative transcription signals and insertion strategy identified in the present example, and this inserted sequence is stably maintained following prolonged replication in tissue culture cells.

A similar strategy was used to generate an HPIV1 vector expressing the HMPV G protein. In this example, a unique NotI site was introduced by PCR mutagenesis at nts 3609-3616, between the HPIV1 P and M ORFs, within the P gene non-coding region. Then the HMPV CAN83 strain G glycoprotein ORF (GenBank Accession No. AF457102) was modified for insertion into the Not I site of rHPIV1. The strategy was to express the heterologous ORF as an additional, separate mRNA, and hence it was important that it be introduced into the rHPIV1 genome so that it was preceded by a functional HPIV1 gene start signal and followed by a functional HPIV1 gene end signal. The cDNA was designed so that the entire inserted gene unit conformed to the "rule of six" and the phasing of the HPIV1 gene start signals were maintained. Hence, for insertion at this site, the HMPV G ORF needed to be modified by insertion of a Not I site followed by a putative HPIV1 gene end signal, intergenic region, gene start signal, the HMPV G ORF, and a Not I site at its downstream end. The inserted sequence was 702 nucleotides in length and thus the length of the modified HPIV1 antigenomic cDNA conformed to the rule of six. Recombinant virus (rHPIV1-G$_{83}$) was readily recovered from transfected HEp-2 cells using the HPIV1 N, P and L protein expression plasmids and MVA-T7 infection, as described above. The virus supernatant was then passaged several times on LLC-MK2 cells grown at 32° C. vRNA isolated from LLC-MK2 cells infected with rHPIV1-G$_{83}$ was used to generate an RT-PCR product flanking the supernumerary gene, and sequence analysis confirmed that the sequence of the supernumerary gene present in rHPIV1-G$_{83}$ was as designed.

Recombinant rHPIV1-F$_{83}$ and rHPIV1-G$_{83}$ expressing the HMPV F protein or HMPV G protein from the supernumerary gene were isolated, biologically cloned, and found to replicate to high titer, $\geqq 7.7$ log$_{10}$ and 9.0 log$_{10}$ TCID$_{50}$/ml, respectively. Expression of the HMPV and HPIV1 glycoproteins was confirmed by indirect immunofluorescence of LLC-MK2 cells infected with either HPIV1, HMPV, rHPIV1-F$_{83}$, or rHPIV1-G$_{83}$. LLC-MK2 cells grown on glass slides were infected with virus, and approximately 72 hours post-infection the cells were fixed and permeabilized. Mouse monoclonal anti-HPIV1 HN and hamster polyclonal anti-HMPV antibodies were used to detect the HPIV1 HN and HMPV glycoproteins, respectively, in LLC-MK2 cells. Fluorescein isothiocyanate (FITC) conjugated anti-mouse or anti-hamster IgG antibody (Jackson Immunochemicals, PA) was used for indirect immunofluorescence of HMPV or HPIV1 glycoproteins. Thus, expression of the HMPV F or G protein was confirmed (Table 12), indicating that supernumerary genes expressing the HMPV F and G glycoproteins inserted either upstream of the HPIV1 N gene or between the P and M genes, respectively, are well tolerated and efficiently translated. Therefore, these recombinant HPIV1 viruses express the protective antigens of two human pathogens, HMPV and HPIV1.

Using the methods outlined herein, the HPIV1 and HPIV2 vectors described herein can now be attenuated by the systematic introduction of deletion and/or point mutations to generate live-attenuated viruses that will protect against two major pediatric respiratory pathogens, for example HPIV1 and HMPV. These rHPIV1-$F_{83}$ and rHPIV1-$G_{83}$ viruses could be used as vectors to induce a primary antibody response to HMPV, or to boost a response induced by prior infection with HMPV or with another PIV vector such as an HPIV3.

TABLE 12

Detection of HMPV or HPIV1 antigens in LLC-MK2 cells infected with recombinant rHPIV1 vectors expressing the HMPV glycoproteins by indirect immunofluorescence

| Virus | Level of immunofluorescence detected using a primary antiserum directed against: | |
|---|---|---|
| | HMPV | HPIV1 |
| rHPIV1$_{LLC4}$ | 0 | +++ |
| rHPIV1 $F_{83}$ | +++ | +++ |
| rHPIV1 $G_{83}$ | +++ | +++ |
| HMPV CAN83 | +++ | 0 |
| uninfected | 0 | 0 |

The virus used to infect LLC-MK2 cells is indicated. The LLC-MK2 monolayers were examined using confocal microscopy. The level of intensity of the immunofluorescence signal obtained from HMPV infected versus rHPIV1 $F_{83}$, or rHPIV1 $G_{83}$ infected cells was equivalent.
A "0" indicates no signal detected.
A "+++" indicates a strong immunofluorescence signal.

Recombinant live attenuated HPIV1 and HPIV2 viruses will be very useful as vectors to express the protective antigens of other human respiratory pathogens, especially those that cause disease in infancy. Since HPIV1 and HPIV2 wild type viruses predominantly cause disease in later infancy. i.e., in infants older than six months of age, they can be administered at four to six months of age to prevent HPIV1- and HPIV2-mediated disease. In contrast, RSV, HMPV, and HPIV3 each cause disease in early as well as later infancy, and vaccination against these viruses will need to be initiated in the first month of life. Thus, the sequential immunization against RSV, HMPV, HPIV3, HPIV1, and HPIV2 will involve giving an RSV, HMPV, and HPIV3 immunogenic composition followed several months later by a bivalent HPIV1 and HPIV2 immunogenic composition. For this reason, HPIV1 and HPIV2 vaccine administration is uniquely positioned to provide an opportunity to boost an immune response to a previously administered RSV, HMPV, or HPIV3 immunogenic composition. Since disease caused by RSV and HPIV3 is more severe and more frequent than that caused by HPIV1 and HPIV2, the ability of a HPIV1 and HPIV2 vaccine to protect against HPIV1 and HPIV2 and to boost an immune response to RSV (or to HMPV or HPIV3) provides added impetus to develop HPIV1 and HPIV2 candidates, i.e., their dual potential will make them more attractive immunogenic compositions for industry to develop and for regulatory agencies to approve. The present example illustrates the ability of a rHPIV1 virus expressing the RSV F glycoprotein to boost the immune response to RSV, an immune response primed by prior infection with an attenuated RSV.

A live attenuated RSV, $RSV_{248/404}$, was administered to hamsters and one month later the animals were administered HPIV1 wild type virus (a control virus), HPIV1-F (HPIV1 expressing the RSV F glycoprotein), or a second dose of $RSV_{248/404}$ (Table 13). The animals boosted with rHPIV1-F, but not those boosted with $RSV_{248/404}$ or the HPIV1 wild type control virus, developed a greater than four fold rise in ELISA and neutralizing antibody titer to RSV. Thus, HPIV1-F was able to boost the immune response to RSV whereas a second dose of $RSV_{248/404}$ was not, presumably because it was not able to infect the RSV immune animals. Thus, the unique ability of rHPIV1-FRSV to boost the response to RSV stems from its ability to replicate in the presence of RSV immunity, whereas this immunity restricted both the replication and immunogenicity of the second dose of the live attenuated $RSV_{248/404}$. The animals immunized with rHPIV1-$F_{RSV}$ developed an immune response to HPIV1, as expected.

A rHPIV2-F vector should be similarly useful as the rHPIV1-F vector at boosting a response to RSV or other such viruses. Furthermore, each of these two viruses should be able to vector other protective antigens of RSV, HMPV and HPIV3 to expand the number of human pathogens that can be protected against, using a relatively small number of live-attenuated viruses.

TABLE 13

Immunization of hamsters with rHPIV1 expressing the RSV F protein following immunization with RSV248/404 induces a boost serum antibodies against RSV F

| First immunizing virus[a] | Second immunizing virus[b] | Serum HAI titer ($\log_2$) to HPIV3 | Serum neut titer ($\log_2$) to HPIV1 | Serum IgG RSV G ELISA titer ($\log_2$) on day: | | Serum IgG RSV F ELISA titer ($\log_2$) on day: | | Serum RSV neutralization titers ($\log_2$ 60% PNT): | |
|---|---|---|---|---|---|---|---|---|---|
| | | 0 | 28 | 28 | 56 | 28 | 56 | 28 | 56 |
| $RSV_{248/404}$ | HPIV1-F | ≤1 | 2.6 | 10.6 | 10.3 | 9.6 | 12.8 | 8.3 ± 0.6 | 10.4 ± 0.5 |
| $RSV_{248/404}$ | HPIV1 | ≤1 | 2.8 | 11.3 | 11.1 | 10.8 | 10.1 | 8.9 ± 0.9 | 9.6 ± 0.9 |
| $RSV_{248/404}$ | $RSV_{248/404}$ | ≤1 | nd | 11.8 | 11.6 | 11.3 | 11.1 | 8.9 ± 0.7 | 9.8 ± 0.4 |

TABLE 13-continued

Immunization of hamsters with rHPIV1 expressing the RSV F protein following immunization with RSV248/404 induces a boost serum antibodies against RSV F

| First immunizing virus[a] | Second immunizing virus[b] | Serum HAI titer ($\log_2$) to HPIV3 | Serum neut titer ($\log_2$) to HPIV1 | Serum IgG RSV G ELISA titer ($\log_2$) on day: | | Serum IgG RSV F ELISA titer ($\log_2$) on day: | | Serum RSV neutralization titers ($\log_2$ 60% PNT): | |
|---|---|---|---|---|---|---|---|---|---|
| 0 | 28 | 28 | 28 | 28 | 56 | 28 | 56 | 28 | 56 |
| HPIV1 | HPIV1-F | ≦1 | 3.8 | 8.3 | 9.8 | 7.1 | 9.8 | — | — |
| — | HPIV1-F | ≦1 | 3.2 | 8.1 | 8.6 | 7.1 | 9.6 | — | — |
| — | HPIV1 | ≦1 | 3.7 | 7.8 | 8.3 | 6.6 | 6.3 | — | — |

[a]Hamsters were immunized intranasally with $10^6$ TCID$_{50}$ of the indicated virus.
[b]After 28 days, hamsters were immunized intranasally with $10^6$ TCID$_{50}$ of the indicated virus.
[c]Serum was collected 28 days and 56 days post-first infection. The serum HPIV3 hemagglutination inhibition titers (HAI), HPIV1 neutralization titers, RSV F and G ELISA and neutralization titers were determined. The mean titer of each group ($\log_2$) is shown.

Although the foregoing invention has been described in detail by way of example for purposes of clarity of understanding, it will be apparent to the artisan that certain changes and modifications may be practiced within the scope of the appended claims which are presented by way of illustration not limitation. In this context, various publications and other references have been cited within the foregoing disclosure for economy of description. Each of these references is incorporated herein by reference in its entirety for all purposes.

```

What is claimed is:

1. An isolated, infectious, self-replicating, recombinant human parainfluenza virus type 2 (HPIV2) comprising a PIV major nucleocapsid (N) protein, a PIV nucleocapsid phosphoprotein (P), a PIV large polymerase protein (L), and a partial or complete, polyhexameric recombinant HPIV2 genome or antigenome encoding one or more attenuating mutation(s) selected from amino acid substitution(s) or deletion(s) in the HPIV2 L polymerase at the amino acid corresponding to residue 11 of SEQ ID NO. 4 and/or residue 11 of SEQ ID NO. 10.

2. The recombinant HPIV2 of claim 1, wherein the recombinant HPIV2 genome or antigenome incorporates one or more additional recombinantly-introduced attenuating mutations.

3. The recombinant HPIV2 of claim 1, wherein the recombinant HPIV2 genome or antigenome incorporates one or more additional recombinantly-introduced attenuating mutations at one or more amino acid position(s) corresponding to an amino acid position of an attenuating mutation identified in a heterologous, mutant nonsegmented negative stranded RNA virus.

4. The recombinant HPIV2 of claim 3, wherein the polynucleotide molecule encoding the recombinant HPIV2 genome or antigenome incorporates one or more mutation(s) of HPIV3 JS cp45.

5. An isolated polynucleotide comprising a partial or complete, polyhexameric recombinant human parainfluenza virus type 2 (HPIV2) genome or antigenome modified by one or more attenuating mutations that are recombinantly introduced into said HPIV2 genome or antigenome at any nucleotide used to encode the amino acid corresponding to residue 11 of SEQ ID NO. 4 and/or residue 11 of SEQ ID NO. 10 in the HPIV2 L polymerase.

6. An expression vector comprising an operably linked transcriptional promoter, a polynucleotide sequence comprising a partial or complete, polyhexameric recombinant human parainfluenza virus type 2 (HPIV2) genome or antigenome modified by one or more attenuating mutations that are recombinantly introduced into said HPIV2 genome or antigenome at any nucleotide used to encode the amino acid corresponding to residue 11 of SEQ ID NO. 4 and/or residue 11 of SEQ ID NO. 10 in the HPIV2 L polymerase, and a transcriptional terminator.

* * * * *

                        SEQUENCE LISTING

<160> NUMBER OF SEQ ID NOS: 70

<210> SEQ ID NO 1
<211> LENGTH: 40
<212> TYPE: PRT
<213> ORGANISM: Human parainfluenza virus 2

<400> SEQUENCE: 1

Ala Glu Ile Ser Tyr Glu Tyr Thr Leu Lys His Trp Lys Glu Ile Ser
 1               5                  10                  15

Leu Ile Glu Phe Arg Lys Cys Phe Asp Phe Asp Pro Gly Glu Glu Leu
            20                  25                  30

Ser Ile Phe Met Lys Asp Lys Ala
        35                  40

<210> SEQ ID NO 2
<211> LENGTH: 40
<212> TYPE: PRT
<213> ORGANISM: Human parainfluenza virus 3

<400> SEQUENCE: 2

Ser Ala Ile Ser Tyr Glu Asn Ala Val Asp Tyr Tyr Gln Ser Phe Ile
 1               5                  10                  15

Gly Ile Lys Phe Asn Lys Phe Ile Glu Pro Gln Leu Asp Glu Asp Leu
            20                  25                  30

Thr Ile Tyr Met Lys Asp Lys Ala
        35                  40

<210> SEQ ID NO 3
<211> LENGTH: 40
<212> TYPE: PRT
<213> ORGANISM: Human parainfluenza virus 1
```

-continued

```
<400> SEQUENCE: 3

Ser Ala Ile Ser Tyr Glu Cys Ala Val Asp Asn Tyr Ser Ser Phe Ile
  1               5                  10                  15

Gly Phe Lys Phe Leu Lys Phe Ile Glu Pro Gln Leu Asp Glu Asp Leu
             20                  25                  30

Thr Ile Tyr Met Lys Asp Lys Ala
         35                  40

<210> SEQ ID NO 4
<211> LENGTH: 21
<212> TYPE: PRT
<213> ORGANISM: Human parainfluenza virus 2

<400> SEQUENCE: 4

Leu Leu Pro Ser Gln Leu Gly Gly Leu Asn Tyr Leu Ala Cys Ser Arg
  1               5                  10                  15

Leu Phe Asn Arg Asn
             20

<210> SEQ ID NO 5
<211> LENGTH: 21
<212> TYPE: PRT
<213> ORGANISM: Human parainfluenza virus 3

<400> SEQUENCE: 5

Leu Ile Pro Ala Ser Val Gly Gly Phe Asn Tyr Met Ala Met Ser Arg
  1               5                  10                  15

Cys Phe Val Arg Asn
             20

<210> SEQ ID NO 6
<211> LENGTH: 21
<212> TYPE: PRT
<213> ORGANISM: Human parainfluenza virus 1

<400> SEQUENCE: 6

Leu Ile Pro Ala Asn Ile Gly Gly Phe Asn Tyr Met Ser Thr Ala Arg
  1               5                  10                  15

Cys Phe Val Arg Asn
             20

<210> SEQ ID NO 7
<211> LENGTH: 21
<212> TYPE: PRT
<213> ORGANISM: Human parainfluenza virus 2

<400> SEQUENCE: 7

Leu Ala Arg Lys Pro Gly Lys Gly Ser Trp Ala Thr Leu Ala Ala Asp
  1               5                  10                  15

Pro Tyr Ser Leu Asn
             20

<210> SEQ ID NO 8
<211> LENGTH: 21
<212> TYPE: PRT
<213> ORGANISM: Human parainfluenza virus 3

<400> SEQUENCE: 8

Met Asn Gln Glu Pro Gly Glu Ser Ser Phe Leu Asp Trp Ala Ser Asp
  1               5                  10                  15

Pro Tyr Ser Cys Asn
```

<210> SEQ ID NO 9
<211> LENGTH: 21
<212> TYPE: PRT
<213> ORGANISM: Human parainfluenza virus 1

<400> SEQUENCE: 9

Met Asn Gln Glu Pro Gly Asp Ser Ser Phe Leu Asp Trp Ala Ser Asp
1               5                   10                  15

Pro Tyr Ser Cys Asn
            20

<210> SEQ ID NO 10
<211> LENGTH: 21
<212> TYPE: PRT
<213> ORGANISM: Human parainfluenza virus 2

<400> SEQUENCE: 10

Asp Ile Ile Thr Pro Ile His Ala Pro Tyr Leu Ala Ser Leu Asp Tyr
1               5                   10                  15

Val Lys Leu Ser Ile
            20

<210> SEQ ID NO 11
<211> LENGTH: 21
<212> TYPE: PRT
<213> ORGANISM: Human parainfluenza virus 3

<400> SEQUENCE: 11

Gly Val Leu Asn Pro Ile Tyr Gly Pro Asn Thr Ala Ser Gln Asp Gln
1               5                   10                  15

Ile Lys Leu Ala Leu
            20

<210> SEQ ID NO 12
<211> LENGTH: 21
<212> TYPE: PRT
<213> ORGANISM: Human parainfluenza virus 1

<400> SEQUENCE: 12

Gly Val Val Glu Pro Val Tyr Gly Pro Asn Leu Ser Asn Gln Asp Lys
1               5                   10                  15

Ile Leu Leu Ala Ile
            20

<210> SEQ ID NO 13
<211> LENGTH: 15
<212> TYPE: PRT
<213> ORGANISM: Human parainfluenza virus 2

<400> SEQUENCE: 13

Glu Gln Leu Glu Thr Asp Ile Ile Leu His Ser Thr Leu Thr Ala
1               5                   10                  15

<210> SEQ ID NO 14
<211> LENGTH: 15
<212> TYPE: PRT
<213> ORGANISM: Human parainfluenza virus 3

<400> SEQUENCE: 14

Glu Asp Asn Ile Leu Asp Asn Ile Val Lys Thr Val Asn Asp Asn
1               5                   10                  15

<210> SEQ ID NO 15
<211> LENGTH: 15
<212> TYPE: PRT
<213> ORGANISM: Human parainfluenza virus 3

<400> SEQUENCE: 15

Glu Asp Asn Met Leu Asp Asn Ile Val Lys Thr Val Asn Asp Asn
 1               5                  10                  15

<210> SEQ ID NO 16
<211> LENGTH: 15
<212> TYPE: PRT
<213> ORGANISM: Human parainfluenza virus 1

<400> SEQUENCE: 16

Ala Asp Ser Met Leu Asp Asn Ile Thr Ala Glu Val Gln His Asn
 1               5                  10                  15

<210> SEQ ID NO 17
<211> LENGTH: 105
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aggtccggaa ccactagatt ccggtgccgg taacgatctc agtttatac tatctgatca    60 ttctttatct ctactaagga tatttctaat ctagcggccg caatg                  105

<210> SEQ ID NO 18
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gcggccgcaa tg                                                       12

<210> SEQ ID NO 19
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tgataataaa tttaagaaaa aaacataggc ccggacgggt tagttaccgc ggccgc        56

<210> SEQ ID NO 20
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tagtaaattt aagaaaaaaa cataggcccg gacgggttag gttaccgcgg ccgc          54

<210> SEQ ID NO 21

-continued

```
<211> LENGTH: 49
<212> TYPE: DNA
<213> ORGANISM: Human parainfluenza virus 2

<400> SEQUENCE: 21
tacgtaggtc cggaaccact agattcggtg ccggtaacga ttccagttt            49

<210> SEQ ID NO 22
<211> LENGTH: 50
<212> TYPE: DNA
<213> ORGANISM: Human parainfluenza virus 2

<400> SEQUENCE: 22
tacgtaggtc cggaaccact agattccggt gccggtaacg attccagttt           50

<210> SEQ ID NO 23
<211> LENGTH: 47
<212> TYPE: DNA
<213> ORGANISM: Human parainfluenza virus 2

<400> SEQUENCE: 23
atgactgctc ctgatcaacc accagtatca gtagcaaaga tggctaa              47

<210> SEQ ID NO 24
<211> LENGTH: 50
<212> TYPE: DNA
<213> ORGANISM: Human parainfluenza virus 2

<400> SEQUENCE: 24
atgactgctc ctgatcaacc accagtatca gtagcaaagc ggatggctaa           50

<210> SEQ ID NO 25
<211> LENGTH: 49
<212> TYPE: DNA
<213> ORGANISM: Human parainfluenza virus 2

<400> SEQUENCE: 25
tctctcataa tttaaagaaa aaatcatagg ccggacgggt tagaaatcc            49

<210> SEQ ID NO 26
<211> LENGTH: 49
<212> TYPE: DNA
<213> ORGANISM: Human parainfluenza virus 2

<400> SEQUENCE: 26
tctctcataa tttaagaaaa aatcataggc ccggacgggt tagaaatcc            49

<210> SEQ ID NO 27
<211> LENGTH: 49
<212> TYPE: DNA
<213> ORGANISM: Human parainfluenza virus 2

<400> SEQUENCE: 27
agtaattgcc ggtccaacta gtggaggctt cacagccgaa caggtgata            49

<210> SEQ ID NO 28
<211> LENGTH: 50
<212> TYPE: DNA
<213> ORGANISM: Human parainfluenza virus 2

<400> SEQUENCE: 28
agtaattgcc ggtccaacta gtggaggctt cacagccgaa ggcagtgata           50
```

<210> SEQ ID NO 29
<211> LENGTH: 50
<212> TYPE: DNA
<213> ORGANISM: Human parainfluenza virus 2

<400> SEQUENCE: 29
ttgatttcaa tggatgaact agctagacct acactctcat caacaaaaag        50

<210> SEQ ID NO 30
<211> LENGTH: 49
<212> TYPE: DNA
<213> ORGANISM: Human parainfluenza virus 2

<400> SEQUENCE: 30
tgatttcaat ggatgaacta gctagaccta cactctcatc aacaaaaag         49

<210> SEQ ID NO 31
<211> LENGTH: 49
<212> TYPE: DNA
<213> ORGANISM: Human parainfluenza virus 2

<400> SEQUENCE: 31
ttatacgttt tggctgtatt agaatgttat agattctgct gttttttccc        49

<210> SEQ ID NO 32
<211> LENGTH: 50
<212> TYPE: DNA
<213> ORGANISM: Human parainfluenza virus 2

<400> SEQUENCE: 32
ttatacgttt tggctgtatt agaatgttat agcattctgc tgttttttccc       50

<210> SEQ ID NO 33
<211> LENGTH: 47
<212> TYPE: DNA
<213> ORGANISM: Human parainfluenza virus 2

<400> SEQUENCE: 33
tggggtcatc ccactcttac tgctgcgcaa gtgggtaaag tgagaga           47

<210> SEQ ID NO 34
<211> LENGTH: 50
<212> TYPE: DNA
<213> ORGANISM: Human parainfluenza virus 2

<400> SEQUENCE: 34
tggggtcatc ccactcttac tgctgcgcaa gctgcaggta aagtgagaga        50

<210> SEQ ID NO 35
<211> LENGTH: 47
<212> TYPE: DNA
<213> ORGANISM: Human parainfluenza virus 2

<400> SEQUENCE: 35
tgatatcttt atagtctcca agggaggtat tgaaggccta tgtcaga           47

<210> SEQ ID NO 36
<211> LENGTH: 50
<212> TYPE: DNA
<213> ORGANISM: Human parainfluenza virus 2

<400> SEQUENCE: 36
tgatatcttt atagtctctc ccaagggagg tattgaaggc ctatgtcaga        50

<210> SEQ ID NO 37
<211> LENGTH: 50
<212> TYPE: DNA
<213> ORGANISM: Human parainfluenza virus 2

<400> SEQUENCE: 37
acagatataa ttcttcactc tactttaact gctccttatg ataattcaga        50

<210> SEQ ID NO 38
<211> LENGTH: 49
<212> TYPE: DNA
<213> ORGANISM: Human parainfluenza virus 2

<400> SEQUENCE: 38
acagatataa ttcttcactc tactttaact gctccttatg ataattcag         49

<210> SEQ ID NO 39
<211> LENGTH: 50
<212> TYPE: DNA
<213> ORGANISM: Human parainfluenza virus 2

<400> SEQUENCE: 39
aaactctaac aaagttcgat ttatcccttt cgacatcttt ccacatccag        50

<210> SEQ ID NO 40
<211> LENGTH: 48
<212> TYPE: DNA
<213> ORGANISM: Human parainfluenza virus 2

<400> SEQUENCE: 40
aaactctaac aaagttcgat ttatcccttg acatctttcc acatccag          48

<210> SEQ ID NO 41
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gatatcgaga ggggtatcga tggcgaagaa ttatgacaac agtga            45

<210> SEQ ID NO 42
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
attgagaggg gtatcgatgg cgaagaatta tgacaacagt ga               42

<210> SEQ ID NO 43
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
attgagaggg gtatcgatgg cgaagaatta tgacaacagt gat              43

<210> SEQ ID NO 44
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
attgagaggg gtatcgatgg cgaagaatta tgacaacagt gata                    44

<210> SEQ ID NO 45
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
attgagaggg gtatcgatgg cgaagaatta tgacaacagt gataa                   45

<210> SEQ ID NO 46
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
attgagaggg gtatcgatgg cgaagaatta tgacaacagt gataac                  46

<210> SEQ ID NO 47
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
attgagaggg gtatcgatgg cgaagaatta tgacaacagt gataact                 47

<210> SEQ ID NO 48
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (53)..(54)
<223> OTHER INFORMATION: may or may not be present

<400> SEQUENCE: 48
ccaattcaat acccattttc ataaaggaac acagtataat ttaatcataa aaaagacctc   60
aaaatctgat acagcttaat ccactcaac                                     89

<210> SEQ ID NO 49
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: misc_feature
<222> LOCATION: (46)
<223> OTHER INFORMATION: may or may not be present

<400> SEQUENCE: 49
aatgaagact ccagattcaa gaataattgg aaggctcttt attttttatgc gatagttata      60 cgttttggct gtattagaat gctatagca                                        89

<210> SEQ ID NO 50
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (75)..(76)
<223> OTHER INFORMATION: may or may not be present

<400> SEQUENCE: 50
ttactaaagt tattctgata tttaagaaaa aataatcttt atataatgta acaatactac      60
taagattata atataggc cagaatggcg                                         90

<210> SEQ ID NO 51
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (33)
<223> OTHER INFORMATION: may or may not be present

<400> SEQUENCE: 51
ttactaaagt tattctgata tttaagaaaa aataatctt tatataatgt aacaatacta      60
ctaagattat aatataggcc agaatggcg                                        89

<210> SEQ ID NO 52
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (9)
<223> OTHER INFORMATION: may or may not be present

<400> SEQUENCE: 52
ttactaaaag ttattctgat atttaagaaa aataatctt tatataatgt aacaatacta      60
ctaagattat aatataggcc agaatggcg                                        89

<210> SEQ ID NO 53
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (43)..(44)
```

<223> OTHER INFORMATION: may or may not be present

<400> SEQUENCE: 53
ttactaaagt tattctgata tttaagaaaa aataatcttt atataatgta acaatactac    60
taagattata ataggcca gaatggcg                                        88

<210> SEQ ID NO 54
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (12)
<223> OTHER INFORMATION: may or may not be present
<220> FEATURE:
<221> NAME/KEY: CDS
<222> LOCATION: (10)..(48)

<400> SEQUENCE: 54 attaatgat ttt gaa gat atc gag agg ggt atc gat ggc gaa gaa tta    48
          Phe Glu Asp Ile Glu Arg Gly Ile Asp Gly Glu Glu Leu
            1               5                  10 tgacaacagt gattataaga actcatga                                    76

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Phe Glu Asp Ile Glu Arg Gly Ile Asp Gly Glu Glu Leu
  1               5                  10

<210> SEQ ID NO 56
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (10)..(72)

<400> SEQUENCE: 56 attaatgat ttg aag ata tcg aga ggg gta tcg atg gcg aag aat tat gac    51
          Leu Lys Ile Ser Arg Gly Val Ser Met Ala Lys Asn Tyr Asp
            1               5                  10 aac agt gat tat aag aac tca tga                                      75
Asn Ser Asp Tyr Lys Asn Ser
 15                  20

<210> SEQ ID NO 57
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

-continued

Leu Lys Ile Ser Arg Gly Val Ser Met Ala Lys Asn Tyr Asp Asn Ser
  1               5                  10                  15

Asp Tyr Lys Asn Ser
            20

<210> SEQ ID NO 58
<211> LENGTH: 15654
<212> TYPE: DNA
<213> ORGANISM: Human parainfluenza virus 2

<400> SEQUENCE: 58

| | | | | | |
|---|---|---|---|---|---|
| accaagggga | gaatcagatg | gcatcgttat | atgacgaatt | gcaaaaagat | tacgtaggtc | 60 |
| cggaaccact | agattccggt | gccggtaacg | atctcagttt | tatactatct | gatcattctt | 120 |
| tatctctact | aaggatattt | ctaatctaag | gttcaaaatg | tcaagtgtct | taaagacatt | 180 |
| tgaaagattt | actatacaac | aggagcttca | ggagcaatct | gaagacactc | caatacctct | 240 |
| tgaaacaatc | agacctacaa | tcagagtatt | tgtcatcaat | aataatgatc | ctattgtaag | 300 |
| atctagactt | ttattcttta | atctacgaat | tattatgagt | aacactgcaa | gagagggaca | 360 |
| tagagctggt | gctctcctca | gtctttatc | actaccttct | gcagctatga | gtaatcacat | 420 |
| caaactagcc | atgcattcac | cagaagccag | catagataga | gtagaaataa | cagggtttga | 480 |
| gaataattca | ttccgagtta | ttccagatgc | tcgatcaact | atgtccagag | agaagtgct | 540 |
| ggccttcgaa | gcattagctg | aggacattcc | tgataccctt | aatcaccaaa | ctccatttgt | 600 |
| aaataatgat | gtggaagatg | acatatttga | tgaaacagag | aaattcttgg | atgtttgcta | 660 |
| tagtgtactt | atgcaggcat | ggatagtaac | atgcaagtgc | atgactgctc | ctgatcaacc | 720 |
| accagtatca | gtagcaaagc | ggatggctaa | atatcaacaa | caagggagaa | tcaatgctag | 780 |
| atatgtacta | caacctgaag | cacaaagact | aattcagaat | gccatccgca | agtcaatggt | 840 |
| agtaaggcat | ttcatgacct | atgagcttca | actttcacaa | tcaagatctt | tgctagcgaa | 900 |
| ccgttattat | gccatggtgg | gagacattgg | caagtatatt | gaacacagcg | gaatgggagg | 960 |
| gttttttctta | acacttaaat | atggacttgg | aacaagatgg | cctacattgg | ctcttgcagc | 1020 |
| attctctggg | gaactccaga | aattaaaggc | tctcatgcta | cattatcaga | gtctaggacc | 1080 |
| catggccaag | tacatggctc | tattagaatc | accaaagctg | atggattttg | tcccatctga | 1140 |
| atatccatta | gtttatagct | atgcaatggg | tattggaact | gtccttgata | caaacatgag | 1200 |
| aaactatgca | tatggtagat | catatctaaa | tccacaatat | tttcagctag | gggtagaaac | 1260 |
| agcaaggaaa | cagcaaggag | ctgttgacaa | caggacagca | gaggacctcg | gcatgactgc | 1320 |
| tgcagataaa | gcagacctca | ctgcaaccat | atcaaagcta | tctttatccc | aattacctag | 1380 |
| gggtagacaa | ccaatatccg | acccatttgc | tggagcaaat | gacagagaaa | caggaggaca | 1440 |
| agcaactgat | acacctgtgt | ataacttcaa | tccaatcaat | aatcggaggt | atgacaacta | 1500 |
| tgacagtgat | agtgaggaca | gaattgacaa | cgatcaagat | caggctatca | gagaaacag | 1560 |
| aggagaacct | ggacaaccaa | acaaccagac | aagcgaaaac | cagcagagac | tcaatctccc | 1620 |
| tgtaccgcaa | agaacatcag | gtatgagtag | tgaaagttc | caacattcaa | tgaatcagta | 1680 |
| catccgtgct | atgcatgagc | aatacagagg | ctcccaggat | gatgatgcca | atgatgccac | 1740 |
| agatgggaat | gacatttcac | ttgagctagt | tggagatttt | gattcctaac | tctcactttc | 1800 |
| acataaccag | acatacacat | ccacaccacc | cagagacata | gctaccatcc | acacactcac | 1860 |
| ccagacaaat | caaactagat | tcaaatcatt | cggaaacaat | tctcctagaa | tttaagaaaa | 1920 |
| aaacataggc | ccggacgggt | tagagatccg | gtgctcgtct | gtggccagac | aacctccaca | 1980 |

```
ccagagccac acaatcatgg ccgaggaacc aacatacacc actgagcaag ttgatgaatt   2040
aatccatgct ggactaggaa cagtagattt cttcctatct agacccatag atgctcagtc   2100
ttctttaggt aaaggcagca tcccaccagg tgtcacggct gttctaacca atgcagcaga   2160
ggcaaaatcc aaaccagttg ctgctggtcc agtaaaaccc agacggaaga aagtgatcag   2220
caataccact ccatacacta ttgcagacaa catcccacct gagaagctac cgatcaacac   2280
tccaataccc aatccattac ttccactggc acgccctcac ggaaagatga cagacattga   2340
cattgtcact gggaacatta cagaaggatc atacaaaggt gtggagcttg ccaaattagg   2400
gaagcaaaca ctactcacaa ggttcacctc gaatgagcca gtctcctcag ctggatccgc   2460
ccaagacccc aactttaaga gggggggagc taatagagaa agagcaagag gcaaccatag   2520
gagagaatgg agtattgcat gggtcggaga tcaggtcaaa gtcttcgagt ggtgtaatcc   2580
caggtgtgcc ccagtcacgg cttcagctcg caagttcacc tgcacatgtg atcctgccc    2640
cagcatctgc ggagaatgtg aaggagatca ttgagctctt aaaagggctt gatcttcgcc   2700
ttcagactgt agaagggaaa gtagataaaa ttcttgcaac ctctgcaact ataatcaatc   2760
ttaaaaatga aatgactagt cttaaggcga gcgttgcaac tgtggaaggt atgataacaa   2820
caattaaaat catggatccc agtacaccaa ccaatgtccc tgtagaggag atcagaaaga   2880
gtttacacaa tgttccagta gtaattgctg gtccgactag tggaggcttc acagccgaag   2940
gcagtgacat gatttcaatg gatgaactag ctaggcctac actctcatca acaaaaaaga   3000
tcacacgaaa gcctgaatcc aagaaagatt taacaggcat aaaactaacc ctgatgcagc   3060
ttgcaaatga ctgcatctcg cgtccagata ccaagactga gtttgtgact aagattcaag   3120
cagcaaccac agaatcacag ctcaacgaaa tcaaacggtc aataatacgc tctgcaatat   3180
aaaatgcggt gcaatcacac aagagacatt caacatgcat ccgatcaaga tccaaactcc   3240
ttccatccga aaacacactc accactgtca acaccaagaa acaactacag ccgaaccatg   3300
ctcaaccaaa agacccaaac aacatctcaa atcgacagaa ggctagacat gataaattta   3360
ataaaaaatt aaaagaagtt aagtaaaatt taaagaacac aatagagaaa acctaggtcc   3420
gaaagcttgc ctttcagaca gatcccaaaa tcatagttca aacttcaaac acagcagcag   3480
acatgcctat aatatcatta ccagcagatc caacttcacc cagtcaatcc cttactccgt   3540
ttccaataca acttgatacc aaagatggca aggcagggaa actccttaaa cagattagaa   3600
ttaggtatct aaatgaacct aactctcgtc ataccaat aactttcatc aatacgtatg     3660
gatttgttta tgctcgagac acttcaggag gcattcacag cgagatcagc agtgacctag   3720
ctgcagggtc cataacggca tgcatgatga cactaggtcc tggtccaaat attcagaatg   3780
caaatctagt gctaagatcc ctgaatgaat tctacgtaaa agtcaagaag acatcaagcc   3840
agagggagga agcagtgttt gaattagtta acattccaac cttattgaga gaacatgctc   3900
tttgcaaacg caaaacgtta gtatgctctg cagaaaaatt cctcaagaac ccatcaaagc   3960
tacaagctgg atttgaatat gtatacatcc caacttttgt ctccattaca tactcaccac   4020
gaaatctgaa ttaccaagtt gccagaccta tccttaagtt cagatcacgc tttgtgtata   4080
gcattcattt ggaattaatc ctgagattgc tatgcaaatc tgactcccct ttgatgaaat   4140
cttataatgc agatcgaaca ggtcgaggat gcctcgcatc agtctggatc cacgtatgta   4200
acattctgaa aaacaaaagc atcaagcaac aaggcagaga atcatatttc atagctaagt   4260
gcatgagtat gcagctgcag gtgtccattg cagatctttg gggaccaaca atcataatta   4320
```

```
aatcattggg tcacatcccc aagactgcac ttccttttt  cagcaaagac gggattgcct  4380
gtcatccact acaagatgtt tcccctactc tgacaaaatc actgtggtca gtgggatgtg  4440
agatagaatc tgccaagttg atacttcaag aatctgatat taatgagcta atgggccacc  4500
aggacttgat tactgataag attgccatta gatcaggtca acggacattt gagaggtcca  4560
aattcagccc attcaaaaaa tacgcatcaa ttccaaactt agaagccatc aactgaatgc  4620
tccagcatct aggaatagaa caacaactaa gtcataccat tattgaccat acaataatca  4680
acaattttag ccaactgatt actaagatat tatcataggt ccgaactgat caatctaaca  4740
aaaaaactaa acattcaata ataaatcaaa gttcaggcca aattatccag ccatgcatca  4800
cctgcatcca atgatagtat gcattttgt  tatgtacact ggaattgtag gttcagatgc  4860
cattgctgga gatcaactcc tcaatgtagg ggtcattcaa tcaaagataa gatcactcat  4920
gtactacact gatggtggcg ctagctttat tgttgtaaaa ttactaccca atcttccccc  4980
aagcaatgga acatgcaaca tcaccagtct agatgcatat aatgttaccc tatttaagtt  5040
gctaacaccc ctgattgaga acctgagcaa aatttctgct gttacagata ccaaaccccg  5100
ccgagaacga tttgcaggag tcgttattgg gcttgctgca ctaggagtag ctacagctgc  5160
acaaataacc gcagctgtag caatagtaaa agccaatgca aatgctgctg cgataaacaa  5220
tcttgcatct tcaattcaat ccaccaacaa ggcagtatcc gatgtgataa ctgcatcaag  5280
aacaattgca accgcagttc aagcgattca ggatcacatc aatggagcca ttgtcaacgg  5340
gataacatct gcatcatgcc gtgcccatga tgcactaatt gggtcaatat taaatttgta  5400
tctcactgag cttactacaa tatttcataa tcaaataaca aaccctgcgc tgacaccact  5460
ttccatccaa gctttaagaa tcctcctcgg tagcaccttg ccaattgtca ttgaatccaa  5520
actcaacaca aaactcaaca cagcagagct gctcagttcc ggactgttaa ctggtcaaat  5580
aatttccatt tccccaatgt acatgcaaat gctaattcaa atcaatgttc cgacatttat  5640
aatgcaaccc ggtgcgaagg taattgatct aattgctatc tctgcaaacc ataaattaca  5700
agaagtagtt gtacaagttc ctaatagaat tctagaatat gcaaatgaac tacaaaacta  5760
cccagccaat gattgtgtcg tgacaccaaa ctctgtattt tgtagataca atgagggttc  5820
cccgatccct gaatcacaat atcaatgctt aagggggaat cttaattctt gcactttttac 5880
ccctattatc gggaactttc tcaagcgatt cgcatttgcc aatggtgtgc tctatgccaa  5940
ctgcaaatct ttgctatgta agtgtgccga ccctcccat  gttgtgtctc aagatgacaa  6000
ccaaggcatc agcataattg atattaagag gtgctctgag atgatgcttg acacttttttc 6060
atttaggatc acatctacat tcaatgctac atacgtgaca gacttctcaa tgattaatgc  6120
aaatattgta catctaagtc ctctagactt gtcaaatcaa atcaattcaa taaacaaatc  6180
tcttaaaagt gctgaggatt ggattgcaga tagcaacttc ttcgctaatc aagccagaac  6240
agccaagaca cttattcac  taagtgcaat cgcattaata ctatcagtga ttactttggt  6300
tgttgtggga ttgctgattg cctacatcat caagctggtt tctcaaatcc atcaattcag  6360
agcactagct gctacaacaa tgttccacag ggagaatcct gccgtctttt ccaagaacaa  6420
tcatggaaac atatatggga tatcttaaga attctatcat aagtccatat atgtccatga  6480
ttgacctta  agagccaacc tccaatgatt atccgttaaa ttcagatata acaattcaaa  6540
aatcaatatt aagcctccag ataccaatga atatgaatat atctcttaga aaacttgatt  6600
attatgtgat aacatagtac aatttaagaa aaaacctaaa ataagcacga acccttaagg  6660
tgtcgtaacg tctcgtgacg ccgggttcag ttcaaacatc gaccctgac  ccaattcaat  6720
```

```
acccattttc ataaaggaac acagtataat ttaatcataa aagacctcaa aatctgatac   6780
agcttaatcc actcaacata taattataag actaataata atggaagatt acagcaatct   6840
atctcttaaa tcaattccta aaaggacatg tagaatcatt ttccgaactg ccacaattct   6900
tggcatatgc acattaattg tgctatgttc aagtattctt catgagataa ttcatcttga   6960
tgtttcctct ggtcttatga attctgatga gtcacagcaa ggcattattc agcctatcat   7020
agaatcatta aaatcattga ttgctttggc caaccagatt ctatataatg ttgcaatagt   7080
aattcctctt aaaattgaca gtatcgaaac tgtaatactc tctgctttaa agatatgca    7140 caccgggagt atgtccaatg ccaactgcac gccaggaaat ctgcttctgc atgatgcagc   7200
atacatcaat ggaataaaca aattccttgt acttgaatca tacaatggga cgcctaaata   7260
tggacctctc ctaaatatac ccagctttat cccctcagca acatctcccc atgggtgtac   7320
tagaatacca tcattttcac tcatcaagac ccattggtgt tacactcaca atgtaatgct   7380
tggagattgt cttgatttca cggcatctaa ccagtattta tcaatgggga taatacaaca   7440
atctgctgca gggtttccaa ttttcaggac tatgaaaacc atttacctaa gtgatggaat   7500
caatcgcaaa agctgttcag tcactgctat accaggaggt tgtgtcttgt attgctatgt   7560
agctacaagg tctgaaaaag aagattatgc cacgactgat ctagctgaac tgagacttgc   7620
tttctattat tataatgata cctttattga aagagtcata tctcttccaa atacaacagg   7680
gcagtgggcc acaatcaacc ctgcagtcgg aagcgggatc tatcatctag gctttatctt   7740
atttcctgta tatggtggtc tcataaatgg gactacttct tacaatgagc agtcctcacg   7800
ctattttatc ccaaaacatc ccaacataac ttgtgccggt aactccagca aacaggctgc   7860
aatagcacgg agttcctatg tcatccgtta tcactcaaac aggttaattc agagtgctgt   7920
tcttatttgt ccattgtctg acatgcatac agaagagtgt aatctagtta tgtttaacaa   7980
ttcccaagtc atgatgggtg cagaaggtag gctctatgtt attggtaata atttgtatta   8040
ttatcaacgc agttcctctt ggtggtctgc atcgctcttt tacaggatca atacagattt   8100
ttctaaagga attcctccga tcattgaggc tcaatgggta ccgtcctatc aagttcctcg   8160
tcctggagtc atgccatgca atgcaacaag ttttttgccct gctaattgca tcacaggggt   8220
gtacgcagat gtgtggccgc ttaatgatcc agaactcatg tcacgtaatg ctctgaaccc   8280
caactatcga tttgctggag cctttctcaa aaatgagtcc aaccgaacta atcccacatt   8340
ctacactgca tcggctaact ccctcttaaa tactaccgga ttcaacaaca ccaatcacaa   8400
agcagcatat acatcttcaa cctgctttaa aaacactgga acccaaaaaa tttattgttt   8460
aataataatt gaaatgggct catctctttt aggggagttc caaataatac cattttttaag  8520 ggaactaatg ctttaatcct attgaatgaa gactccagat tcaagaataa ttggaaggct   8580
cttttattta tgcgatagtt atacgttttg gctgtattag aatgctatag cattctgctg   8640
tttttcccat atggaaaaat ccttcaacac caacttaggt tcaattttct catcatttac   8700
tgttgtaatt caatcttact aaagttattc tgatatttaa gaaaaaataa tctttatata   8760
atgtaacaat actactaaga ttataatata ggccagaatg gcggcctctt ctgagatact   8820
ccttcctgaa gtccatttga actcaccaat agtcaaacac aaactcatat actacttatt   8880
actagggcac ttcccgcatg atcttgacat ttctgaaata agccccttc acaataatga    8940 ttgggatcag attgccagag aagaatccaa tcttgctgaa cgactcggag tagctaaatc   9000
tgaattaatt aaacgtgtgc ccgcatttag agcaaccaga tggcgtagtc atgcagccgt   9060
```

```
ccttatatgg ccttcttgta taccattcct tgttaaattc ctaccccatt ctaagcttca    9120
accaatagaa caatggtaca agttgatcaa tgcttcatgc aatactatat ctgactcaat    9180
tgatagatgt atggagaata tttctattaa gcttactggg aaaaacaatc tattctctcg    9240
atccagagga actgcaggcg caggtaaaaa cagtaaaatc accctcaatg atatccaatc    9300
tatttgggaa tcaaacaaat ggcagcctaa tgtatcttta tggcttacaa ttaaatacca    9360
aatgcgacaa cttataatgc atcaaagttc tcgtcagcca actgatttag ttcacattgt    9420
tgacacacga tctggtctaa tagttatcac ccctgaactt gttatttgct ttgatcggtt    9480
gaataatgtt ttaatgtatt ttacatttga gatgacttta atggtaagtg acatgtttga    9540
gggacggatg aatgttgccg cgctctgcac tattagtcat tacttatcac cactagggcc    9600
aaggatagat agattgtttt ctattgtaga tgaattagca caactattgg gtgacactgt    9660
atataaaatt attgcatctc ttgaatcttt agtatatggg tgtctacaac ttaaagatcc    9720
agtggttgaa ttaacaggat catttcattc ctttattacg caagagatta tagatatcct    9780
aattgggtca aaagcccttg ataaggatga atcaataact gtcactacac aattgctaga    9840
tatattttcc aacctttctc cagatttaat cgctgagatg ttgtgtctca tgagactttg    9900
gggtcatccc actcttactg ctgcgcaagc tgcaggtaaa gtgagagaat ctatgtgtgc    9960
aggtaagtta cttgatttcc ctacaataat gaaaactctt gcttttttcc acacaatttt    10020
aatcaatggt tatcgtagaa agaagaatgg aatgtggcct ccacttatac ttcctaaaaa    10080
tgcatcaaaa agcttaatag agtttcaaca tgataatgct gaaatatctt atgagtatac    10140
actcaagcat tggaaagaaa tctctctcat agaatttaga aagtgctttg actttgatcc    10200
tggtgaggag ctaagcattt ttatgaaaga caaggcaata agtgctccaa aaagtgattg    10260
gatgagtgta ttccgtagaa gtctaataaa acaacgacat cagagacatc atattcctat    10320
gcccaatcca tttaacagac gtctattact caatttctta aagatgacaa gttttgatcc    10380
agttgctgag cttcaatatg ttaccagtgg tgaatatctc cgagatgaca cattttgtgc    10440
atcttactca ttaaaagaga agaaataaa accagatgga aggatatttg ctaagcttac    10500
taatagaatg cggtcttgtc aagtaattgc ggaagcaatt cttgcaaatc acgcaggtac    10560
tctaatgaag gaaaacggag ttgtcttgaa tcaattatct ctgactaaat cattgctta c   10620 tatgagtcaa attggcataa tatcagaaaa agcaaagaga tatacccgag ataacatctc    10680
atctcaaggt ttccatacaa tcaagactga ctcaaaaaat aagaagaaaa gcaaaattgc    10740
atcatcatac ctcacagatc ctgatgatac atttgaactt agtgcatgtt ttataactac    10800
tgatcttgct aaaatactgtc ttcaatggag atatcagacc ataatccatt ttgctcgaac    10860
attaaacaga atgtatggag ttccacattt atttgaatgg attcatcttc gtttgattag    10920
atctacatta tatgttggtg atccattcaa tcctcctgcc acaactgatg ccttcgatct    10980
agataaagta ttaaatggtg atatcttat agtctctccc aagggaggta ttgaaggcct    11040
atgtcagaaa atgtggacaa tgatctctat ttctgtgatc atcctttctt cagccgaatc    11100
caaaacaaga gtaatgagca tggttcaagg agataatcag gcgattgcag ttacaacaag    11160
agttcctaga tcattgccta gtgttcagaa aaaggagtta gcctacgcag caagcaagtt    11220
attctttgaa agactagggg caaataatta tggtttgggt catcaactaa aggctcaaga    11280
gactataata agttccacgt tcttcatata tagtaaacgg gtattctatc aaggacgtat    11340
actaacacag gcacttaaaa atgctagcaa gttatgtctt actgcagatg tattaggtga    11400
atgtactcag gcttcctgct caaattctgc tactacaatc atgagattaa cagaaaatgg    11460
```

```
ggttgagaaa gatacatgtt ataagcttaa tatttatcaa tctattcgtc aactcacata   11520
tgatctaata tttccccaat actccatacc aggtgaaaca ataagtgaaa ttttcttaca   11580
gcatccaaga ttaatctcac gtattgttct gctcccttca cagctaggtg gtcttaatta   11640
cctcgcatgt agcagattat ttaaccgcaa tatcggagat ccccttggta cagccgtggc   11700
agacctcaag aggttaatta aatgtggtgc tcttgaatca tggatactgt acaatttact   11760
ggcaagaaaa ccagggaaag gttcatgggc cactttagca gccgatccat actcattgaa   11820
tcaagaatat ctttatcctc ctactactat acttaaaaga catactcaaa atactttaat   11880
ggagatatgt cggaatccta tgttaaaggg agttttttaca gataatgcaa agaggagga   11940 aaatctcctt gcaaaatttc ttcttgatcg tgatatagta ttgccaagag tcgcacacat   12000
tataatagat caatccagca ttggaaggaa gaaacagata caagggtttt ttgacaccac   12060
aaggaccata atgagacgat catttgagat caaaccactc tcaactaaga agacactttc   12120
agtcatagaa tataatacta attatttatc ttataactac cctgtcatac ttaatccttt   12180
acctattcct ggatatttaa attatattac tgaccaaact tgcagtattg atatatctag   12240
aagtttaaga aaattatcat ggtcttcttt attgaatgga agaactttag aaggattaga   12300
aactccagat ccaattgaag ttgtcaatgg ttccttgatt gtaggtacag agattgtga   12360 cttttgtatg cagggtgacg ataaaattcac ttggttcttt ttacctatgg ggataattat   12420
tgatggaaat cctgaaacta atccacccat cagagttcca tacattgggt ctagaacaga   12480
ggaaagaaga gttgcatcaa tggcatatat taaaggtgcc acacacagtt tgaaggctgc   12540
tcttagaggc gcaggggtat acatttgggc attcggagat acagtagtga actggaatga   12600
tgcacttgat atcgcaaata ctagggttaa gatatcccta gagcaacttc agactcttac   12660
acctcttcct acatctgcaa acattacaca tcgtttagat gatggagcca caacacttaa   12720
attcactcca gctagttcct atgcattttc tagttatact catatatcaa atgatcaaca   12780
atatttagaa atagatcaga gagtagtcga ttccaatatt atttatcaac aattaatgat   12840
aacagggctt gggatcattg agacctacca taacccacct atcaggacct ctacacagga   12900 aatcacccctc catttgcaca ctagctcatc ttgttgtgtt agaagtgtag atggttgcct   12960
tatatgtgag agcaatggag aggttcctca gatcactgtt ccctacacta attcattgt   13020 atatgatcct gatccactag cagattatga gattgcacat ctagattatc tctcctacca   13080
agctaaaatt ggaagtacag attactactc acttactgat aaaattgatc tattggcaca   13140
tttaactgca aaacaaatga taaactcaat aattgggtta gatgaaacag tatcaattgt   13200
caatgatgcg gttattctat ctgattatac taataactgg attagtgaat gttcttatac   13260
taagatagat ttagttttta aattaatggc atggaatttc cttcttgagc ttgcattcca   13320
gatgtactac ctaagaatat catccttggac aaatatattt gactatactt acatgacttt   13380
acgcaggata cccggaactg ctctaaataa tattgcagct actattagcc acccaaaatt   13440
attaagacgt gcaatgaatc ttgatattat cactcctata catgcaccgt atttggcttc   13500
attagattat gtcaaattaa gtattgatgc aattcagtgg gggggttaaac aagttcttgc   13560 tgatttatca aatggaattg atcttgaaat cttgattctt tcagaggatt caatggaaat   13620
tagtgatagg gcaatgaatc tcattgctag aaaaactaact ctccttgcac ttgttaaagg   13680
tgagaactat acatttccaa aaattaaagg gatgccacca gaggaaaagt gtttagtctt   13740
aactgaatac ctagcaatgt gttatcagaa tactcaccac ttagatccag atcttcaaaa   13800
```

-continued

```
gtatttatat aatctaacta atccaaaatt gactgcattt cccagtaaca acttctactt    13860
aacaaggaaa atccttaatc aaattagaga atcagacgaa ggacaatata ttatcacctc    13920
atattatgaa tccttcgaac aattagaaac agatataatt cttcactcta ctttaactgc    13980
tccttatgat aattcagaaa ctctaacaaa gtttgattta tcccttgaca tctttccaca    14040
tccagaatct ctcgagaaat atcctcttcc agttgatcat gactctcaat ctgcaatttc    14100
aacactaatt ccaggccctc cctctcatca tgtattacga ccactaggag tgtcatctac    14160
agcttggtat aaaggataa gttattgcag atacctggaa acgcaaaaga tacagactgg    14220
tgatcatctt tatttagctg aaggaagcgg tgcttcaatg tcacttctag aactcctatt    14280
tccaggagat actgtctatt ataatagtct ttttagtagt ggagagaatc ctccacagag    14340
aaattatgct cctcttccaa ctcaatttgt acagagtgtt ccatataaat tgtggcaagc    14400
tgatcttgct gatgatagta acttaataaa agattttgtc ccattatgga atggaaacgg    14460
agcagttaca gacttatcga caaaggatgc agttgcattc ataatacata agtaggagc    14520 ggagaaagca tcccttgttc atatagatct cgaatcgact gctaatataa atcagcaaac    14580
tctgtccaga tcccgattcc attcgttaat tatagcaact actgttctta agaggggtgg    14640
gatattagtt tacaaaacat catggcttcc gttttctagg tttagtcaac tagcaagcct    14700
actttggtgc tttttgacc ggatccatct aatacgtagt agttattctg atcctcacag    14760
tcatgaggtt tatcttgtat gtagacttgc tgcggatttt agaactatcg gtttcagtgc    14820
agctctagta actgctacta ctcttcacaa tgacggattc acaacaatac atcctgatgt    14880
tgtttgtagt tattggcaac accatcttga gaatgttggg agagtcgaaa agtaattga    14940 tgagatactc gatggtttag ccaccaactt cttcgcagga gataatgggc ttattctaag    15000
atgtggagga actcccagct ctagaaaatg gttagagatt gatcagttag catcatttga    15060
ttcagttcaa gatgctctag tgacacttat caccatacac ctaaaggaaa ttatagaagt    15120
gcagtcatca catacagagg attatacatc tctccttttc acacttata atattggtgc    15180 agcagggaaa gtaagaacta tcatcaaatt aattctagaa cgatctttaa tgtatacagt    15240
ccgaaattgg ttagttttac ccagttccat ccgggattcc gtacgacaag atctagagtt    15300
agggtcattt agattaatgt ctattttaag tgaacagaca tttcttaaaa agacacccac    15360
caaaaaatac ttacttgatc agcttacaag gacatatata tcaaccttct ttaattctca    15420
ctcagtcctc cccctccacc gtccatatca aaaacaaata tggaaagcct taggtagtgt    15480
aatatattgt tcggagacgg ttgatatacc tctaattaga gacattcaga tagaagatat    15540
taatgatttt gaagatatcg agaggggtat cgatggcgaa gaattatgac aacagtgatt    15600
ataagaactc atgatagttt tatttaagaa aaacatattg attttcccct tggt          15654
```

<210> SEQ ID NO 59
<211> LENGTH: 15654
<212> TYPE: DNA
<213> ORGANISM: Human parainfluenza virus 2

<400> SEQUENCE: 59

```
accaagggga gaattagatg gcatcgttat atgacgaatt gcaaaaagat tacgtaggtc     60
cggaaccact agattccggt gccggtaacg attccatttt tatactatct gatcattctc    120
tatctctact aaggatattt ctagtctaaa gttcaaaatg tcaagtgtct taaagacatt    180
tgaaaggttt actatacaac aagagcttca ggagcaatct gatgacactc cagtaccttct   240 tgagacaatc aaacctacaa taagggtatt tgtcatcaat aataatgatc ctgccataag    300
```

```
gtctagactt ttattcttta atctacgaat tattatgagt aacaccgcaa gagagggaca    360
tagagctggt gctctcctca gtctcttatc actaccttct gcagctatga gtaatcacat    420
caaactagcc atgcattcac cagaagccag catagataga gtagagataa cagggtttga    480
gaataattca ttccgagtta ttccagatgc tcgatcaact atgtccagag gagaggtgct    540
ggcctttgaa gcattagctg aagacattcc tgatacccct aatcaccaaa ctccatttgt    600
aaataatgat gtagaagatg acatgtttga tgaaacagag aaattcttag atgtttgcta    660
cagtgtactt atgcaggcat ggatagtaac atgcaagtgt atgactgctc ctgatcagcc    720
gccagtatca gtagcaaagc ggatggctaa atatcaacaa caagggagaa tcaatgctag    780
gtatgtacta cagcctgaag cacaaagact aattcagaat gccatccgca agtcaatggt    840
agtgaggcat ttcatgactt atgagcttca actttcacaa tcaagatctt tgctagcaaa    900
ccgctactat gctatggtgg gagacattgg caagtacatt gaacacagcg aatgggagg     960
tttttttctta acacttaaat atggacttgg aacaagatgg cctacattgg ctcttgcagc   1020
attctctggg gaactccaga aattaaaagc tctcatgcta cattatcaga gcctaggacc   1080
catggccaag tacatggctc tattagaatc accaaagctg atggattttg tcccatctga   1140
atatccatta gtttatagtt atgcaatggg tattggaact gtccttgata caaatatgag   1200
aaactatgca tatggtagat catatttaaa tccgcaatat tttcagctag gagtagaaac   1260
agcaaggaaa cagcagggag ctgttgacaa caggacagca gaggacctcg gcatgactgc   1320
tgcagacaaa gcagacctca ctgcaaccat atcaaagcta tctttgtccc aattacctag   1380
gggtagacaa ccaatatctg acccatttgc tggagcaaat gacagagaaa taggaggcca   1440
agcaaatgat acacctgtat acaacttcaa tccaatcaat actcggaggt atgcaacta    1500
tgacagtgat ggtgaggaca gaattgacaa cgatcaagat caagctatca gagagaacag   1560
aggagagcct ggacaactaa acaaccagac aagtgacaac cagcagagac tcaatctctc   1620
cataccgcaa agaacatcag gtatgagcag tgaagagttc caacattcaa tgaatcagta   1680
catccgtgcc atgcatgagc aatacagagg accccaggat gatgatacca atgatgccgc   1740
agatgggaat gacatttctc ttgagctagt tggggatttt gattcctaat tctcaatgtc   1800
atacaaccag atatacacat ccacatcact taaagataca gctgccaccc acacactcat   1860
ccagacaaat caaccagacc tcacatcatt cagaaacaat tctctcataa tttaagaaaa   1920
aaacataggc ccggacgggt ttaaaatctg gtgctcgttc gtggtctgac aacctccaaa   1980
ccagaatcac acaattatgg ccgaggaacc aacatacacc actgagcaag ttgatgaact   2040
aatccatgct ggactgggaa cagtagattt cttcctatct agacccatag atgctcaatc   2100
ttccctaggc aagggcagca tcccaccagg tgtcacagct gttctaacta gtgcagcaga   2160
ggcaaaatcc aaaccagttg ccgctggtcc agtgaaaccc aggcggaaga aagtgatcag   2220
caatgctacc ccatacactg ttgcagacaa tactccacct gagaagctac caatcaacac   2280
cccaataccc aatccattac ttccactggc acgcccccaa ggaaagatga cagacattga   2340
cattgtcact gggaccatta cagaaggatc gtacaaaggt gtggagcttg ctaaattagg   2400
gaagcaaaca ctactcacaa ggttcacctc gaacgagcca gtctcctcag ctggatccgc   2460
ccaagacccc aactttaaga ggggggagc taatagagaa agagcaagag gcaaccatag   2520
gagagaatgg agtattgcat gggtcggaga tcaggtcaaa gtcttcgagt ggtgtaatcc   2580
caggtgtgcc ccagtcacgg cctcagctcg caagttcacc tgcacatgcg gatcctgccc   2640
```

```
cagcatctgc ggagaatgtg aaggagatca ttgagctctt aaaggggctt gatcttcgcc   2700
ttcagactgt agaagggaag gtagataaaa ttcttgcaac ttccgcaact ataatcaatc   2760
ttaaaaatga aatgactagt ctcaaggcga gcgttgcaac tgtggaaggt atgataacaa   2820
caattaaaat catggatccc agcacaccaa ccaatgtccc tgtagaggag atcagaaaga   2880
gcttacacaa tgctccagta gtaattgccg gtccaactag tggaggcttc acagccgaag   2940
gcagtgatat gatttcaatg gatgaactag ctagacctac actctcatca acaaaaaaga   3000
tcacacgaaa gcctgaatcc aagaaagact taacaggcac aaaactaacc ttgatgcagc   3060
ttgcaaatga ctgcatctcg cgtccagata ccaagactga gttcgtgact aagattcaag   3120
cagcaaccac agaatcacag cttaatgaaa tcaagcggtc aataatacgc tctgcaatat   3180
aaaatgaggt gcaatcacac aagagacact caacatgcat ccaatcaaga tccaaattct   3240
gtccatccga aaacacaccc acaattgtta acaccaagaa acaaccacag ccgaaccatg   3300
cttaatcaaa agatccaaac aacatctcac atcgacagaa ggctggacat gataaattta   3360 ataaaaaga aaaaaaagtc aagtaaaatt taaaggacac aatagagaaa atctaggtcc   3420
gaaagcttgc ttcccggaca gatctcaaaa tcatagtcta aacctcaaac acagcagcag   3480
acatgcccat aatatcatta ccagcagatc caacttcacc cagtcaatcc cttactccgt   3540
ttccaataca acttgacacc aaagatggca aggcagggaa actccttaaa cagattcgaa   3600
ttaggtatct aaatgagcct aattctcgcc atacaccaat aactttcatc aatacgtatg   3660
gatttgttta tgctcgagac acttcagggg gcattcacag tgagcttagt agtgacctag   3720
ctgcagggtc tataacagca tgcatgatga cgctaggccc tggtccaaat attcagaatg   3780
caaatctagt gctaagatct ctgaatgaat tctacgtgaa agtcaagaag acatcaagcc   3840
agagagagga agcagtgttt gaattagtta acattccaac tttattgaga gaacatgctc   3900
tttgcaaacg caaaatgtta gtttgctctg cagaaaagtt cctcaagaac ccgtcaaagc   3960
tacaagctgg atttgagtat gtatacatac caacttttgt ctccattaca tactcaccac   4020
gaaatctgaa ttaccaagtt gccagaccta tccttaagtt cagatcacgt tttgtgtata   4080
gcattcattt ggaattaatt ctgagattgc tatgcaaatc tgaatccccc ttaatgaaat   4140
cctacaatgc agacaaaaca ggtcggggat gccttgcatc agtctggatc catgtatgta   4200
acattctgaa aaacaaaagc atcaagcaac aaggcagaga atcatatttc atagccaagt   4260
gcatgagcat gcagctgcag gtgtccattg cagatctttg gggaccaaca atcataatca   4320
aatcattggg tcacatcccc aagactgcac ttccttttt cagcaaagat gggattgcct   4380
gtcatccatt acaagatgtt ccccccactc tgacaaaatc actgtggtca gttggatgtg   4440
agatagaatc tgccaagttg atacttcaag aatctgatct taatgagcta atgggccacc   4500
aggaccttat cactgataag attgccatca gatcaggtca acggacattt gagaggtcca   4560
aattcagccc atttaaaaaa tatgcatcaa ttccaaactt ggaagccatc aactgaatgc   4620
tccagcatct gagaatagaa ccacaattaa atcatactat tagtaactat acaataataa   4680
acaattttag tcaacagatt accaagatgt tatcataggt ccgaactgat caatctaaca   4740
aaaaaactaa acgttccata ataaatcaac gttcaggtca aaatactcaa ccatgcatca   4800
cctacatcca atgatagtat gcatctttgt tatgtacact ggaattgtag gttcaggtgc   4860
cattgccgga gaccaactac ttaatatagg ggtcattcaa tcaaagataa gatcactcat   4920
gtactatact gatggtggtg ctagctttat tgttgttaaa ttgctaccta atcttccccc   4980
aagcaatgga acatgcaaca ttaccagtct agatgcatac aatgttaccc tatttaaatt   5040
```

```
actgacaccc ctgattgaga acctgagcaa aatctccgct gttacagata ccaaaacccg    5100
ccaagaacga tttgcaggag tcgttgttgg acttgctgca ttaggagtag ccacagctgc    5160
acaaataacc gcagctgtag caatagttaa agctaatgca aatgctgccg cgattaataa    5220
tcttgcatct tcaattcaat caacaaacaa ggcagtatcc gatgtgatag atgcatcaaa    5280
aacaattgca actgcagttc aagcaatcca ggatcatatc aatggagcta ttgttaatgg    5340
gataacatct gcatcatgcc gtgcccatga tgcactcatt gggtcaatat taaatcttta    5400
tctcactgag cttaccacaa tatttcacaa tcaaataaca aaccctgcgc tgacaccgct    5460
ctccatccaa gctttaagaa ttctcctcgg tagcaccttg ccaattgtca ttgagtccaa    5520
actcaacaca aacctcaaca cagcagagct gctcagctcc ggactgttaa ctggtcaaat    5580
aatttcaatt tccccaatgt acatgcaaat gctaattcaa atcaatgttc cgacatttat    5640
aatgcaaccc ggtgcgaagg taattgatct aattgctatc tctgcaaacc ataaattgca    5700
agaagtagtt gtacaagttc cgaataggat tctagagtat gcaaatgaac tacaaaatta    5760
tccagccaat gactgtgttg tgacaccgaa ctctgtattc tgtagataca atgagggttc    5820
ccctatccct gaatcacaat accaatgctt gaggggaat cttaattctt gcactttac    5880 ccctattatc gggaactttc ttaagcgatt tgcatttgcc aatggtgtgc tctatgccaa    5940
ctgcaaatct ttgctatgta agtgtgccga ccctccccat gtggtgtccc aagatgatac    6000
ccaaggcatc agcataattg atattaagag atgctctgag atgatgcttg acactttctc    6060
atttaggatc acatctacgt tcaatgctac atacgtgaca gacttctcaa tgattaatgc    6120
aaatattgta catctaagtc ctctagattt gtcaaaccaa atcaattcaa taaacaaatc    6180
tcttaaaagt gctgaggatt ggattgcaga tagcaacttc tttgctaatc aagccaggac    6240
agccaagaca ctttattcat taagtgcaat agcattaata ctatcagtga ttaccttggt    6300
tgttgtggga ttgctgattg cctacatcat caaactagtt tcccaaatcc atcaattcag    6360
agcgctagct gctacaacaa tgttccacag ggaaaatcct gccttctttt ccaagaacaa    6420
tcatggaaac atatatggga tatcttaaga aatctatcac aagtccatat atgtccacaa    6480
ttgattctta agaaccaact tccaatgatt atcctttaaa cttaagtata atagtttaaa    6540
aattaacatt aagcctccag ataccaatga atatgaatat atctctaaga aaacctgatt    6600
attatgtgat agtgtagtac aatttaagaa aaaacctaaa ataagcacga acccttaagg    6660
tgtcgtaacg tctcgtgaca ctgggttcag ttcaaaaatc gacttctaat ctaatttaac    6720
acccattctt atataagaac acagtataac ttaattacaa aagacctcaa aaactgacac    6780
agcttaatcc actcaacata taattgtaag attaataata atggaagatt acagcaatct    6840
atctcttaaa tcaattccta aaaggacatg tagaatcatt ttccgaactg ccacaattct    6900
tggaatatgc acattgattg ttctatgttc aagtattctt catgaaataa ttcatcttga    6960
tgcttcctct ggtctcatga attctgatga ttcacagcaa ggcattattc agcctattgt    7020
agaatcatta aaatcattga ttgctttggc taaccagatt ctgtacaatg ttgcaataat    7080
aattcctctt aaaattgaca gtattgagac cgtaatactc tctgcttyaa aggayatgca    7140
tactgggagc atgtccaaca ccaactgtac acccggaaat ctgcttctgc atgatgcagc    7200
atacatcaat ggaataaaca aattccttgt acttaaatca tacaatggta cgcctaaata    7260
tggacctctc ctaaatattc ctagctttat cccctcagca acatctcccc acgggtgcac    7320
tagaatacca tcatttttcac tcagtaagac tcattggtgt tacactcaca atgtaatact    7380
```

```
tggagattgc ctcgatttca cgacatctaa tcagtattta gcaatgggga taatacaaca    7440
atctgctgca gcatttccaa tcttcaggac tatgaaaacc atttacctaa gtgatggaat    7500
caatcgcaaa agctgttcag tcactgccat accaggaggt tgtgtcttgt actgctatgt    7560
agctacaaga tctgagaaag aagattatgc cacaactgat ctagctgaac tgagacttgc    7620
tttctattat tataatgata cctttgttga aagagtcata tctcttccaa atacaacagg    7680
gcaatgggcc acaatcaatc ctgcagttgg aagcgggatc tatcatctag gctttatttt    7740
atttcctgta tatggtggtc tcataaatgg gactccttcc tacaacgagc agtcctcacg    7800
ctattttatc ccaacacatc ccaacataac ctgtgccgga aactccagtg aacgggctgc    7860
agcagcacgg ggttcctatg tcatccgtta tcattcaaac aggttgattc agagtgctat    7920
tcttatttgc ccattatctg acatgcaaac agcaaggtgt gatctagtta tgtttaacaa    7980
ttctcaagtc atgatgggtg cagaaggtag gctctatgtt attgacaaca atttgtatta    8040
ttatcaacgt agttcctctt ggtggtctgc atcgcttttc tacaggatca atacagattt    8100
ctctaaagga attcctccta tcattgaggc tcaatgggta ccgtcctatc aagttccccg    8160
ccctggagtc atgccatgta atgcaacaag tttttgccct gctaattgca tcacaggagt    8220
gtatgcagat gtgtggccgc ttaacgatcc agaactcaca tcacaaaatg ctctgaatcc    8280
caactatcga tttgctggag cctttctaaa aaatgagtcc aaccgaacca atcccacatt    8340
ttacactgca tcagccaact ccctactaaa tactaccgga ttcaacaaca ccaatcacaa    8400
agcagcatat acgtcttcaa cctgctttaa gaatactgga actcagaaga tttattgttt    8460
gataataatc gaaatgggct catctctttt aggggagttc caaataatac catttctaag    8520
ggaactaata ccttaatact attgaatgaa aacttaagat tcaataataa ttgaaaggct    8580
ctctatctta tgtaatagtt atacgttttg gctgtattag aatgttatag cattctgctg    8640
tgtttcccat atgaagcaag ccttcaacac cgacttaggt tcaattttct catcatttac    8700
tgttgtaatc caatcttact aaagttattc tgatatttaa gaaaaaataa cctttatata    8760
atataacaat actattaaga ttatgatata ggccagaatg gcggcctctt ctgagatact    8820
ccttcctgaa gtccacttga actcaccaat agtcaaacac aaactcatat actacttatt    8880
actagggcac ttcccgcatg atcttgacat ttctgaaata agccctcttc acaataatga    8940
ttgggatcaa attgccagag aagaatccaa tcttgctgaa cgacttggag tagctaaatc    9000
tgaattaatt aaacgtgtgc ccgcatttag agcaactaga tggcgtagtc atgcagctgt    9060
ccttatatgg ccttcttgta taccatttct tgttaaattc ctacctcatt ctaagcttca    9120
accaatagaa caatggtaca agttgatcaa tgcttcatgt aatactatat ctgactcaat    9180
tgatagatgt atggagaata tttctattaa gcttactggg aaaaacaatc tattctctcg    9240
atccagagga actgcaggtg caggtaaaaa cagtaaaatc accctcaatg atatccaatc    9300
tatttgggaa tcaaacaagt ggcagcctaa tgtatcttta tggcttacaa ttaaatatca    9360
aatgcgacaa cttataatgc atcaaagttc tcgtcagccg actgatttag ttcacattgt    9420
tgacacacga tctggtctaa tagttatcac ccctgaactt gttatttgtt ttgatcggtt    9480
gaatagtgtt ttaatgtatt ttacatttga gatgactttta atggtaagcg acatgttcga    9540
ggggaggatg aatgtcactg ctctctgcac tattagtcat tacttatctc cactagggcc    9600
aaggatcgat agattgtttt ccattgtaga tgaattagca caactattag gtgacactgt    9660
atataaagtt attgcatctc ttgaatcttt agtatatggg tgtctacaac ttaaagatcc    9720
agtagtggaa ttagcagggt catttcattc ctttattaca caagagatta tagatatcct    9780
```

```
aattggttca aaagcccttg ataaggatga atcaataact gttactacac aattgttaga    9840
tatattttcc aacctttctc cagatttaat tgctgagatg ttgtgtctca tgagactttg    9900
gggtcatcct actcttactg ctgcgcaagc tgcaggtaaa gtgagagaat ctatgtgtgc    9960
aggtaagttg cttgatttcc ctacaataat gaaaactctt gctttttttcc acacaatttt   10020 aattaatggt taccgtagaa agaaaaatgg aatgtggcct ccacttatac ttcctaaaaa   10080
tgcatcaaaa agcttaatag aatttcaaca tgataatgct gaaatatctt acgaatatac   10140
actcaagcat tggaaagaga tctctctcat agaatttaga aagtgctttg actttgatcc   10200
tggtgaggag ctaagcattt ttatgaagga caaggcaata agtgctccaa aaagtgattg   10260
gatgagtgta tttcgtagaa gtctaataaa acaacgacat cagagacatc atattcctat   10320
gcccaatcca tttaatagac gtctattact caatttctta gaagatgaca gttttgaccc   10380
agttgctgag ctccaatatg ttaccagtgg tgaatacctc caagatgaca cattttgtgc   10440
atcttactca ttaaaagaga aagaaataaa accagatgga aggatattcg ctaagcttac   10500
taatagaatg cggtcctgtc aagtaattgc ggaagcaatt cttgcaaatc atgcaggtac   10560
tctaatgaag gaaaacggag ttgtcttgaa tcaattatca ctgaccaagt cattgcttac   10620
tatgagtcaa attggcataa atcagaaaaa ggcaaagaga tatacgcgag ataacatctc   10680
atctcaaggt ttccatacaa tcaagactga ctctaaaaat aagaggaaaa gcaaaactgc   10740
atcatcatac ctcacagatc ctgatgatac atttgaactt agtgcatgtt ttataactac   10800
tgatcttgct aaatactgtc ttcaatggag atatcagacc ataatccatt ttgctcgaac   10860
attaaacaga atgtatggag ttccacattt atttgaatgg attcatcttc gtttaattag   10920
gtctacatta tatgttggtg atccattcaa tcccctgct cgactgatg ctttcgatct    10980 agataaagta ttaatggtg atatcttttat agtctctccc aaaggaggta ttgaaggcct   11040
atgtcagaaa atgtggacaa tgatctctat ttctgtgatc atcctctcct cagccgaatc   11100
caaaacaaga gtaatgagca tggttcaagg agataatcag gcaattgcag ttacaacaag   11160
agttcctaga tcattaccta gtattcagaa aaaggagtta gcctatgcag caagcaagtt   11220
attttttgaa agacttaggg caaataatta tgggttgggt catcagctaa aggctcaaga   11280
aactataata agttccacat tcttcatata tagtaaacgg gtattttatc aaggacgtat   11340
actaacacag gcactcaaaa acgctagcaa gctatgtctt actgcggatg tattaggtga   11400
atgtactcaa gcttcctgtt caaattctgc tactaccatc atgagattaa cagaaaatgg   11460
ggttgagaaa gatacatgtt ataagcttaa tatttatcag tccattcgtc aactcacata   11520
tgatctaata tttccccaat attccatacc aggtgaaacg ataagtggga ttttcctgca   11580
gcatccaaga ctaatctcac gtattgttct gctcccttca cagctaggtg gtcttaatta   11640
cctcgcatgc agcagattat ttaaccgcaa tatcggagat cctcttggta cagctgtggc   11700
ggacctcaag aggttaatta atgtggtgc tcttgaatca tggatactgt acaatttact   11760
agcaagaaaa ccagggaaag gttcatgggc aactttagca gccgatccgt actcattgaa   11820
tcaagaatat ctttatcctc ctactactat acttaaaaga catactcaac atactttaat   11880
ggagatatgt aggaatccta tgttaaaggg agttttcaca gataatgcaa aagaggagga   11940
aaatctcctt gcaaaatttc ttcttgatcg tgatatagta ttgccaagag ttgcgcacat   12000
tataatagat caatctagca tcggaaggaa gaaacagata caaggatttt ttgacaccac   12060
aaggaccatt atgagacgat catttgaaat caaaccactc tcaactaaga agactctttc   12120
```

```
agttatagaa tataatacaa attacttatc ttataactac cctgtcatac ttaatccttt   12180
acctattccc ggatatttaa attatattac tgaccaaact tgcagtattg atatatctag   12240
aagtttaaga aaattatcat ggtcttcttt attgaatgga agaactttag aaggattaga   12300
aactccagat ccaattgaag ttgtcaatgg ttccttgatt gtaggtacag agattgtga    12360
tttttgtatg cagggtgatg acaaatttac ttggttcttt ttacctatgg ggataattat   12420
tgatggaaat cctgaaacta atccacccat cagagttcca tacattgggt ctagaacaga   12480
ggaaagaaga gttgcatcaa tggcatatat taaaggtgcc acacacagtt tgaaggctgc   12540
tcttaggggt gcaggggtat atatttgggc attcggggat actatagtga actggaatga   12600
tgcacttgat attgcaaata ctagagttaa gatatcccta gagcaacttc agactctcac   12660
acctcttcct acatctgcaa acattacaca ccgtttagat gatggagcca caacacttaa   12720
attcactcca gctagttcct atgcattttc tagttatact catatatcaa atgatcaaca   12780
atatttagaa atagatcaga gagtagttga ttccaatatt atttatcaac aattaatgat   12840
aacaggactt gggattattg agacctacca taacccacct ataagaactt ctacacaaga   12900
aatcactctc catttgcaca ctagctcatc ttgttgtgtt agaagtgtag atggctgcct   12960
tatatgtgaa agcaatggag aggttcccca gatcactgtt ccctatacta atacatttgt   13020
atatgatcct gacccactag cagattatga gattgcacat ctagattacc tctcctacca   13080
agctaaaatt ggaagtacag attactactc actcactgat aaaattgacc tattagcaca   13140
tttaactgca aaacaaatga taaactcaat aattgggtta gatgaaacag tatcgattgt   13200
caatgatgcg gttatcctat ctgactatac taataactgg attagtgaat gttcttatac   13260
taaaatagat ctagttttta aattaatggc atggaatttt cttcttgagc ttgcattcca   13320
gatgtactac ttaaggatat catcttggac aaatatattt gactatactt acatgacttt   13380
acgcagaata cccggaactg ctctaaataa tattgcagct actattagcc atccaaaatt   13440
actgagacgt gcaatgaatc ttgatattat cactcctata catgcaccgt atctagcttc   13500
attagattat gtcaaattaa gtattgatgc aattcagtgg ggagttaaac aagttcttgc   13560
tgatttatca aatggaattg atcttgaaat cttgattctt tcagaggatt caatggaaat   13620
tagtgatagg gcaatgaatc tcattgctag aaaactaact ctccttgcac ttgttaaagg   13680
tgagaactac acttttccaa aaattaaagg gatgccacca gaagaaaagt gtttagtctt   13740
aactgaatat ctagcaatgt gttatcaaaa tactccaccac ttagatccag atcttcaaaa   13800
gtatttatat aatctaacta atccaaaatt gaccgcattt cccagtaaca acttctactt   13860
aactaggaaa atcctcaatc aaattagaga atcagacgaa ggacaatata ttatcacctc   13920
atattatgaa tccttcgaac aattagaaac agatataatt cttcattcta ctttaactgc   13980
tccttatgat aattcagaaa ctctaacaaa gtttgattta tcccttgaca tctttccaca   14040
tccagaatct ctcgagaaat atcctcttcc agttgatcat gactctcaat ctgcaatttc   14100
aacactaatt ccaggccctc cttctcatca tgtattacga ccactgggag tgtcctctac   14160
agcttggtat aaaggataa gttattgtag gtatctagaa acacaaaaga tacagactgg   14220
tgatcatctt tatttagctg aaggaagcgg cgcttcaatg tcactcctag aactcctatt   14280
tccaggagat actgtctatt ataatagtct ttttagtagt ggagagaatc ctccacagag   14340
aaactacgcc cctcttccaa ctcaatttgt acagagtgtt ccatataaat tgtggcaagc   14400
tgatcttgct gatgatagca acttgataaa agatttgtc ccattatgga atggaaatgg   14460
tgcagttaca gacttatcaa caaaggatgc agttgcattc ataatacata agtaggagc    14520
```

-continued

```
agaaaaagca tctcttgtcc atatagatct cgaatcgact gctaatataa atcagcaaac    14580
tctgtccaga tcccagattc attcattaat tatagcaact actgttctta agagggtgg    14640 gatattaatt tataagacat catggcttcc tttttctaga tttagtcaac tagcaagcct    14700
tctttggtgc ttttttgacc ggatccatct aatacgtagt agctattctg atcctcacag    14760
tcatgaggtt tatcttgtat gtagacttgc cgcagatttt agaactatcg gtttcagtgc    14820
agctctagta actgctacta ctcttcacaa tgacggattc acaacaatac atcctgatgt    14880
tgtttgtagt tattggcaac accatcttga aaatgttggg agagtcggaa aagtaattga    14940
tgagatactt gatggtttag ccaccaactt ctttgcagga gataatggac ttattctaag    15000
atgtggagga actcccagct ccagaaaatg gttggagatt gaccagttag catcatttga    15060
tttggttcaa gatgctctgg tgacacttat cactatacac ctaaaggaaa ttatagaagt    15120
gcaatcatca catacagaag attatacatc tctcctcttc acaccttata atattggtgc    15180
agcagggaaa gttagaacta tcatcaaatt aattctagaa cgatctttaa tgtatacagt    15240
ccgaaattgg ttagtgttac ccagttccat ccgggattct gtacgacaag atttggaatt    15300
agggtcattt agattaatgt ctattttaag tgaacagaca tttcttaaaa agacacccac    15360
aaaaaaatac ttacttgatc agcttacaag gacatatata tcaaccttct ttaactctca    15420
ctcagtcctt cctcttcacc gtccatatca aaaacaaata tggaaagcct aggtagtgt    15480 aatatattgt tcggagacag ttgatatacc tctaattaaa gacattcaga tagaagatat    15540
taatgatttt gaggatatcg agaggggtat cgatggcgaa gaattatgac aacaatgatt    15600
ataagaactc atgatagttt tatttaagaa aaacatattg attttccccct tggt           15654
```

<210> SEQ ID NO 60
<211> LENGTH: 15654
<212> TYPE: DNA
<213> ORGANISM: Human parainfluenza virus 2

<400> SEQUENCE: 60

```
accaaggga gaatcagatg gcatcgttat atgacgaatt gcaaaaagat tacgtaggtc      60
cggaaccact agattccggt gccggtaacg attccagttt tatactatct gatcattctc     120
tatctctatt aaggatattt ctagtctaaa gttcaaaatg tcaagtgttt taaagacatt     180
tgaaagattt actatacaac aggagcttca ggagcaatct gatgacactc cagtacctct     240
tgagacaatc aaacctacaa tcagggtatt tgtcatcaat aataatgatc ctgtcgtaag     300
atctagactt ttattcttta atctacgaat cattatgagt aacactgcaa gagagggaca     360
tagagctggt gctctcctca gtcttttatc actaccttct gcagctatga gtaatcacat     420
caaattagcc atgcattcac cagaagccag catagataga gtagagataa cagggtttga     480
gaataattca ttccgagtca ttccagatgc tcgatcaact atgtccagag gagaggtgct     540 ggctttgaa gcattagctg aggacattcc tgatacccct aatcaccaaa ctccatttgt      600
aaataatgat gtagaagatg acatatttga tgaaacagag aaattcttag atgtttgcta     660
cagtgtgctt atgcaggcat ggatagtaac atgcaagtgt atgactgctc ctgatcaacc     720
accagtatca gtagcaaagc ggatggctaa atatcaacaa caaggagaa tcaatgctag     780 gtatgtacta caacctgaag cacaaagact aattcagaat gccatccgca agtcaatggt     840
agtaaggcat ttcatgactt atgagcttca actttcacaa tcaagatctt tgctagcaaa     900
ccgctactat gctatggtgg gagacattgg caagtacatt gaacacagcg gaatgggagg     960
```

```
atttttctta acacttaaat atggacttgg aacaagatgg cctacattgg ctccttgcagc    1020 attttctggg gaactccaga aattaaaagc tctcatgcta cattatcaga gtctaggacc    1080
catggccaag tacatggctc tattagaatc accaaaactg atggattttg tcccatctga    1140
atatccatta gtttatagct atgcaatggg tattggaact gtccttgata caaatatgag    1200
aaattatgca tacggtagat catatttaaa tccgcaatat tttcagctag agtagaaaac    1260
agcaaggaaa cagcagggag ctgttgacaa caggacagca gaggacctcg gcatgactgc    1320
tgcagacaaa gcagacctca ctgcaaccat atcaaagcta tccttgtccc aattacctag    1380
gggtagacaa ccaatatctg acccatttgc tggagcaaat gacagagaaa tgggaggaca    1440
agcaaatgat acacctgtgt ataacttcaa tccaatcaat actcggaggt atgacaacta    1500
tgacagtgat ggtgaggaca gaattgacaa cgatcaagaa caagctatca gagagaatag    1560
aggagagcct ggacaaccaa acaaccagac aagtgacaac cagcagagat caacccccc     1620 cataccgcaa agaacatcag gtatgagcag tgaagagttc caacattcaa tgaatcagta    1680
catccgtgct atgcatgagc aatacagagg ctcccaggat gatgatgcca atgatgccac    1740
agatgggaat gacatttctc ttgagctagt tggagatttt gattcctaac tctcaatgtc    1800
atacaaccag atatacacat ccacatcact cagagataca gctgccactc acacactcat    1860
ccagacaaat caaactagac tcacatcatt cggaaacaat tctctcataa tttaagaaaa    1920
aatcataggc ccggacgggt tagaaatccg gtgcttgttc gtgatcagat aacctccaca    1980
ccagaatcat acaatcatgg ccgaggaacc aacatacacc actgagcaag ttgatgaatt    2040
aatccatgct ggactgggaa cagtagattt cttcctatct agacccatag atgctcagtc    2100
ttctttaggc aaaggcagca tcccaccagg tgtcacagct gttctaacta gtgcagcgga    2160
ggcaaaatcc aaaccagttg ctgctggtcc agttaaaccc aggcggaaga aagtgatcag    2220
caatactact ccatacacta ttgcagacaa tattccacct gagaagctac cgatcaacac    2280 tccaatacc  aatccattac ttccactggc acgccctcac ggaaagatga cagacattga    2340
cattgtcact gggaacatta cagaaggatc gtacaaaggt gtggagcttg ctaaattagg    2400
gaagcagaca ctactcacaa ggttcacctc gaatgagcca gtctcctcag ctggatccgc    2460
ccaagacccc aactttaaga ggggggagc  taatagagaa agagcaagag gcaaccatag    2520
gagagaatgg agtattgcat gggtcggaga tcaggtcaaa gtcttcgagt ggtgtaatcc    2580
caggtgtgcc ccagtcacgg cctcagctcg caagttcacc tgcacatgcg gatcctgccc    2640
cagcatctgc ggagaatgtg aaggagatca ttgagctctt aaagggactt gatcttcgcc    2700
ttcagactgt agaagggaaa gtagataaaa ttcttgcaac ttctgcaact ataatcaatc    2760
ttaaaaatga aatgactagt ctcaaggcga gtgttgcaac tgtggaaggt atgataacaa    2820
caattaaaat catggatccc agtacaccaa ctaatgtccc tgtagaggag atcagaaaga    2880
gtttacacaa tgttccagta gtaattgccg gtccaactag tggaggcttc acagccgaag    2940
gcagtgatat gatttcaatg gatgaactag ctagacctac actctcatca acaaaaagga    3000
tcacacgaaa gcctgaatcc aagaaagatt aacaggcat  aaaactaact ttgatgcagc    3060
ttgcaaatga ctgcatctcg cgtccagata ccaagactga gttcgtgact aagattcagg    3120
cagcaaccac agaatcacag cttaacgaaa ttaaacggtc aataatacgc tctgcaatat    3180
aaaatgaggt gcagtcacac aagagacact caacatgcat ccaatcaaga tccagactcc    3240
atccatccaa aaacacgccc acaattgtca acaccaagaa acaaccacag ccgaaccatg    3300
ctcaaccaaa agacccaaac aacacctcac atcaatagaa ggctggacat gataaattta    3360
```

```
ataaaaaaag aaaagaagtt aagtaaaatt taaaggacac aatagagaaa atctaggtcc    3420
gaaagcttgc ctctcagaca gatcccaaaa tcatagtcca aaccccaaac acagcagcag    3480
acatgcctat aatatcatta ccagcagatc caacttcacc cagtcaatcc cttactccgt    3540
ttccaataca acttgacacc aaagatggca aggcagggaa actccttaaa cagattcgaa    3600
ttaggtatct aaatgagcct aattctcgcc atacaccaat aactttcatc aatacgtatg    3660
gatttgttta tgctcgagac acttcagggg gcattcacag tgagatcagc agtgacctag    3720
ctgcagggtc cataacagca tgcatgatga cgctaggtcc tggtccaaat attcagaatg    3780
caaatctagt gctaagatct ctgaatgaat tctacgtaaa agtcaagaag acatcaagcc    3840
agagagagga agcagtgttt gaattagtta acattccaac tttattgaga gaacatgctc    3900
tttgcaaacg caaaatgtta gtatgctctg cagaaaaatt cctcaagaac ccgtcaaagc    3960
tacaagctgg atttgagtat gtatacatac caacttttgt ctccattaca tactcaccac    4020
gaaatctgaa ttaccaagtt gccagaccta tccttaagtt cagatcacgc tttgtgtata    4080
gcattcattt ggaattaatc ctgagattgc tatgcaaatc tgactccccc ttgatgaaat    4140
cctacaatgc agacagaaca ggtcggggat gcctcgcatc agtctggatc cttgtatgta    4200
acattctgaa aaacaaaagc atcaagcaac aaggcagaga atcatatttc atagctaagt    4260
gcatgagcat gcagctgcag gtgtccattg cagatctttg ggaccaaca atcataatca    4320 aatcattggg tcacatcccc aagactgcac ttcctttttt cagcaaagat gggattgcct    4380
gtcatccatt acaagatgtt tcccctaatc tgacaaaatc actgtggtca gttggatgtg    4440
agatagaatc tgccaagttg atacttcaag aatctgatct taatgagcta atgggccacc    4500
aggaccttat cactgataag attgccatta gatcaggtca acggacattt gagaggtcca    4560
aattcagccc attcaaaaaa tatgcatcaa ttccaaactt ggaagccatc aactgaatgc    4620
tccagcatct gagaatagaa ccacaatcaa gtcatactac tagtcactat acaataatca    4680
acaattttag tcaactgatt accaagatgt tatcataggt ccgaactgat caatctaaca    4740
aaaaaactaa acgttccaca ataaatcaac gttcaggcca aaatattcag ccatgcatca    4800
cctgcatcca atgatagtat gcatctttgt tatgtacact ggaattgtag gttcagatgc    4860
cattgctgga gatcaactac ttaatatagg ggtcattcaa tcaaagataa gatcactcat    4920
gtactatact gatggtggtg ctagctttat tgttgtaaaa ttgctaccta atcttccccc    4980
aagcaatgga acatgcaaca tcaccagtct agatgcatat aatgttaccc tatttaagtt    5040
actaacaccc ctgattgaga acctgagtaa aatttccact gttacagata ccaaaacccg    5100
ccaagaacga tttgcaggag tagttgttgg acttgctgca ttaggagtag ccacagccgc    5160
acaaataact gcagctgtag caatagtgaa agctaatgca aatgctgctg cgataaacaa    5220
tcttgcatct tcaattcaat ccaccaacaa ggcagtatcc gatgtgatag atgcatcaag    5280
aacaattgca accgcagttc aagcaattca ggatcacatc aatggagcta ttgttaatgg    5340
gataacatct gcatcatgcc gtgcccatga tgcactcatt gggtcaatat taaatctttta    5400 tctcactgag cttaccacaa tatttcataa tcaaataaca aaccctgcgc tgacaccact    5460
ctccatccaa gctttaagaa tcctcctcgg tagcaccttg ccaattgtca ttgagtccaa    5520
actcaacaca aacctcaaca cagcagagct gctcagttcc ggactgttaa ctggtcaaat    5580
aatttccatt tccccaatgt acatgcaaat gctaattcaa atcaatgttc cgacatttat    5640
aatgcaaccc ggtgcgaagg taattgatct aattgctatc tccgcaaacc ataaattgca    5700
```

```
agaagtggtt gtacaagttc cgaataggat tctagagtat gcaaatgaac tacaaaatta    5760
cccagccaat gactgtgtcg tgacaccgaa ctctgtattt tgtagataca atgagggttc    5820
ccctatccct gaatcacaat atcaatgctt gaggggggaat cttaattctt gcacttttac   5880
ccctattatc gggaactttc ttaagcgatt cgcatttgct aatggtgtgc tctatgccaa    5940
ctgcaaatct ttgctatgta ggtgtgccga ccccccccat gttgtatccc aggatgatac    6000
ccaaggcatc agcataattg atattaagag atgctctgag atgatgcttg acactttttc    6060
atttaggatc acatctactt tcaatgctac gtacgtgaca gacttctcaa tgattaatgc    6120
aaatattgta catctaagtc ctctagattt gtcaaatcaa atcaattcaa taaacaaatc    6180
tcttaaaagt gctgaggatt ggattgcaga tagcaacttc tttgctaatc aagccaggac    6240
agccaagaca ctttattcac taagtgcaat agcattaata ctatcagtga ttactttggt    6300
tgtcgtggga ttgctgattg cctacatcat caagctggtt tctcaaatcc atcaattcag    6360
atcgctagct gctacaacaa tgttccacag ggaaaatcct gccttctttt ccaagaataa    6420
ccatggaaac atatatggga tatcttaaga atctatcac aagtctatat atgtccacaa     6480 ttgacccctta agaaccaact tccaacgatt atccgttaaa tttaagtata atagttaaa    6540 aattaacatt aagcctccag ataccaatga atatgaatat atctcttaga aaacctgatt   6600
attatgtgat agcgtagtac aatttaagaa aaaacctaaa ataagcacga acccttaagg   6660
tgtcgtaacg tctcgtgaca ccgggttcag ttcaaatatc gacctctaac ccaatttaac   6720
acccattctt atataagaac acagtataat ttaatcacaa aagacctcaa aaactgacac   6780
agcttgatcc actcaacata taattgtaag attaataata atggaagatt acagcaatct   6840
atctcttaaa tcaattccta aaaggacatg tagaatcatt ttccgaactg ccacaattct   6900
tggaatatgc acattgattg ttctatgttc aagtattctt catgagataa ttcatcttga    6960
tgtttcctct ggtctcatgg attccgatga ttcacagcaa ggcattattc agcctattat   7020
agaatcatta aaatcattaa ttgctttggc taaccagatt ctgtacaatg ttgcaataat   7080
aattcctctt aaaattgaca gtatcgagac tgtaatatac tctgctttaa aggatatgca   7140
tactgggagc atgtccaaca ccaactgtac acccggaaat ctgcttctgc atgatgcagc   7200
gtacatcaat ggaataaaca aattccttgt acttaaatca tacaatggga cgcctaaata   7260
tggacctctc ctaaatattc ccagctttat ccccctcagca acatctccca acgggtgcac   7320
tagaatacca tcattttcac tcattaagac ccattggtgt tacactcaca atgtaatact   7380
tggagattgc ctcgatttca cgacatctaa tcagtattta gcaatgggga taatacaaca   7440
atctgctgca gcatttccaa tcttcaggac tatgaaaacc atttacctaa gtgatggaat   7500
caatcgcaaa agctgttcag tcactgctat accaggaggt tgtgtcttgt attgctatgt   7560
agctacaaga tctgagaaag aagattatgc cacaactgat ctagctgaac tgagacttgc   7620
tttctattat tataatgata cctttattga aagagtcata tctcttccaa atacaacagg   7680
gcaatgggcc acaatcaatc ctgcagttgg aagcgggatc tatcatctag ctttatttt    7740 atttcctgta tatggtggtc tcataaaggg gactccttcc tacaacaagc agtcctcacg   7800 ctatttatc ccaaaacatc ccaacataac ctgtgccggt aaatccagcg aacaggctgc    7860
agcagcacgg agttcctatg taatccgtta tcactcaaac aggttgattc agagtgctgt   7920
tcttatttgc ccattgtctg acatgcacac agcaaggtgt aatctagtta tgtttaacaa    7980
ttctcaagtc atgatgggtg cagaaggtag gctctatgtt attgacaata atttgtatta   8040
ttatcaacgt agttcctctt ggtgggctgc atcgcttttt tacaggatca atacagattt   8100
```

```
ttctaaagga attcctccta tcattgaggc tcaatgggta ccgtcctatc aagttccccg   8160
tcctggagtc atgccatgca atgcaacaag tttttgccct gctaattgca tcacaggggt   8220
gtacgcagat gtgtggccgc ttaacgatcc agaacccaca tcacaaaatg ctctgaatcc   8280
caactatcga tttgctggag cctttctcag aaatgagtcc aaccgaacca atcccacatt   8340
ctacactgca tcagccagcg ccctactaaa tactaccgga ttcaacaaca ccaatcacaa   8400
agcagcatat acgtcttcaa cctgctttaa gaatactgga actcaaaaga tttattgttt   8460
gataataatt gaaatgggct catctctttt aggggagttc caaataatac catttctaag   8520
ggaactaata ccttaatact attgaatgaa gactccagat tcaataataa ttgaaaggct   8580
ctctatctta tgcaatagtt atacgttttg gctgtattag aatgttatag cattctgctg   8640
tttttcccat atgaagcaat ccttcaacac cgacttaggt tcaattttct catcatttac   8700
tgttgtaatt caatcttact aaagttattc cgatatttaa gaaaaaataa cctttatata   8760
atgtaacaat actattaaga ttatgatata ggccagaatg gcggcctctt ctgagatact   8820
ccttcctgaa gtccacttga actcaccaat agtcaaacac aaactcatat actacttatt   8880
actagggcac ttcccgcatg atcttgacat ttctgaaata gccccccttc acaataatga   8940
ttgggatcaa attgccagag aagaatccaa tcttgctgaa cgacttggag tagctaaatc   9000
tgaattaatt aaacgtgtgc ccgcatttag agcaactaga tggcgtagtc atgcagccgt   9060
ccttatatgg ccttcttgta taccatttct tgttaaattc ctacctcatt ctaagcttca   9120
accagtagaa caatggtaca agttgatcaa tgcttcatgt aatactatat ctgactcaat   9180
tgatagatgt atggagaata tttctattaa gcttactggg aaaaacaatc tattctctcg   9240
atccagagga actgcaggtg caggtaaaaa cagtaaaatc accctcaatg atatccaatc   9300
tatttgggaa tcaaacaagt ggcaacctaa tgtatctttta tggcttacaa ttaaatacca   9360
aatgcgacaa cttataatgc atcaaagttc tcgtcagccg actgatttag ttcacattgt   9420
tgacacacga tctggtctaa tagttatcac ccctgaactt gttatttgtt ttgatcggtt   9480
aaatagtgtt ttaatgtatt ttacatttga gatgacttta atggtaagtg acatgtttga   9540
gggaaggatg aatgtcaccg ctctctgcac tattagtcat tacttatctc cactagggcc   9600
aaggatagat agattgtttt ccattgtaga tgaattagca caactattag gtgacactgt   9660
atataaagtt attgcatctc ttgaatcttt agtatatggg tgtctacaac ttaaagatcc   9720
agtagtggaa ttagcagggt catttcattc ctttattaca caagagatta tagatatcct   9780
aattggttca aaagcccttg ataaggatga atcaataact gttactacac aattgttaga   9840
tatattttcc aacctttctc cagatttaat tgctgagatg ttgtgtctca tgagactttg   9900
gggtcatccc actcttactg ctgcgcaagc tgcaggtaaa gtgagagaat ctatgtgtgc   9960
aggtaagtta cttgatttcc ctacaataat gaaaactctt gcttttttcc acacaatttt  10020
aattaatggt taccgtagaa agaaaaatgg aatgtggcct ccacttatac ttcctaaaaa  10080
tgcatcaaaa agcttaatag aatttcaaca tgataatgct gaaatatctt acgaatatac  10140
actcaagcat tggaaagaga tctctctcat agaatttaga aagtgctttg actttgatcc  10200
tggtgaggag ctaagcattt ttatgaaaga caaggcaata agtgctccaa gaagtgattg  10260
gatgagtgta tttcgtagaa gtctaataaa acaacgacat cagagacatc atattcctat  10320
gcccaatcca tttaatagac gtctattact caatttctta aagatgaca gttttgatcc  10380
agttgccgag cttcaatatg ttaccagtgg tgaatatctc caagatgaca cattttgtgc  10440
```

```
atcttactca ttaaaagaga aagaaataaa accagatgga aggatatttg ctaagcttac    10500
taatagaatg cggtcctgtc aagtaattgc ggaagcaatt ctcgcaaatc atgcaggtac    10560
tctaatgaag gaaaacggag ttgtcttgaa tcaattatca ctgactaaat cattgcttac    10620
tatgagtcaa attggcataa tatcagaaaa ggcgaagaga tatacgcgag ataacatctc    10680
atcccaaggt ttccatacaa tcaagactga ttctaaaaat aagaggaaaa gcaaaactgc    10740
atcatcatac ctcacagatc ctgatgatac atttgaactt agtgcatgtt ttataactac    10800
tgatcttgct aaatactgtc ttcaatggag atatcagacc ataatccatt ttgctcgaac    10860
attaaacaga atgtatggag ttccacattt atttgaatgg attcatcttc gtttaattag    10920
atctacatta tatgttggtg atccattcaa tcctcctgcc gcaactgatg ctttcgatct    10980
agataaagta ttaaatggtg atatcttat agtctctccc aagggaggta ttgaaggcct    11040
atgtcagaaa atgtggacaa tgatctctat ttctgtgatc atcctctctt cagccgaatc    11100
caaaacaaga gtaatgagca tggttcaagg agataatcag gcgattgcag ttacaacaag    11160
agttcctaga tcattaccta gtattcagaa aaaggagtta gcctatgcag caagcaagtt    11220
attttttgaa agacttaggg caaataatta tgggttgggt catcagctaa aggctcaaga    11280
aactataata agttccacgt tcttcatata tagtaaacgg gtattttatc aaggacgtat    11340
actaacacag gcactcaaaa atgctagcaa gttatgtctt actgcagatg tattaggtga    11400
atgtactcaa gcttcctgtt caaattctgc tactaccatc atgagattaa cagaaaatgg    11460
ggttgagaaa gatacatgtt ataagcttaa tatttatcag tccattcgtc aactcacata    11520
tgatctaata tttccccaat actccatacc aggtgaaact ataagtgaga ttttcctaca    11580
gcatccaaga ctaatctcac gtattgttct gctcccttca cagctaggtg gtcttaatta    11640
cctcgcatgt agcagattat ttaaccgcaa tatcggagat cctcttggta cagctgtggc    11700
agatctcaag aggttaatta atgtggtgc tcttgaatca tggatactgt ataatttact    11760
agcaagaaaa ccagggaaag gttcatgggc aactttagca gccgatccat actcattgaa    11820
tcaagaatat ctttatcctc ctactactat acttaaaaga catactcaaa atactttaat    11880
ggagatatgt cggaatccta tgttaaaggg agtttttaca gataatgcaa aagaggagga    11940
aaatctcctt gcaaaatttc ttcttgatcg tgatatagta ttgccaagag ttgcacacat    12000
tataatagat caatctagca tcggaaggaa gaaacagata caaggatttt ttgacaccac    12060
aaggaccata atgagacgat catttgaaat caaaccactc tcaactaaga agactctttc    12120
agtcatagaa tataatacta attacttatc ttataactac cctgtcatac ttaatccttt    12180
acctattcct ggatatttaa attatattac tgaccaaact tgcagtattg atatatctag    12240
aagtttaaga aaattatcat ggtcttcttt attgaatgga agaactttag aaggattaga    12300
aactccagat ccaattgaag ttgtcaatgg ttccttgatt gtaggtacag gagattgtga    12360
tttttgtatg caggggtgacg acaaatttac ttggttcttt ttacctatgg ggataattat    12420
tgatggaaat cctgaaacta atccaccat cagagttcca tacattgggt ctagaacaga    12480
ggaaagaaga gttgcatcaa tggcatatat taaaggtgcc acacacagtt tgaaggctgc    12540
tcttagaggc gcagggggtat atatttgggc attcggggat actgtagtga actggaatga    12600
tgcacttgat atcgcaaata ctaggggttaa gatatccca gagcaacttc agacccttac    12660
acctcttcct acatctgcaa acattacaca ccgtttagat gatggagcca caacacttaa    12720
attcactcca gctagttcct atgcattttc tagttatact catatatcaa atgatcaaca    12780
atatttagaa atagatcaga gagtagtcga ttctaatatt atttatcaac aattaatgat    12840
```

```
aacaggactt gggattattg agacctacca taacccacct ataaggactt ctacacaaga   12900
aatcactctc catttgcaca ctagctcatc ttgttgtgtt agaagtgtag atggttgcct   12960
tatatgtgag agcaatggag aggttcctca gatcactgtt ccctatacta atacatttgt   13020
atatgatcct gatccactag cagattatga gattgcacac ctagattatc tctcctacca   13080
agctaaaatt ggaagtacag attactactc actcactgat aaaattgacc tattagcaca   13140
tttaactgca aaacaaatga taaactcaat aattgggtta gatgaaacag tatcaattgt   13200
caatgatgcg gttatcctat ctgactatac taataactgg attagtgaat gttcttatac   13260
taagatagat ttagtttta aattaatggc atggaatttc cttcttgagc ttgcattcca    13320
gatgtactac ttaaggatat catcttggac aaatatattt gactatactt atatgacttt   13380
acgcaggata cccggaactg ctctaaataa tattgcagct actattagcc atccaaaatt   13440
attaagacgt gcaatgaatc ttgatattat cactcctata catgcaccgt atttagcttc   13500
attagattat gtcaaattaa gtattgatgc aattcagtgg ggagttaaac aagttcttgc   13560
tgatttatca aatggaattg atcttgaaat cttgattctt tcagaggatt caatggaaat   13620
tagtgatagg gcaatgaatc tcattgctag aaaactaact ctccttgcac ttgttaaagg   13680
tgagaactat acttttccaa aaattaaagg gatgccacca gaagaaaagt gtttagtctt   13740
aactgaatat ctagcaatgt gttatcaaaa tactcatcac ttagatccag atcttcaaaa   13800
gtatttatat aatctaacta atccaaaatt gactgcattt cccagtaaca acttctactt   13860
aactagaaaa atccttaatc aaattagaga atcagacgaa ggacaatata ttatcacctc   13920
atattatgaa tccttcgaac aattagaaac agatataatt cttcactcta ctttaactgc   13980
tccttatgat aattcagaaa ctctaacaaa gttcgattta tcccttgaca tctttccaca   14040
tccagaatct ctcgagaaat atcctcttcc agttgatcat gactctcgat ctgcaatttc   14100
aacactaatt ccaggccctc cttctcatca tgtattacga ccactaggag tgtcatccac   14160
agcttggtat aaagggataa gttattgtag atacctagaa acacaaaaga tacagactgg   14220
tgatcatctt tatttagccg aaggaagcgg tgcttcaatg tcacttctag aactcttatt   14280
tccaggagat actgtctatt ataatagtct ttttagtagt ggagagaatc ctccacagag   14340
aaactatgcc cctcttccaa ctcaatttgt acagagtgtt ccatataaat tgtggcaagc   14400
tgatcttgct gatgatagca atttgataaa agattttgtc ccattatgga atggaaacgg   14460
tgcagttaca gacttatcaa caaaggatgc agttgcattc ataatacata agtaggagc    14520
agagaaagca tcccttgtcc atatagatct cgaatcaact gctaatataa atcagcaaac   14580
tctgtccaga tccagattc attcattaat tatagcaact actgttctta agaggggtgg    14640
gatattaatt tataaaacat catggcttcc gttttctagg tttagtcaac tagcaagtct   14700
actttggtgc ttcttttgacc ggatccatct aatacgtagt agctattctg atcctcacag   14760
tcatgaggtt tatcttgtat gtagacttgc cgcagatttt agaactatcg gtttcagtgc   14820
agctctagta actgctacta ctcttcacaa tgacggattc acaacaatac atcctgatgt   14880
tgtttgtagt tattggcaac accatcttga aaatgttggg agagtcggaa aagtaattga   14940
tgagatactt gatggtttag ccaccaactt cttcgcagga gataatgggc ttattctaag   15000
atgtggagga actcccagct ccagaaaatg gttagagatt gaccagttag catcatttga   15060
tttggttcaa gatgctctgg ttacacttat cactatacac ctaaaggaaa ttatagaagt   15120
gcagtcatca catacagagg attatacatc tctcctcttc acaccttata atattggtgc   15180
```

```
agcagggaaa gtcagaacta tcatcaaatt aattctagaa cgatctttaa tgtatacagt    15240
ccgaaattgg ttagttttac ccagttccat ccgggattct gtacgacaag atttagaatt    15300
agggtcattt agattaatgt ctattttaag tgaacagaca tttcttaaaa agacacccac    15360
aaaaaaatac ttacttgatc agcttacaag gacatatata tcaaccttct ttaactctca    15420
ctcagtcctt cccctccacc gtccatatca aaaacaaata tggaaagcct taggtagtgt    15480
aatatattgt tcggagacag ttgatatacc tctaattaaa gacattcaga tagaagatat    15540
taatgatttt gaagatatcg agagggtat cgatggcgaa gaattatgac aacaatgatt     15600
ataagaactc atgatagttt tatttaagaa aaacatattg attttcccct tggt          15654
```

<210> SEQ ID NO 61
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61

```
acgcgtaatg                                                              10
```

<210> SEQ ID NO 62
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62

```
tagtaataag taagaaaaac ttagggttaa agacgcgt                               38
```

<210> SEQ ID NO 63
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63

```
agggttaaag taatacttta aagggacaag tcacagacat ttgatcttag tataaatacg       60
cgtaatg                                                                 67
```

<210> SEQ ID NO 64
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64

```
gcggccgcta gcaaattaag aaaaacttag ggtcaaagaa atg                         43
```

<210> SEQ ID NO 65
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 65
tagtagcggc cgc                                                        13

<210> SEQ ID NO 66
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
aatcaatatc cagagccaac tcaaaaagcg gccgcaaaac aattaagaaa aacttagggt    60
taaag                                                                 65

<210> SEQ ID NO 67
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Ser Asp Met
  1

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Val Ile Leu
  1

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Thr Leu Thr Lys Phe Asp Leu Ser Leu
  1               5

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asn Ser Asn Lys Val Arg Phe Ile Pro Phe
  1               5                  10
```